US007157451B2

(12) United States Patent
Atwal et al.

(10) Patent No.: US 7,157,451 B2
(45) Date of Patent: *Jan. 2, 2007

(54) HETEROCYCLIC DIHYDROPYRIMIDINE COMPOUNDS

(75) Inventors: Karnail S. Atwal, Newtown, PA (US); Wayne Vaccaro, Yardley, PA (US); John Lloyd, Yardley, PA (US); Heather Finlay, Lawrenceville, NJ (US); Lin Yan, Princeton, NJ (US); Rao S. Bhandaru, Belle Mead, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/660,878

(22) Filed: Sep. 12, 2003

(65) Prior Publication Data

US 2004/0063687 A1  Apr. 1, 2004

Related U.S. Application Data

(62) Division of application No. 09/729,731, filed on Dec. 5, 2000, now Pat. No. 6,706,720.

(60) Provisional application No. 60/236,037, filed on Sep. 28, 2000, provisional application No. 60/169,091, filed on Dec. 6, 1999.

(51) Int. Cl.
*C07D 401/06* (2006.01)
*A61K 31/4025* (2006.01)
*A61K 31/4162* (2006.01)
*C07D 487/04* (2006.01)

(52) U.S. Cl. .............. 514/217.06; 514/183; 514/228.5; 514/233.2; 514/252.16; 514/259.3; 540/481; 540/600; 544/61; 544/117; 544/281

(58) Field of Classification Search ................ 544/281; 514/259.3
See application file for complete search history.

(56) References Cited

U.S. PATENT DOCUMENTS

| 4,298,734 | A | 11/1981 | Temple, Jr. ............ 544/251 |
| 4,472,398 | A | 9/1984 | Meszaros et al. .......... 424/251 |
| 4,918,074 | A | 4/1990 | Tsuda et al. ................ 514/258 |
| 6,150,356 | A | 11/2000 | Lloyd et al. ................ 514/218 |
| 6,660,742 | B1 | 12/2003 | Lee | |

FOREIGN PATENT DOCUMENTS

| DE | 3309432 A1 | 9/1983 |
| EP | 0 163 240 A2 | 12/1985 |
| EP | 0 183 848 A1 | 6/1986 |
| EP | 0 217 142 A2 | 4/1987 |
| EP | 0 254 119 A1 | 1/1988 |
| EP | 0 304 001 A2 | 2/1989 |
| EP | 0 565 096 B1 | 10/1993 |
| GB | 1596320 | 8/1981 |
| JP | 61-227584 | 10/1986 |
| JP | 63-60985 | 3/1988 |
| JP | 63-107983 | 5/1988 |
| JP | 1-271751 | 10/1989 |
| JP | 8-301871 | 11/1996 |
| WO | WO 85/04172 | 9/1985 |
| WO | WO 90/10632 | 9/1990 |
| WO | WO 93/14083 | 7/1993 |
| WO | WO 97/35550 | 10/1997 |
| WO | WO 98/18475 | 5/1998 |
| WO | WO 98/18476 | 5/1998 |

OTHER PUBLICATIONS

Yi et al., Controlling Potassium Channel activities, PNAS, vol. 98, No. 20, pp. 11016-23, Sep. 2001.*
Bremner et al., Therapy of Crohn's Disease in childhood, Expert Opin. Pharmacother. 3(7), pp. 809-825, 2002.*
Singh et al., Immune therapy in inflammatory bowel disease and models of colitis, British Journal of Surgery, 88, 1558-1569, 2001.*
Robinson, Medical Therapy of Inflammatory Bowel Disease for the 21st Century, Eur. J. Surg. Suppl 582, pp. 90-98, 1998.*
Li G-R, Feng J, Yue L, Carrier M, Nattel S. *Evidence for two components of delayed rectifier K+ current in human ventricular myocytes.* Circ Res. 1996; 78:689-696.
Feng J, Wible B, Li GR, Wang Z, Nattel S. *Antisense oligodeoxynucleotides directed against Kv1.5 mRNA specifically inhibit ultrarapid delayed rectifier K+ Current in cultured adult human atrial myocytes.* Circ. Res. 1997 Apr.: 80(4):572-579.
Amos GJ, Wettwer E. Metzger F, LiQ, Himmel HM, Ravens U. *Differences between outward currents of human atrial and subepicardial ventricular myocytes.* J Physiol (Lond). 1996; 4911:31-50.
Cochran et al., "Regionally selective alterations in local cerebral glucose utilization evoked by charybdotoxin, a blocker of central voltage-activated K+-channels," Eur J Neurosci: Nov. 2001:14(9):1455-63.
Coleman et al., "Subunit composition of Kv1 channels in human CNAS," J Neurochem. Aug. 1999;73(2):849-58.

(Continued)

Primary Examiner—Deepak Rao
(74) *Attorney, Agent, or Firm*—Terence J. Bogie; Maureen P. O'Brien

(57) ABSTRACT

Novel heterocyclic dihydropyrimidine compounds useful as inhibitors of potassium channel function (especially inhibitors of the $K_v1$ subfamily of voltage gated $K^+$ channels, especially inhibitors $K_v1.5$ which has been linked to the ultra-rapidly activating delayed rectifier $K^+$ current $I_{Kur}$), methods of using such compounds in the prevention and treatment of arrhythmia and $I_{Kur}$-associated conditions, and pharmaceutical compositions containing such compounds.

15 Claims, No Drawings

OTHER PUBLICATIONS

Davies et al., "Kv channel subunit expression in rat pulmonary arteries," Lung. 2001;179(3):147-61. Epub Feb. 4, 2002.

Frey et al., "Blocking of cloned and native delayed rectifier K channels from visceral smooth muscles by phencyclidine," Neurogastroenterol Motif. Dec. 2000;12(6):509-16.

Hanson et al., "UK-78,282, a novel piperidine compound that potently blocks the Kv1.3 voltage-gated potassium channel and inhibits human T cell activation," British Journal of Pharmacology (1999), 128, 1707-1716.

Hatton et al., "Functional and molecular expression of a voltage-dependent K(+) channel (Kv1.1) in interstitial cells of Cajal," J Physiol. Jun. 1, 2001;533 (Pt 2):215-27.

Koh et al., "Contribution of delayed rectifier potassium currents to the electrical activity of murine colonic smooth muscle," J Physiol. Mar. 1, 1999; 515 (Pt 2):475-87.

Kourrich et al., "Kallotoxin, a Kv1.1 and Kv1.3 channel blocker, improves associative learning in rats," Behav Brain Res. Apr. 8, 2001;120(1):35-46.

Lopantsev et al., "Hyperexcitability of CA3 pyramidal cells in mice lacking the potassium channel subunit Kv1.1." Epilepsia. Dec. 2003;44(12):1506-12.

MacDonald et al., "Members of the Kv1 and Kv2 voltage-dependent K(+) channel families regulate insulin secretion," Mol Endocrinol. Aug. 2001;15(8):1423-35.

MacDonald et al., "Voltage-dependent K(+( channels in pancreatic beta cells; role, regulation and potential as therapeutic targets," Diabetologia. Aug. 2003;46(8):1048-62. Epub Jun. 27, 2003.

Pozeg et al., "In vivo gene transfer of the O2-sensitive potassium channel Kv1.5 reduces pulmonary hypertension and restores hypoxic pulmonary vasoconstriction in chronically hypoxic rats," Circulation. Apr. 22, 2003;107(15):2037-44, Epub Apr. 14, 2003.

Rho et al., "Developmental seizure susceptibility of kv1.1 potassium channel knockout mice," Dev Neurosci. Nov. 1999;21 (3-5):320-7.

Shah et al., "Immunosuppressiv effects of a Kv1.3 ubgubutirm" Cellular Immunology 221, (2003), 100-106.

Vianna-Jorge et al., "Shaker-type Kv1 channel blockers increase the peristatic activity of guinea-pig ileum by stimulating acetylcholine and tachykinins release by the enterio nervous system," Br J Pharmacol. Jan. 2003; 138(1):57-62.

Wickenden, "Potassium channels as anti-epileptic drug targets," Neuropharmacology. Deb. 2002;43(7):1055-60.

Wulff et al., "Potassium channels as therapeutic targets for autoimmune disorders," Current Opinion in Drug Discovery & Develpment 2003 6(5):640-647.

Xu et al., "The voltage-gated potassium channel Kv1.3 regulates peripheral insulin sensitivity," Proc natl Acad Sci U S A. mar. 2, 2004;101(9):3112-7. Epub Feb. 23, 2004 (epublished Feb. 23, 2004).

* cited by examiner

HETEROCYCLIC DIHYDROPYRIMIDINE COMPOUNDS

This application is a Divisional of U.S. Ser. No. 09/729,731 filed Dec. 5, 2000 now U.S. Pat. No. 6,706,720 which claims priority to U.S. Provisional application Ser. No. 60/236,037 filed Sep. 28, 2000 and U.S. Provisional application Ser. No. 60/169,091 filed Dec. 6, 1999. The entirety of each of these applications is incorporated herein by reference.

FIELD OF THE INVENTION

The present invention provides for heterocyclic dihydropyrimidine compounds useful as inhibitors of potassium channel function (especially inhibitors of the $K_v1$ subfamily of voltage gated $K^+$ channels, more especially inhibitors $K_v1.5$ which has been linked to the ultra-rapidly activating delayed rectifier $K^+$ current $I_{Kur}$) and to pharmaceutical compositions containing such compounds. The present invention further provides for methods of using such compounds in the treatment of arrhythmia, $I_{Kur}$-associated disorders, and other disorders mediated by ion channel function.

BACKGROUND OF THE INVENTION

The importance of potassium channels was first recognized aproximately fifty years ago when Hodgkin and Huxley discovered that potassium ions contributed to the current that excited the squid giant axon. Research in the area, however, was hampered by the lack of selective, high affinity ligands for potassium channels. But the advent of recombinant DNA techniques and single cell and whole cell voltage clamp techniques has changed the slow pace of the field. Indeed, potassium channels that exhibit functional, pharmacological and tissue distribution characteristics have been cloned. These cloned potassim channels are useful targets in assays for identifying candidate compounds for the treatment of various disease states. Potassium channels have turned out to be the most diverse family of ion channels discovered to date. They modulate a number of cellular events such as muscle contraction, neuro-endocrine secretion, frequency and duration of action potentials, electrolyte homeostatis, and resting membrane potential.

Potassium channels are expressed in eukaryotic and procaryotic cells and are elements in the control of electrical and non-electrical cellular functions. Potassium channels have been classified according to their biophysical and pharmacological characteristics. Subclasses of these channels have been named based on amino acid sequence and functional properties. Salient among these are the voltage dependent potassium channels, for example voltage gated potassium channels (e.g., $K_v1$, $K_v2$, $K_v3$, $K_v4$). Subtypes within these subclasses have been characterized as to their putative function, pharmacology and distribution in cells and tissues (Chandy and Gutman, "Voltage-gated potassium channel genes" in Handbook of Receptors and Channels—Ligand and Voltage-gated Ion Channels, ed. R. A. North, 1995; Doupnik et al., Curr. Opin. Neurobiol. 5:268, 1995). For example, the $K_v1$ class of potassium channels is further subdivided depending on the molecular sequence of the channel, for example $K_v1.1$, $K_v1.2$, $K_v1.3$, $K_v1.4$, $K_v1.5$, $K_v1.6$, and $K_v1.7$. Functional voltage-gated $K^+$ channels can exist as multimeric structures formed by the association of either identical or dissimilar subunits. This phenomena is thought to account for the wide diversity of $K^+$ channels. However, subunit compositions of native $K^+$ channels and the physiologic role that particular channels play are, in most cases, still unclear.

Membrane depolarization by $K_v1.3$ inhibition has been shown to be an effective method to prevent T-cell proliferation and therefore has applications in many autoimmune conditions. Inhibition of $K^+$ channels in the plasma membrane of human T-lymphocytes has been postulated to play a role in eliciting immunosuppressive responses by regulating intracellular $Ca^{++}$ homeostasis, which has been found to be important in T-cell activation.

The $K_v1.3$ voltage-gated potassium channel is found in neurons, blood cells, osteoclasts and T-lymphocytes. The Chandy and Cahalan laboratories proposed a hypothesis that blocking the $K_v1.3$ channel would elicit an immunosuppressant response. (Chandy et al., J. Exp. Med. 160, 369, 1984; Decoursey et al., Nature, 307, 465, 1984). However, the $K^+$ channel blockers employed in their studies were non-selective. Until research with the peptide margatoxin, a peptide found in scorpion venom, no specific inhibitor of the $K_v1.3$ channel existed to test this hypothesis. Although a laboratory (Price et al., Proc. Natl, Acad, Sci. USA, 86, 10171, 1989) showed that charybdotoxin would block $K_v1.3$ in human T-cells, charybdotoxin was subsequently shown to inhibit four different $K^+$ channels ($K_v1.3$ and three distinct small conductance $Ca^{++}$ activated $K^+$ channels) in human T-lymphocytes, limiting the use of this toxin as a probe for the physiological role of $K_v1.3$ (Leonard et al., Proc. Natl, Acad. Sci. USA, 89, 10094, 1992). Margatoxin, on the other hand, blocks only Kv1.3 in T-cells, and has immunosuppressant activity on both in in vitro and in vivo models. (Lin et al., J. exp. Med, 177, 637, 1993). The therapeutic utility of this compound, however, is limited by its potent toxicity. Recently, a class of compounds has been reported that may be an attractive alternative to the above mentioned drugs, see for example U.S. Pat. Nos. 5,670,504; 5,631,282; 5,696,156; 5,679,705; and 5,696,156. While addressing some of the activity/toxicity problems of previous drugs, these compounds tend to be of large molecular weight and are generally produced by synthetic manipulation of a natural product, isolation of which is cumbersome and labor intensive.

Immunoregulatory abnormalities have been shown to exist in a wide variety of autoimmune and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves ophthalmopathy and asthma.

Although the underlying pathogenesis of each of these conditions may be quite different, they have in common the appearance of a variety of auto-antibodies and self-reactive lymphocytes. Such self-reactivity may be due, in part, to a loss of the homeostatic controls under which the normal immune system operates. Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Anti-inflammatory agents such as NSAID's act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A(CsA), which was approved by the US FDA in 1983 is currently the leading drug used to prevent rejection of transplanted organs. In 1993, FK-506 (Prograf) was approved by the US FDA for the prevention of rejection in liver transplantation. CsA and FK-506 act by inhibiting the body's immune system from mobilizing its vast arsenal of natural protecting agents to reject the transplant's foreign protein. In 1994, CsA was approved by the US FDA for the treatment of severe psoriasis and has been approved by European regulatory agencies for the treatment of atopic dermatitis. Though they are effective in fighting transplant rejection, CsA and FK-506 are known to cause several undesirable side effects including nephrotoxicity, neurotoxicity, and gastrointestinal discomfort. Therefore, a selective immunosuppressant without these side effects still remains to be developed. Potassium channel inhibitors promise to be the solution to this problem.

Atrial fibrillation (AF) and atrial flutter are the most common cardiac arrhythmias in clinical practice and are likely to increase in prevalence with the aging of the population. Currently, AF affects more than 1 million Americans annually, represents over 5% of all admissions for cardiovascular diseases and causes more than 80,000 strokes each year in the United States. While AF is rarely a lethal arrhythmia, it is responsible for substantial morbidity and can lead to complications such as the development of congestive heart failure or thromboembolism. Currently available Class I and Class III antiarrhythmic drugs reduce the rate of recurrence of AF, but are of limited use because of a variety of potentially adverse effects including ventricular proarrhythmia. Because current therapy is inadequate and fraught with side effects, there is a clear need to develop new therapeutic approaches Antiarrhythmic agents of Class III are drugs that cause a selective prolongation of the duration of the action potential without significant cardiac depression. Available drugs in this class are limited in number. Examples such as sotalol and amiodarone have been shown to possess interesting Class III properties (Singh B. N., Vaughan Williams E. M. "A Third Class of Anti-Arrhythmic Action: Effects On Atrial And Ventricular Intracellular Potentials And Other Pharmacological Actions On Cardiac Muscle, of MJ 1999 and AH 3747" Br. J. Pharmacol 1970; 39:675–689, and Singh B. N., Vaughan Williams E. M, "The Effect of Amiodarone, A New Anti-Anginal Drug, On Cardiac Muscle", Br J. Pharmacol 1970; 39:657–667), but these are not selective Class III agents. Sotalol also possesses Class II effects which may cause cardiac depression and is contraindicated in certain susceptible patients. Amiodarone, also is not a selective Class III antiarrhythmic agent because it possesses multiple electrophysiological actions and is severely limited by side effects (Nademanee, K. "The Amiodarone Odessey". J. Am. Coll. Cardiol. 1992;20:1063–1065.) Drugs of this class are expected to be effective in preventing ventricular fibrillation. Selective class III agents, by definition, are not considered to cause myocardial depression or an induction of arrhythmias due to inhibition of conduction of the action potential as seen with Class I antiarrhythmic agents.

Class III agents increase myocardial refractoriness via a prolongation of cardiac action potential duration. Theoretically, prolongation of the cardiac action potential can be achieved by enhancing inward currents (i.e. Na$^+$ or Ca$^{2+}$ currents; hereinafter I$_{Na}$ and I$_{Ca}$, respectively) or by reducing outward repolarizing potassium (K$^+$) currents. The delayed rectifier (I$_K$) K$^+$ current is the main outward current involved in the overall repolarization process during the action potential plateau, whereas the transient outward (I$_{to}$) and inward rectifier (I$_{KI}$) K$^+$ currents are responsible for the rapid initial and terminal phases of repolarization, respectively. Cellular electrophysiologic studies have demonstrated that I$_K$ consists of two pharmacologically and kinetically distinct K$^+$ current subtypes, I$_{Kr}$ (rapidly activating and deactivating) and I$_{Ks}$ (slowly activating and deactivating) (Sanguinetti and Jurkiewicz, Two Components Of Cardiac Delayed Rectifier K$^+$ Current: Differential Sensitivity To Block By Class III Antiarrhythmic Agents, J Gen Physiol 1990, 96:195–215). Class III antiarrhythmic agents currently in development, including d-sotalol, dofetilide (UK-68,798), almokalant (H234/09), E-4031 and methanesulfonamide-N-[1'-6-cyano-1,2,3,4-tetrahydro-2-naphthalenyl)-3,4-dihydro-4-hydroxyspiro[2H-1-benzopyran-2,4'-piperidin]-6yl]monochloride, predominantly, if not exclusively, block I$_{Kr}$. Although, amiodarone is a blocker of I$_{Ks}$ (Balser J. R. Bennett, P. B., Hondeghem, L. M. and Roden, D. M. "Suppression Of Time-Dependent Outward Current In Guinea Pig Ventricular Myocytes: Actions Of Quinidine And Amiodarone. Circ. Res. 1991, 69:519–529), it also blocks I$_{Na}$ and I$_{Ca}$, effects thyroid function, is as a nonspecific adrenergic blocker, and acts as an inhibitor of the enzyme phospholipase (Nademanee, K. "The Amiodarone Odessey", J. Am. Coll. Cardiol. 1992; 20:1063–1065). Therefore its method of treating arrhythmia is uncertain. Most Class III agents that are known to be in development predominantly block I$_{Kr}$.

Reentrant excitation (reentry) has been shown to be a prominent mechanism underlying supraventricular arrhythmias in man. Reentrant excitation requires a critical balance between slow conduction velocity and sufficiently brief refractory periods to allow for the initiation and maintenance of multiple reentry circuits to coexist simultaneously and sustain AF. Increasing myocardial refractoriness by prolonging action potential duration (APD), prevents and/or terminates reentrant arrhythmias. Most selective Class III antiarrhythmic agents currently in development, such as d-sotalol and dofetilide predominantly, if not exclusively, block I$_{kr}$, the rapidly activating component of I$_K$ found both in the human atrium and ventricle.

Since these I$_{kr}$ blockers increase APD and refractoriness both in atria and ventricle without affecting conduction per se, theoretically they represent potential useful agents for the treatment of arrhythmias like AF. These agents have a liability in that they have an enhanced risk of proarrhythmia at slow heart rates. For example, torsades de points has been observed when these compounds are utilized (Roden, D. M. "Current Status of Class III Antiarrhythmic Drug Therapy", Am J. Cardiol, 1993; 72:44B–49B). This exaggerated effect at slow heart rates has been termed "reverse frequency-dependence", and is in contrast to frequency-independent or frequency-dependent actions (Hondeghem, L. M. "Development of Class III Antiarrhythmic Agents". J. Cadiovasc. Cardiol. 20 (Suppl.2):S17–S22).

The slowly activating component of the delayed rectifier (I$_{ks}$) potentially overcomes some of the limitations of I$_{kr}$ blockers associated with ventricular arrhythmias. Because of its slow activation kinetics however, the role of I$_{ks}$ in atrial repolarization may be limited due to the relatively short APD of the atrium. Consequently, although I$_{ks}$ blockers may provide distinct advantage in the case of ventricular arrhythmias, their ability to affect SVT is considered to be minimal.

The ultra-rapidly activating delayed rectifier K$^+$ current (I$_{kur}$) is believed to represent the native counterpart to a cloned potassium channel designated Kv1.5 and, while present in human atrium, it appears to be absent in human ventricle. Furthermore, because of its rapidity of activation and limited slow inactivation, $I_{kur}$ is believed to contribute significantly to repolarization in human atrium. Consequently, a specific blocker of $I_{kur}$, that is a compound which blocks Kv1.5, would overcome the short coming of other compounds by prolonging refractoriness by retarding repolarization in the human atrium without causing the delays in ventricular reporlarization that underlie arrhythmogenic after depolarizations and acquired long QT syndrome observed during treatment with current Class III drugs.

In intact human atrial myocytes an ultra-rapidly activating delayed rectifier K+ current $I_{kur}$ which is also known as the sustained outward current, $L_{SUS}$ or $I_{SO}$, has been identified and this current has properties and kinetics identical to those expressed by the human K+ channel clone (hKv1.5, HK2) when isolated from human heart and stably expressed in human (HEK-293) cell lines. (Wang et al., 1993, Circ Res 73:1061–1076; Fedida et al., 1993, Circ Res 73:210–216; Snyders et al., 1993, J Gen Physiol 101:513–543) and originally cloned from rat brain (Swanson et al., 10, Neuron 4:929–939). Although various antiarythmic agents are now available on the market, those having both satisfactory efficacy and a high margin of safety have not been obtained. For example, antiarrythmic agents of Class I according to the classification scheme of Vaughan-Williams ("Classification Of Antiarrhythmic Drugs: In: Cardiac Arrhythmias, edited by: E. Sandoe, E. Flensted-Jensen, K. Olesen; Sweden, Astra, Sodertalje, pp449–472, 1981) which cause a selective inhibition of the maximum velocity of the upstroke of the action potential $(_{max})$ are inadequate for preventing ventricular fibrillation. In addition, they have problems regarding safety, namely, they cause a depression of myocardial contractility and have a tendency to induce arrhythmias due to an inhibition of impulse conduction. Beta-adrenoceptor blockers and calcium antagonists which belong to Class II and IV, respectively, have a defect in that their effects are either limited to a certain type of arrhythmia or are contraindicated because of their cardiac depressant properties in certain patients with cardiovascular disease. Their safety, however, is higher than that of the antiarrythmic agents of Class I.

SUMMARY OF THE INVENTION

The present invention provides heterocyclic dihydropyrimidine compounds of the following formula I, including enantiomers, diastereomers, and salts thereof, useful as inhibitors of potassium channel function (especially inhibitors of the $K_v1$ subfamily of voltage gated K+ channels, more especially inhibitors $K_v1.5$ which has been linked to the ultra-rapidly activating delayed rectifier K+ current $I_{Kur}$) for the treatment of disorders such as arrhythmia and $I_{Kur}$-associated disorders:

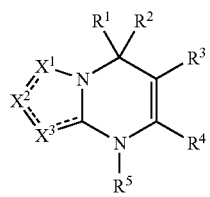

(I)

where $X^1$, $X^2$ and $X^3$ are independently selected from N, $NR^6$, $(CR^7)_q$, $(CHR^7)_q$, or C=O, wherein the bonds connecting $X^1$, $X^2$ and $X^3$ to adjacent atoms may be single or double bonds forming a 5 to 7-membered saturated, partially unsaturated or aromatic ring;

$R^1$, $R^2$, $R^3$, $R^4$, $R^5$, $R^6$ and $R^7$ are the same or different and are independently selected from groups of the formula —$(CH_2)_n$-$(Z^1)_m$—$(CH_2)_p$-$Z^2$; or $R^1$, $R^2$, $R^3$, $R^4$ and $R^5$ may, in one or more pairs of two (such as $R^1$ and $R^2$, $R^1$ and $R^3$, $R^2$ and $R^3$, $R^3$ and $R^4$ or $R^4$ and $R^5$), together with the atoms to which they are bonded, form a carbocyclic, substituted carbocyclic, heterocyclic or substituted heterocyclic group; or $R^6$ and $R^7$ may, in one or more pairs of two (such as $R^6$ and $R^7$, $R^6$ and $R^6$, or $R^7$ and $R^7$), together with the atoms to which they are bonded, form a carbocyclic, substituted carbocyclic, heterocyclic or substituted heterocyclic group;

$Z^1$ is —$CZ^3Z^4$-, —O—, —$NZ^3$-, —S—, —SO—, —$SO_2$—, —C(O)—, —C(O)$Z^3$-, —C(O)$NZ^4$-, —C(S)—, —C(=$NOZ^3$)—, alkyl, substituted alkyl, alkenyl, substituted alkenyl, alkynyl, substituted alkynyl, carbocyclo, substituted carbocyclo, aryl, substituted aryl, heterocyclo, or substituted heterocyclo;

$Z^2$ is hydrogen, —$OZ^5$, —OC(O)$Z^5$, —$NZ^5$-C(O)-$Z^6$, —$NZ^5$-$CO_2$-$Z^6$, —$NZ^5$(C=O)—$NZ^6Z^7$, —$NZ^5Z^6$, —$NO_2$, halo, —CN, —C(O)$Z^5$, —$CO_2Z^5$, —C(S)$Z^5$, —(C=$NOZ^5$)$Z^6$, —C(O)$NZ^5Z^6$, —C(S)$NZ^5Z^6$, —$SZ^5$, —$SOZ^5$, —$SO_2Z^5$, —$SO_2NZ^5Z^6$, alkyl, substituted alkyl, alkenyl, substituted alkenyl, alkynyl, substituted alkynyl, carbocyclo, substituted carbocyclo, aryl, substituted aryl, heterocyclo (such as heteroaryl), or substituted heterocyclo;

$Z^3$, $Z^4$, $Z^5$, $Z^6$ and $Z^7$ are independently hydrogen, halo, alkyl, substituted alkyl, alkenyl, substituted alkenyl, alkynyl, substituted alkynyl, carbocyclo, substituted carbocyclo, aryl, substituted aryl, heterocyclo, or substituted heterocyclo; or $Z^1$, $Z^4$, $Z^5$, $Z^6$ and $Z^7$ may, in one or more pairs of two (such as $Z^3$ and $Z^4$, $Z^5$ and $Z^6$ or $Z^6$ and $Z^7$), together with the atoms to which they are bonded, form a carbocyclic, substituted carbocyclic, heterocyclic or substituted heterocyclic group;

n and p are independently selected from integers from 0 to 10 wherein, when m is 0, p is also 0;

m is an integer selected from 0 or 1; and q is an integer selected from 1 to 3.

The present invention provides novel methods for the prevention and treatment of arrhythmia and $I_{Kur}$-associated disorders employing one or more compounds of the formula I, enantiomers, diastereomers or pharmaceutically acceptable salts thereof. In particular the present invention provides a novel method for the selective prevention and treatment of supraventricular arrhythmias.

In addition, compounds within the formula I, as well as enantiomers, diastereomers and salts thereof are novel compounds, including compounds of formula I* and salts thereof:

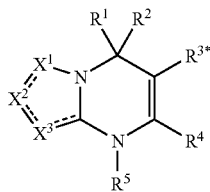

(I*)

where
X¹, X², X³, R¹, R², R⁴ and R⁵ are as defined above;
R³* is —OZ⁵, —OC(O)-Z⁵, —NZ⁵-C(O)₂-Z⁶, —NZ⁵(C=O)—NZ⁶Z⁷, —NZ⁵Z⁶, —(C=NOZ⁵)Z⁶, —C(O)NZ⁵*Z⁶*, —C(S)NZ⁵*Z⁶*, —SZ⁵, —SOZ⁵, —SO₂Z⁵, —SO₂NZ⁵Z⁶, —C(O)Z³*-Z²*, halo, alkyl, substituted alkyl, alkenyl, substituted alkenyl, alkynyl, substituted alkynyl, carbocyclo, substituted carbocyclo, aryl, substituted aryl, heterocyclo or substituted heterocylco;
Z²* is other than hydrogen when Z³* is heterocyclo;
Z³* is heterocyclo or substituted heterocyclo;
Z⁵* is substituted alkyl, alkenyl, substituted alkenyl, alkynyl, substituted alkynyl, carbocyclo, substituted carbocyclo, aryl, substituted aryl, heterocyclo, or substituted heterocyclo; and
Z⁶* is hydrogen, alkyl, substituted alkyl, alkenyl, substituted alkenyl, alkynyl, substituted alkynyl, carbocyclo, substituted carbocyclo, aryl, substituted aryl, heterocyclo, or substituted heterocyclo, provided that Z⁶* is not hydrogen when Z⁵* is unsubstituted cycloalkyl, unsubstituted aryl, or unsubstituted benzyl;
or Z⁵* and Z⁶* may together with the nitrogen atom to which they are bonded form a heterocyclic group or substituted heterocyclic group, provided that Z⁵* and Z⁶* do not together form unsubstituted piperidinyl, unsubstituted pyrrolidinyl, or unsubstituted morpholinyl, and further provided that when
(i) R¹ and R⁵ are each hydrogen; and
(ii) R² is aryl or substituted aryl; and
(iii) R⁴ is heterocyclo-substituted aryl; and
(iv) X¹, X² and X³ form the ring

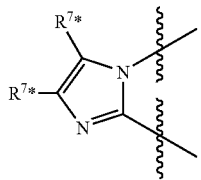

where R⁷* is H or alkyl
Z⁵* and Z⁶* do not together form unsubstituted piperazinyl or N-alkyl-substituted piperazinyl;

Preferred Compounds

Compounds of the formula I and salts thereof wherein one or more, and especially all, of X¹, X², X³, R¹, R², R³, R⁴ and R⁵ are selected from the following definitions, are preferred compounds of the present invention:
R¹ is hydrogen;
R² is hydrogen, alkyl, substituted alkyl, aryl, substituted aryl, heterocyclo, substituted heterocyclo, carbocyclo or substituted carbocyclo;

R³ is —(CH₂)ₙ-Z², —(CH₂)ₙ—C(O)Z³-(CH₂)ₚ-Z², or —(CH₂)ₙ—C(O)NZ⁴-(CH₂)ₚ-Z²;
R⁴ is alkyl or substituted alkyl; and
R⁵ is hydrogen, or —(CH₂)ₙ-Z²; and
X¹, X² and X³, together with the atoms to which they are bonded, form a ring selected from:

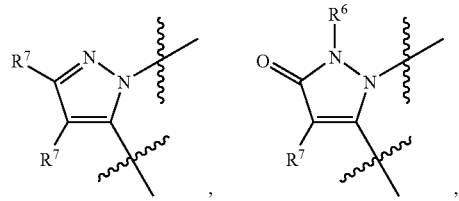

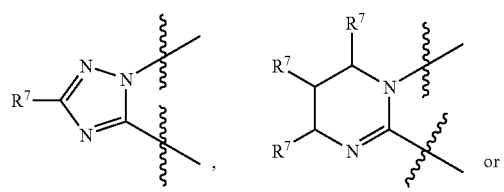

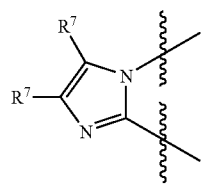

where R⁶ and/or R⁷ are the same or different, as defined above.

Compounds of the formula I and salts thereof wherein one or more, and especially all, of X¹, X², X³, R¹, R², R³, R⁴ and R⁵ are selected from the following definitions, are more preferred compounds of the present invention:
R¹ is hydrogen;
R² is aryl (especially where aryl is phenyl), substituted aryl, heterocyclo, substituted heterocyclo, carbocyclo or substituted carbocyclo;
R³ is —(CH₂)ₙ-Z², —(CH₂)ₙ—C(O)Z³-(CH₂)ₚ-Z², or —(CH²)ₙ—C(O)NZ⁴-(CH₂)ₚ-Z² wherein
Z² is selected from —C(O)NZ⁵Z⁶, —CO₂Z⁵, —SO₂Z⁵, —NZ⁵Z⁶, —NZ⁵CO₂Z⁶, —NZ⁵C(O)Z⁶, —OZ⁵, aryl, substituted aryl, heterocyclo, substituted heterocyclo, alkyl or substituted alkyl;
Z³ is heterocyclo or substituted heterocyclo; and
n and p are independently selected from integers 0 to 3;
R⁴ is alkyl, or substituted alkyl;
R⁵ is hydrogen, or —(CH₂)ₙ-Z² wherein Z² is selected from —C(O)NZ⁵Z⁶, —CO₂Z⁵, —NZ⁵Z⁶, aryl, substituted aryl, alkyl, or substituted alkyl; and $X^1$, $X^2$ and $X^3$, together with the atoms to which they are bonded, form a ring selected from:

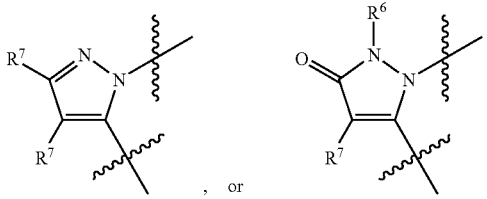

, or

Compounds of the formula I and salts thereof wherein one or more, and especially all, of $X^1$, $X^2$, $X^3$, $R^1$, $R^2$, R, $R^4$ and $R^5$ are selected from the following definitions, are most preferred compounds of the present invention:

$R^1$ is hydrogen;

$R^2$ is aryl (especially where aryl is phenyl), substituted aryl, heterocyclo, substituted heterocyclo, carbocyclo or substituted carbocyclo;

$R^3$ is heterocyclo or substituted heterocyclo, —C(O)N$Z^5Z^6$, —C(O)$Z^3$-CON$Z^5Z^6$, —C(O)$Z^3$-$Z^2$, or —C(O)$Z^3$-CO$_2Z^5$, wherein $Z^3$ is heterocyclo or substituted heterocyclo, and $Z^2$ is aryl or substituted aryl;

$R^4$ is alkyl (especially lower alkyl) or substituted alkyl (especially halo-substituted alkyl or alkoxy-substituted alkyl);

$R^5$ is hydrogen, alkyl or substituted alkyl; and $X^1$, $X^2$ and $X^3$, together with the atoms to which they are bonded, form a ring selected from:

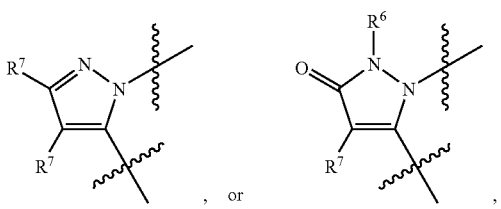

, or wherein $R^6$ is H or C(O)$Z^5$, where $Z^5$ is alkyl or carbocyclo; and $R^7$ is independently selected from H, alkyl, substituted alkyl (especially halo-substituted), halo, or CN

DETAILED DESCRIPTION OF THE INVENTION

The following are definitions of terms used in this specification. The initial definition provided for a group or term herein applies to that group or term throughout the present specification, individually or as part of another group, unless otherwise indicated.

The terms "alk" or "alkyl" refer to straight or branched chain hydrocarbon groups having 1 to 12 carbon atoms, preferably 1 to 8 carbon atoms, such as methyl, ethyl, n-propyl, i-propyl, n-butyl, i-butyl, t-butyl, pentyl, hexyl, heptyl, octyl, etc. Lower alkyl groups, that is, alkyl groups of 1 to 6 carbon atoms, are generally most preferred. The term "substituted alkyl" refers to alkyl groups substituted with one or more groups (such as by groups described above in the definition of $R^1$), preferably selected from aryl, substituted aryl, heterocyclo, substituted heterocyclo, carbocyclo, substituted carbocyclo, halo, hydroxy, alkoxy (optionally substituted), aryloxy (optionally subsituted), alkylester (optionally substituted), arylester (optionally substituted), alkanoyl (optionally substituted), aryol (optionally substituted), cyano, nitro, amino, substituted amino, amido, lactam, urea, urethane, sulfonyl, etc.

The term "alkenyl" refers to straight or branched chain hydrocarbon groups having 2 to 12 carbon atoms, preferably 2 to 4 carbon atoms, and at least one double carbon to carbon bond (either cis or trans), such as ethenyl. The term "substituted alkenyl" refers to alkenyl groups substituted with one or more groups (such as by groups described above in the definition of $R^1$), preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, etc.

The term "alkynyl" refers to straight or branched chain hydrocarbon groups having 2 to 12 carbon atoms, preferably 2 to 4 carbon atoms, and at least one triple carbon to carbon bond, such as ethynyl. The term "substituted alkynyl" refers to alkynyl groups substituted with one or more groups (such as by groups described above in the definition of $R^1$), preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, etc.

The terms "ar" or "aryl" refer to aromatic homocyclic (i.e., hydrocarbon) mono-, bi- or tricyclic ring-containing groups preferably having 6 to 12 members such as phenyl, naphthyl and biphenyl. Phenyl is a preferred aryl group. The term "substituted aryl" refers to aryl groups substituted with one or more groups (such as by groups described above in the definition of $R^1$), preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, etc., where optionally one or more pair of substituents together with the atoms to which they are bonded form a 3 to 7 member ring.

The terms "cycloalkyl" and "cycloalkenyl" refer to mono-, bi- or tri homocylcic ring groups of 3 to 15 carbon atoms which are, respectively, fully saturated and partially unsaturated. The term "cycloalkenyl" includes bi- and tricyclic ring systems that are not aromatic as a whole, but contain aromatic portions (e.g. fluorene, tetrahydronapthalene, dihydroindene, and the like). The rings of multi-ring cycloalkyl groups may be either fused, bridged and/or joined through one or more spiro unions. The terms "substituted cycloalkyl" and "substituted cycloalkenyl" refer, respectively, to cycloalkyl and cycloalkenyl groups substituted with one or more groups (such as by groups described above in the definition of $R^1$), preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, etc.

The terms "carbocyclo", "carbocyclic" or "carbocyclic group" refer to both cycloalkyl and cycloalkenyl groups. The terms "substituted carbocyclo", "substituted carbocyclic" or "substituted carbocyclic group" refer to carbocyclo or carbocyclic groups substituted with one or more groups as described in the definition of cycloalkyl and cycloalkenyl.

The terms "halogen" and "halo" refer to fluorine, chlorine, bromine and iodine.

The terms "heterocycle", "heterocyclic", "heterocyclic group" or "heterocyclo" refer to fully saturated or partially or completely unsaturated, including aromatic ("heteroaryl") or nonaromatic cyclic groups (for example, 3 to 13 member monocyclic, 7 to 17 member bicyclic, or 10 to 20 member tricyclic ring systems, preferably containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be either fused, bridged and/or joined through one or more spiro unions.

Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, triazinyl, tetrahydropyranyl, tetrazoyl, triazolyl, morpholinyl, thiamorpholinyl, thiamorpholinyl sulfoxide, thiamorpholinyl sulfone, 1,3-dioxolane and tetrahydro-1,1-dioxothienyl,

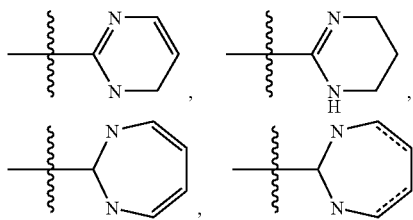

and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, benzofuranly, dihydrobenzofuranyl, chromonyl, coumarinyl, benzodioxolyl, dihydrobenzodioxolyl, benzodioxinyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl, azabicycloalkyls (such as 6-azabicyclo[3.2.1]octane), azaspiroalkyls (such as 1,4 dioxa-8-azaspiro[4.5]decane), imidazopyridinyl (such as imidazo[1,5-a]pyridin-3-yl), triazolopyridinyl (such as 1,2,4-triazolo[4,3-a]pyridin-3-yl), and hexahydroimidazopyridinyl (such as 1,5,6,7,8,8a-hexahydroimidazo[1,5-a]pyridin-3-yl),

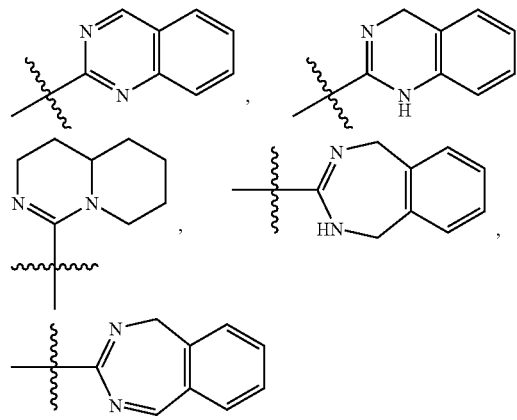

and the like.

Exemplary tricyclic heterocyclic groups include carbazolyl, benzidolyl, phenanthrolinyl, acridinyl, phenanthridinyl, xanthenyl and the like.

The terms "substituted heterocycle", "substituted heterocyclic", "substituted heterocyclic group" and "substituted heterocyclo" refer to heterocycle, heterocyclic and heterocyclo groups substituted with one or more groups (such as by groups described above in the definition of $R^1$), preferably selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, etc., where optionally one or more pair of substituents together with the atoms to which they are bonded form a 3 to 7 member ring.

The term "alkanoyl" refers to alkyl group (which may be optionally substituted as described above) linked to a carbonyl group (i.e. —C(O)-alkyl). Similarly, the term "aroyl" refers to an aryl group (which may be optionally substituted as described above) linked to a carbonyl group (i.e., —C(O)-aryl).

Throughout the specification, groups and substituents thereof may be chosen to provide stable moieties and compounds.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound 1 with an amount of acid or base, such as an equivalent amount, in a medium such as one in which the salt precipitates or in an aqueous medium followed by lyophilization.

The compounds of formula I which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug", as employed herein, denotes a compound which, upon administration to a subject, undergoes chemical conversion by metabolic or chemical processes to yield a compound of the formula I, or a salt and/or solvate thereof. Solvates of the compounds of formula I are preferably hydrates.

To the extent that compounds of the formula I, and salts thereof, may exist in their tautomeric form, all such tautomeric forms are contemplated herein as part of the present invention.

All stereoisomers of the present compounds, such as those which may exist due to asymmetric carbons on the various R and Z substituents, including enantiomeric forms (which may exist even in the absence of asymmetric carbons) and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

The terms "including", "such as", "for example" and the like are intended to refer to exemplary embodiments and not to limit the scope of the present invention.

Schemes

Compounds of formula I may be prepared using the sequence of steps outlined below.

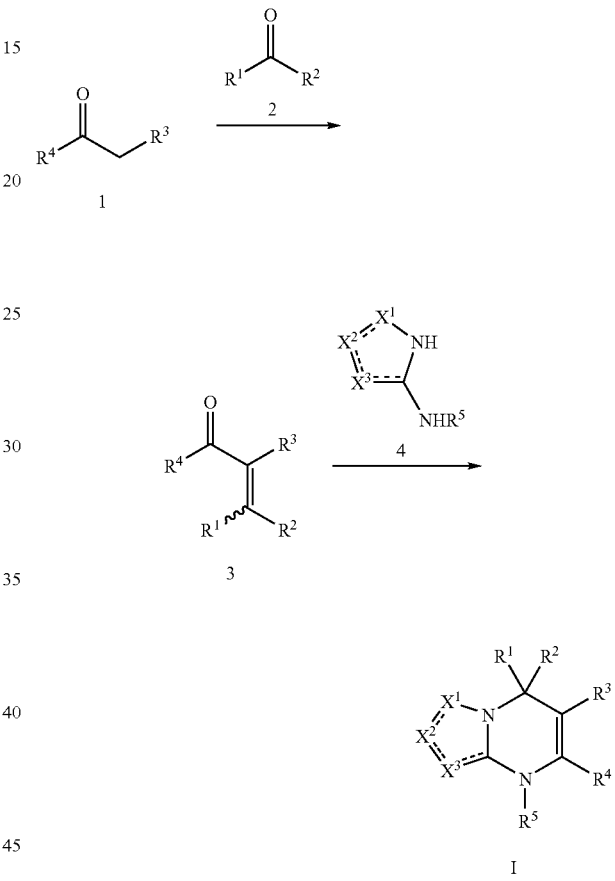

Compounds 1, 2 and 4 used in this preparation are commercially available or are readily prepared by methods well known to those skilled in the art. For example compounds of formula 1 where $R^3$=$CONZ^5Z^6$ can be prepared by the method of Witzeman (JOC 1991, 56(5), 1713) which involves warming an amine and a t-butoxy-β-ketoester neat or in a suitable solvent (xylenes, toluene, etc.)

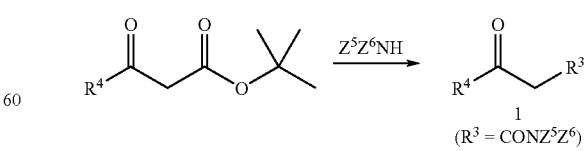

Alternately compounds of formula 1 where $R^4$=methyl and $R^3$=$CONZ^5Z^6$ may be prepared by reaction of an amine with diketene in a suitable solvent such as dichloromethane at temperatures between −100–22° C.

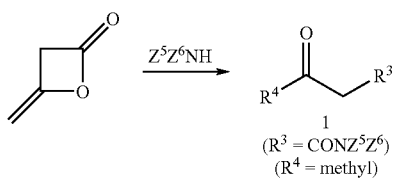

Compounds of formula 3 can be prepared by modification of the Knovenagel condensation. For example condensation of a compound of formula 1 and a compound of formula 2 at temperatures between 22–170° C. in solvents such as toluene or dimethylformamide in the presence of an acid such as acetic acid and an a base such as piperidine with removal of water generated during the reaction by the use of 4 Å dry molecular sieves or a Dean-Stark trap affords compounds of formula 3 as a mixture of cis and trans stereoisomers.

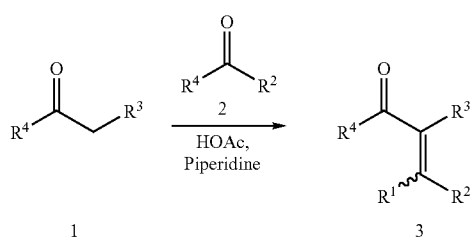

Compounds of formula I may also be prepared by condensation of compounds of formula 3 with compounds of formula 4 by warming at temperatures between 30–150° C. in alcoholic solvents such as ethanol or propanol or by warming between 30–150° C. in a solvent such as dimethylformamide and in the presence of a base such as sodium acetate.

Compounds of formula I where $R^3$=ester may be prepared by condensation of compounds of formula 1, formula 2 and heterocycles of formula 4 by warming between temperatures of 30–150° C. in the presence of a base such as sodium carbonate or sodium bicarbonate in a suitable solvent such as dimethylformamide.

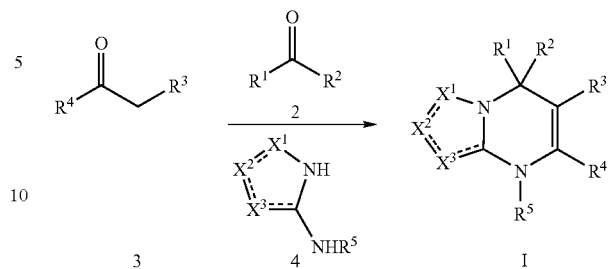

Compounds of formula I where $R^3$=amide maybe prepared by treating compounds of formula I where $R^3$=ester with a suitable amine and trimethylaluminium in a solvent such as toluene at temperatures between 0–150° C.

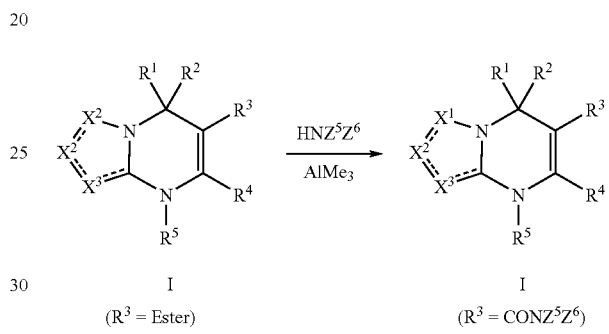

Compounds of formula I where $R^3$=amide may also be prepared by condensing compounds of formula I where $R^3$=COOH with a suitable amine by amidation methods well known to those skilled in the art. For example treatment of a compound of formula I where $R^3$=COOH with 1-[3-(dimethylamino)propyl]-3-ethylcarbodiimide hydrochloride (EDCI) and dimethylaminopyridine (DMAP) in a solvent such as dichloromethane affords compounds of formula I where $R^3$=amide.

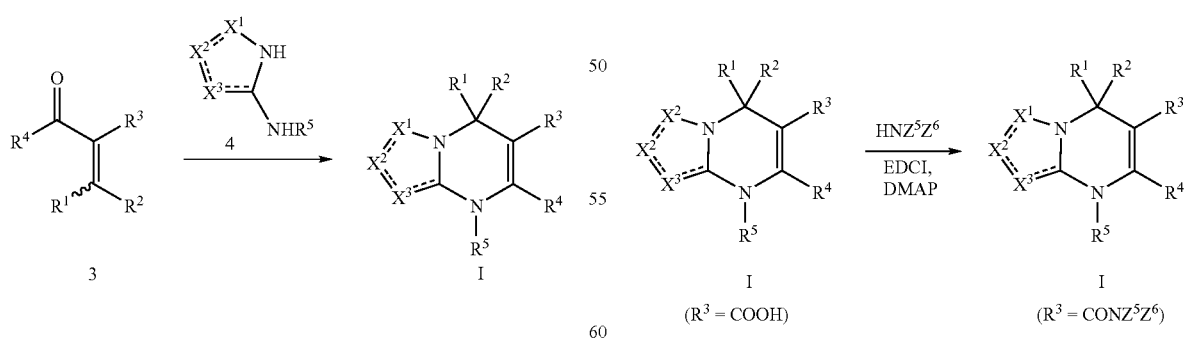

Compounds of formula I where $R^5$ is a substituent other than hydrogen may be formed by reacting a compound of formula 5 with a reactive species M-$R^5$ such that a compound of formula Ia is obtained, where M is Cl, Br, OR etc., and $R^5$ is as defined above (other than hydrogen).

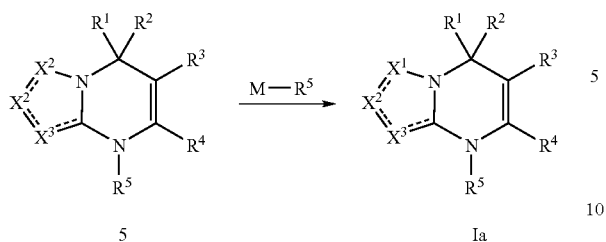

Compounds of formula I where $X^1$, $X^2$ and $X^3$ form a ring of the structure

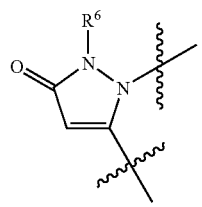

where $R^6$ is a substituent other than hydrogen may be formed by reacting a compound of formula 7 with a reactive species M-$R^6$ such that a compound of formula Ib is obtained where M is Cl, Br, OR, etc. and $R^6$ is as defined above.

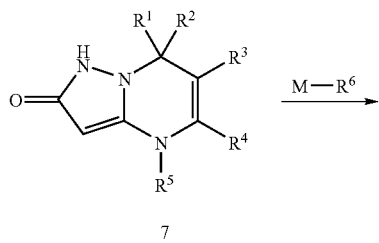

Compounds of formula Ic where $R^3$ is a amino containing heterocycle may be formed by condensing compounds of formula i where $R^3$ is an acid or ester with an amine which is attached through a linker to M. M may be $NH_2$, NHR, SH, or OH. The linker unit may be selected such that unsubstituted, substituted or fused heterocycles are formed.

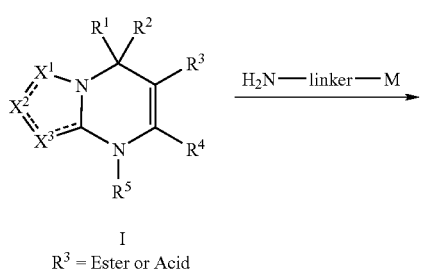

-continued

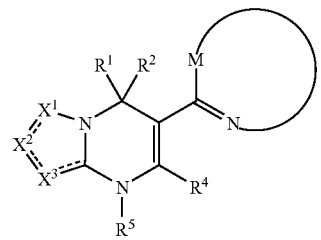

Additional compounds within the scope of the present invention can be prepared from the compounds obtained by the above described methods through conversion of the substituent groups to other functionality by the usual methods of chemical synthesis, as illustrated in the following examples.

Compounds of formula I that contain chiral centers maybe obtained in non-racemic form by non-racemic synthesis or resolution by methods well known to those skilled in the art. Compounds that are non-racemic are designated as "chiral" in the examples.

In the examples described below it may be necessary to protect reactive functionality such as hydroxy, amino, thio or carboxy groups, where these are desired in the final product, to avoid their unwanted participation in reactions. The introduction and removal of protecting groups are well known to those skilled in the art, for example see (Green, T. W. in "Protective Groups in Organic Synthesis", John Wiley and Sons, 1991).

Utility

Compounds within the scope of the present invention inhibit the $K_v1$ subfamily of voltage-gated $K^+$ channels, and as such are useful in the treatment and/or prevention of various disorders: cardiac arrhythmias, including supraventricular arrhythmias, atrial arrhythmias, atrial flutter, atrial fibrillation, complications of cardiac ischemia, and use as heart rate control agents; angina pectoris including relief of Prinzmetal's symptoms, vasospastic symptoms and variant symptoms; gastrointestinal disorders including reflux esauphagitis, functional dispepsia, motility disorders (including constipation and diarrhea), and irritable bowel syndrome; disorders of vascular and visceral smooth muscle including asthma, chronic obstructive pulmonary disease, adult respiratory distress syndrome, peripheral vascular disease (including intermittent claudication), venous insufficiency, impotence, cerebral and coronary spasm and Raynaud's disease; inflammatory and immunological disease including inflammatory bowel disease, rheumatoid arthritis, graft rejection, asthma. chronic obstructive pulmonary disease, cystic fibrosis and atherosclerosis; cell poliferative disorders including restenosis and cancer (including leukemia); disorders of the auditory system; disorders of the visual system including macular degeneration and cataracts; diabetes including diabetic retinopathy, diabetic nephropathy and diabetic neuropathy; muscle disease including myotonia and wasting; peripheral neuropathy; cognitive disorders; migraine; memory loss including Alzheimer's and dementia; CNS mediated motor dysfunction including Parkinson's disease, and ataxia; epilepsy; and other ion channel mediated disorders.

As inhibitors of the $K_v1$ subfamily of voltage-gated $K^+$ channels compounds of the present invention are useful to treat a variety of disorders including resistance by transplantation of organs or tissue, graft-versus-host diseases brought about by medulla ossium transplantation, rheumatoid arthritis, systemic lupus erythematosus, hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenicmicroorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer Scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases, Coeliaz diseases, proctitis, eosinophilic gastroenteritis, mastocytosis, Crohn's disease, ulcerative colitis, migraine, rhinitis, eczema, interstitial nephritis, Good-pasture's syndrome, hemolyticuremic syndrome, diabetic nephropathy, multiple myositis, Guillain-Barre syndrome, Meniere's disease, polyneuritis, multiple neuritis, mononeuritis, radiculopathy, hyperthroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Weekend's granuloma, Sjogren's syndrome, adiposis, eosinophilic fascitis, lesions of gingiva, periodontium, alveolar bone, substantia osses dentis, glomerulonephritis, male pattern alopecia or alopecia senilis by preventing epilation or providing hair germination and/or promoting hair generation and hair growth, muscular dystrophy; Pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis, pigentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenis, metastatis of carcinoma and hypobaropathy, disease caused by histamine or leukotriene-$C_4$ release, Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augention of chemotherapeutic effect, cytomegalovirus infection, HCMV infection, AIDS, cancer, senile dementia, trauma, and chronic bacterial infection.

The compounds of the present invention are antiarrhythmic agents which are useful in the prevention and treatment (including partial alleviation or cure) of arrhythmias. As inhibitors of $K_v1.5$ compounds within the scope of the present invention are particularly useful in the selective prevention and treatment of supraventricular arrhythmias such as atrial fibrillation, and atrial flutter. By "selective prevention and treatment of supraventricular arrhythmias" is meant the prevention or treatment of supraventricular arrhythmias wherein the ratio of the prolongation of the atrial effective refractory period to the prolongation of the ventricular effective refractory period is greater than 1:1. This ratio is preferably greater than 4:1, more preferably greater than 10:1, and most preferably such that prolongation of the atrial effective refractory response period is achieved without significantly detectable prolongation of the ventricular effective refractory period.

In addition, the compounds within the scope of the present invention block $I_{Kur}$, and thus may be useful in the prevention and treatment of all $I_{Kur}$-associated conditions. An "$I_{Kur}$-associated condition" is a disorder which may be prevented, partially alleviated or cured by the administration of an $I_{Kur}$ blocker. The $K_v1.5$ gene is known to be expressed in stomach tissue, intestinal/colon tissue, the pulmonary artery, and pancreatic beta cells. Thus, administration of an $I_{Kur}$ blocker could provide useful treatment for disorders such as: reflux esauphagitis, functional dispepsia, constipation, asthma, and diabetes. Additionally, $K_v1.5$ is known to be expressed in the anterior pituitary. Thus, administration of an $I_{Kur}$ blocker could stimulate growth hormone secretion. $I_{Kur}$ inhibitors can additionally be useful in cell poliferative disorders such as leukemia, and autoimmune diseases such as rheumatoid arthritis and transplant rejection.

The present invention thus provides methods for the prevention or treatment of one or more of the aforementioned disorders, comprising the step of administering to a subject in need thereof an effective amount of at least one compound of the formula I. Other therapeutic agents such as those described below may be employed with the inventive compounds in the present methods. In the methods of the present invention, such other therapeutic agent(s) may be administered prior to, simultaneously with or following the administration of the compound(s) of the present invention.

The present invention also provides pharmaceutical compositions comprising at least one of the compounds of the formula I or salts thereof capable of preventing or treating one or more of the aforementioned disorders in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula I may be administered by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. In the case where the compounds of formula I are being administered to prevent or treat arrhythmias, the compounds may be administered to achieve chemical conversion to normal sinus rhythm, or may optionally be used in conjunction with electrical cardioconversion.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The compounds of formula I may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.001 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to the aforementioned disorders.

The compounds of the present invention may be employed alone or in combination with each other and/or other suitable therapeutic agents useful in the treatment of the aforementioned disorders or other disorders, including: other antiarrhythmic agents such as Class I agents (e.g., propafenone), Class II agents (e.g., carvadiol and propranolol), Class III agents (e.g., sotalol, dofetilide, amiodarone, azimilide and ibutilide), Class IV agents (e.g., diltiazem and verapamil), 5HT antagonists (e.g., sulamserod, serraline and tropsetron), and dronedarone; calcium channel blockers (both L-type and T-type) such as diltiazem, verapamil, nifedipine, amlodipine and mybefradil; Cyclooxygenase inibitors (i.e., COX-1 and/or COX-2 inhibitors) such as aspirin, indomethacin, ibuprofen, piroxicam, naproxen, celebrex, vioxx and NSAIDs; anti-platelet agents such as GPIIb/IIIa blockers (e.g., abciximab, eptifibatide and tirofiban), P2Y$_{12}$ antagonists (e.g., clopidogrel, ticlopidine and CS-747), thromboxane receptor antagonists (e.g., ifetroban), aspirin, and PDE-III inhibitors (e.g., dipyridamole) with or without aspirin; diruetics such as chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone; anti-hypertensive agents such as alpha adrenergic blockers, beta adrenergic blockers, calcium channel blockers, diuretics, renin inhibitors, ACE inhibitors, (e.g., captropril, zofenopril, fosinopril, enalapril, ceranopril, cilazopril, delapril, pentopril, quinapril, ramipril, lisinopril), A II antagonists (e.g., losartan, irbesartan, valsartan), ET antagonists (e.g. sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), nitrates, and combinations of such anti-hypertensive agents; antithrombotic/thrombolytic agents such as tissue plasminogen activator (tPA), recombinant tPA, tenecteplase (TNK), lanoteplase (nPA), factor VIIa inhibitors, factor Xa inhibitors, thromin inibitors (e.g., hirudin and argatroban), PAI-1 inhibitors (i.e., inactivators of tissue plasminogen activator inhibitors), α2-antiplasmin inhibitors, streptokinase, urokinase, prourokinase, anisoylated plasminogen streptokinase activator complex, and animal or salivary gland plasminogen activators; anticoagulants such as warfarin and heparins (including unfractionated and low molecular weight heparins such as enoxaparin and dalteparin); HMG-COA reductase inhibitors such as pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin); other cholesterol/ lipid lowering agents such as squalene synthetase inhibitors, fibrates, and bile acid sequestrants (e.g., questran); antipoliferative agents such as cyclosporin A, taxol, FK 506, and adriamycin; antitumor agents such as taxol, adriamycin, epothilones, cisplatin and carboplatin; anti-diabetic agents such as biguanides (e.g. metformin), glucosidase inhibitors (e.g. acarbose), insulins, meglitinides (e.g. repaglinide), sulfonylureas (e.g. glimepiride, glyburide and glipizide), biguanide/glyburide combinations (i.e,. glucovance), thiozolidinediones (e.g. troglitazone, rosiglitazone and pioglitazone), PPAR-gamma agonists, aP2 inhibitors, and DP4 inhibitors; thyroid mimetics (including thyroid receptor antagonists) (e.g., thyrotropin, polythyroid, KB-130015, and dronedarone); Mineralocorticoid receptor antagonists such as spironolactone and eplerinone; growth hormone secretagogues; anti-osteoporosis agents (e.g., alendronate and raloxifene); hormone replacement therapy agents such as estrogen (including conjugated estrogens in premarin), and estradiol; antidepressants such as nefazodone and sertraline; antianxiety agents such as diazepam, lorazepam, buspirone, and hydroxyzine pamoate; oral contraceptives; anti-ulcer and gastroesophageal reflux disease agents such as famotidine, ranitidine, and omeprazole; anti-obesity agents such as orlistat; cardiac glycosides including digitalis and ouabain; phosphodiesterase inibitors including PDE III inhibitors (e.g. cilostazol), and PDE V inhibitors (e.g., sildenafil); protein tyrosine kinase inhibitors; steroidal anti-inflammatory agents such as prednisone, and dexamethasone; and other anti-inflammatory agents such as enbrel.

The above other therapeutic agents, when employed in combination with the compounds of the present invention, may be used, for example, in those amounts indicated in the Physicians' Desk Reference (PDR) or as otherwise determined by one of ordinary skill in the art.

Assays to determine the degree of activity of a compound as an $I_{Kur}$ inhibitor are well known in the art and are described in references such as *J. Gen. Physiol.* April; 101(4):513–43, and *Br. J. Pharmacol.* 1995 May; 115(2): 267–74.

Assays to determine the degree of activity of a compound as an inhibitor of other members of the $K_v1$ subfamily are also well known in the art. For example, inhibition of Kv1.1, $K_v1.2$ and $K_v1.3$ can be measured using procedures described by Grissmer S, et al., *Mol Pharmacol* 1994 June; 45(6):1227–34. Inhibition of Kv1.4 can be measured using procedures described by Petersen K R, and Nerbonne J M, *Pflugers Arch* 1999 February; 437(3):381–92. Inhibition of Kv1.6 can be measured using procedures described by Bowlby M R, and Levitan I B, *J Neurophysiol* 1995 June; 73(6):2221–9. And inhibition of Kv1.7 can be measured using procedures described by Kalman K, et al., *J Biol Chem* 1998 Mar. 6;273(10):5851–7.

Compounds within the scope of the present invention demonstrate activity in $K_v1$ assays such as the ones described above.

All documents cited in the present specification are incorporated herein by reference in their entirety.

The following examples and preparations describe the manner and process of making and using the invention and are illustrative rather than limiting. It is to be understood that there may be other embodiments which fall within the spirit and scope of the invention as defined by the claims appended hereto. Abbreviations employed herein are defined below.

CDI=carbonyl diimidazole

DCM=dichloromethane

DMAP=dimethylaminopyridine

DMF=dimethylformamide

DMPU=1,3-Dimethyl-3,4,5,6-tetrahydro-2(1H)-pyrimidinone

EDCI (or EDC)=1-(3-Dimethylaminopropyl)-3-ethylcarbodiimide hydrochloride

M+H=monoisotopic mass plus one proton

Et=ethyl h=hours

HPLC=high performance liquid chromatography

HOBT=hydroxybenzotriazole

LC/MS=liquid chromatography/mass spectrometry

Me=methyl min=minutes

MS=mass spectrometry

NaOAc=sodium acetate

Ph=phenyl

PPA=poly phosphoric acid

Pr=propyl

Py=pyridine

PyBrOP=bromo-tris-pyrrolidino-phosphonium hexafluorophosphate

RT=room temperature

Rt=retention time

TEA=triethylamine

TFA=trifluoroacetic acid

TLC=thin layer chromatography

THF=tetrahydrofuran

TMSOTf=trimethylsilyl trifluoromethanesulfonate

EXAMPLE 1

7-(2,3-Dichlorophenyl)-4,7-dihydro-5-methylpyrazolo[1,5-a]pyrimidine-6-carboxylic acid methyl ester

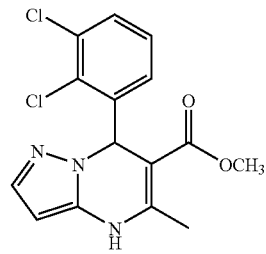

Method:

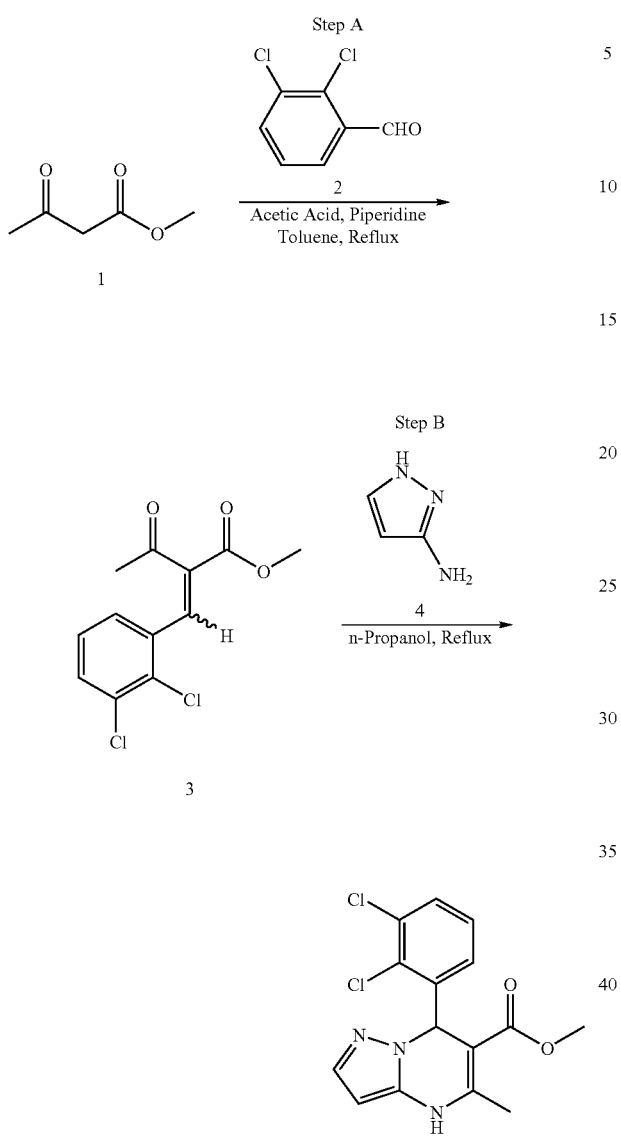

Step A: A mixture of methyl acetoacetate 1 (5 mL, 46 mmol), 2,3-dichlorobenzaldehyde 2 (8.1 g, 46 mmol), piperidine (1.1 ml, 12 mmol), and acetic acid (0.6 mL, 11 mmol) in toluene (200 mL) was refluxed overnight with azeotropic removal of water via a Dean-Stark trap. The mixture was cooled to room temperature, quenched with water, transferred to a separatory funnel, diluted with ethyl acetate, washed with aqueous NaOH (1M), aqueous HCl (1M), water and brine and concentrated in vacuo. The residue was purified by flash chromatography (silica gel, 33% Ethyl acetate/hexanes) to afford 10.8 g (85% yield) of compound 3 as a mixture of diasteromers. Reverse Phase LC/MS: YMC S5 ODS 4.6×50 mm Ballistic column, UV detection at 220λ, 4 min. gradient (10% MeOH/H$_2$O with 0.1% TFA-90% MeOH/H$_2$O with 0.1% TFA), 4 mL/min. Diastereomer A, Rt=3.51 min,(53%) Diastereomer B, Rt=3.70 min (45%). MS (M+H: 273).

Step B: A mixture of compound 3 (5 g, 18.3 mmol), 3-aminopyrazole 4 (1.5 g, 18.3 mmol) in 1-propanol (60 mL) was refluxed for 6 h. The mixture was cooled to room temperature and concentrated and recrystallized from ethyl acetate/hexanes to give 1.25 g (20%) of the title compound as a yellow solid. The mother liquor was concentrated and purified by flash chromatography (silica gel, 5% methanol/dichloromethane) to give an additional 1.62 g (26%) of the title compound. Combined yield 2.87 g (46%). Reverse Phase LC/MS: YMC S5 ODS 4.6×50 mm Ballistic column, UV detection at 220λ, 4 min. gradient (10% MeOH/H$_2$O with 0.1% TFA-90% MeOH/H$_2$O with 0.1% TFA), 4 mL/min. Rt=3.38 min, (96% pure). MS (M+H: 338). HMR (CDCl$_3$, 400 MHz) 7.98 (1H, app. s), 7.15(3H, m), 6.91(1H,s), 5.52(1H, app. s), 3.61(3H, s), 2.39(3H,s).

EXAMPLES 2 AND 3

The compounds of Examples 2 and 3, shown in the table provided below, were prepared in a manner similar to that described in Example 1.

| Example | Structure | Name | (M + H) |
|---|---|---|---|
| 2 | 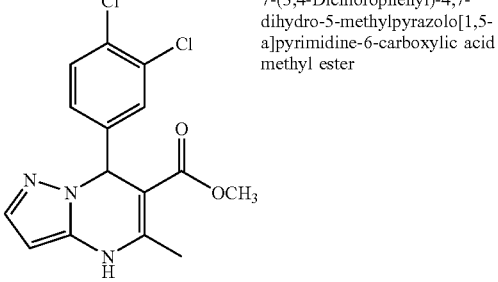 | 7-(3,4-Dichlorophenyl)-4,7-dihydro-5-methylpyrazolo[1,5-a]pyrimidine-6-carboxylic acid methyl ester | 338 |

-continued

| Example | Structure | Name | (M + H) |
|---|---|---|---|
| 3 | 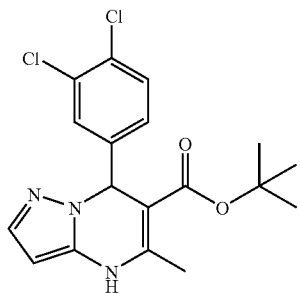 | 7-(4-Chlorophenyl)-4,7-dihydro-5-methylpyrazolo[1,5-a]pyrimidine-6-carboxylic acid methyl ester | 303 |

EXAMPLE 4

7-(3,4-Dichlorophenyl)-4,7-dihydro-5-methylpyrazolo[1,5-a]pyrimidine-6-carboxylic acid 1,1-dimethylethyl ester Method 1:

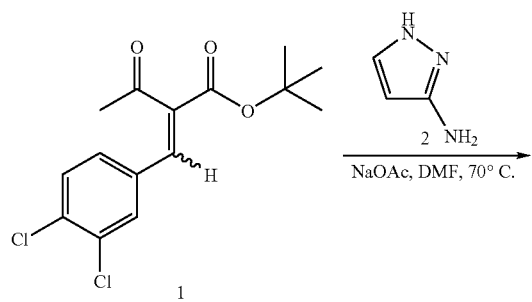

Compound 1: Compound 1 was prepared by condensing t-butoxyacetoacetate and 2,4-dichlorobenzaldehyde as described in Example 1 step A.

Title Compound: A mixture of compound 1 (44.4 g, 141 mmol), 3-aminopyrazole 2 (17.6 g 212 mmol) and sodium acetate (46.3 g, 564 mmol) in dimethylformamide (300 mL) was stirred at 70° C. overnight (17 h). The mixture was cooled to room temperature, transferred to a separatory funnel, diluted with water and ethyl acetate, washed with water (a small amount of methanol was added to breakup emulsions that formed) and brine, dried over anhydrous sodium sulfate and concentrated. A precipitate formed. The precipitate was collected and washed with ethyl acetate, ethyl ether and hexanes and dried to give 8.93 g. The mother liquor was concentrated to give a second crop of precipitate 9.32 g. LC/MS analysis indicated the precipitates were not pure. The precipitates were combined, dissolved in dichloromethane and concentrated onto enough silica gel such that a free flowing powder was obtained. The resulting powder was loaded onto a chromatography column prepacked with silica gel and dichloromethane. Elution with 100% dichloromethane followed by 3% methanol/dichloromethane gave 15.1 g (29% yield) of the title compound. Reverse Phase LC/MS: YMC S5 ODS 4.6×50 mm Ballistic column, UV detection at 220 λ, 4 min. gradient (10% MeOH/H$_{2O}$ with 0.1% TFA-90% MeOH/H$_2$O with 0.1% TFA), 4 mL/min. Rt=4.63 min, (97% pure). MS (M+H: 380). HMR (CD$_3$OD, 400 MHz) 7.41(2H, m), 7.33(1H, d, J=2 Hz), 7.08(1H, m), 6.21(1H,s), 5.68(1H, d, J=2 Hz), 2.43(3H, s), 1.37(9H,s).

Method 2:

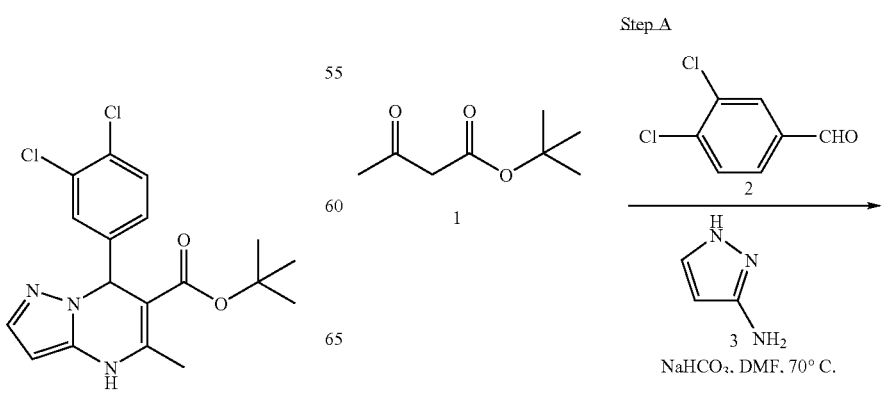

Step A

-continued

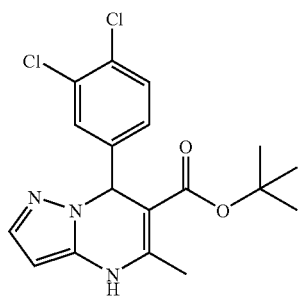

A mixture of t-butoxyacetoacetate 1 (22.6 g, 143 mmol), 3,4-dichlorobenzaldehyde 2 (25.0 g, 143 mmol), 3-aminopyrazole 3 (15.4 g, 185 mmol) and sodium bicarbonate (36 g, 428 mmol) in dimethylformamide (250 mL) was stirred at 70° C. overnight (18 h). The mixture was cooled to room temperature, quenched with ethyl acetate and water, transferred to a separatory funnel, washed with water and brine, dried over sodium sulfate, filtered and concentrated. The residue was recrystallized from ethyl acetate/hexanes to give 16.8 g (31% yield) of the title compound as a white solid. Data for the title compound is given in method 1.

EXAMPLES 5 AND 6

The compounds of Examples 5 and 6, shown in the table provided below, were prepared in a manner similar to that described in Example 4, Method 1.

| Example | Structure | Name | (M + H) |
|---|---|---|---|
| 5 | 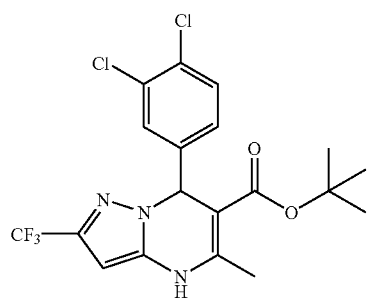 | 7-(3,4-Dichlorophenyl)-4,7-dihydro-5-methyl-2-(trifluoromethyl)pyrazolo[1,5-a]pyrimidine-6-carboxylic acid 1,1-dimethylethyl ester | 448 |
| 6 | 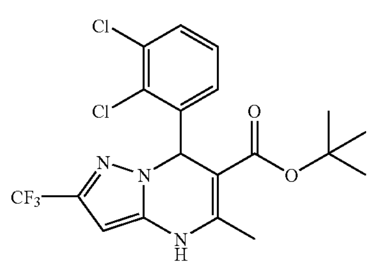 | 7-(2,3-Dichlorophenyl)-4,7-dihydro-5-methyl-2-(trifluoromethyl)pyrazolo[1,5-a]pyrimidine-6-carboxylic acid 1,1-dimethylethyl ester | 448 |

EXAMPLE 7–11

The compounds of Examples 7–11, shown in the table provided below, were prepared in a manner similar to that described in Example 4, Method 2. The compound of Example 4, method 2 could be resolved into the corresponding enantiomers A (Example 8) and B (Example 9) by preparative chiral HPLC (Chiralcel OD column (50×500 mm), eluting with 7% isopropanol/hexanes containing 0.1% triethylamine amine at 50 mL/min), UV detection at 254λ. Analytical HPLC (Chiralcel OD column (4.6×250 mm) eluting with 10% isopropanol/hexanes containing 0.1% triethylamine amine at 1 mL/min), UV detection at 254λ, enantiomer A (Rt=6.98 min, 98% ee) enantiomer B (Rt=9.22 min, 98% ee).

| Example | Structure | Name | (M + H) |
| --- | --- | --- | --- |
| 7 | 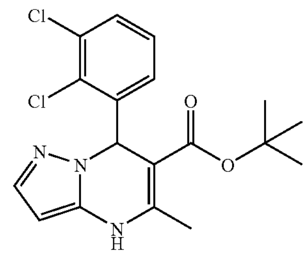 | 7-(2,3-Dichlorophenyl)-4,7-dihydro-5-methylpyrazolo[1,5-a]pyrimidine-6-carboxylic acid 1,1-dimethylethyl ester | 380 |
| 8 | chiral | 7-(3,4-Dichlorophenyl)-4,7-dihydro-5-methylpyrazolo[1,5-a]pyrimidine-6-carboxylic acid 1,1-dimethylethylester, enantiomer A | 380 |
| 9 | chiral | 7-(3,4-Dichlorophenyl)-4,7-dihydro-5-methylpyrazolo[1,5-a]pyrimidine-6-carboxylic acid 1,1-dimethylethylester, enantiomer B | 380 |
| 10 | 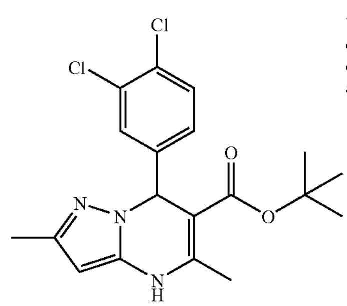 | 7-(3,4-Dichlorophenyl)-4,7-dihydro-2,5-dimethylpyrazolo[1,5-a]pyrimidine-6-carboxylic acid 1,1-dimethylethyl ester | 394 |

| Example | Structure | Name | (M + H) |
|---|---|---|---|
| 11 | 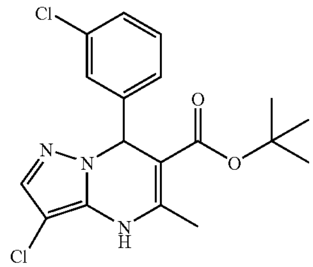 | 3-Chloro-7-(3-chlorophenyl)-4,7-dihydro-5-methylpyrazolo[1,5-a]pyrimidine-6-carboxylic acid 1,1-dimethylethyl ester | 380 |

Example 12

7-(2,3-Dichlorophenyl)-4,7-dihydro-4,5-dimethylpyrazolo[1,5-a]pyrimidine-6-carboxylic acid 1,1-dimethylethyl ester

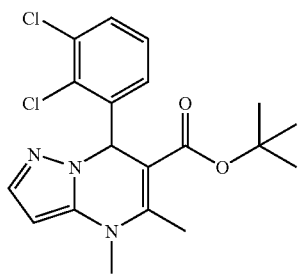

Method:

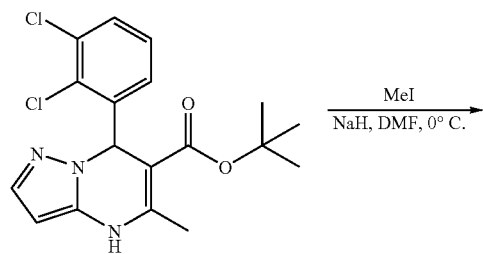

Compound 1: Compound 1 was prepared as described in Example 4, method 1.

Title Compound: Sodium hydride (0.186 g, 7.76 mmol) was added to a 0° C. solution of 1 (2.27 g, 5.97 mmol) in dimethylformamide (30 mL). After 10 min., methyl iodide (0.41 mL, 6.57 mmol) was added. After an additional 85 min, the mixture was quenched with saturated ammonium chloride solution, diluted with ethyl acetate, transferred to a separatory funnel, washed with saturated ammonium chloride, water and brine, dried over anhydrous sodium sulfate and concentrated onto enough silica gel such that a free flowing powder was obtained. The resulting powder was loaded onto a chromatography column prepacked with 100% dichloromethane. Elution with 0–10% ethyl acetate/dichloromethane gave 1.16 g (49%) of the tile compound as a slightly yellow solid. Reverse Phase LC/MS: YMC S5 ODS 4.6×50 mm Ballistic column, UV detection at 220 λ, 4 min. gradient 40–100% Solvent B/A (Solvent A: 10% MeOH/H20 with 0.1% TFA, Solvent B: 90% MeOH/H$_2$O with 0.1% TFA), 4 mL/min. Rt=3.46 min, (96% pure). MS (M+H: 394). HMR (CD$_3$Cl, 400 MHz) 7.39(1H, d, J=2 Hz), 7.35(1H, m), 7.23(1H, m), 7.11(1H, m), 6.91(1H,s), 5.58 (1H, d, J=2 Hz), 2.38(3H, s), 2.62(3H, s), 1.27(9H,s).

EXAMPLE 13

7-(3,4-Dichlorophenyl)-4,7-dihydro-4,5-dimethylpyrazolo[1,5-a]pyrimidine-6-carboxylic acid 1,1-dimethylethyl ester

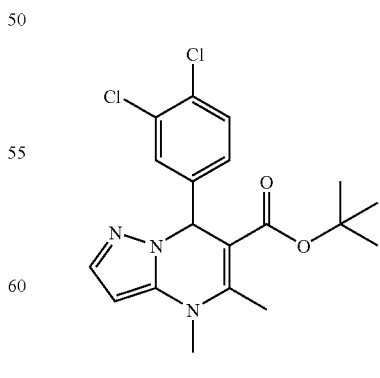

The title compound was prepared in a similar manner to that provided in Example 12 yielding a compound with (M+H): 394.

EXAMPLE 14

4,7-Dihydro-5-methyl-7-(1-methylethyl)pyrazolo[1,5-a]pyrimidine-6-carboxylic acid 1,1-dimethylethyl ester

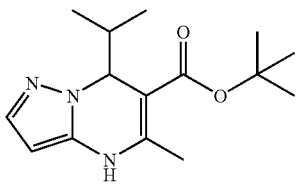

Method:

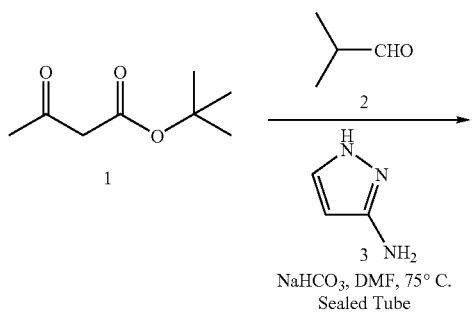

NaHCO₃, DMF, 75° C.
Sealed Tube

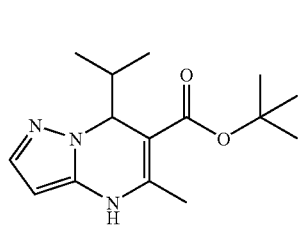

A pressure tube was dried with a heat gun under nitrogen. The pressure tube was charged in the following order with isobutyraldehyde 2 (0.262 g, 3.63 mmol), dimethylformamide (3 mL), t-butylacetoacetate 1 (0.574 g, 3.63 mmol), 3-aminopyrazole 3 (0.362 g, 4.36 mmol) and sodium acetate (1.22 g, 14.5 mmol). The mixture was flushed with nitrogen. The tube was sealed and warmed to 75° C. and stirred overnight. The mixture was cooled to room temperature, diluted with ethyl acetate to a volume of 20 mL, washed with lithium chloride (2.4M, 10 mL) and brine, dried over anhydrous sodium sulfate, filtered and concentrated to give 1.02 of a yellow oil. The oil was purified by flash chromatography (silica, 45% ethyl acetate/heptane) to give 0.42 g (41% yield) of the title compound. Reverse Phase HPLC: YMC S5 ODS 4.6×50 mm Ballistic column, UV detection at 220 λ, 4 min. gradient 0–100% Solvent B/A (Solvent A: 10% MeOH/H₂O with 0.2% PPA, Solvent B: 90% MeOH/H₂O with 0.2% PPA), 4 mL/min. Rt=3.83 min, (100% pure). Reverse Phase LC/MS: YMC S5 ODS 4.6×50 mm Ballistic column, UV detection at 220 λ, 4 min. gradient 0–100% Solvent B/A (Solvent A: 10% MeOH/H₂O with 0.1% TFA, Solvent B: 90% MeOH/H₂O with 0.1% TFA), 4 mL/min. Rt=3.06 min. MS (EM, M+1: 278). HMR (CDCl₃, 400 MHz): 7.37(1H,d,J=2.2 Hz), 6.35(1H,s), 5.55(1H,d,J=1.8 Hz), 5.29(1H,d,J=2.2 Hz), 2.41(3H,s), 1.50(9H,s), 1.28–1.19(1H,m), 1.07(3H,d,J=7.0 Hz), 0.60(3H,d,J=7.0 Hz).

EXAMPLE 15

7-Cyclopropyl-4,7-dihydro-5-methylpyrazolo[1,5-a]pyrimidine-6-carboxylic Acid 1,1-dimethylethyl ester

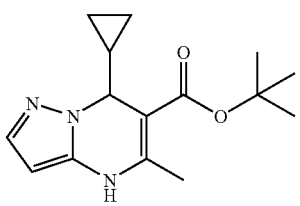

The title compound was prepared in a similar manner to that provided in Example 14 yielding a compound with (M+H): 275.

EXAMPLE 16

7-(3,4-Dichlorophenyl)-4,7-dihydro-5-methylpyrazolo[1,5-a]pyrimidine-6-carboxylic acid

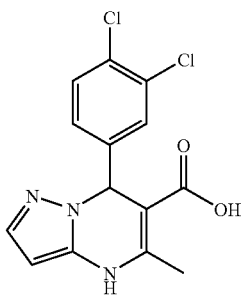

Method:

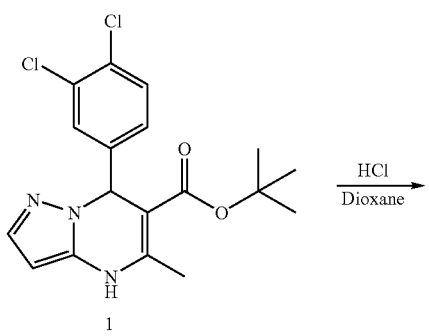

-continued

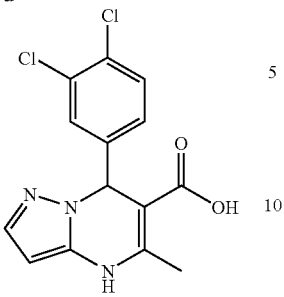

Compound 1: Compound 1 was prepared as described in Example 4.

Title Compound: HCl (4M in dioxane) was added to solid compound 1 (1.13 g, 2.97 mmol) at room temperature. The solid dissolves and a precipitate forms. The resulting thick reaction mixture was allowed to stir overnight and was concentrated in vacuo to give 1.14 g (120% contains dioxane) of the title compound as a white solid. Reverse Phase LC/MS: YMC S5 ODS 4.6×50 mm Ballistic column, UV detection at 220 λ, 4 min. gradient 0–100% Solvent B/A (Solvent A: 10% MeOH/H20 with 0.1% TFA, Solvent B: 90% MeOH/H$_2$O with 0.1% TFA), 4 mL/min. Rt=3.54 min, (93% pure). MS (M+H: 324). HMR (CD$_3$OD, 400 MHz) 7.96(1H, d, J=3 Hz), 7.51(2H, m), 7.21(1H, m), 6.49(1H, s), 6.11(1H, d, J=3 Hz), 2.51(3H, s). The title compound was used in subsequent reactions without further purification.

EXAMPLE 17

7-(3,4-Dichlorophenyl)-4,7-dihydro-5-methyl-2-(trifluoromethyl)pyrazolo[1,5-a]pyrimidine-6-carboxyl acid

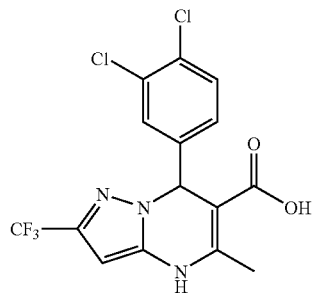

Method:

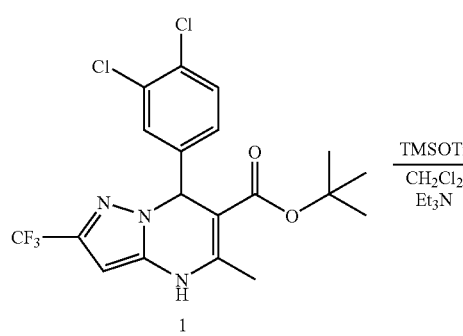

Compound 1: Compound 1 (the compound of Example 5) was prepared in a manner similar to that described in Example 4.

Title Compound: Trimethylsilyl trifluoromethanesulfonate (0.873 mL, 4.82 mmol) was added to a room temperature solution of compound 1 (1.08 g, 2.41 mmol) in dichloromethane (50 mL). After 2 h triethylamine (0.672 ml, 4.82 mmol) was added and the reaction mixture was poured into water. The organic layer was separated and dried over Na$_2$SO$_4$, concentrated, and purified by flash chromatography (50% ethylacetate/hexane→100% ethyl acetate) to give 0.71 g (75% yield) of the title compound as a white solid. MS (M+H: 392).

EXAMPLE 18

1-[[7-(2,3-Dichlorophenyl)-4,7-dihydro-5-methylpyrazolo[1,5-a]pyrimidin-6-yl]carbonyl]-4-phenylpiperazine

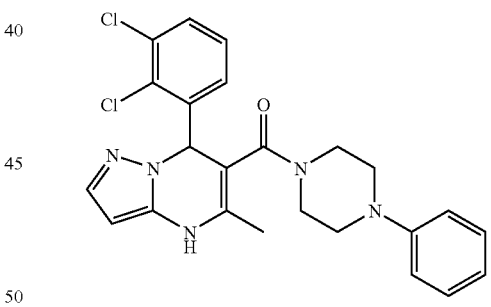

Method 1:

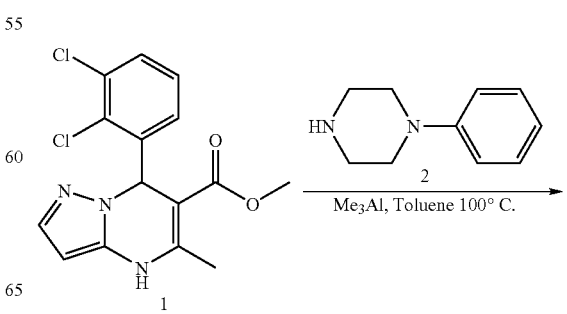

-continued

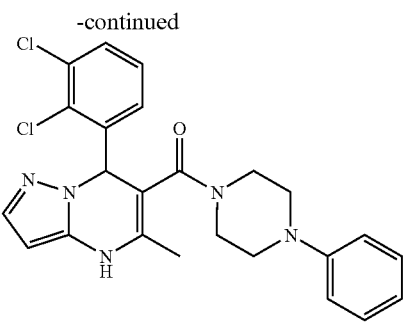

Compound 1: Compound 1 was prepared as described in Example 1.

Title Compound: Trimethylaluminium (1.1 mL, 2.2 mmol, 2 M in toluene) was dropwise added to a room temperature solution of 1-phenypiperazine 2 (0.4 mL, 2.2 mmol) in toluene (7 mL). After one hour compound 1 (0.50 g, 1.5 mmol) was added and the resulting mixture was stirred at 100° C. for 18 h. The mixture was cooled to room temperature, quenched with water, diluted with ethyl acetate, transferred to a separatory funnel, washed with aqueous HCl (1M), water and brine, dried over anhydrous sodium sulfate and concentrated in vacuo. The residue was purified by flash chromatography (silica gel, 50% ethyl acetate/hexanes followed by 5% methanol/dichloromethane to provide 0.22 g (32%) of a solid which was further purified by recrystallization from methanol/ethyl ether to give 0.15 g (22%) of the title compound. Reverse Phase LC/MS: YMC S5 ODS 4.6×50 mm Ballistic column, UV detection at 220 λ, 4 min. gradient 0–100% Solvent B/A (Solvent A: 10% MeOH/H20 with 0.1% TFA, SolventB: 90% MeOH/H$_2$O with 0.1% TFA), 4 mL/min. Rt=3.58 min, (92% pure). MS (M+H: 468). Additional Data for the title compound is reported in Method 2, step C variation 1.

Method 2:

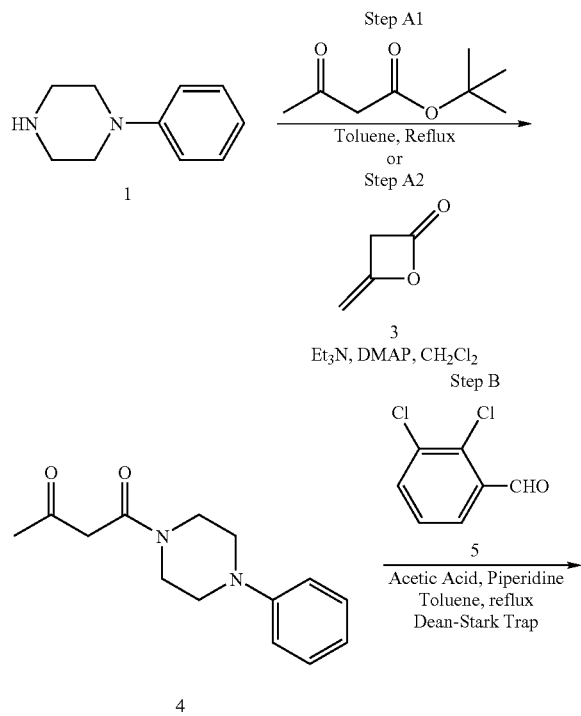

-continued

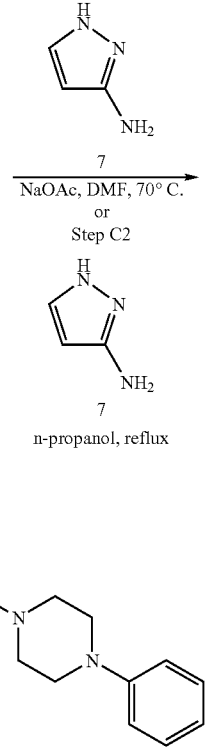

Step A Variation 1: A mixture of N-phenylpiperazine 1 (6.7 mL, 41 mmol) and t-butoxyacetoacetate 2 (6.8 mL, 45 mmol) in toluene (50 mL) was refluxed overnight. The mixture was cooled to room temperature, transferred to a separatory funnel, diluted with ethyl ether and extracted (3×) with aqueous HCl (1M). The HCl extracts were combined and washed with ethyl ether (2×), made basic (pH 9) with aqueous NaOH (50% w/w) and extracted with ethyl acetate. The ethyl acetate extracts were combined, washed with water and brine, dried over anhydrous sodium sulfate, filtered and concentrated to give 9.76 g (97.6%) of compound 4 as a thick amber oil. Reverse Phase LC/MS: YMC S5 ODS 4.6×50 mm Ballistic column, UV detection at 220 λ, 4 min. gradient 0–100% Solvent B/A (Solvent A: 10% MeOH/H20 with 0.1% TFA, SolventB: 90% MeOH/H$_2$O with 0.1% TFA), 4 mL/min. Rt=1.65 min, (100% pure). MS (M+H: 247). HMR (CDCl$_3$, 400 MHz) 7.28(2H, m), 6.91 (3H, m), 3.80(2H, m), 3.78(2H, m), 3.59(4H, m), 3.19(4H, m), 2.30(3H, s).

Step A Variation 2: Diketene 3 (5.50 g, 65.5 mmol) was slowly added over 15 min. to a 0° C. solution of 4-phenylpiperazine 1 (5.31 g, 32.7 mmol) in dichloromethane (50 mL). TLC after 4 h indicated compound 1 was not completely consumed. Additional diketene (5.50 g, 65.5 mmol) was added. After an additional 1.5 h the reaction was quenched with 1N NaOH, transferred to a separatory funnel, washed with 1H NaOH and brine, dried over sodium sulfate, concentrated onto enough silica gel such that a free flowing powder was obtained. The resulting powder was loaded onto a chromatography column prepacked with silica and 50% ethyl acetate/hexanes. Elution with 50–100% ethylacetate/hexanes gave 8.2 g (100%) of compound 4 as a thick yellow oil. Data for compound 4 is given above in step A variation 1.

Step B: A mixture of compound 4 (9.76 g, 40 mmol), 2,3-dichlorobenzaldehyde 6 (7.89 g, 45 mmol), piperidine (1.0 ml, 10 mmol), acetic acid (0.59 mL, 10 mmol) in toluene (100 mL) was refluxed overnight with azeotropic removal of water via a Dean-Stark trap. The mixture was cooled to room temperature and concentrated in vacuo and was typically used in subsequent reactions without purification. Compound 6 may be Purified by silica gel chromatography (30–40% ethyl acetate/hexanes). Reverse Phase LC/MS: YMC S5 ODS 4.6×50 mm Ballistic column, UV detection at 220 λ, 4 min. gradient 0–100% Solvent B/A (Solvent A: 10% MeOH/H20 with 0.1% TFA, SolventB: 90% MeOH/H$_2$O with 0.1% TFA), 4 mL/min. Rt=3.83 min, (96% pure). MS (M+H: 404). HMR (CDCl$_3$, 400 MHz) 7.82(1H, s), 7.55(1H, dd, J=1, 8 Hz), 7.48(1H, dd, J=1, 8 Hz), 7.23(3H, m), 6.89(1H, app. t, 7 Hz), 6.81(2H, d, J=8 Hz), 3.78(2H, m), 3.34(1H, m), 3.23(2H, m), 2.96(1H, m), 2.85(1H, m), 2.50(3H, s), 2.42(1H, M).

Step C Variation 1: A mixture of compound 6 (16 g, 40 mmol), 3-aminopyrazole 7 (5.1 g 62 mmol) and sodium acetate (10.1 g, 123 mmol) in dimethylformamide (100 mL) was stirred at 70° C. overnight (17 h). The mixture was cooled to room temperature, transferred to a separatory funnel, diluted with water and ethyl acetate, washed with water (a small amount of methanol was added to breakup emulsions that formed) and brine, dried over anhydrous sodium sulfate and concentrated. The resulting residue was purified by silica gel chromatography. Elution with 50% ethyl acetate/hexanes followed by 100% ethyl acetate afforded 6.2 g (33% yield from compound 1) of the title compound. The title compound could be resolved into the corresponding enantiomers A (Example 28) and B (Example 29) by preparative chiral HPLC (Chiracel OD column (50×500 mm), eluting with 30% isopropanol/hexanes containing 0.1% triethylamine amine at 50 mL/min), UV detection at 254λ, enantiomer A Rt=42 min, enantiomer B Rt=54 min. Analytical HPLC (Chiracel OD column (4.6×250 mm) eluting with 30% isopropanol/hexanes containing 0.1% triethylamine amine at 1 mL/min), UV detection at 254λ, enantiomer A Rt=11.7 min, enantiomer B Rt=17.6 min. Data given for enantiomer A: Reverse Phase LC/MS: YMC S5 ODS 4.6×50 mm Ballistic column, UV detection at 220λ, 4 min. gradient 0–100% Solvent B/A (Solvent A: 10% MeOH/H20 with 0.1% TFA, Solvent B: 90% MeOH/H$_2$O with 0.1% TFA), 4 mL/min. Rt=3.54 min, (91% pure). MS (M+H: 468). HMR (HCl salt of 8a, CD$_3$OD, 400 MHz) 7.94(1H, d, J=3 Hz), 7.56(8H, m), 7.38(1H, m), 6.05(1H, d, J=3 Hz), 4.23(1H,m), 3.57(7H, m), 2.01(3H, s).

Step C Variation 2: A mixture of compound 5 (6.0 g, 15 mmol), 3-aminopyrazole 7 (1.24 g, 15 mmol) in n-propanol (50 mL) was refluxed overnight (19 h). The mixture was cooled to room temperature, transferred to a separatory funnel, diluted with ethyl acetate. An attempt to wash the solution with saturated ammonium chloride resulted in the formation of a precipitate. The precipitate was dissolved with water and methanol. The resulting mixture was washed with water and brine, dried over anhydrous sodium sulfate and concentrated. The resulting residue was purified by silica gel chromatography. Elution with 70% ethyl acetate/hexanes followed by 100% ethyl acetate afforded 2.7 g (39% yield) of the title compound as a white solid. The title compound could be resolved into the corresponding enantiomers A and B as described in Step C variation 1.

EXAMPLES 19–27

Compounds of Examples 19–27, shown in the table provided below, were prepared in a manner similar to that described in Example 18, Method 1.

| Example | Structure | Name | (M + H) |
| --- | --- | --- | --- |
| 19 | 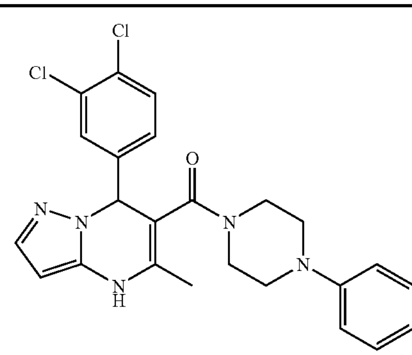 | 1-[[7-(3,4-Dichlorophenyl)-4,7-dihydro-5-methylpyrazolo[1,5-a]pyrimidin-6-yl]carbonyl]-4-phenylpiperazine | 468 |
| 20 | 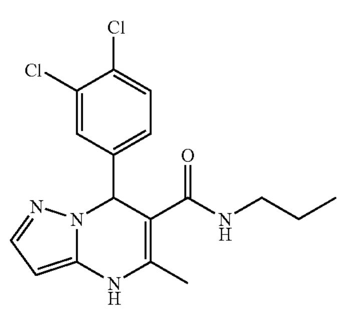 | 7-(3,4-Dichlorophenyl)-4,7-dihydro-5-methyl-N-propylpyrazolo[1,5-a]pyrimidine-6-carboxamide | 365 |

| Example | Structure | Name | (M + H) |
|---|---|---|---|
| 21 | 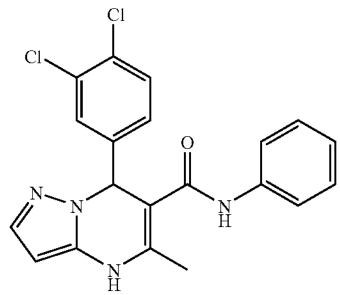 | 7-(3,4-Dichlorophenyl)-4,7-dihydro-5-methyl-N-phenyl-pyrazolo[1,5-a]pyrimidine-6-carboxamide | 399 |
| 22 | 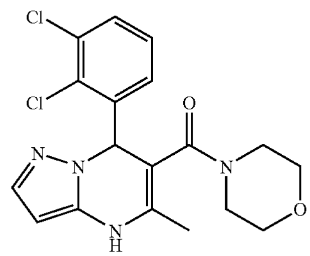 | 4-[[7-(2,3-Dichlorophenyl)-4,7-dihydro-5-methyl-pyrazolo[1,5-a]pyrimidin-6-yl]carbonyl]morpholine | 393 |
| 23 | 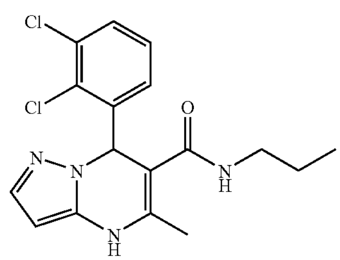 | 7-(2,3-Dichlorophenyl)-4,7-dihydro-5-methyl-N-propylpyrazolo[1,5-a]pyrimidine-6-carboxamide | 365 |
| 24 | 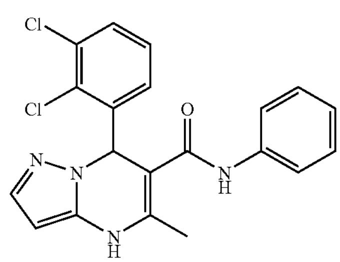 | 7-(2,3-Dichlorophenyl)-4,7-dihydro-5-methyl-N-phenylpyrazolo[1,5-a]pyrimidine-6-carboxamide | 399 |
| 25 | 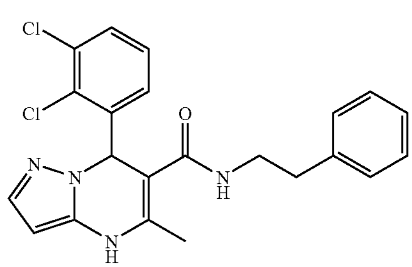 | 7-(2,3-Dichlorophenyl)-4,7-dihydro-5-methyl-N-(2-phenylethyl)pyrazolo[1,5-a]pyrimidine-6-carboxamide | 427 |

-continued

| Example | Structure | Name | (M + H) |
|---|---|---|---|
| 26 | 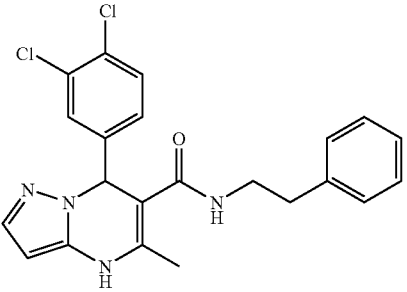 | 7-(3,4-Dichlorophenyl)-4,7-dihydro-5-methyl-N-(2-phenylethyl)pyrazolo[1,5-a]pyrimidine-6-carboxamide | 427 |
| 27 | 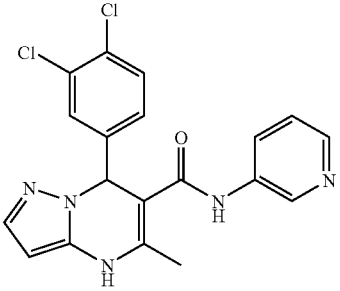 | 7-(3,4-Dichlorophenyl)-4,7-dihydro-5-methyl-N-3-pyridinylpyrazolo[1,5-a]pyrimidine-6-carboxamide | 400 |

EXAMPLES 28–82

The compounds of Examples 28–82, shown in the table provided below, were prepared in a manner similar to that described in Example 18, Method 2.

HPLC resolution of Example 47, Chiralcel OD column (50×500 mm), eluting with 30% isopropanol/hexanes containing 0.1% triethylamine at 50 mL/min), UV detection at 254λ, provided enantiomers A (Example 50) and B (Example 51). Chiralcel OD column (4.6×250 mm) eluting with 30% isopropanol/hexanes containing 0.1% triethylamine at 1 mL/min), UV detection at 254λ, enantiomer A Rt=9.8 min, >99% ee. Enantiomer B Rt=14.2 min, >99% ee.

HPLC resolution of Example 70, Chiralpak AD column (50×500 mm), eluting with 15% ethanol/hexanes containing 0.1% triethylamine at 50 mL/min), UV detection at 254λ, provided enantiomers A (Example 72) and B (Example 71). Chiralpak AD column (4.6×250 mm) eluting with 15% ethanol/hexanes containing 0.1% triethylamine at 1 mL/min), UV detection at 254λ, enantiomer A Rt=6.9 min, >99% ee. Enantiomer B Rt=13.4 min, >99% ee.

HPLC resolution of Example 80, Chiralpak AD column (50×500 mm), eluting with 25% isopropanol/hexanes containing 0.1% triethylamine at 50 mL/min), UV detection at 254λ, provided enantiomers A (Example 81) and B (Example 82). Chiralpak AD column (4.6×250 mm) eluting with 30% isopropanol/hexanes containing 0.1% triethylamine at 1 mL/min), UV detection at 254λ, enantiomer A Rt=5.3 min, >99% ee. Enantiomer B Rt=7.1 min, >99% ee.

| Example | Structure | Name | (M + H) |
|---|---|---|---|
| 28 | 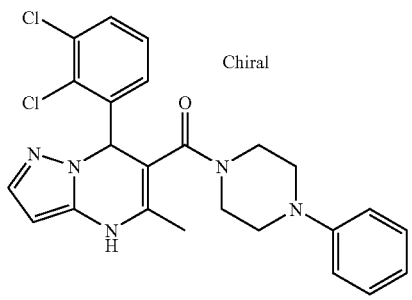 Chiral | 1-[[7-(2,3-Dichlorophenyl)-4,7-dihydro-5-methyl-pyrazolo[1,5-a]pyrimidin-6-yl]carbonyl]-4-phenyl-piperazine, enantiomer A | 468 |

-continued

| Example | Structure | Name | (M + H) |
|---|---|---|---|
| 29 | 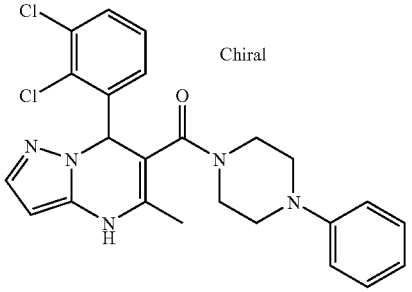 | 1-[[7-(2,3-Dichlorophenyl)-4,7-dihydro-5-methyl-pyrazolo[1,5-a]pyrimidin-6-yl]carbonyl]-4-phenyl-piperazine, enantiomer B | 468 |
| 30 | 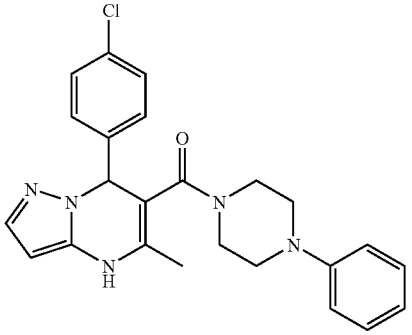 | 1-[[7-(4-Chlorophenyl)-4,7-dihydro-5-methylpyrazolo[1,5-a]pyrimidin-6-yl]carbonyl]-4-phenylpiperazine | 433 |
| 31 | 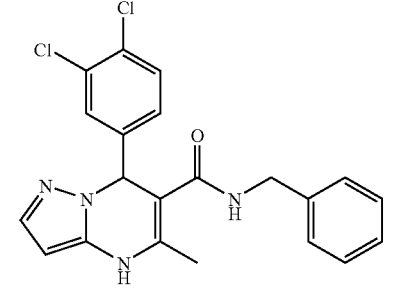 | 1-[[7-(3,4-Dichlorophenyl)-4,7-dihydro-5-methyl-N-(phenylmethyl)pyrazolo[1,5-a]pyrimidine-6-carboxamide | 413 |
| 32 | 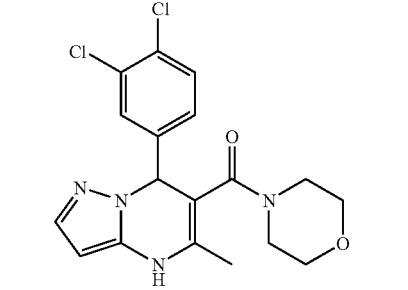 | 4-[[7-(3,4-Dichlorophenyl)-4,7-dihydro-5-methyl-pyrazolo[1,5-a]pyrimidin-6-yl]carbonyl]morpholine | 393 |
| 33 | 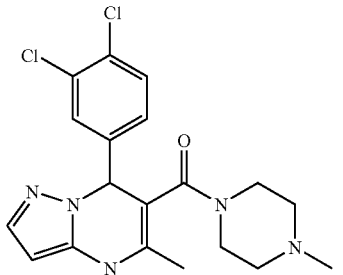 | 1-[[7-(3,4-Dichlorophenyl)-4,7-dihydro-5-methyl-pyrazolo[1,5-a]pyrimidin-6-yl]carbonyl]-4-methyl-piperazine | 406 |

-continued

| Example | Structure | Name | (M + H) |
|---|---|---|---|
| 34 | 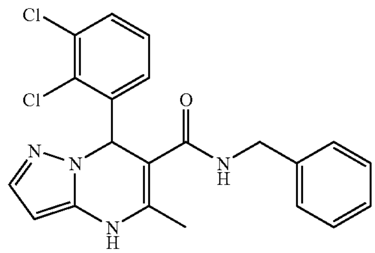 | 7-(2,3-Dichlorophenyl)-4,7-dihydro-5-methyl-N-(phenylmethyl)pyrazolo[1,5-a]pyrimidine-6-carboxamide | 413 |
| 35 | 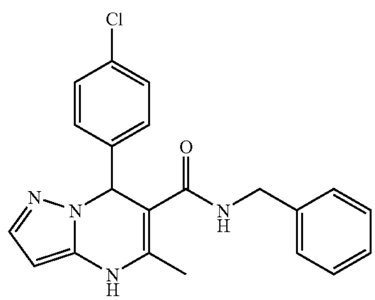 | 7-(4-Chlorophenyl)-4,7-dihydro-5-methyl-N-(phenylmethyl)pyrazolo[1,5-a]pyrimidine-6-carboxamide | 378 |
| 36 | 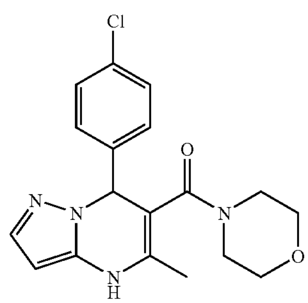 | 4-[[7-(4-Chlorophenyl)-4,7-dihydro-5-methylpyrazolo[1,5-a]pyrimidin-6-yl]carbonyl]morpholine | 358 |
| 37 | 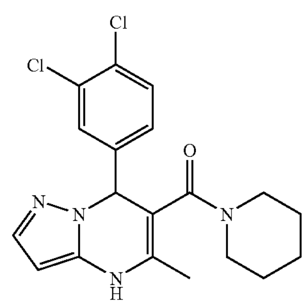 | 1-[[7-(3,4-Dichlorophenyl)-4,7-dihydro-5-methyl-pyrazolo[1,5-a]pyrimidin-6-yl]carbonyl]piperidine | 391 |
| 38 | 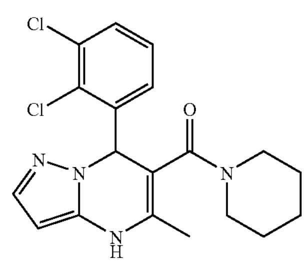 | 1-[[7-(2,3-Dichlorophenyl)-4,7-dihydro-5-methyl-pyrazolo[1,5-a]pyrimidin-6-yl]carbonyl]piperidine | 391 |

-continued

| Example | Structure | Name | (M + H) |
| --- | --- | --- | --- |
| 39 | 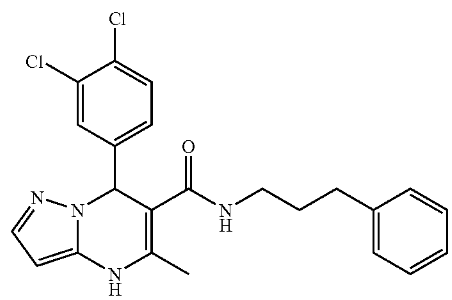 | 7-(3,4-Dichlorophenyl)-4,7-dihydro-5-methyl-N-(3-phenylpropyl)pyrazolo[1,5-a]pyrimidine-6-carboxamide | 441 |
| 40 | 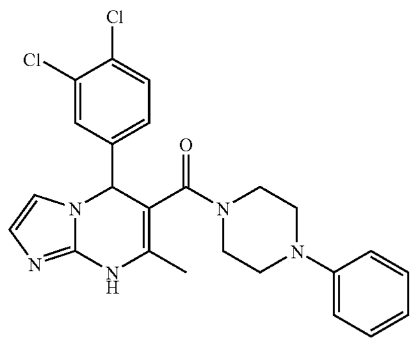 | 1-[[5-(3,4-Dichlorophenyl)-5,8-dihydro-7-methyl-imidazo[1,2-a]pyrimidin-6-yl]carbonyl]-4-phenyl-piperazine | 468 |
| 41 | 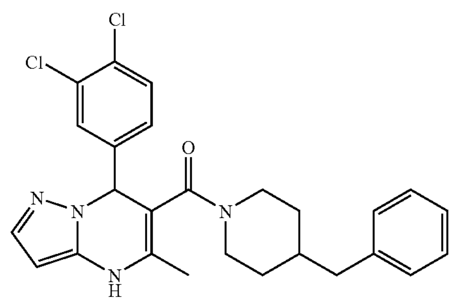 | 1-[[7-(3,4-Dichlorophenyl)-4,7-dihydro-5-methyl-pyrazolo[1,5-a]pyrimidin-6-yl]carbonyl]-4-(phenyl-methyl)piperidine | 481 |
| 42 | 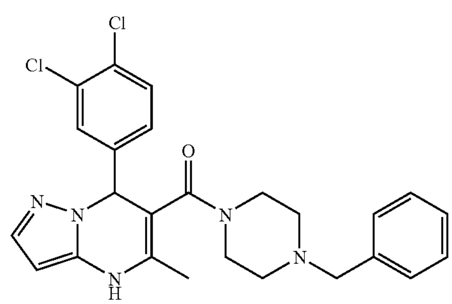 | 1-[[7-(3,4-Dichlorophenyl)-4,7-dihydro-5-methyl-pyrazolo[1,5-a]pyrimidin-6-yl]carbonyl]-4-(phenyl-methyl)piperazine | 482 |
| 43 | 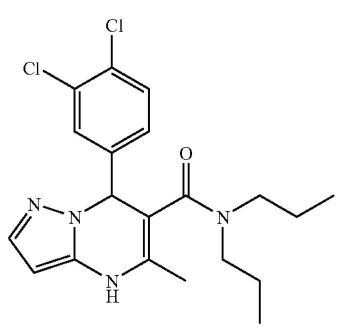 | 7-(3,4-Dichlorophenyl)-4,7-dihydro-5-methyl-N,N-dipropylpyrazolo[1,5-a]pyrimidine-6-carboxamide | 407 |

-continued

| Example | Structure | Name | (M + H) |
|---------|-----------|------|---------|
| 44 | 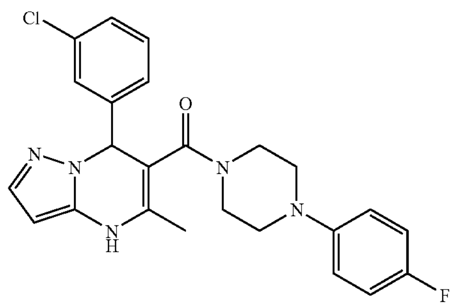 | 1-[[7-(3-Chlorophenyl)-4,7-dihydro-5-methylpyrazolo[1,5-a]pyrimidin-6-yl]carbonyl]-4-(4-fluorophenyl)piperazine | 451 |
| 45 | 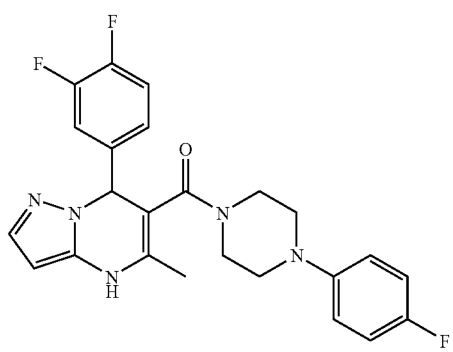 | 1-[[7-(3,4-Difluorophenyl)-4,7-dihydro-5-methylpyrazolo[1,5-a]pyrimidin-6-yl]carbonyl]-4-(4-fluorophenyl)piperazine | 453 |
| 46 | 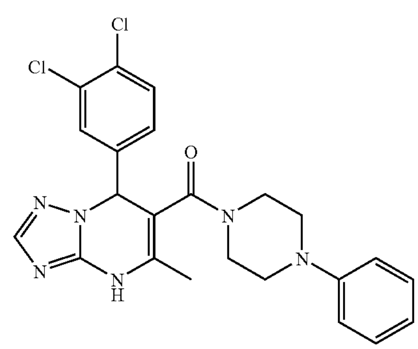 | 1-[[7-(3,4-Dichlorophenyl)-4,7-dihydro-5-methyl[1,2,4]triazolo[1,5-a]pyrimidin-6-yl]carbonyl]-4-phenylpiperazine | 469 |
| 47 | 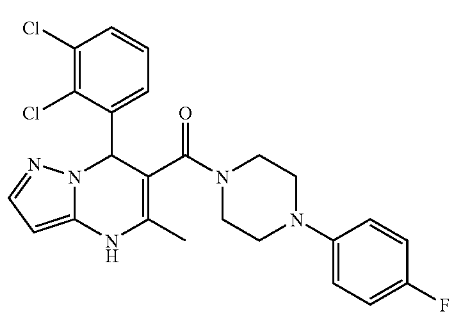 | 1-[[7-(2,3-Dichlorophenyl)-4,7-dihydro-5-methyl-pyrazolo[1,5-a]pyrimidin-6-yl]carbonyl]-4-(4-fluoro-phenyl)piperazine | 486 |

| Example | Structure | Name | (M + H) |
|---|---|---|---|
| 48 | 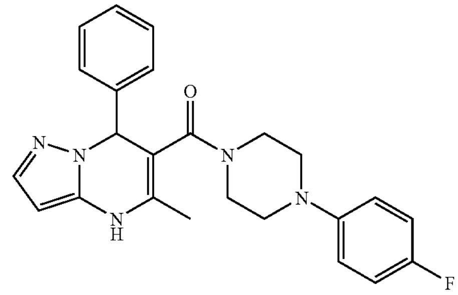 | 1-(4-Fluorophenyl)-4-[(4,7-dihydro-5-methyl-7-phenylpyrazolo[1,5-a]pyrimidin-6-yl)carbonyl]piperazine | 417 |
| 49 | 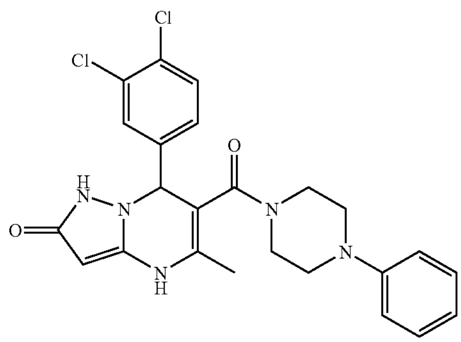 | 1-[[7-(3,4-Dichlorophenyl)-1,2,4,7-tetrahydro-5-methyl-2-oxopyrazolo[1,5-a]pyrimidin-6-yl]carbonyl]-4-phenylpiperazine | 484 |
| 50 | Chiral | 1-[[7-(2,3-Dichlorophenyl)-4,7-dihydro-5-methyl-pyrazolo[1,5-a]pyrimidin-6-yl]carbonyl]-4-(4-fluoro-phenyl)piperazine, enantiomer A | 486 |
| 51 | Chiral | 1-[[7-(2,3-Dichlorophenyl)-4,7-dihydro-5-methyl-pyrazolo[1,5-a]pyrimidin-6-yl]carbonyl]-4-(4-fluoro-phenyl)piperazine, enantiomer B | 486 |
| 52 | 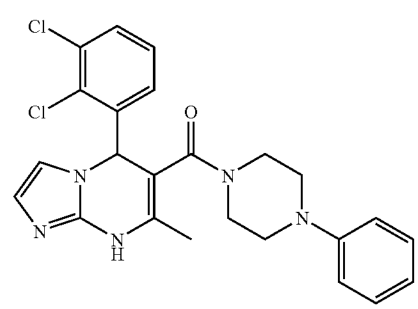 | 1-[[5-(2,3-Dichlorophenyl)-5,8-dihydro-7-methyl-imidazo[1,2-a]pyrimidin-6-yl]carbonyl]-4-phenyl-piperazine | 468 |

| Example | Structure | Name | (M + H) |
|---|---|---|---|
| 53 | 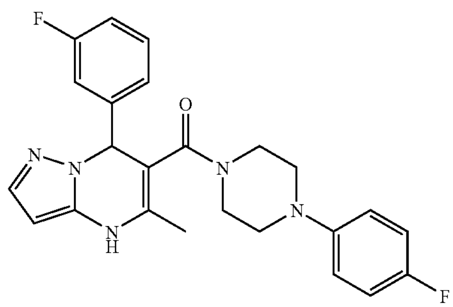 | 1-(4-Fluorophenyl)-4-[[7-(3-fluorophenyl)-4,7-dihydro-5-methylpyrazolo[1,5-a]pyrimidin-6-yl]carbonyl]-piperazine | 435 |
| 54 | 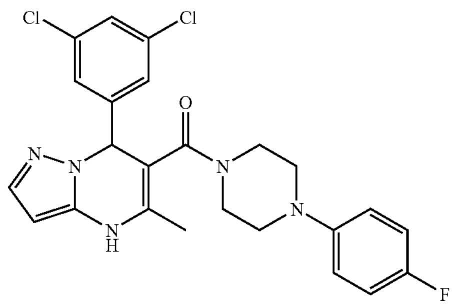 | 1-[[7-(3,5-Dichlorophenyl)-4,7-dihydro-5-methyl-pyrazolo[1,5-a]pyrimidin-6-yl]carbonyl]-4-(4-fluorophenyl)piperazine | 486 |
| 55 | 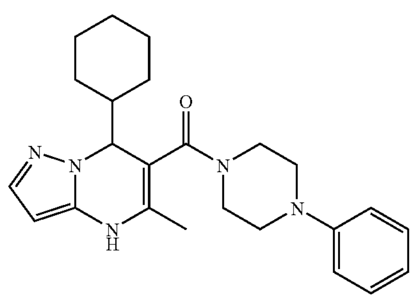 | 1-[(7-Cyclohexyl-4,7-dihydro-5-methylpyrazolo[1,5-a]pyrimidin-6-yl)carbonyl]-4-phenylpiperazine | 405 |
| 56 | 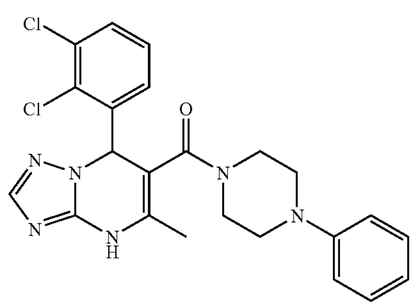 | 1-[[7-(2,3-Dichlorophenyl)-4,7-dihydro-5-methyl-[1,2,4]triazolo[1,5-a]pyrimidin-6-yl)carbonyl]-4-phenyl-piperazine | 469 |
| 57 | 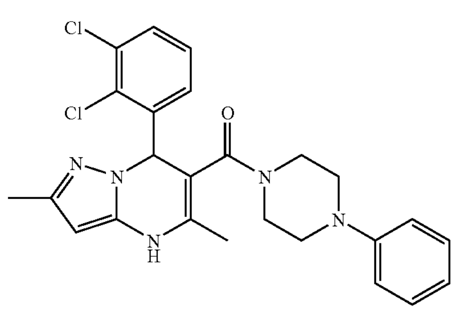 | 1-[[7-(2,3-Dichlorophenyl)-4,7-dihydro-2,5-dimethyl-pyrazolo[1,5-a]pyrimidin-6-yl]carbonyl]-4-phenyl-piperazine | 482 |

-continued

| Example | Structure | Name | (M + H) |
|---|---|---|---|
| 58 | 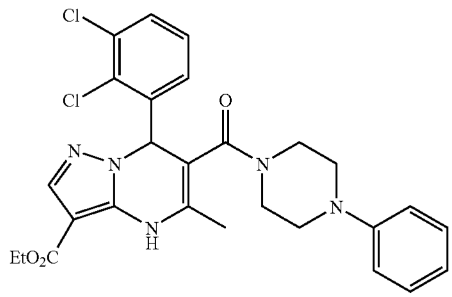 | 7-(2,3-Dichlorophenyl)-4,7-dihydro-5-methyl-6-[(4-phenyl-1-piperazinyl)-carbonyl]pyrazolo[1,5-a]pyrimidine-3-carboxylic acid ethyl ester | 540 |
| 59 | 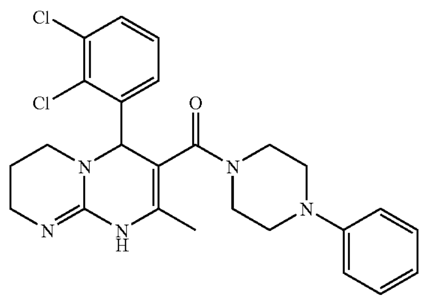 | 1-[[4-(2,3-Dichlorophenyl)-4,6,7,8-tetrahydro-2-methyl-1H-pyrimido[1,2-a]pyrimidin-3-yl]carbonyl]-4-phenyl-piperazine | 484 |
| 60 | 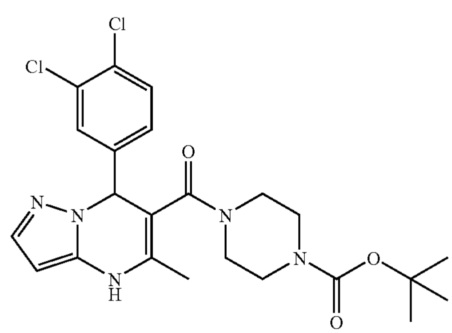 | 4-[[7-(3,4-Dichlorophenyl)-4,7-dihydro-5-methyl-pyrazolo[1,5-a]pyrimidin-6-yl]carbonyl]-1-piperazinecarboxylic acid 1,1-dimethylethyl ester | 492 |
| 61 | 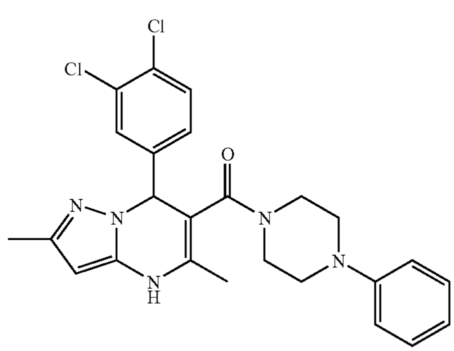 | 1-[[7-(3,4-Dichlorophenyl)-4,7-dihydro-2,5-dimethylpyrazolo[1,5-a]pyrimidin-6-yl]carbonyl]-4-phenylpiperazine | 482 |

| Example | Structure | Name | (M + H) |
|---|---|---|---|
| 62 | 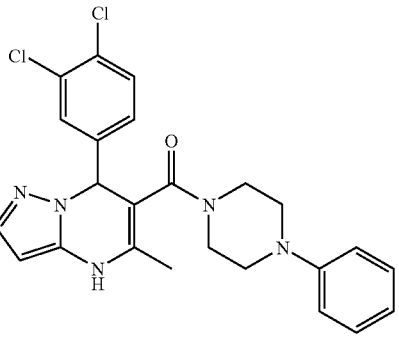 | 1-[[7-(3,4-Dichlorophenyl)-4,7-dihydro-5-methyl-2-phenylpyrazolo[1,5-a]pyrimidin-6-yl]carbonyl]-4-phenylpiperazine | 544 |
| 63 | 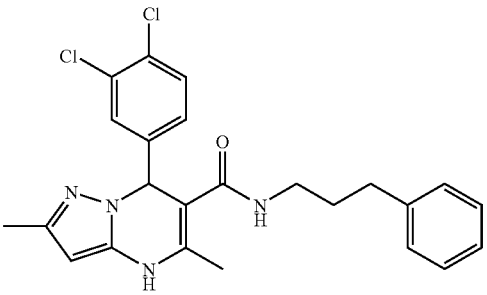 | 7-(3,4-Dichlorophenyl)-4,7-dihydro-2,5-dimethyl-N-(3-phenylpropyl)pyrazolo[1,5-a]pyrimidine-6-carboxamide | 455 |
| 64 | 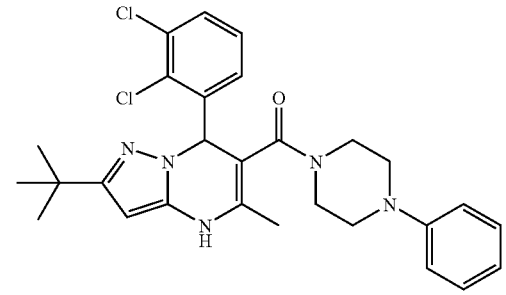 | 1-[[7-(2,3-Dichlorophenyl)-2-(1,1-dimethylethyl)-4,7-dihydro-5-methylpyrazolo[1,5-a]pyrimidin-6-yl]carbonyl]-4-phenylpiperazine | 524 |
| 65 | 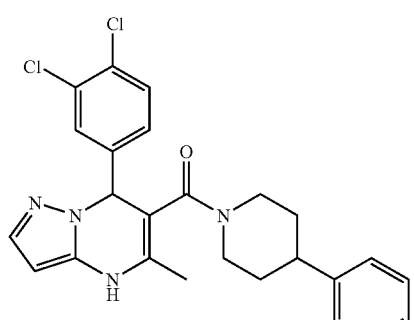 | 1-[[7-(3,4-Dichlorophenyl)-4,7-dihydro-5-methyl-pyrazolo[1,5-a]pyrimidin-6-yl]carbonyl]-4-phenyl-piperidine | 467 |

| Example | Structure | Name | (M + H) |
|---|---|---|---|
| 66 | 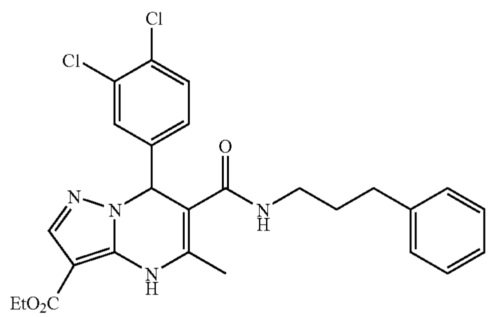 | 7-(3,4-Dichlorophenyl)-4,7-dihydro-5-methyl-6-[[(3-phenylpropyl)amino]carbonyl]pyrazolo[1,5-a]pyrimidine-3-carboxylic acid ethyl ester | 513 |
| 67 | 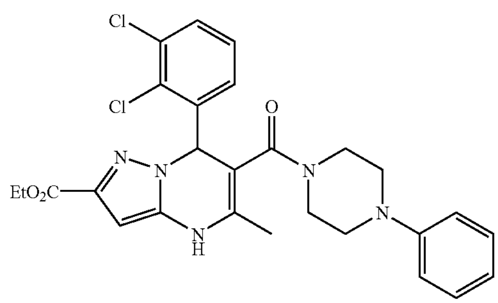 | 7-(2,3-Dichlorophenyl)-4,7-dihydro-5-methyl-6-[(4-phenyl-1-piperazinyl)carbonyl]pyrazolo[1,5-a]pyrimidine-2-carboxylic acid ethyl ester | 540 |
| 68 | 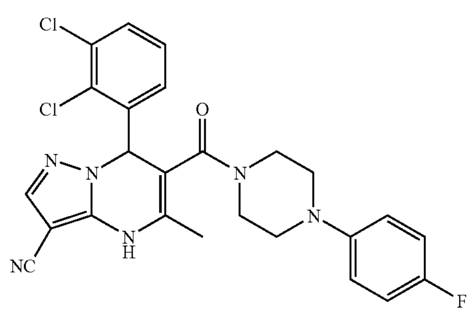 | 1-[[3-Cyano-7-(2,3-dichlorophenyl)-4,7-dihydro-5-methylpyrazolo[1,5-a]pyrimidin-6-yl]carbonyl]-4-(4-fluorophenyl)piperazine | 511 |
| 69 | 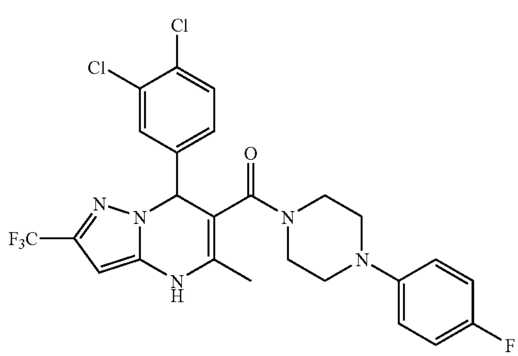 | 1-[[7-(3,4-Dichlorophenyl)-4,7-dihydro-5-methyl-2-(trifluoromethyl)pyrazolo[1,5-a]pyrimidin-6-yl]carbonyl]-4-(4-fluorophenyl)piperazine | 554 |
| 70 | 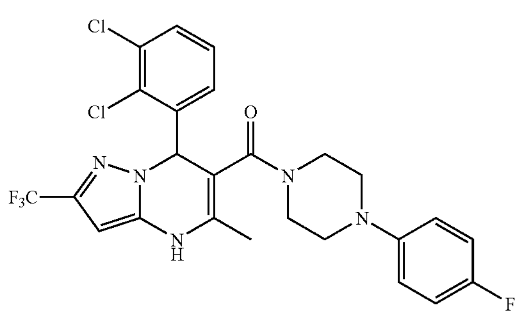 | 1-[[7-(2,3-Dichlorophenyl)-4,7-dihydro-5-methyl-2-(trifluoromethyl)pyrazolo[1,5-a]pyrimidin-6-yl]carbonyl]-4-(4-fluorophenyl)piperazine | 554 |

-continued

| Example | Structure | Name | (M + H) |
|---|---|---|---|
| 71 | Chiral | 1-[[7-(2,3-Dichlorophenyl)-4,7dihydro-5-methyl-2-(trifluoromethyl)pyrazolo[1,5-a]pyrimidin-6-yl]carbonyl]-4-(4-fluorophenyl)piperazine, enantiomer B | 554 |
| 72 | Chiral | 1-[[7-(2,3-Dichlorophenyl)-4,7-dihydro-2,5-dimethyl-pyrazolo[1,5-a]pyrimidin-6-yl]carbonyl]-4-(4-fluoro-phenyl)piperazine, enantiomer B | 554 |
| 73 | 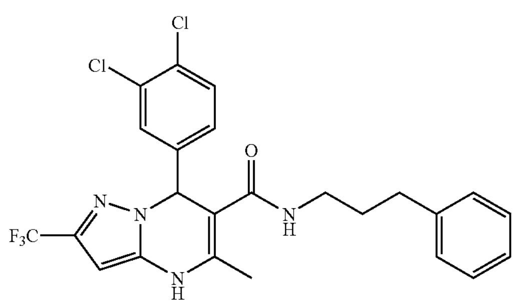 | 7-(3,4-Dichlorophenyl)-4,7-dihydro-5-methyl-N-(3-phenylpropyl)-2-(trifluoro-methyl)pyrazolo[1,5-a]pyrimidine-6-carboxamide | 509 |
| 74 | 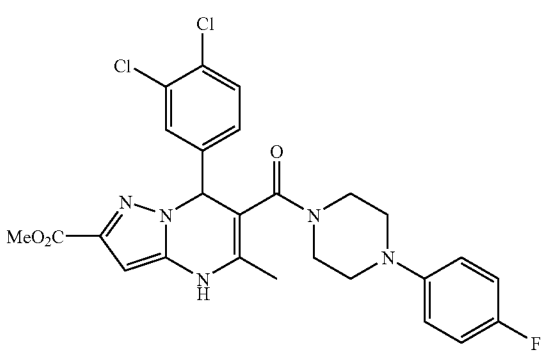 | 7-(3,4-Dichlorophenyl)-6-[[4-(4-fluorophenyl)-1-pipera-zinyl]carbonyl]-4,7-dihydro-5-methylpyrazolo[1,5-a]pyri-midine-2-carboxylic acid methyl ester | 544 |
| 75 | 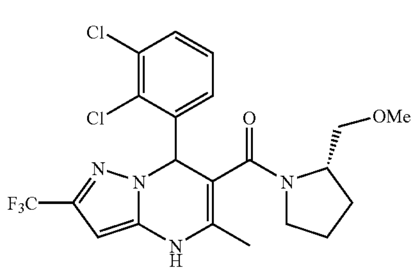 | (2S)-1-[[7-(2,3-Dichlorophenyl)-4,7-dihydro-5-methyl-2-(trifluoro-methyl)pyrazolo[1,5-a]pyrimidin-6-yl]carbonyl]-2-(methoxymethyl)pyrrolidine | 489 |

| Example | Structure | Name | (M + H) |
| --- | --- | --- | --- |
| 76 | 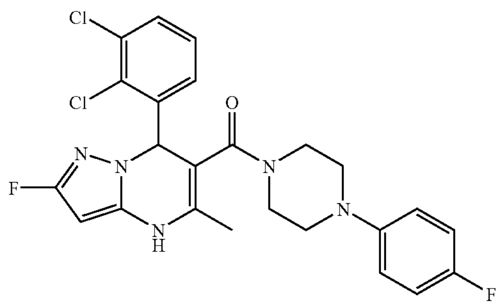 | 1-[[7-(2,3-Dichlorophenyl)-2-fluoro-4,7-dihydro-5-methylpyrazolo[1,5-a]pyrimidin-6-yl]carbonyl]-4-(4-fluorophenyl)piperazine | 504 |
| 77 | 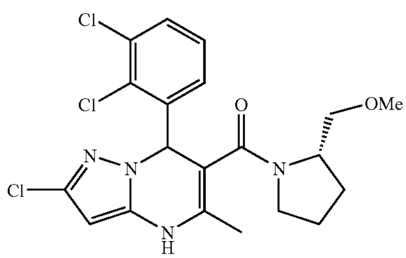 | (2S)-1-[[2-Chloro-7-(2,3-dichlorophenyl)-4,7-dihydro-5-methyl-pyrazolo[1,5-a]pyrimidin-6-yl]carbonyl]-2-(methoxymethyl)-pyrrolidine | 455 |
| 78 | 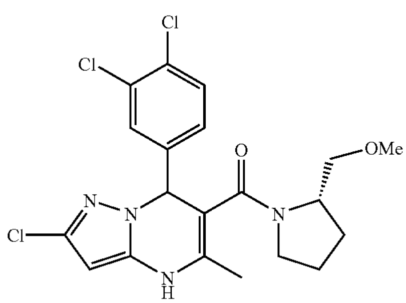 | (2S)-1-[[2-Chloro-7-(3,4-dichlorophenyl)-4,7-dihydro-5-methyl-pyrazolo[1,5-a]pyrimidin-6-yl]carbonyl]-2-(methoxymethyl)-pyrrolidine | 455 |
| 79 | 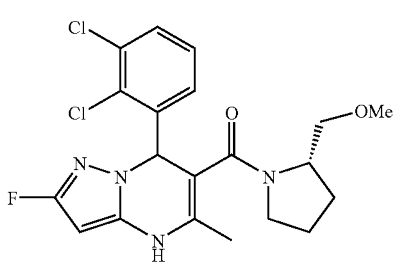 | (2S)-1-[[7-(2,3-Dichloro-phenyl)-2-fluoro-4,7-dihydro-5-methyl-pyrazolo[1,5-a]pyrimidin-6-yl]carbonyl]-2-(methoxy-methyl)pyrrolidine | 439 |

| Example | Structure | Name | (M + H) |
|---|---|---|---|
| 80 | 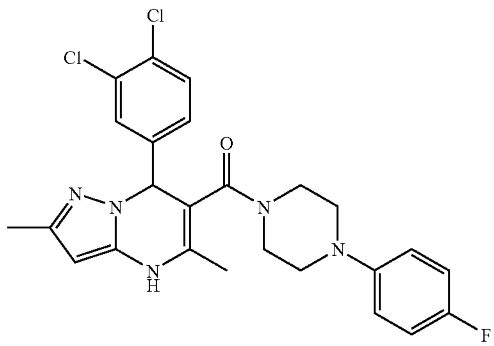 | 1-[[7-(3,4-Dichlorophenyl)-4,7-dihydro-2,5-dimethylpyrazolo[1,5-a]pyrimidin-6-yl]carbonyl]-4-(4-fluorophenyl)piperazine | 500 |
| 81 | Chiral | 1-[[7-(3,4-Dichlorophenyl)-4,7-dihydro-2,5-dimethylpyrazolo[1,5-a]pyrimidin-6-yl]carbonyl]-4-(4-fluorophenyl)piperazine, enantiomer A | 500 |
| 82 | Chiral | 1-[[7-(3,4-Dichlorophenyl)-4,7-dihydro-2,5-dimethyl-pyrazolo[1,5-a]pyrimidin-6-yl]carbonyl]-4-(4-fluoro-phenyl)piperazine, enantiomer B | 500 |

EXAMPLE 83

7-(2,3-Dichlorophenyl)-4,7-dihydro-5-methyl-N,N-dipropylpyrazolo[1,5-a]pyrimidine-6-carboxamide

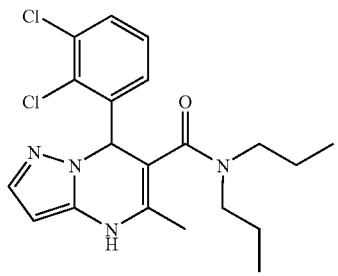

Method:

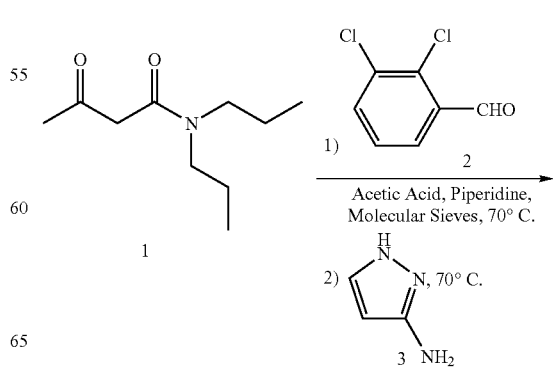

-continued

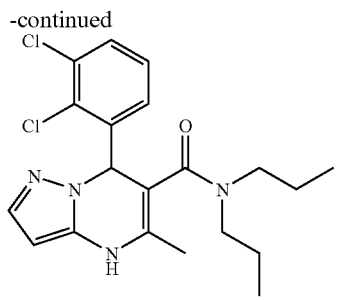

Compound 1: Compound 1 was prepared as described in Example 18, Method 2 Step A1 from t-butoxyacetoacetate and dipropylamine.

Title Compound: A mixture of compound 1 (0.2 g, 1.1 mmol), 2,3-dichlorobenzaldehyde 2 (0.23 g, 1.3 mmol), piperidine (0.015 ml, 0.27 mmol), acetic acid (0.027 mL, 0.27 mmol) and 4 A Molecular Sieves (spatula tip) in dimethylformamide (1 mL) was stirred at 70° C. overnight. The mixture was cooled to room temperature. 3-aminopyrazole 3 (0.13 g, 1.6 mmol) and sodium acetate (0.28 g, 3.5 mmol) were added and the mixture was stirred overnight at 70° C. The mixture was cooled to room temperature, transferred to a separatory funnel, diluted with water and ethyl acetate, washed with water (a small amount of methanol was added to breakup emulsions that formed) and brine, dried over anhydrous sodium sulfate and concentrated. The resulting residue was purified by silica gel chromatography (50% ethyl acetate/hexanes followed by 100% ethyl acetate) to afford 0.10 g (23% yield from compound 1) of the title compound. Reverse Phase LC/MS: YMC S5 ODS 4.6×50 mm Ballistic column, UV detection at 220 λ, 4 min. gradient 40–100% Solvent B/A (Solvent A: 10% MeOH/H20with 0.1% TFA, Solvent B: 90% MeOH/$H_2O$ with 0.1% TFA), 4 mL/min. Rt=2.94 min, (96% pure). MS (M+H: 407).

EXAMPLES 84–169

The compounds of Examples 84–169, shown in the table provided below, were prepared in a manner similar to that described in Example 83.

HPLC resolution of Example 84, Chiralpak AS column (50×500 mm), eluting with 30% isopropanol/hexanes containing 0.1% triethylamine at 50 mL/min), UV detection at 254λ, provided enantiomers A (Example 166) and B (Example 167). Chiralpak AS column (4.6×250 mm) eluting with 40% isopropanol/hexanes containing 0.1% triethylamine at 1 mL/min), UV detection at 254λ, enantiomer A Rt=5.53 min, >99% ee. Enantiomer B Rt=12.0 min, 98% ee.

HPLC resolution of Example 165, Chiralpak AD column (50×500 mm), eluting with 20% isopropanol/hexanes containing 0.1% triethylamine at 50 mL/min), UV detection at 254λ provided enantiomers A (Example 169) and B (Example 168). Chiralpak AD column (4.6×250 mm) eluting with 20% isopropanol/hexanes containing 0.1% triethylamine at 1 mL/min), UV detection at 254λ, enantiomer A Rt=8.3 min, >99% ee. Enantiomer B Rt=12.8 min, 98% ee.

| Example | Structure | Name | (M + H) |
|---|---|---|---|
| 84 | 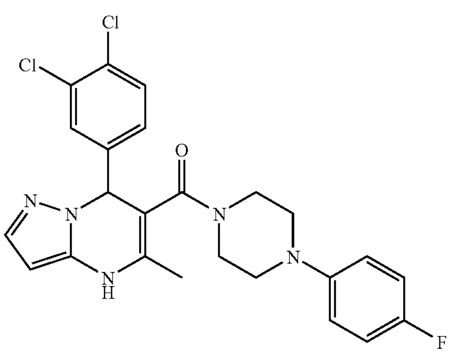 | 1-[[7-(3,4-Dichlorophenyl)-4,7-dihydro-5-methylpyrazolo[1,5-a]pyrimidin-6-yl]carbonyl]-4-(4-fluorophenyl)piperazine | 486 |
| 85 | 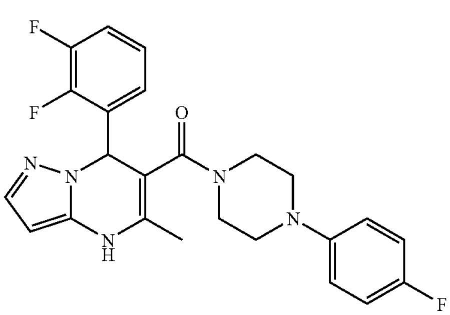 | 1-[[7-(2,3-Difluorophenyl)-4,7-dihydro-5-methylpyrazolo[1,5-a]pyrimidin-6-yl]carbonyl]-4-(4-fluorophenyl)piperazine | 453 |

-continued

| Example | Structure | Name | (M + H) |
|---|---|---|---|
| 86 | 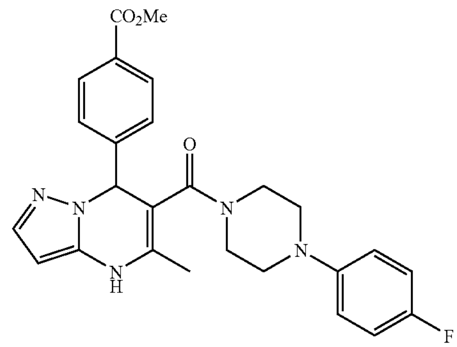 | 4-[6-[[4-(4-Fluorophenyl)-1-piperazinyl]carbonyl]-4,7-dihydro-5-methylpyrazolo[1,5-a]pyrimidin-7-yl]benzoic acid methyl ester | 475 |
| 87 | 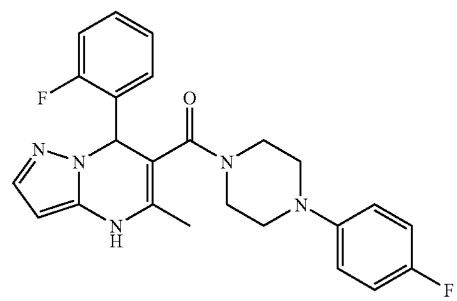 | 1-(4-Fluorophenyl)-4-[[7-(2-fluorophenyl)-4,7-dihydro-5-methylpyrazolo[1,5-a]pyrimidin-6-yl]carbonyl]-piperazine | 435 |
| 88 | 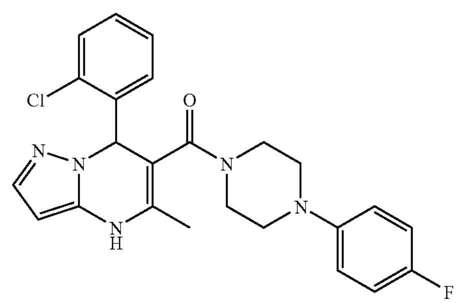 | 1-[[7-(2-Chlorophenyl)-4,7-dihydro-5-methylpyrazolo[1,5-a]pyrimidin-6-yl]carbonyl]-4-(4-fluorophenyl)piperazine | 451 |
| 89 | 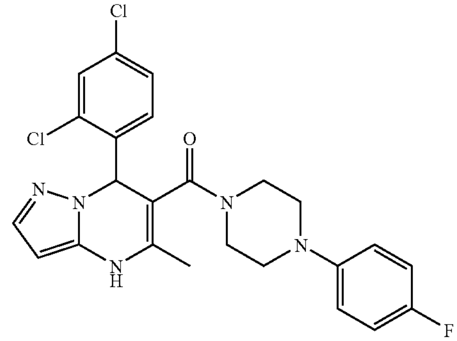 | 1-[[7-(2,4-Dichlorophenyl)-4,7-dihydro-5-methyl-pyrazolo[1,5-a]pyrimidin-6-yl]carbonyl]-4-(4-fluorophenyl)piperazine | 486 |

-continued

| Example | Structure | Name | (M + H) |
|---|---|---|---|
| 90 | 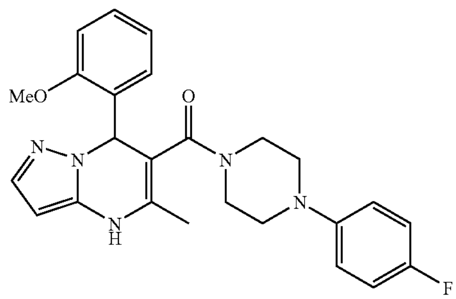 | 1-[[4,7-Dihydro-7-(2-methoxyphenyl)-5-methylpyrazolo[1,5-a]pyrimidin-6-yl]carbonyl]-4-(4-fluorophenyl)piperazine | 447 |
| 91 | 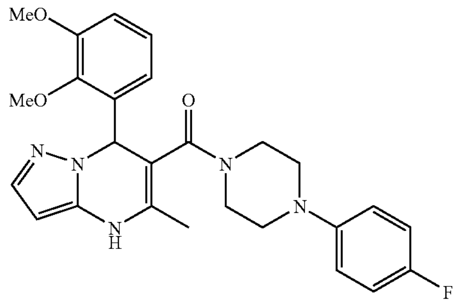 | 1-[[7-(2,3-Dimethoxyphenyl)-4,7-dihydro-5-methyl-pyrazolo[1,5-a]pyrimidin-6-yl]carbonyl]-4-(4-fluoro-phenyl)piperazine | 477 |
| 92 | 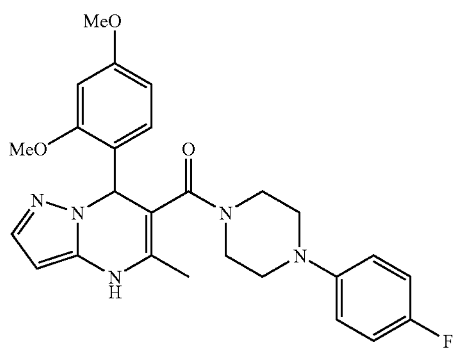 | 1-[[7-(2,4-Dimethoxyphenyl)-4,7-dihydro-5-methyl-pyrazolo[1,5-a]pyrimidin-6-yl]carbonyl]-4-(4-fluoro-phenyl)piperazine | 477 |
| 93 | 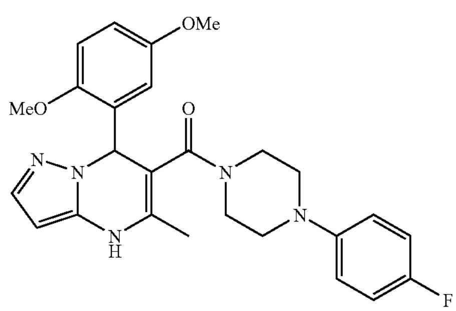 | 1-[[7-(2,5-Dimethoxyphenyl)-4,7-dihydro-5-methyl-pyrazolo[1,5-a]pyrimidin-6-yl]carbonyl]-4-(4-fluoro-phenyl)piperazine | 477 |
| 94 | 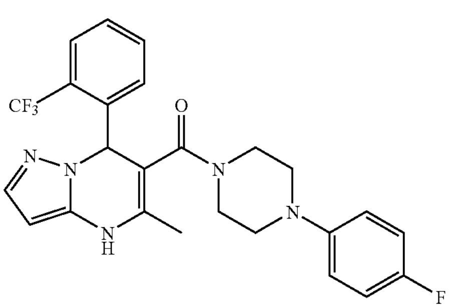 | 1-[[4,7-Dihydro-5-methyl-7-[2-(trifluoromethyl)phenyl]pyrazolo[1,5-a]pyrimidin-6-yl]carbonyl]-4-(4-fluorophenyl)piperazine | 485 |

-continued

| Example | Structure | Name | (M + H) |
|---|---|---|---|
| 95 | 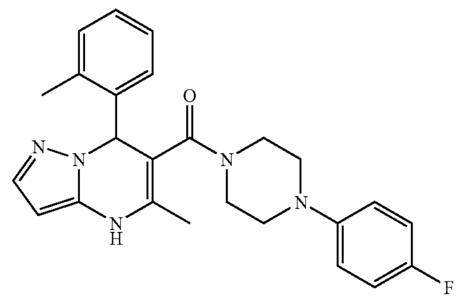 | 1-[[4,7-Dihydro-5-methyl-7-(2-methylphenyl)pyrazolo[1,5-a]pyrimidin-6-yl]carbonyl]-4-(4-fluorophenyl)piperazine | 431 |
| 96 | 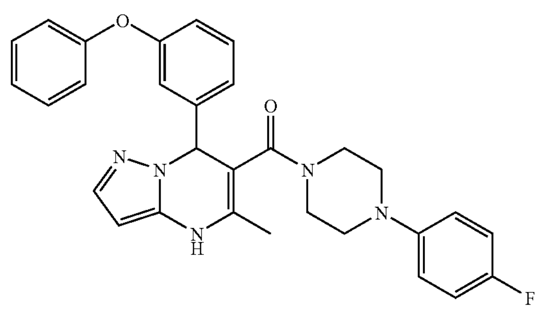 | 1-[[4,7-Dihydro-5-methyl-7-(3-phenoxyphenyl)pyrazolo[1,5-a]pyrimidin-6-yl]carbonyl]-4-(4-fluorophenyl)piperazine | 509 |
| 97 | 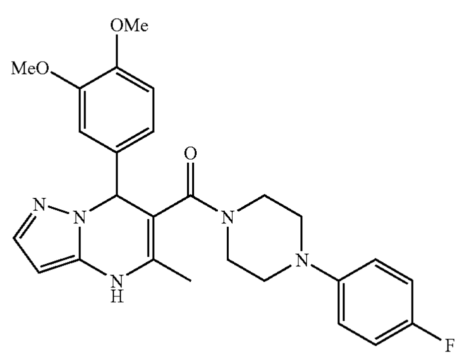 | 1-[[7-(3,4-Dimethoxyphenyl)-4,7-dihydro-5-methyl-pyrazolo[1,5-a]pyrimidin-6-yl]carbonyl]-4-(4-fluorophenyl)piperazine | 477 |
| 98 | 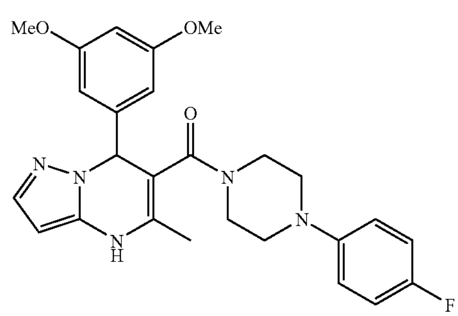 | 1-[[7-(3,5-Dimethoxyphenyl)-4,7-dihydro-5-methyl-pyrazolo[1,5-a]pyrimidin-6-yl]carbonyl]-4-(4-fluorophenyl)piperazine | 477 |

-continued

| Example | Structure | Name | (M + H) |
| --- | --- | --- | --- |
| 99 | 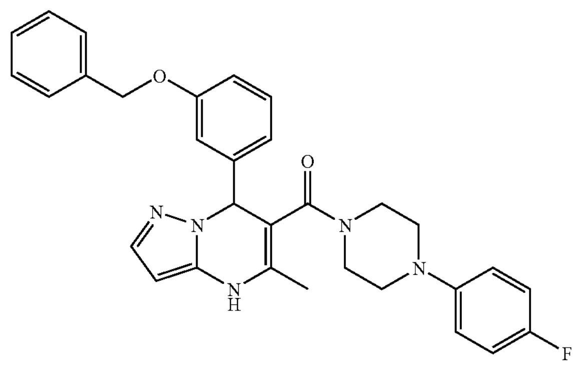 | 1-[[4,7-Dihydro-5-methyl-7-[3-(phenylmethoxy)phenyl]pyrazolo[1,5-a]pyrimidin-6-yl]carbonyl]-4-(4-fluorophenyl)piperazine | 523 |
| 100 | 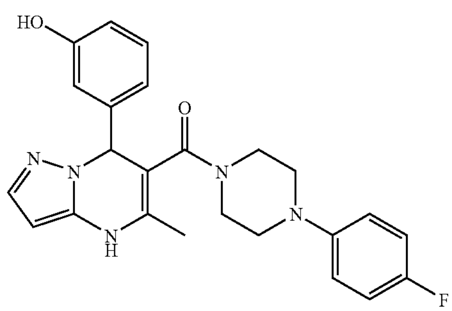 | 1-[[4,7-Dihydro-7-(3-hydroxyphenyl)-5-methyl-pyrazolo[1,5-a]pyrimidin-6-yl]carbonyl]-4-(4-fluorophenyl)piperazine | 433 |
| 101 | 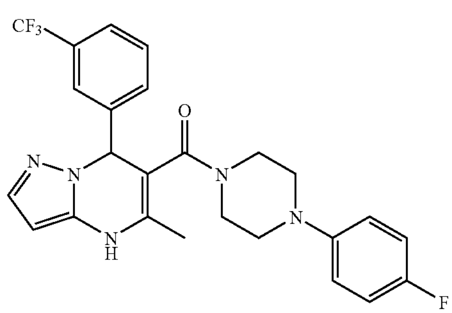 | 1-[[4,7-Dihydro-5-methyl-7-[3-(trifluoromethyl)phenyl]pyrazolo[1,5-a]pyrimidin-6-yl]carbonyl]-4-(4-fluorophenyl)piperazine | 485 |
| 102 | 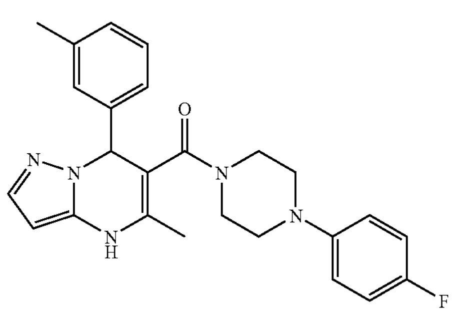 | 1-[[4,7-Dihydro-5-methyl-7-(3-methylphenyl)pyrazolo[1,5-a]pyrimidin-6-yl]carbonyl]-4-(4-fluorophenyl)piperazine | 431 |

-continued

| Example | Structure | Name | (M + H) |
|---|---|---|---|
| 103 | 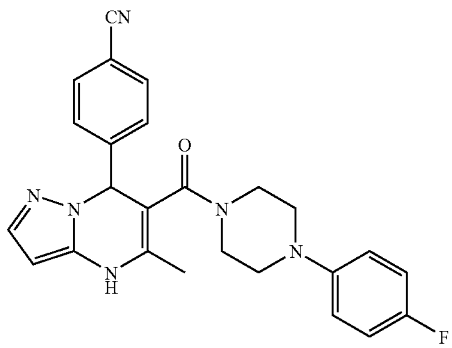 | 1-[[7-(4-Cyanophenyl)-4,7-dihydro-5-methylpyrazolo[1,5-a]pyrimidin-6-yl]carbonyl]-4-(4-fluorophenyl)piperazine | 442 |
| 104 | 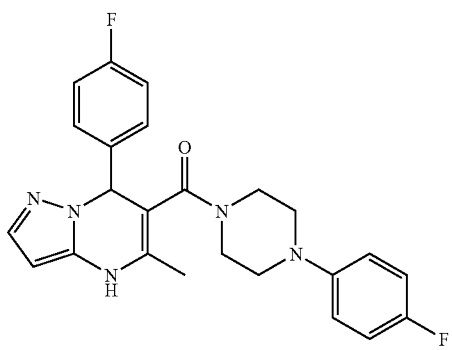 | 1-(4-Fluorophenyl)-4-[[7-(4-fluorophenyl)-4,7-dihydro-5-methylpyrazolo[1,5-a]pyrimidin-6-yl]carbonyl]-piperazine | 435 |
| 105 | 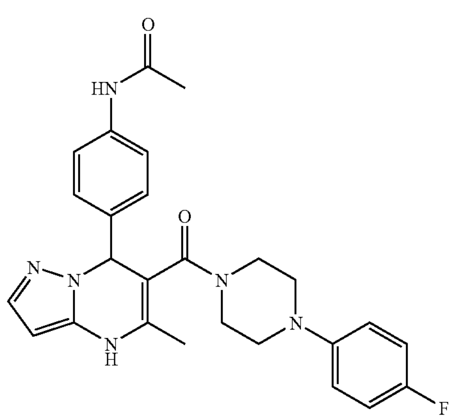 | N-[4-[6-[[4-(4-Fluorophenyl)-1-piperazinyl]carbonyl]-4,7-dihydro-5-methylpyrazolo[1,5-a]pyrimidin-7-yl]phenyl]acetamide | 474 |
| 106 | 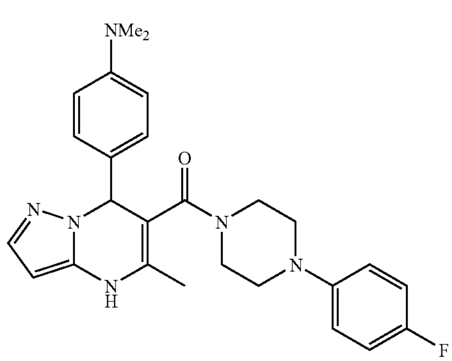 | 1-[[7-[4-(Dimethylamino)phenyl]-4,7-dihydro-5-methylpyrazolo[1,5-a]pyrimidin-6-yl]carbonyl]-4-(4-fluorophenyl)piperazine | 460 |

-continued

| Example | Structure | Name | (M + H) |
|---|---|---|---|
| 107 | 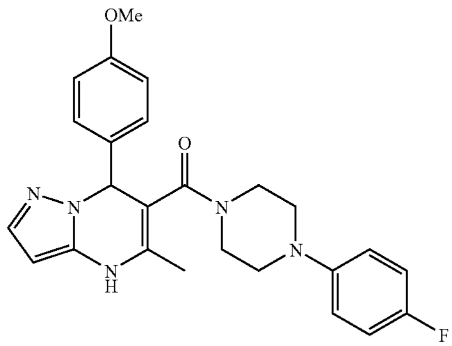 | 1-[[4,7-Dihydro-7-(4-methoxyphenyl)-5-methylpyrazolo[1,5-a]pyrimidin-6-yl]carbonyl]-4-(4-fluorophenyl)piperazine | 447 |
| 108 | 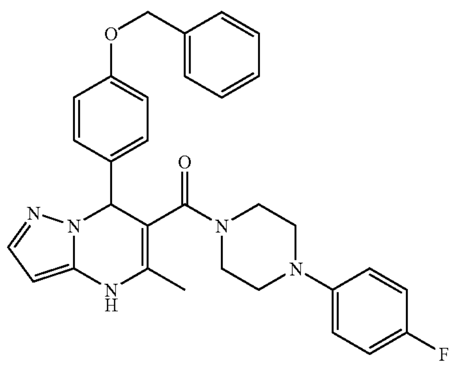 | 1-[[4,7-Dihydro-5-methyl-7-[4-(phenylmethoxy)phenyl]pyrazolo[1,5-a]pyrimidin-6-yl]carbonyl]-4-(4-fluorophenyl)piperazine | 523 |
| 109 | 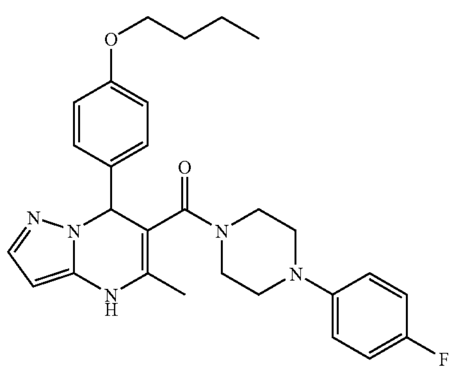 | 1-[[7-(4-Butoxyphenyl)-4,7-dihydro-5-methylpyrazolo[1,5-a]pyrimidin-6-yl]carbonyl]-4-(4-fluorophenyl)piperazine | 489 |
| 110 | 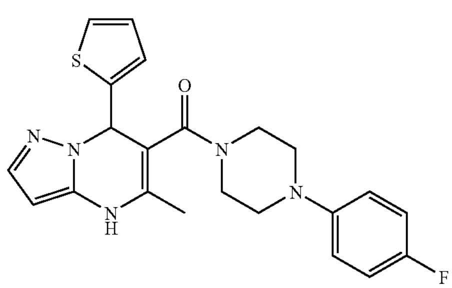 | 1-[[4,7-Dihydro-5-methyl-7-(2-thienyl)pyrazolo[1,5-a]pyrimidin-6-yl]carbonyl]-4-(4-fluorophenyl)piperazine | 423 |

-continued

| Example | Structure | Name | (M + H) |
|---|---|---|---|
| 111 | 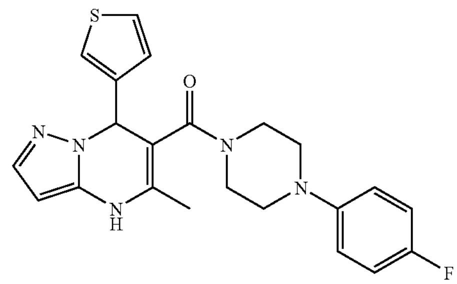 | 1-[[4,7-Dihydro-5-methyl-7-(3-thienyl)pyrazolo[1,5-a]pyrimidin-6-yl]carbonyl]-4-(4-fluorophenyl)piperazine | 423 |
| 112 | 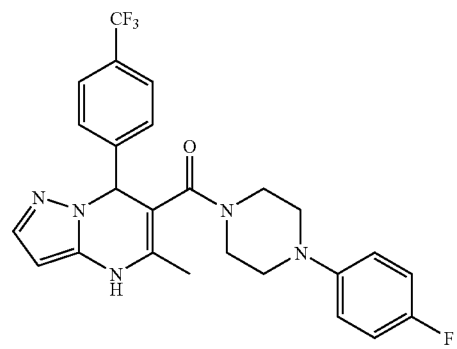 | 1-[[4,7-Dihydro-5-methyl-7-[4-(trifluoromethyl)phenyl]pyrazolo[1,5-a]pyrimidin-6-yl]carbonyl]-4-(4-fluorophenyl)piperazine | 485 |
| 113 | 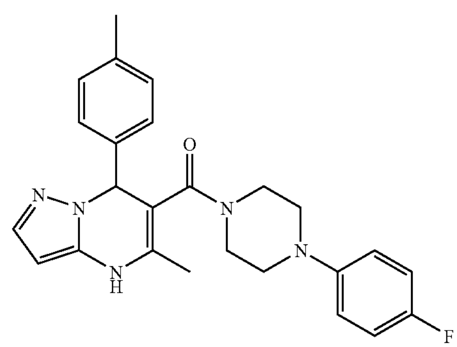 | 1-[[4,7-Dihydro-5-methyl-7-(4-methylphenyl)pyrazolo[1,5-a]pyrimidin-6-yl]carbonyl]-4-(4-fluorophenyl)piperazine | 431 |
| 114 | 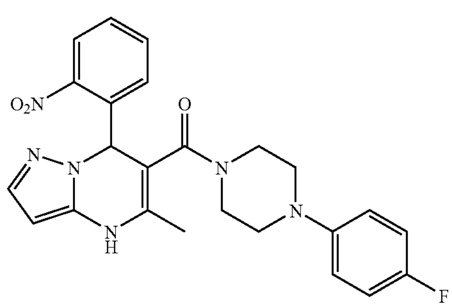 | 1-[[4,7-Dihydro-5-methyl-7-(2-nitrophenyl)pyrazolo[1,5-a]pyrimidin-6-yl]carbonyl]-4-(4-fluorophenyl)piperazine | 462 |

-continued

| Example | Structure | Name | (M + H) |
|---|---|---|---|
| 115 | 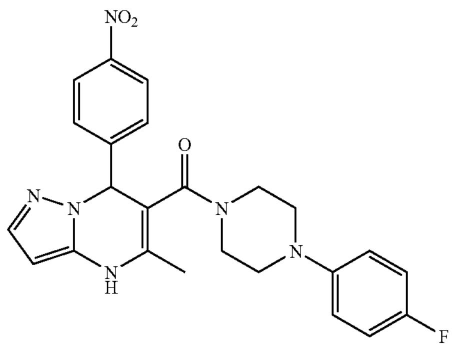 | 1-[[4,7-Dihydro-5-methyl-7-(4-nitrophenyl)pyrazolo[1,5-a]pyrimidin-6-yl]carbonyl]-4-(4-fluorophenyl)piperazine | 462 |
| 116 | 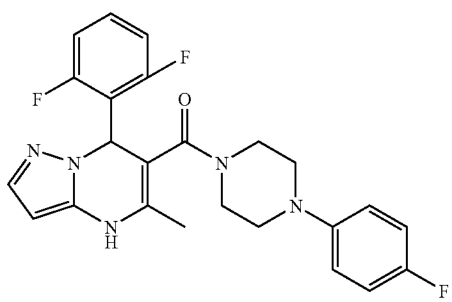 | 1-[[7-(2,6-Difluorophenyl)-4,7-dihydro-5-methylpyrazolo[1,5-a]pyrimidin-6-yl]carbonyl]-4-(4-fluorophenyl)piperazine | 453 |
| 117 | 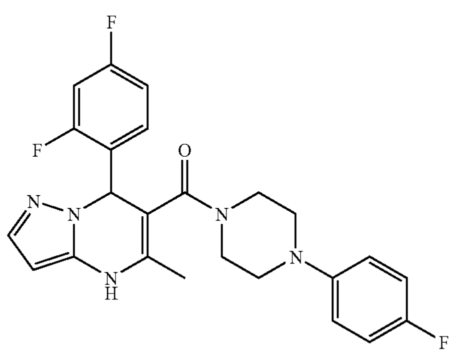 | 1-[[7-(2,4-Difluorophenyl)-4,7-dihydro-5-methylpyrazolo[1,5-a]pyrimidin-6-yl]carbonyl]-4-(4-fluorophenyl)piperazine | 453 |
| 118 | 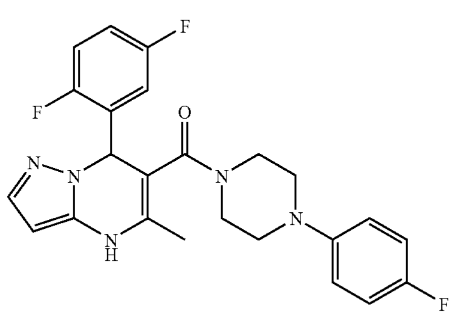 | 1-[[7-(2,5-Difluorophenyl)-4,7-dihydro-5-methylpyrazolo[1,5-a]pyrimidin-6-yl]carbonyl]-4-(4-fluorophenyl)piperazine | 453 |

-continued

| Example | Name | (M + H) |
|---|---|---|
| 119 | 1-[[7-(3,5-Difluorophenyl)-4,7-dihydro-5-methylpyrazolo[1,5-a]pyrimidin-6-yl]carbonyl]-4-(4-fluorophenyl)piperazine | 453 |
| 120 | 1-[[4,7-Dihydro-5-methyl-7-[2-(phenylmethoxy)phenyl]pyrazolo[1,5-a]pyrimidin-6-yl]carbonyl]-4-(4-fluorophenyl)piperazine | 523 |
| 121 | 1-[[7-(3,4-Dimethylphenyl)-4,7-dihydro-5-methyl-pyrazolo[1,5-a]pyrimidin-6-yl]carbonyl]-4-(4-fluorophenyl)piperazine | 445 |
| 122 | 1-[[4,7-Dihydro-5-methyl-7-[4-(trifluoromethoxy)phenyl]pyrazolo[1,5-a]pyrimidin-6-yl]carbonyl]-4-(4-fluorophenyl)piperazine | 501 |

-continued

| Example | Structure | Name | (M + H) |
|---|---|---|---|
| 123 | 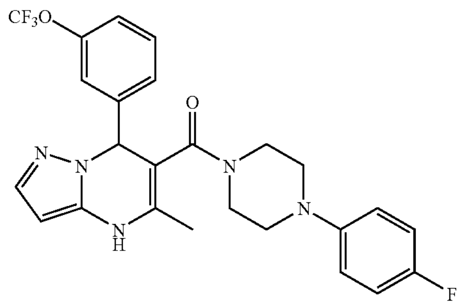 | 1-[[4,7-Dihydro-5-methyl-7-[3-(trifluoromethoxy)phenyl]pyrazolo[1,5-a]pyrimidin-6-yl]carbonyl]-4-(4-fluorophenyl)piperazine | 501 |
| 124 | 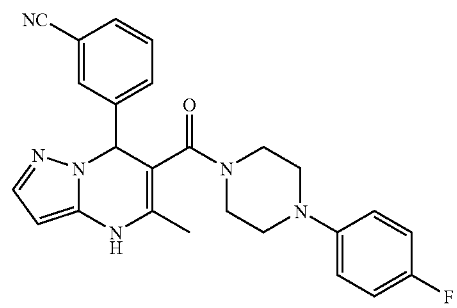 | 1-[[7-(3-Cyanophenyl)-4,7-dihydro-5-methylpyrazolo[1,5-a]pyrimidin-6-yl]carbonyl]-4-(4-fluorophenyl)piperazine | 442 |
| 125 | 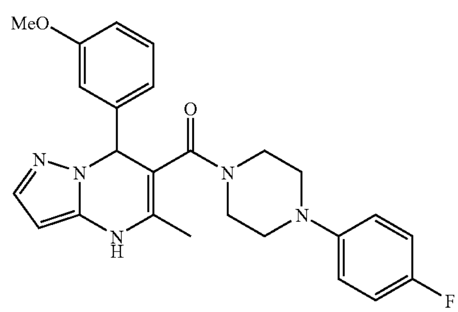 | 1-[[4,7-Dihydro-7-(3-methoxyphenyl)-5-methylpyrazolo[1,5-a]pyrimidin-6-yl]carbonyl]-4-(4-fluorophenyl)piperazine | 447 |
| 126 | 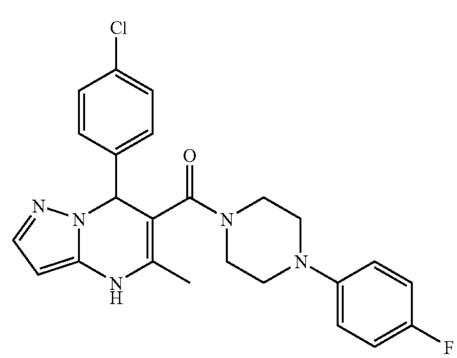 | 1-[[7-(4-Chlorophenyl)-4,7-dihydro-5-methylpyrazolo[1,5-a]pyrimidin-6-yl]carbonyl]-4-(4-fluorophenyl)piperazine | 451 |

-continued

| Example | Structure | Name | (M + H) |
|---------|-----------|------|---------|
| 127 | 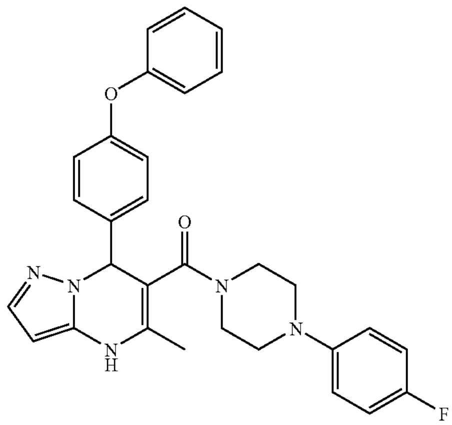 | 1-[[4,7-Dihydro-5-methyl-7-(4-phenoxyphenyl)pyrazolo[1,5-a]pyrimidin-6-yl]carbonyl]-4-(4-fluorophenyl)piperazine | 509 |
| 128 | 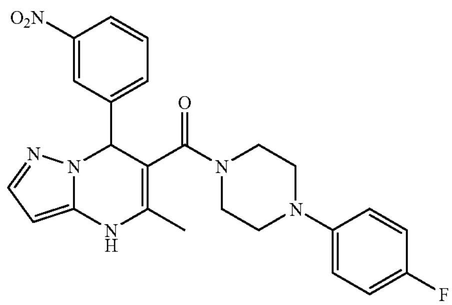 | 1-[[4,7-Dihydro-5-methyl-7-(3-nitrophenyl)pyrazolo[1,5-a]pyrimidin-6-yl]carbonyl]-4-(4-fluorophenyl)piperazine | 462 |
| 129 | 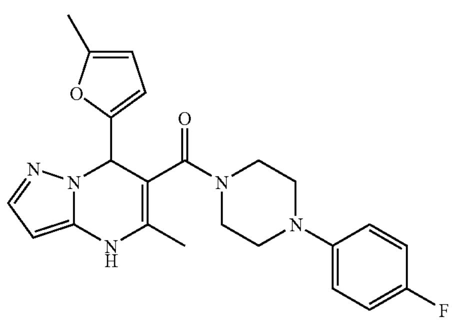 | 1-[[4,7-Dihydro-5-methyl-7-(5-methyl-2-furanyl)pyrazolo[1,5-a]pyrimidin-6-yl]carbonyl]-4-(4-fluorophenyl)piperazine | 421 |
| 130 | 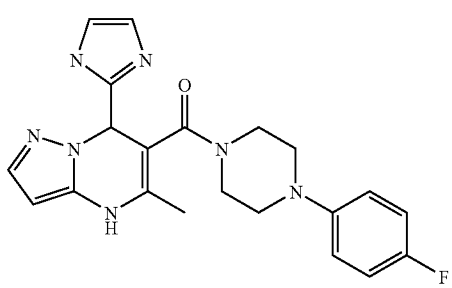 | 1-[[4,7-Dihydro-7-(1H-imidazol-2-yl)-5-methylpyrazolo[1,5-a]pyrimidin-6-yl]carbonyl]-4-(4-fluorophenyl)piperazine | 407 |

-continued

| Example | Structure | Name | (M + H) |
|---|---|---|---|
| 131 | 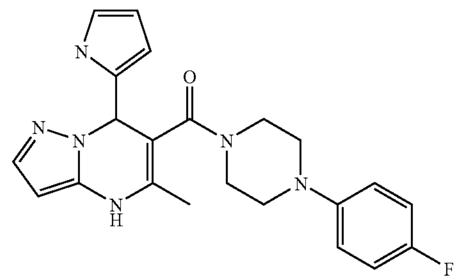 | 1-[[4,7-Dihydro-5-methyl-7-(1H-pyrrol-2-yl)pyrazolo[1,5-a]pyrimidin-6-yl]carbonyl]-4-(4-fluorophenyl)piperazine | 406 |
| 132 | 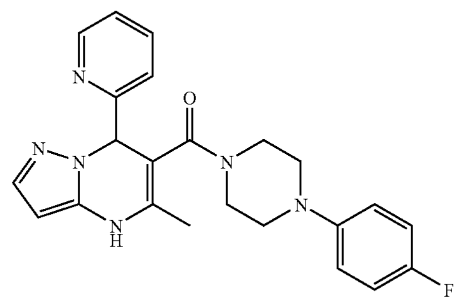 | 1-[[4,7-Dihydro-5-methyl-7-(2-pyridinyl)pyrrolo[1,5-a]pyrimidin-6-yl]carbonyl]-4-(4-fluorophenyl)piperazine | 418 |
| 133 | 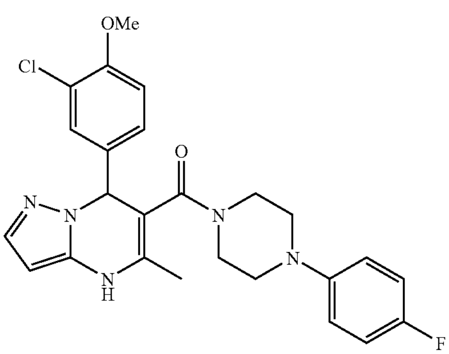 | 1-[[7-(3-Chloro-4-methoxyphenyl)-4,7-dihydro-5-methylpyrazolo[1,5-a]pyrimidin-6-yl]carbonyl]-4-(4-fluorophenyl)piperazine | 481 |
| 134 | 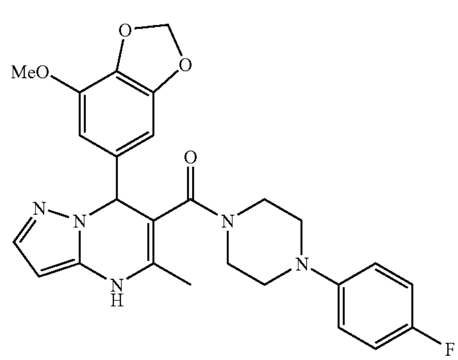 | 1-[[4,7-Dihydro-7-(4-methoxy-1,3-benzodioxol-6-yl)-5-methylpyrazolo[1,5-a]pyrimidin-6-yl]carbonyl]-4-(4-fluorophenyl)piperazine | 491 |

-continued

| Example | Structure | Name | (M + H) |
|---|---|---|---|
| 135 | 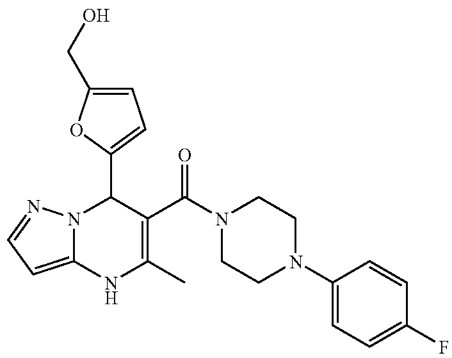 | 1-[[4,7-Dihydro-7-[5-(hydroxymethyl)-2-furanyl]-5-methylpyrazolo[1,5-a]pyrimidin-6-yl]carbonyl]-4-(4-fluorophenyl)piperazine | 437 |
| 136 | 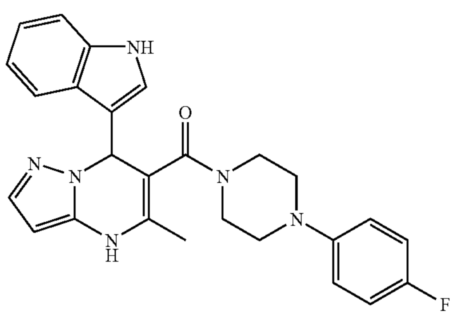 | 1-[[4,7-Dihydro-7-(1H-indol-3-yl)-5-methylpyrazolo[1,5-a]pyrimidin-6-yl]carbonyl]-4-(4-fluorophenyl)piperazine | 456 |
| 137 | 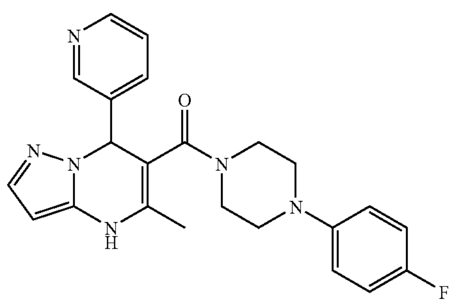 | 1-[[4,7-Dihydro-5-methyl-7-(3-pyridinyl)pyrazolo[1,5-a]pyrimidin-6-yl]carbonyl]-4-(4-fluorophenyl)piperazine | 418 |
| 138 | 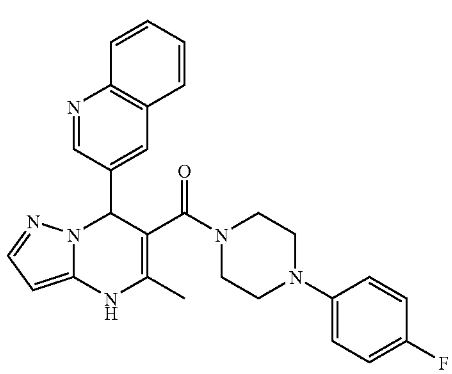 | 1-[[4,7-Dihydro-5-methyl-7-(3-quinolinyl)pyrazolo[1,5-a]pyrimidin-6-yl]carbonyl]-4-(4-fluorophenyl)piperazine | 468 |

-continued

| Example | Structure | Name | (M + H) |
|---|---|---|---|
| 139 | 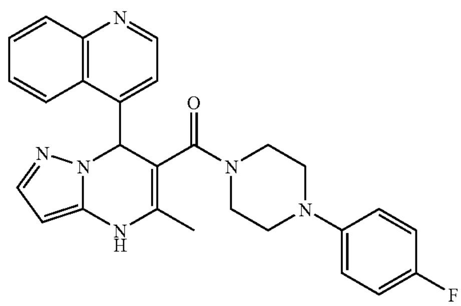 | 1-[[4,7-Dihydro-5-methyl-7-(4-quinolinyl)pyrazolo[1,5-a]pyrimidin-6-yl]carbonyl]-4-(4-fluorophenyl)piperazine | 468 |
| 140 | 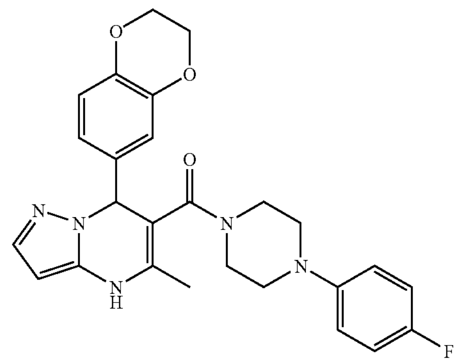 | 1-[[7-(2,3-Dihydro-1,4-benzodioxin-6-yl)-4,7-dihydro-5-methylpyrazolo[1,5-a]pyrimidin-6-yl]carbonyl]-4-(4-fluorophenyl)piperazine | 475 |
| 141 | 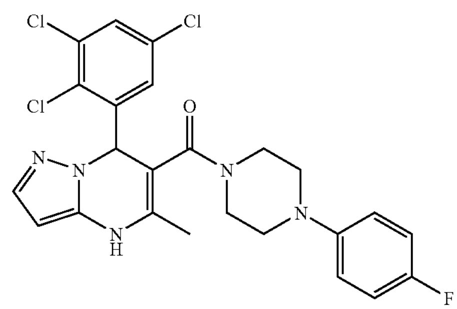 | 1-[[4,7-Dihydro-5-methyl-7-(2,3,5-trichlorophenyl)pyrazolo[1,5-a]pyrimidin-6-yl]carbonyl]-4-(4-fluorophenyl)piperazine | 520 |
| 142 | 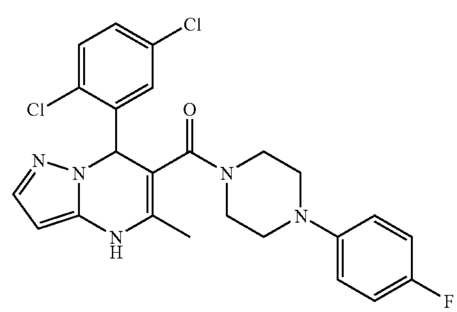 | 1-[[7-(2,5-Dichlorophenyl)-4,7-dihydro-5-methylpyrazolo[1,5-a]pyrimidin-6-yl]carbonyl]-4-(4-fluorophenyl)piperazine | 486 |
| 143 | 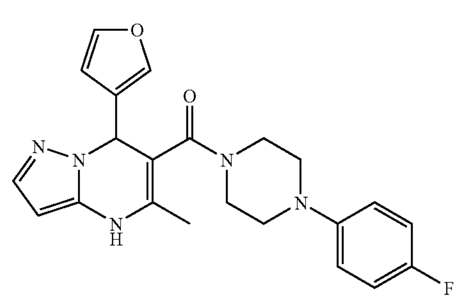 | 1-(4-Fluorophenyl)-4-[[7-(3-furanyl)-4,7-dihydro-5-methylpyrazolo[1,5-a]pyrimidin-6-yl]carbonyl]-piperazine | 407 |

-continued

| Example | Structure | Name | (M + H) |
|---|---|---|---|
| 144 | 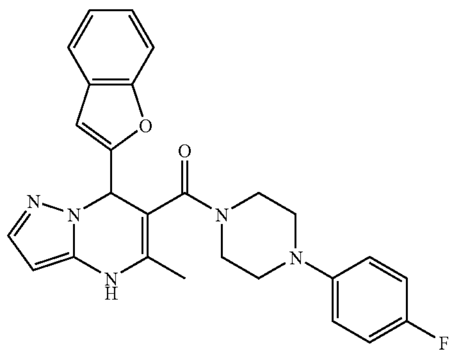 | 1-[[7-(2-Benzofuranyl)-4,7-dihydro-5-methylpyrazolo[1,5-a]pyrimidin-6-yl]carbonyl]-4-(4-fluorophenyl)piperazine | 457 |
| 145 | 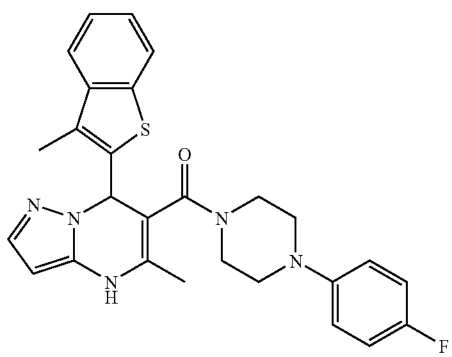 | 1-[[4,7-Dihydro-5-methyl-7-(3-methylbenzo[b]thiophen-2-yl)pyrazolo[1,5-a]pyrimidin-6-yl]carbonyl]-4-(4-fluorophenyl)piperazine | 487 |
| 146 | 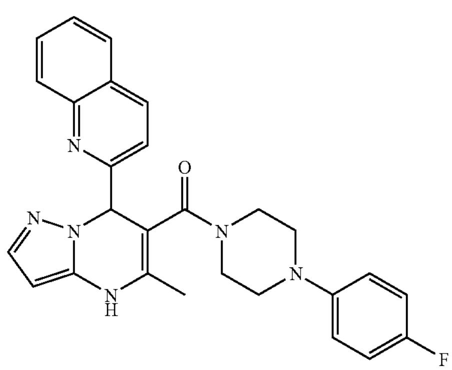 | 1-[[4,7-Dihydro-5-methyl-7-(2-quinolinyl)pyrazolo[1,5-a]pyrimidin-6-yl]carbonyl]-4-(4-fluorophenyl)piperazine | 468 |
| 147 | 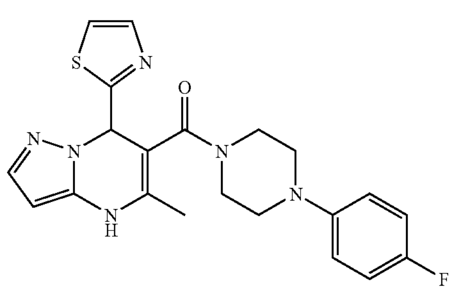 | 1-[[4,7-Dihydro-5-methyl-7-(2-thiazolyl)pyrazolo[1,5-a]pyrimidin-6-yl]carbonyl]-4-(4-fluorophenyl)piperazine | 424 |

-continued

| Example | Structure | Name | (M + H) |
|---|---|---|---|
| 148 | 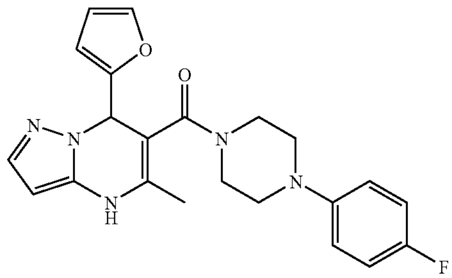 | 1-(4-Fluorophenyl)-4-[[7-(2-furanyl)-4,7-dihydro-5-methylpyrazolo[1,5-a]pyrimidin-6-yl]carbonyl]-piperazine | 407 |
| 149 | 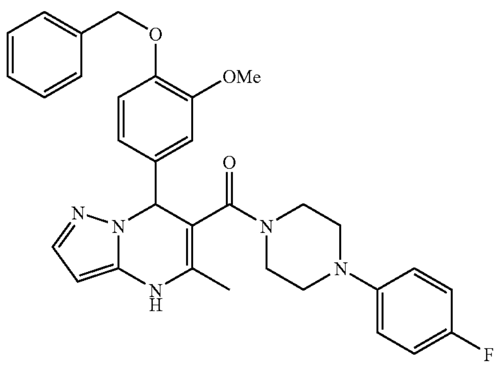 | 1-[[4,7-Dihydro-7-[3-methoxy-4-(phenylmethoxy)phenyl]-5-methylpyrazolo[1,5-a]pyrimidin-6-yl]carbonyl]-4-(4-fluorophenyl)piperazine | 553 |
| 150 | 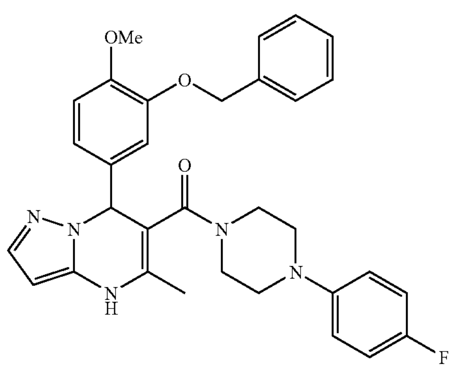 | 1-[[4,7-Dihydro-7-[4-methoxy-3-(phenylmethoxy)phenyl]-5-methylpyrazolo[1,5-a]pyrimidin-6-yl]carbonyl]-4-(4-fluorophenyl)piperazine | 553 |
| 151 | 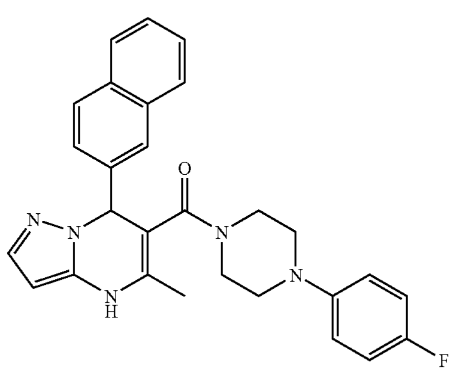 | 1-[[4,7-Dihydro-5-methyl-7-(2-naphthalenyl)pyrazolo[1,5-a]pyrimidin-6-yl]carbonyl]-4-(4-fluorophenyl)piperazine | 467 |

-continued

| Example | Structure | Name | (M + H) |
|---|---|---|---|
| 152 | 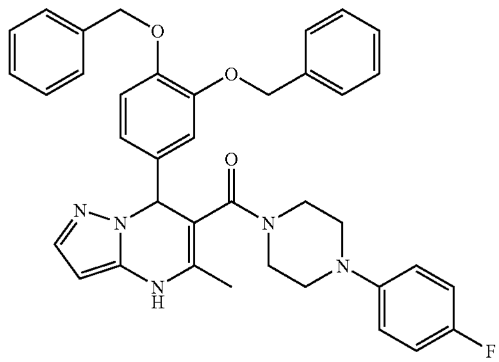 | 1-[[7-[3,4-Bis(phenyl-methoxy)phenyl]-4,7-dihydro-5-methylpyrazolo[1,5-a]pyrimidin-6-yl]carbonyl]-4-(4-fluorophenyl)piperazine | 629 |
| 153 | 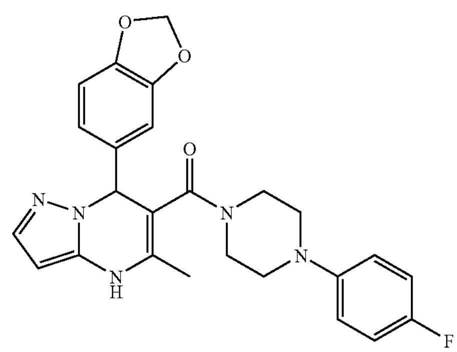 | 1-[[7-(1,3-Benzodioxol-5-yl)-4,7-dihydro-5-methyl-pyrazolo[1,5-a]pyrimidin-6-yl]carbonyl]-4-(4-fluoro-phenyl)piperazine | 461 |
| 154 | 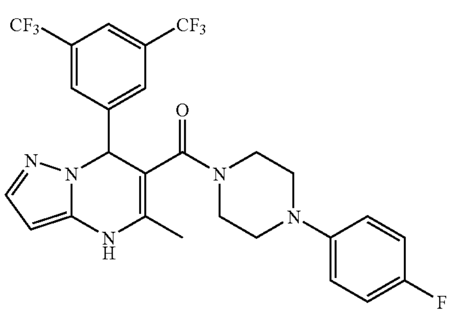 | 1-[[7-[3,4-Bis(trifluoro-methyl)phenyl]-4,7-dihydro-5-5-methylpyrazolo[1,5-a]pyri-midin-6-yl]carbonyl]-4-(4-fluorophenyl)piperazine | 553 |
| 155 | 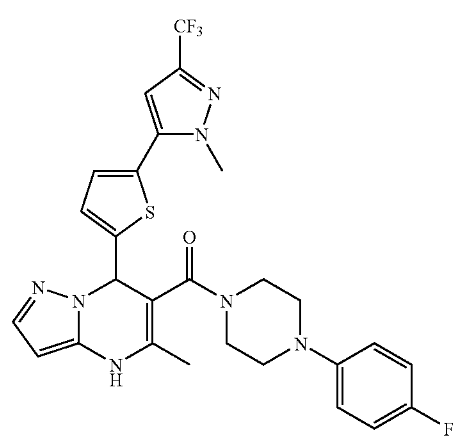 | 1-[[4,7-Dihydro-5-methyl-7-[5-[1-methyl-3-(trifluoromethyl)-1H-pyrazol-5-yl]-2-thienyl]pyrazolo[1,5-a]pyrimidin-6-yl]carbonyl]-4-(4-fluorophenyl)piperazine | 571 |

-continued

| Example | Structure | Name | (M + H) |
|---|---|---|---|
| 156 | 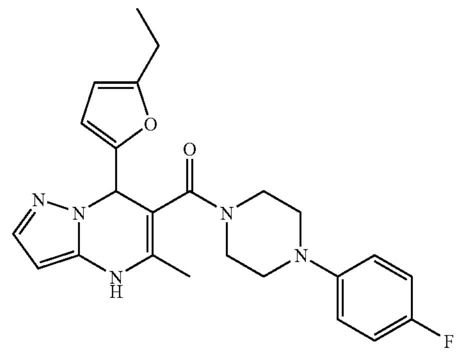 | 1-[[7-(5-Ethyl-2-furanyl)-4,7-dihydro-5-methylpyrazolo[1,5-a]pyrimidin-6-yl]carbonyl]-4-(4-fluorophenyl)piperazine | 435 |
| 157 | 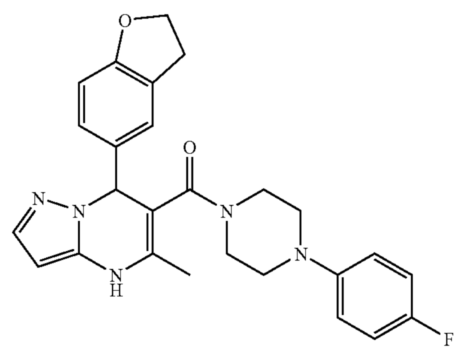 | 1-[[7-(2,3-Dihydro-5-benzofuranyl)-4,7-dihydro-5-methylpyrazolo[1,5-a]pyrimidin-6-yl]carbonyl]-4-(4-fluorophenyl)piperazine | 459 |
| 158 | 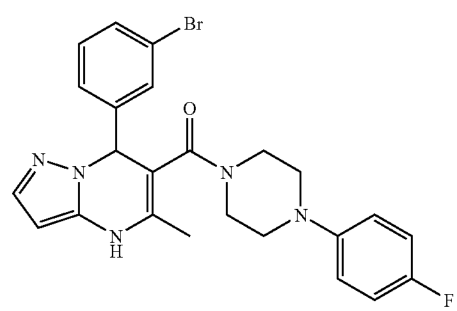 | 1-[[7-(3-Bromophenyl)-4,7-dihydro-5-methylpyrazolo[1,5-a]pyrimidin-6-yl]carbonyl]-4-(4-fluorophenyl)piperazine | 496 |
| 159 | 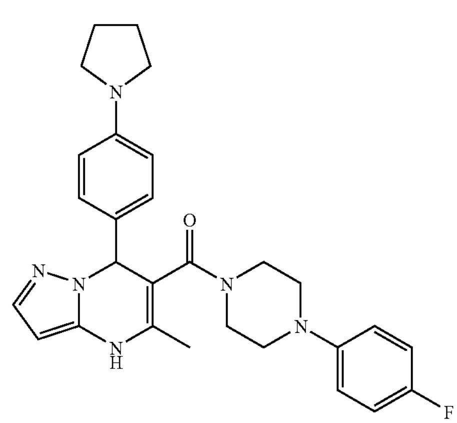 | 1-[[4,7-Dihydro-5-methyl-7-[4-(1-pyrrolidinyl)-phenyl]pyrazolo[1,5-a]pyrimidin-6-yl]carbonyl]-4-(4-fluorophenyl)piperazine | 486 |

-continued

| Example | Structure | Name | (M + H) |
|---|---|---|---|
| 160 | 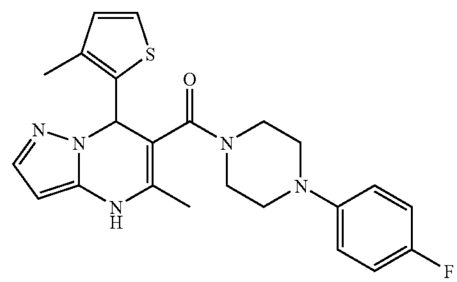 | 1-[[4,7-Dihydro-5-methyl-7-(3-methyl-2-thienyl)pyrazolo[1,5-a]pyrimidin-6-yl]carbonyl]-4-(4-fluorophenyl)piperazine | 437 |
| 161 | 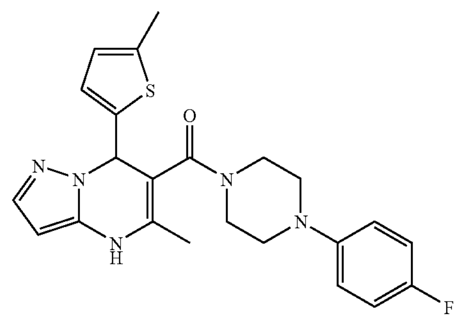 | 1-[[4,7-Dihydro-5-methyl-7-(5-methyl-2-thienyl)pyrazolo[1,5-a]pyrimidin-6-yl]carbonyl]-4-(4-fluorophenyl)piperazine | 437 |
| 162 | 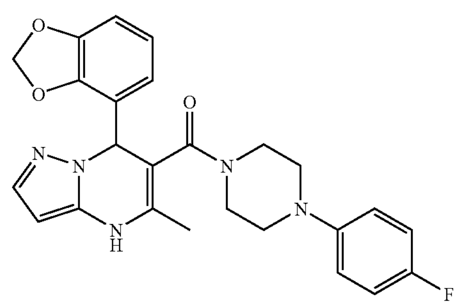 | 1-[[7-(1,3-Benzodioxol-4-yl)-4,7-dihydro-5-methyl-pyrazolo[1,5-a]pyrimidin-6-yl]carbonyl]-4-(4-fluorophenyl)piperazine | 461 |
| 163 | 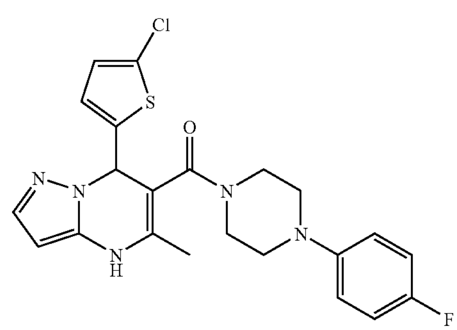 | 1-[[7-(5-Chloro-2-thienyl)-4,7-dihydro-5-methyl-pyrazolo[1,5-a]pyrimidin-6-yl]carbonyl]-4-(4-fluorophenyl)piperazine | 457 |
| 164 | 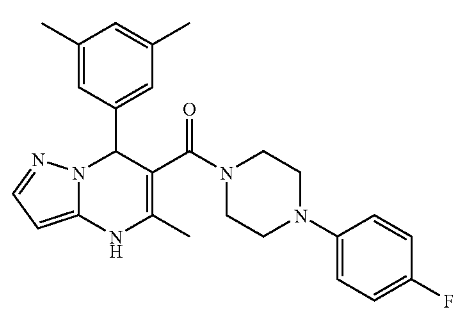 | 1-[[7-(3-Dimethylphenyl)-4,7-dihydro-5-methyl-pyrazolo[1,5-a]pyrimidin-6-yl]carbonyl]-4-(4-fluorophenyl)piperazine | 445 |

-continued

| Example | Structure | Name | (M + H) |
|---|---|---|---|
| 165 | 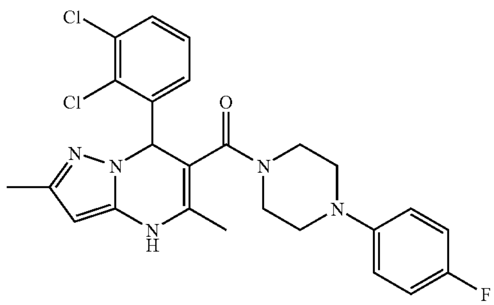 | 1-[[7-(2,3-Dichlorophenyl)-4,7-dihydro-2,5-dimethylpyrazolo[1,5-a]pyrimidin-6-yl]carbonyl]-4-(4-fluorophenyl)piperazine | 500 |
| 166 | Chiral | 1-[[7-(3,4-Dichlorophenyl)-4,7-dihydro-5-methyl-pyrazolo[1,5-a]pyrimidin-6-yl]carbonyl]-4-(4-fluorophenyl)piperazine, enantiomer A | 486 |
| 167 | Chiral | 1-[[7-(3,4-Dichlorophenyl)-4,7-dihydro-5-methyl-pyrazolo[1,5-a]pyrimidin-6-yl]carbonyl]-4-(4-fluorophenyl)piperazine, enantiomer B | 486 |
| 168 | Chiral | 1-[[7-(2,3-Dichlorophenyl)-4,7-dihydro-2,5-dimethyl-pyrazolo[1,5-a]pyrimidin-6-yl]carbonyl]-4-(4-fluorophenyl)piperazine, enantiomer B | 500 |

| Example | Structure | Name | (M + H) |
|---|---|---|---|
| 169 | 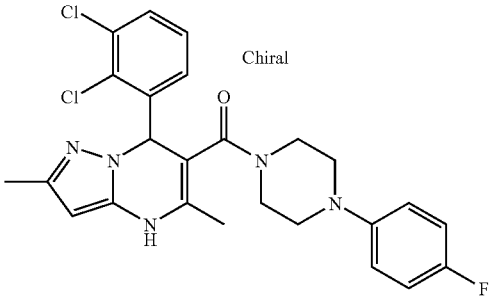 Chiral | 1-[[7-(2,3-Dichlorophenyl)-4,7-dihydro-2,5-dimethyl-pyrazolo[1,5-a]pyrimidin-6-yl]carbonyl]-4-(4-fluorophenyl)piperazine, enantiomer A | 500 |

EXAMPLE 170

8-[[7-(3,4-Dichlorophenyl)-4,7-dihydro-5-methylpyrazolo[1,5-a]pyrimidin-6-yl]carbonyl]-1,4-dioxa-8-azaspiro[4.5]decane

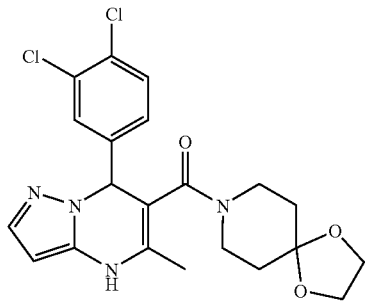

Method:

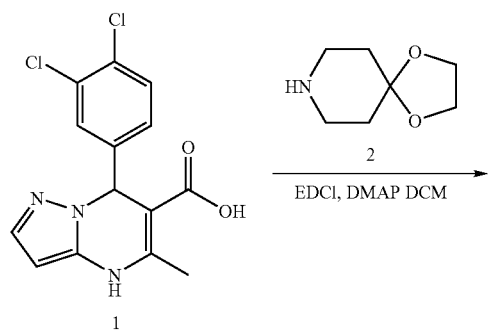

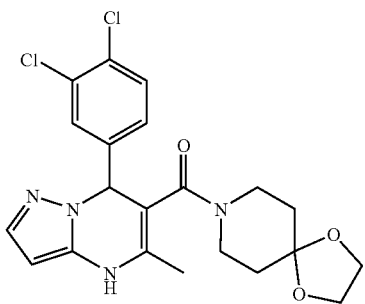

Compound 1: Compound 1 was prepared as described in Example 16.

Title Compound: Compound 2 (0.068 g, 0.47 mmol) was added to a suspension of compound 1 (0.10 g, 0.32 mmol), EDCI (0.09 g, 0.47 mmol), DMAP(0.004 g, 0.03 mmol) in dichloromethane (1 mL). When LC/MS indicated the reaction was complete the mixture was loaded directly onto a Worldwide Monitoring CLEAN-UP CARTRIDGE (silica gel, CUSIL12M6) which had been equilibrated with 100% hexanes. Elution with 100% hexanes (40 mL), followed by 50% Ethyl acetate/hexanes (40 mL) and 100% ethyl acetate (70 mL). The purest fractions (TLC analysis) were combined to give 0.043 g (30% yield) of the title compound as a white solid. Reverse Phase LC/MS: YMC S5 ODS 4.6×50 mm Ballistic column, UV detection at 220 λ, 4 min. gradient 40–100% Solvent B/A (Solvent A: 10% MeOH/H20with 0.1% TFA, Solvent B: 90% MeOH/$H_2O$ with 0.1% TFA), 4 mL/min. Rt=2.12 min, (97% pure). MS (M+H: 449). HMR (DMSO-$d_6$, 400 MHz, 100° C.) 9.02(1H, bs), 7.49(1H, d, J=8 Hz), 7.26(1H, d, J=2 Hz), 7.14(1H, d, J=2 Hz), 6.95(1H, d, J=8 Hz), 6.08(1H, s), 5.55(1H, d, J=2 Hz), 3.84(4H, m), 3.55(2H,m), 3.20(2H, m), 1.86(3H, s), 1.37(2H, m), 1.26 (2H, m).

EXAMPLES 171–377

The compounds of Examples 171–377, shown in the table provided below, were prepared in a manner similar to that described in Example 170.

HPLC resolution of Example 194, Chiralpak AD column (50×500 mm), eluting with 30% isopropanol/hexanes containing 0.1% triethylamine at 50 mL/min), UV detection at 254λ, provided enantiomers A (Example 250)and B (Example 251). Chiralpak AD column (4.6×250 mm) eluting with 30% isopropanol/hexanes containing 0.1% triethylamine at 1 mL/min), UV detection at 254λ, enantiomer A Rt=5.32 min, 99% ee. Enantiomer B Rt=8.59 min, 98% ee.

HPLC resolution of Example 221, Chiralpak AS column (50×500 mm), eluting with 50% isopropanol/hexanes containing 0.1% triethylamine at 42 mL/min, UV detection at 254λ provided enantiomers A (Example 328) and B (Example 329). Chiralpak AS column (4.6×250 mm) eluting with 30% isopropanol/hexanes containing 0.1% triethylamine amine at 1 mL/min), UV detection at 254λ, enantiomer A Rt=5.12 min, >99% ee. Enantiomer B Rt=8.70 min, >99% ee.

HPLC resolution of Example 288, Chiralpak AD column (50×500 mm), eluting with 30% isopropanol/hexanes containing 0.1% triethylamine at 50 mL/min), UV detection at 254λ provided enantiomers A (Example 376) and B (Example 377). Chiralpak AD column (4.6×250 mm) eluting with 30% isopropanol/hexanes containing 0.1% triethylamine at 1 mL/min), UV detection at 254λ, enantiomer A Rt=3.8 min, >99% ee. Enantiomer B Rt=5.6 min, >99% ee.

HPLC resolution of Example 333, Chiralpak AD column (50×500 mm), eluting with 40% isopropanol/hexanes containing 0.1% triethylamine at 50 mL/min), UV detection at 254λ, provided enantiomers A (Example 364) and B (Example 365). Chiralpak AD column (4.6×250 mm) eluting with 40% isopropanol/hexanes containing 0.1% triethylamine at 1 mL/min), UV detection at 254λ, enantiomer A Rt=4.92 min, >99% ee. Enantiomer B Rt=8.0 min, >97% ee.

The compound of Example 360 was separated into pure diastereo-isomers by column chromatography (silica gel eluted with 75% ethyl acetate, hexane). The faster eluting isomer is diastereomer 1, the slower eluting isomer is diastereomer 2. When separated by TLC (20% acetone, dichloromethane), diasteriomer 1 has an $R_f$ of 0.26 and diastereromer 2 has an $R_f$ of 0.17. Diastereomer 2 was further separated into pure chiral form via preparative chiral HPLC (Chiralpak AD 5 cm×50 cm column eluted with 13% ethanol in hexane with 0.1% TEA at 50 mL/min with UV detection at 254 nM). The faster eluting isomer is enantiomer A (HPLC retention time 8.1 min, 4.6×250 mm Chiralpak AD column eluted with 10% ethanol, hexane with 0.1% triethylamine at 2 mL/min with UV detection at 254 nm) and the slower eluting isomer is enantiomer B (HPLC retention time 10.6 min, 4.6×250 mm Chiralpak AD column eluted with 10% ethanol, hexane with 0.1% triethylamine at 2 mL/min with UV detection at 254 nm). Diasteromer 1 can also be further separated into chiral pure form by similar methodology as that descibed for diastereomer 2 above to provide enantiomers C and D.

| Example | Structure | Name | (M + H) |
| --- | --- | --- | --- |
| 171 | 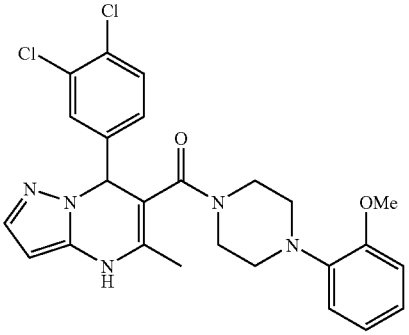 | 1-[[7-(3,4-Dichloro-phenyl)-4,7-dihydro-5-methyl-pyrazolo[1,5-a]-pyrimidin-6-yl]carbonyl]-4-(2-methoxyphenyl)piperazine | 498 |
| 172 | 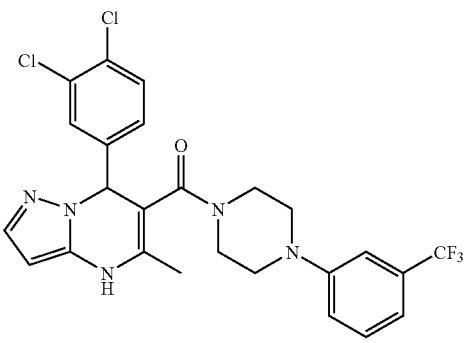 | 1-[[7-(3,4-Dichloro-phenyl)-4,7-dihydro-5-methylpyrazolo[1,5-a]-pyrimidin-6-yl]carbonyl]-4-[3-(trifluoromethyl)-phenyl]piperazine | 536 |

-continued

| Example | Structure | Name | (M + H) |
|---|---|---|---|
| 173 | 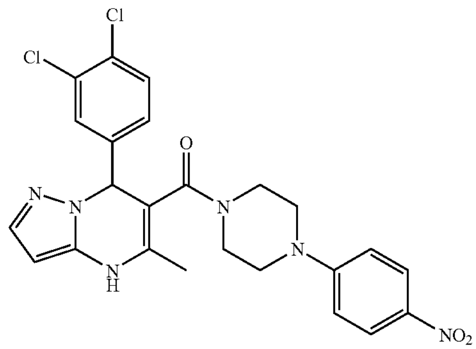 | 1-[[7-(3,4-Dichloro-phenyl)-4,7-dihydro-5-methylpyrazolo[1,5-a]-pyrimidin-6-yl]carbonyl]-4-(4-nitrophenyl)piperazine | 513 |
| 174 | 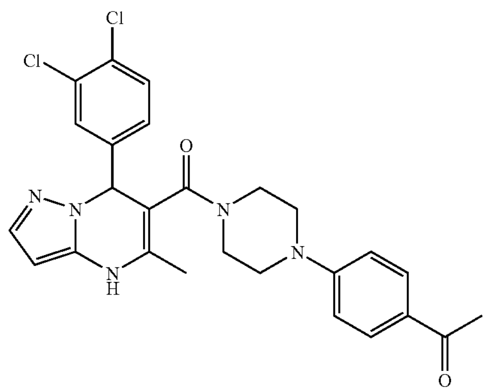 | 1-(4-Acetylphenyl)-4-[[7-(3,4-dichlorophenyl)-4,7-dihydro-5-methyl-pyrazolo[1,5-a]-pyrimidin-6-yl]carbonyl]piperazine | 510 |
| 175 | 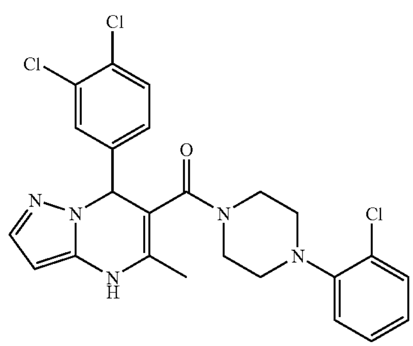 | 1-(2-Chlorophenyl)-4-[[7-(3,4-dichlorophenyl)-4,7-dihydro-5-methyl-pyrazolo[1,5-a]-pyrimidin-6-yl]carbonyl]piperazine | 502 |
| 176 | 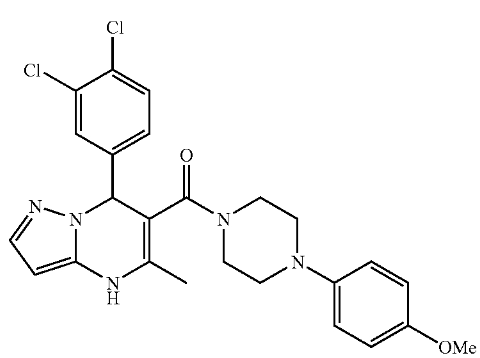 | 1-[[7-(3,4-Dichloro-phenyl)-4,7-dihydro-5-methylpyrazolo[1,5-a]-pyrimidin-6-yl]carbonyl]-4-(4-methoxyphenyl)piperazine | 498 |

| Example | Structure | Name | (M + H) |
|---|---|---|---|
| 177 | 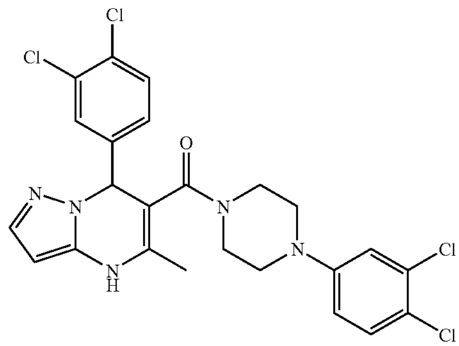 | 1-(3,4-Dichlorophenyl)-4-[[7-(3,4-dichlorophenyl)-4,7-dihydro-5-methylpyrazolo[1,5-a]-pyrimidin-6-yl]carbonyl]-piperazine | 537 |
| 178 | 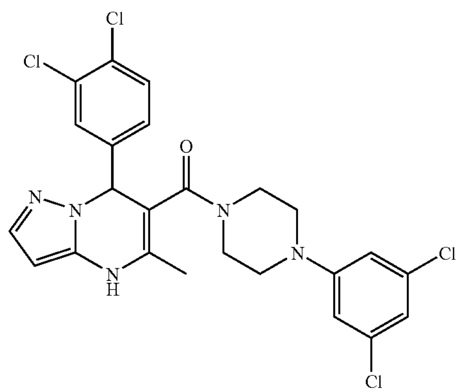 | 1-(3,5-Dichlorophenyl)-4-[[7-(3,4-dichlorophenyl)-4,7-dihydro-5-methylpyrazolo[1,5-a]pyrimidin-6-yl]carbonyl]piperazine | 537 |
| 179 | 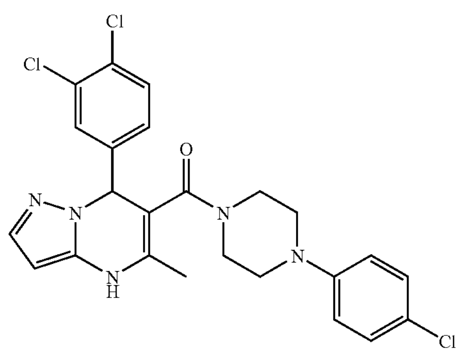 | 1-(4-Chlorophenyl)-4-[[7-(3,4-dichlorophenyl)-4,7-dihydro-5-methyl-pyrazolo[1,5-a]pyrimidin-6-yl]carbonyl]piperazine | 502 |
| 180 | 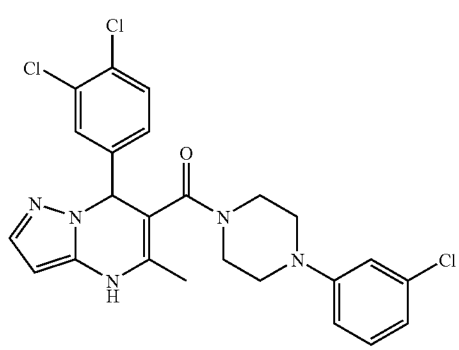 | 1-(3-Chlorophenyl)-4-[[7-(3,4-dichlorophenyl)-4,7-dihydro-5-methylpyrazolo-[1,5-a]pyrimidin-6-yl]-carbonyl]piperazine | 502 |

-continued

| Example | Structure | Name | (M + H) |
|---|---|---|---|
| 181 | 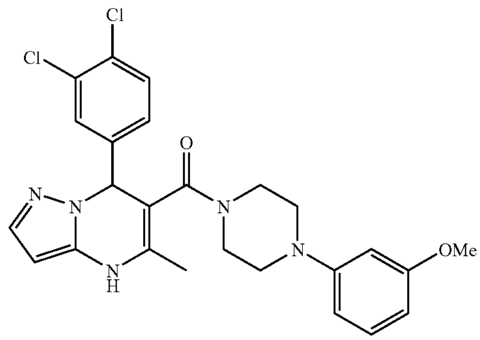 | 1-[[7-(3,4-Dichloro-phenyl)-4,7-dihydro-5-methylpyrazolo[1,5-a]-pyrimidin-6-yl]carbonyl]-4-(3-methoxyphenyl)piperazine | 498 |
| 182 | 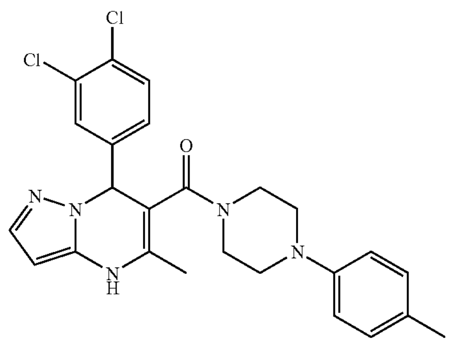 | 1-[[7-(3,4-Dichloro-phenyl)-4,7-dihydro-5-methylpyrazolo[1,5-a]-pyrimidin-6-yl]carbonyl]-4-(4-methylphenyl)piperazine | 482 |
| 183 | 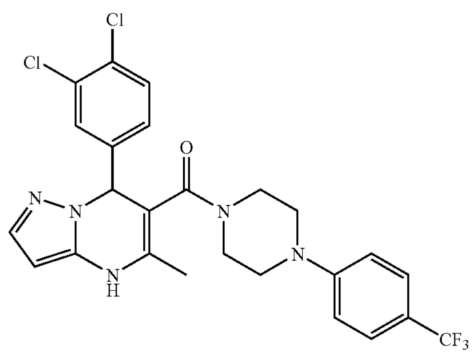 | 1-[[7-(3,4-Dichloro-phenyl)-4,7-dihydro-5-methylpyrazolo[1,5-a]-pyrimidin-6-yl]carbonyl]-4-[4-(trifluoromethyl)-phenyl]piperazine | 536 |
| 184 | 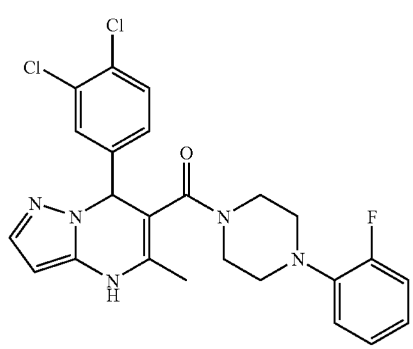 | 1-[[7-(3,4-Dichloro-phenyl)-4,7-dihydro-5-methylpyrazolo[1,5-a]-pyrimidin-6-yl]carbonyl]-4-(2-fluorophenyl)piperazine | 486 |

-continued

| Example | Structure | Name | (M + H) |
|---|---|---|---|
| 185 | 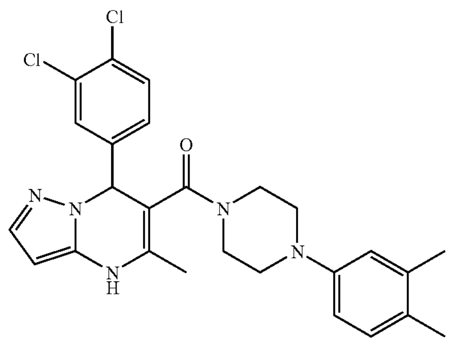 | 1-[[7-(3,4-Dichloro-phenyl)-4,7-dihydro-5-methylpyrazolo[1,5-a]pyrimidin-6-yl]carbonyl]-4-(3,4-dimethylphenyl)piperazine | 496 |
| 186 | 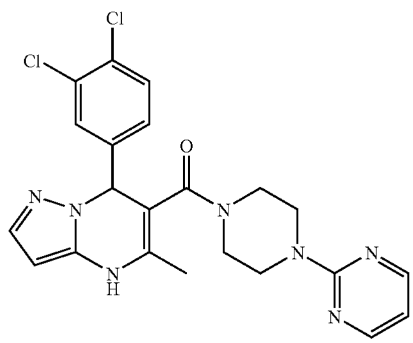 | 1-[[7-(3,4-Dichlorophenyl)-4,7-dihydro-5-methylpyrazolo[1,5-a]pyrimidin-6-yl]carbonyl]-4-(2-pyrimidinyl)piperazine | 470 |
| 187 | 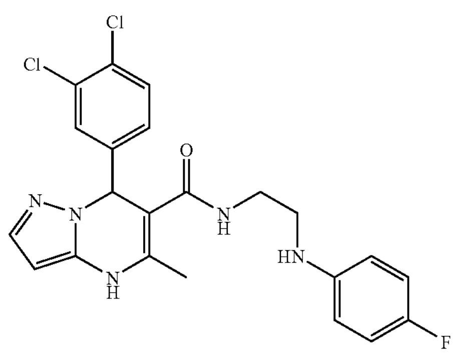 | 7-(3,4-Dichlorophenyl)-N-[2-[(4-fluoro-phenyl)amino]ethyl]-4,7-dihydro-5-methyl-pyrazolo[1,5-a]pyrimidine-6-carboxamide | 460 |
| 188 | 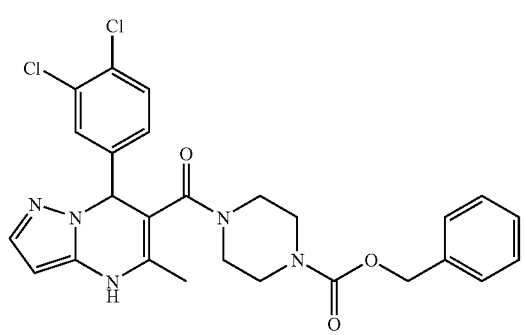 | 4-[[7-(3,4-Dichlorophenyl)-4,7-dihydro-5-methyl-pyrazolo[1,5-a]pyrimidin-6-yl]carbonyl]-1-piperazinecarboxylic acid phenylmethyl ester | 526 |

| Example | Structure | Name | (M + H) |
|---|---|---|---|
| 189 | 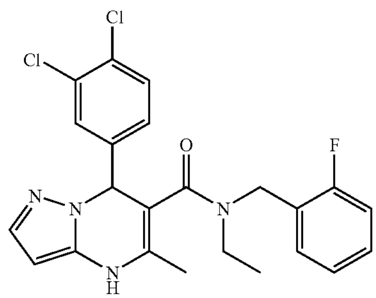 | 7-(3,4-Dichlorophenyl)-N-ethyl-N-[(2-fluorophenyl)methyl]-4,7-dihydro-5-methyl-pyrazolo[1,5-a]pyrimidine-6-carboxamide | 459 |
| 190 | 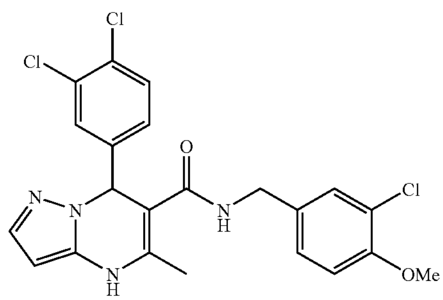 | N-[[(3-Chloro-4-methoxyphenyl)methyl]-7-(3,4-dichlorophenyl)-4,7-dihydro-5-methyl-pyrazolo[1,5-a]pyrimidine-6-carboxamide | 477 |
| 191 | 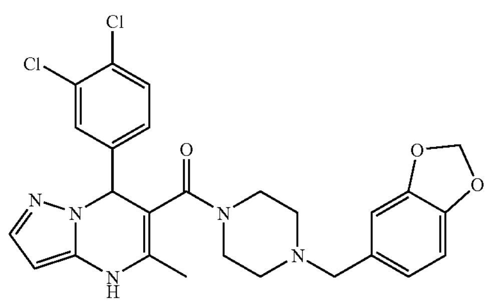 | 1-(1,3-Benzodioxol-5-ylmethyl)-4-[[7-(3,4-dichlorophenyl)-4,7-dihydro-5-methylpyrazolo[1,5-a]-pyrimidin-6-yl]carbonyl]-piperazine | 526 |
| 192 | 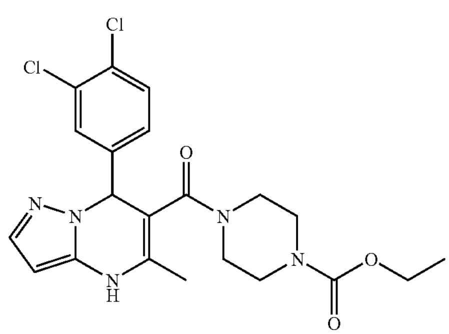 | 4-[[7-(3,4-Dichlorophenyl)-4,7-dihydro-5-methylpyrazolo[1,5-a]-pyrimidin-6-yl]carbonyl]-1-piperazinecarboxylic acid ethyl ester | 464 |
| 193 | 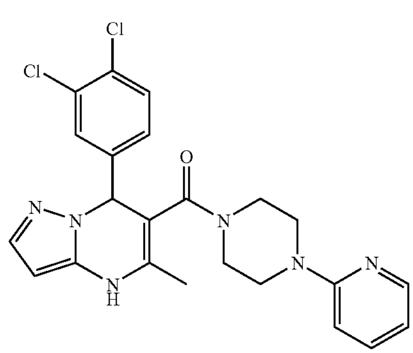 | 1-[[7-(3,4-Dichlorophenyl)-4,7-dihydro-5-methylpyrazolo[1,5-a]-pyrimidin-6-yl]carbonyl]-4-(2-pyridinyl)piperazine | 469 |

-continued

| Example | Structure | Name | (M + H) |
|---|---|---|---|
| 194 | 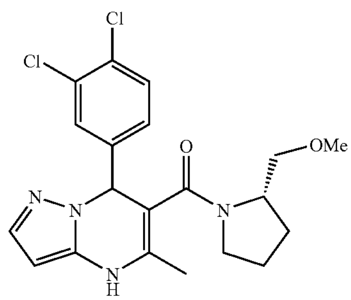 | (2S)-1-[[7-(3,4-Dichlorophenyl)-4,7-dihydro-5-methylpyrazolo[1,5-a]-pyrimidin-6-yl]carbonyl]-2-(methoxymethyl)pyrrolidine | 421 |
| 195 | 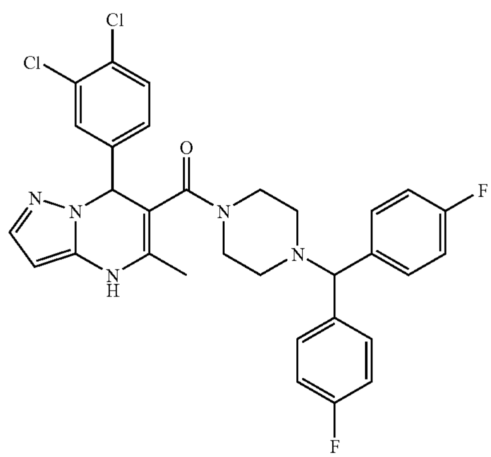 | 1-[Bis(4-fluorophenyl)-methyl]-4-[[7-(3,4-dichlorophenyl)-4,7-dihydro-5-methyl-pyrazolo[1,5-a]pyrimidin-6-yl]carbonyl]piperazine | 594 |
| 196 | 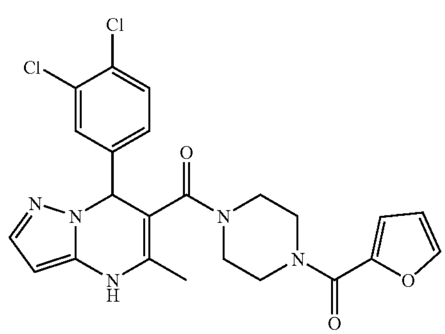 | 1-[[7-(3,4-Dichloro-phenyl)-4,7-dihydro-5-methyl-pyrazolo[1,5-a]-pyrimidin-6-yl]carbonyl]-4-(2-furanylcarbonyl)piperazine | 486 |
| 197 | 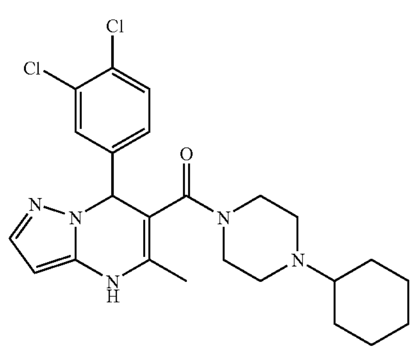 | 1-Cyclohexyl-4-[[7-(3,4-dichlorophenyl)-4,7-dihydro-5-methylpyrazolo[1,5-a]pyrimidin-6-yl]carbonyl]piperazine | 474 |

-continued

| Example | Structure | Name | (M + H) |
|---|---|---|---|
| 198 | 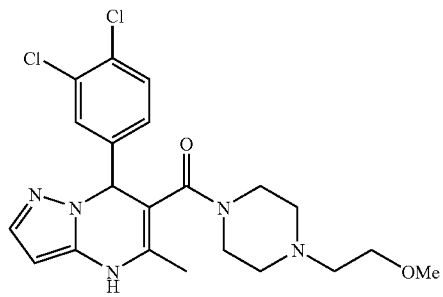 | 1-[[7-(3,4-Dichloro-phenyl)-4,7-dihydro-5-methylpyrazolo[1,5-a]pyrimidin-6-yl]carbonyl]-4-(2-methoxyethyl)piperazine | 450 |
| 199 | 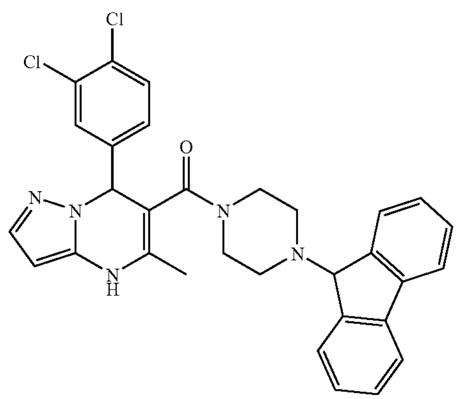 | 1-[[7-(3,4-Dichloro-phenyl)-4,7-dihydro-5-methylpyrazolo[1,5-a]pyrimidin-6-yl]carbonyl]-4-(9H-fluoren-9-yl)-piperazine | 556 |
| 200 | 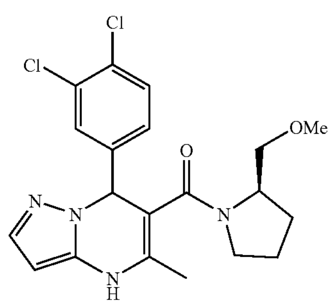 | (2R)-1-[[7-(3,4-Dichloro-phenyl)-4,7-dihydro-5-methyl-pyrazolo[1,5-a]pyrimidin-6-yl]carbonyl]-2-(methoxy-methyl)pyrrolidine | 421 |
| 201 | 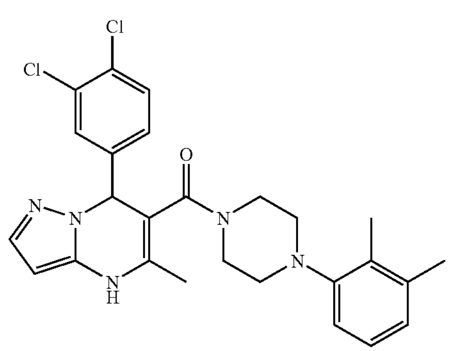 | 1-[[7-(3,4-Dichloro-phenyl)-4,7-dihydro-5-methylpyrazolo[1,5-a]pyrimidin-6-yl]carbonyl]-4-(2,3-dimethyl-phenyl)piperazine | 496 |

-continued

| Example | Structure | Name | (M + H) |
|---|---|---|---|
| 202 | 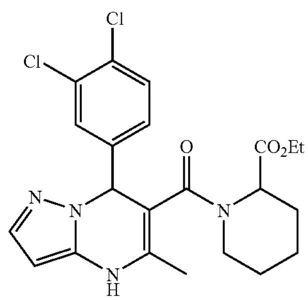 | 1-[[7-(3,4-Dichloro-phenyl)-4,7-dihydro-5-methylpyrazolo[1,5-a]pyrimidin-6-yl]carbonyl]-2-piperidine-carboxylic acid ethyl ester | 463 |
| 203 | 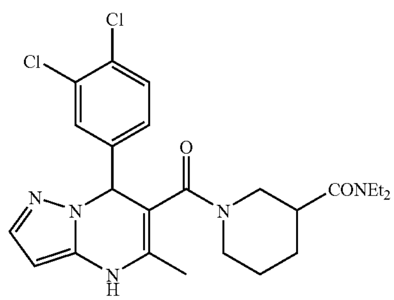 | 1-[[7-(3,4-Dichloro-phenyl)-4,7-dihydro-5-methylpyrazolo[1,5-a]pyrimidin-6-yl]carbonyl]-N,N-diethyl-3-piperidinecarboxamide | 490 |
| 204 | 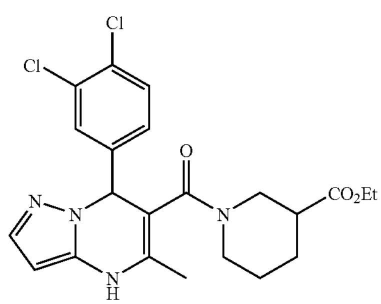 | 1-[[7-(3,4-Dichloro-phenyl)-4,7-dihydro-5-methylpyrazolo[1,5-a]pyrimidin-6-yl]carbonyl]-3-piperidine-carboxylic acid ethyl ester | 463 |
| 205 | 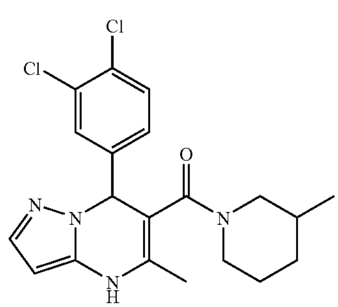 | 1-[[7-(3,4-Dichloro-phenyl)-4,7-dihydro-5-methylpyrazolo[1,5-a]pyrimidin-6-yl]carbonyl]-3-methyl-piperidine | 405 |
| 206 | 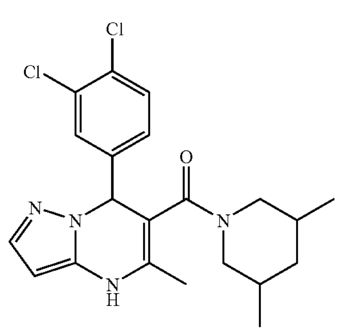 | 1-[[7-(3,4-Dichloro-phenyl)-4,7-dihydro-5-methylpyrazolo[1,5-a]pyrimidin-6-yl]carbonyl]-3,5-dimethyl-piperidine | 419 |

-continued

| Example | Structure | Name | (M + H) |
|---|---|---|---|
| 207 | 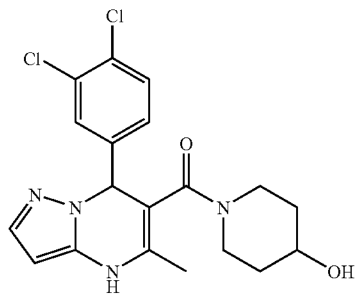 | 1-[[7-(3,4-Dichloro-phenyl)-4,7-dihydro-5-methylpyrazolo[1,5-a]pyrimidin-6-yl]carbonyl]-4-hydroxy-piperidine | 407 |
| 208 | 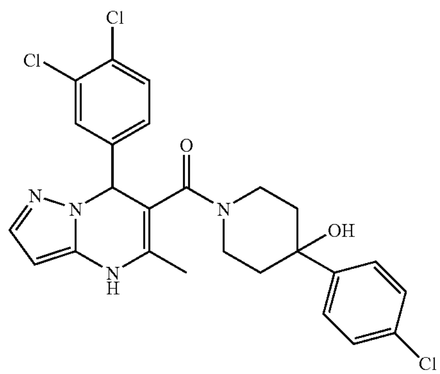 | 4-(4-Chlorophenyl)-1-[[7-(3,4-dichlorophenyl)-4,7-dihydro-5-methyl-pyrazolo[1,5-a]pyrimidin-6-yl]-carbonyl]-4-hydroxypiperidine | 517 |
| 209 | 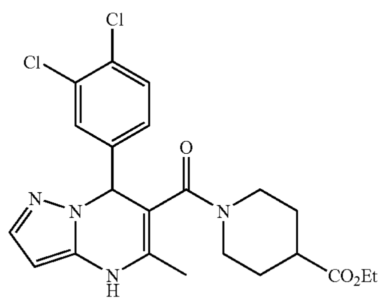 | 1-[[7-(3,4-Dichloro-phenyl)-4,7-dihydro-5-methylpyrazolo[1,5-a]pyrimidin-6-yl]-carbonyl]-4-piperidine-carboxylic acid ethyl ester | 463 |
| 210 | 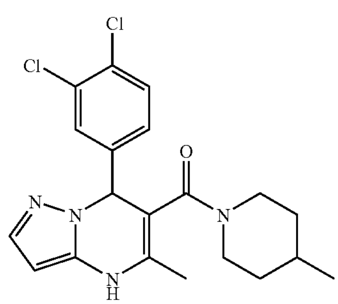 | 1-[[7-(3,4-Dichloro-phenyl)-4,7-dihydro-5-methylpyrazolo[1,5-a]pyrimidin-6-yl]carbonyl]-4-methylpiperidine | 405 |
| 211 | 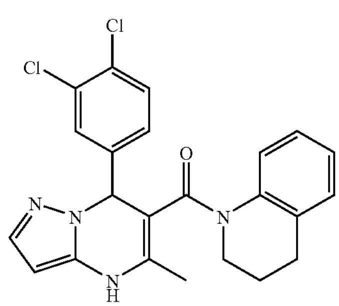 | 1-[[7-(3,4-Dichloro-phenyl)-4,7-dihydro-5-methylpyrazolo[1,5-a]pyrimidin-6-yl]carbonyl]-1,2,3,4-tetrahydroquinoline | 439 |

-continued

| Example | Structure | Name | (M + H) |
|---|---|---|---|
| 212 | 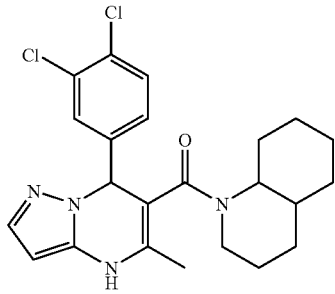 | 1-[[7-(3,4-Dichloro-phenyl)-4,7-dihydro-5-methylpyrazolo[1,5-a]pyrimidin-6-yl]carbonyl]-decahydroquinoline | 445 |
| 213 | 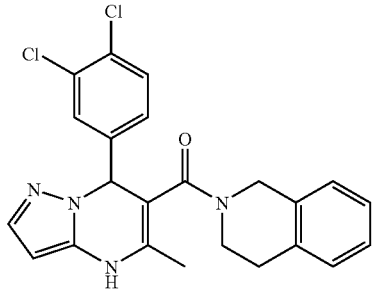 | 2-[[7-(3,4-Dichloro-phenyl)-4,7-dihydro-5-methylpyrazolo[1,5-a]pyrimidin-6-yl]carbonyl]-1,2,3,4-tetrahydroisoquinoline | 439 |
| 214 | 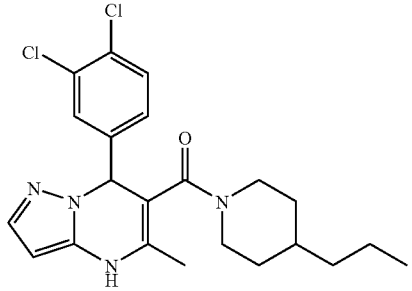 | 1-[[7-(3,4-Dichloro-phenyl)-4,7-dihydro-5-methylpyrazolo[1,5-a]pyrimidin-6-yl]carbonyl]-4-propylpiperidine | 433 |
| 215 | 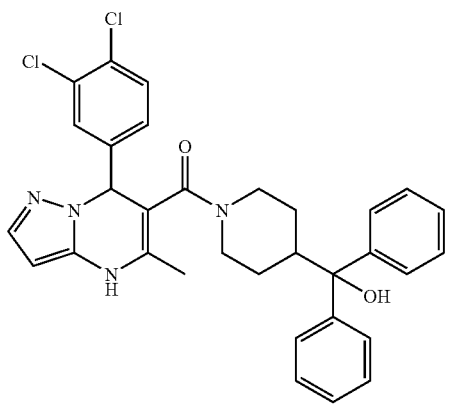 | 1-[[7-(3,4-Dichloro-phenyl)-4,7-dihydro-5-methylpyrazolo[1,5-a]pyrimidin-6-yl]carbonyl]-4-(hydroxydiphenylmethyl)piperidine | 573 |

-continued

| Example | Structure | Name | (M + H) |
|---|---|---|---|
| 216 | 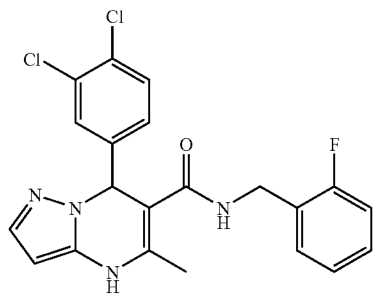 | 7-(3,4-Dichlorophenyl)-N-[(2-fluorophenyl)methyl]-4,7-dihydro-5-methyl-pyrazolo[1,5-a]-pyrimidine-6-carboxamide | 431 |
| 217 | 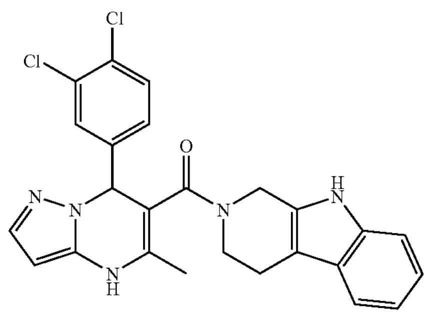 | 2-[[7-(3,4-Dichlorophenyl)-4,7-dihydro-5-methylpyrazolo-[1,5-a]pyrimidin-6-yl]-carbonyl]-2,3,4,9-tetrahydro-1H-pyrido[3,4-b]indole | 478 |
| 218 | 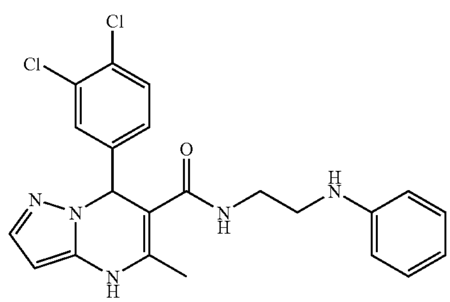 | 7-(3,4-Dichlorophenyl)-4,7-dihydro-5-methyl-N-[2-(phenylamino)-ethyl]-pyrazolo[1,5-a]pyrimidine-6-carboxamide | 442 |
| 219 | 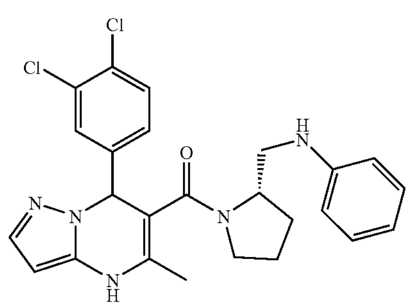 | (2S)-1-[[7-(3,4-Dichlorophenyl)-4,7-dihydro-5-methylpyrazolo-[1,5-a]-pyrimidin-6-yl]carbonyl]-2-[(phenylamino)methyl]-pyrrolidine | 482 |
| 220 | 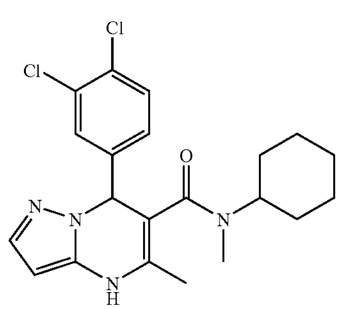 | N-Cyclohexyl-7-(3,4-dichlorophenyl)-4,7-dihydro-N,5-dimethyl-pyrazolo[1,5-a]pyrimidine-6-carboxamide | 419 |

-continued

| Example | Structure | Name | (M + H) |
|---|---|---|---|
| 221 | 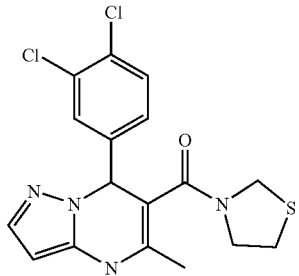 | 3-[[7-(3,4-Dichloro-phenyl)-4,7-dihydro-5-methylpyrazolo[1,5-a]pyrimidin-6-yl]carbonyl]thiazole | 395 |
| 222 | 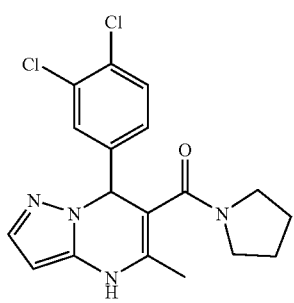 | 1-[[7-(3,4-Dichloro-phenyl)-4,7-dihydro-5-methylpyrazolo[1,5-a]pyrimidin-6-yl]carbonyl]pyrrolidine | 377 |
| 223 | 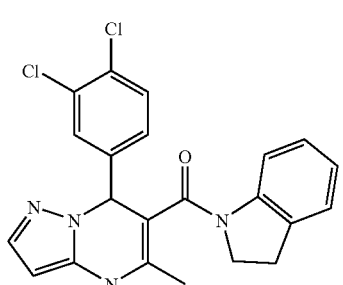 | 1-[[7-(3,4-Dichloro-phenyl)-4,7-dihydro-5-methylpyrazolo[1,5-a]pyrimidin-6-yl]carbonyl]-3,4-dihydo-1H-indole | 425 |
| 224 | 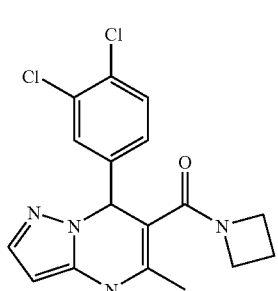 | 1-[[7-(3,4-Dichloro-phenyl)-4,7-dihydro-5-methylpyrazolo[1,5-a]pyrimidin-6-yl]carbonyl]azetidine | 363 |
| 225 | 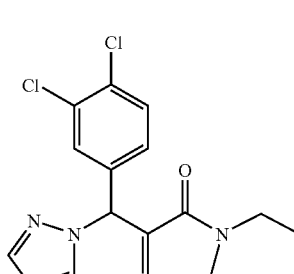 | 1-[[7-(3,4-Dichloro-phenyl)-4,7-dihydro-5-methylpyrazolo[1,5-a]pyrimidin-6-yl]carbonyl]hexahydro-1H-azepine | 405 |

-continued

| Example | Structure | Name | (M + H) |
|---|---|---|---|
| 226 | 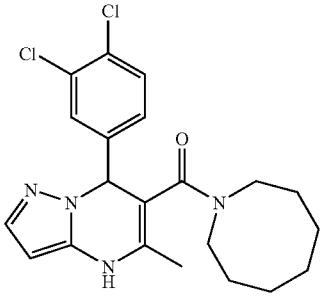 | 1-[[7-(3,4-Dichloro-phenyl)-4,7-dihydro-5-methylpyrazolo[1,5-a]pyrimidin-6-yl]carbonyl]octahydroazocine | 419 |
| 227 | 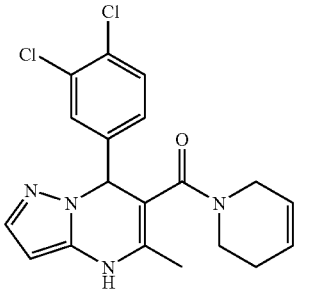 | 1-[[7-(3,4-Dichloro-phenyl)-4,7-dihydro-5-methylpyrazolo[1,5-a]pyrimidin-6-yl]carbonyl]-1,2,3,6-tetrahydropyridine | 389 |
| 228 | 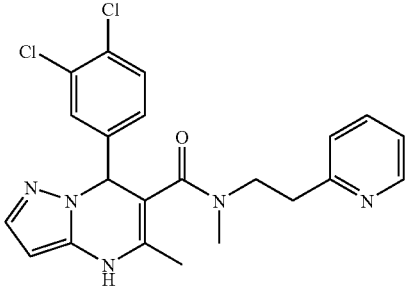 | 7-(3,4-Dichlorophenyl)-4,7dihydro-N,5-dimethyl-N-[2-(2-pyridinyl)-ethyl]pyrazolo[1,5-a]pyrimidine-6-carboxamide | 442 |
| 229 | 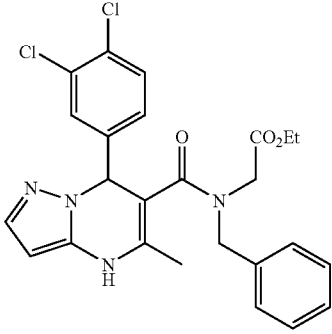 | N-[[7-(3,4-Dichloro-phenyl)-4,7-dihydro-5-methylpyrazolo[1,5-a]pyrimidin-6-yl]carbonyl]-N-(phenylmethyl)glycine ethyl ester | 499 |
| 230 | 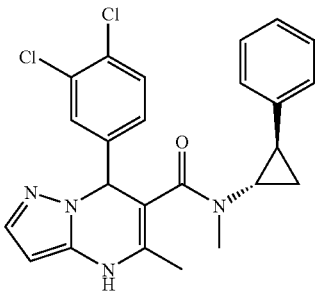 | trans-7-(3,4-Dichlorophenyl)-4,7-dihydro-5-methyl-N-(2-phenylcyclopropyl)-pyrazolo[1,5-a]pyrimidine-6-carboxamide | 439 |

-continued

| Example | Structure | Name | (M + H) |
|---|---|---|---|
| 231 | 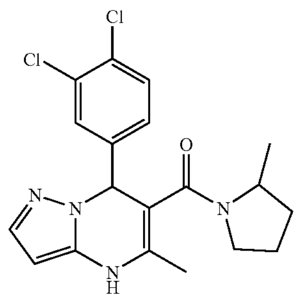 | 1-[[7-(3,4-Dichloro-phenyl)-4,7-dihydro-5-methylpyrazolo[1,5-a]pyrimidin-6-yl]carbonyl]-2-methylpyrrolidine | 391 |
| 232 | 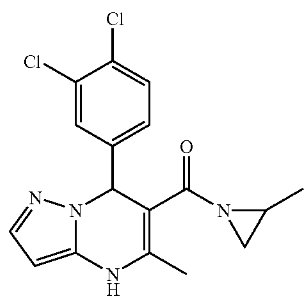 | 1-[[7-(3,4-Dichlorophenyl)-4,7-dihydro-5-methylpyrazolo[1,5-a]-pyrimidin-6-yl]carbonyl]-2-methylaziridine | 363 |
| 233 | 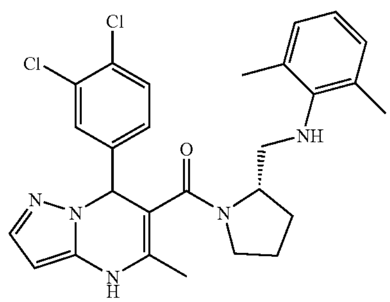 | (2S)-1-[[7-(3,4-Dichlorophenyl)-4,7-dihydro-5-methylpyrazolo[1,5-a]pyrimidin-6-yl]carbonyl]-2-[[(2,6-dimethylphenyl)amino]-methyl]pyrrolidine | 510 |
| 234 | 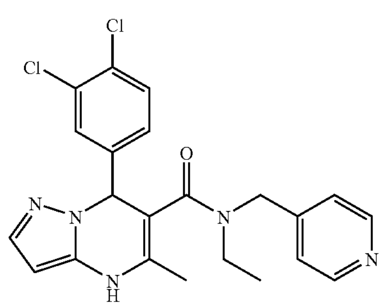 | 7-(3,4-Dichlorophenyl)-N-ethyl-4,7-dihydro-5-methyl-N-(4-pyridinylmethyl)pyrazolo[1,5-a]-pyrimidine-6-carboxamide | 442 |
| 235 | 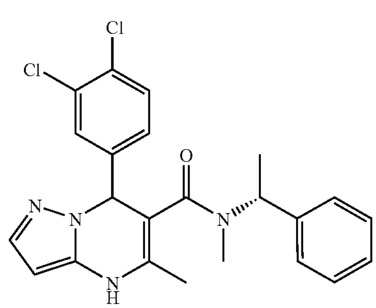 | 7-(3,4-Dichlorophenyl)-4,7-dihydro-N,5-dimethyl-N-[(1R)-1-phenylethyl]pyrazolo-[1,5-a]pyrimidine-6-carboxamide | 441 |

-continued

| Example | Structure | Name | (M + H) |
|---|---|---|---|
| 236 | 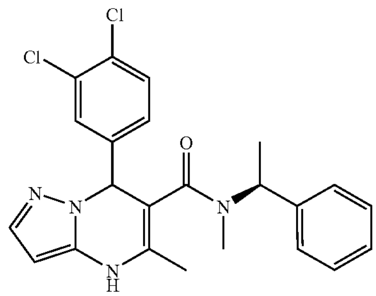 | 7-(3,4-Dichlorophenyl)-4,7-dihydro-N,5-dimethyl-N-[(1S)-1-phenylethyl]pyrazolo-[1,5-a]pyrimidine-6-carboxamide | 441 |
| 237 | 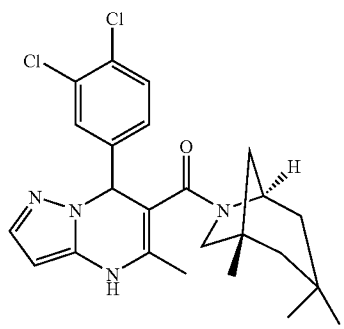 | 6-[[7-(3,4-Dichlorophenyl)-4,7-dihydro-5-methylpyrazolo[1,5-a]-pyrimidin-6-yl]carbonyl]-1,3,3-trimethyl-6-azabicyclo[3.2.1]-octane | 459 |
| 238 | 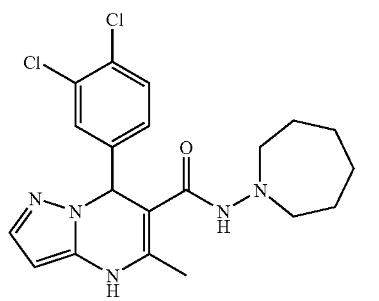 | 7-(3,4-Dichlorophenyl)-N-(hexahydro-1H-azepin-1-yl)-4,7-dihydro-5-methylpyrazolo[1,5-a]-pyrimidine-6-carboxamide | 420 |
| 239 | 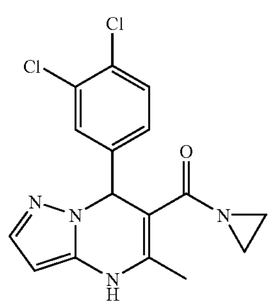 | 1-[[7-(3,4-Dichlorophenyl)-4,7-dihydro-5-methylpyrazolo[1,5-a]-pyrimidin-6-yl]carbonyl]aziridine | 349 |
| 240 | 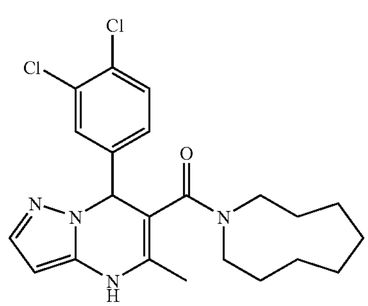 | 1-[[7-(3,4-Dichlorophenyl)-4,7-dihydro-5-methylpyrazolo[1,5-a]-pyrimidin-6-yl]carbonyl]-octahydro-1H-azonine | 433 |

-continued

| Example | Structure | Name | (M + H) |
|---|---|---|---|
| 241 | 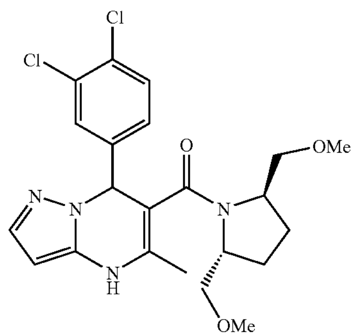 | (2R-trans)-1-[[7-(3,4-Dichlorophenyl)-4,7-dihydro-5-methyl-pyrazolo[1,5-a]-pyrimidin-6-yl]carbonyl]-2,5-bis(methoxymethyl)pyrrolidine | 465 |
| 242 | 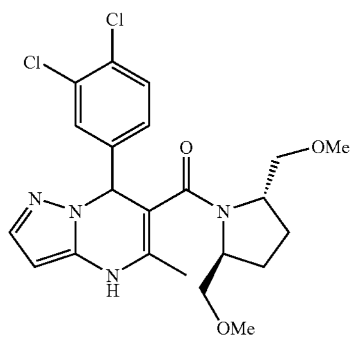 | (2S-trans)-1-[[7-(3,4-Dichlorophenyl)-4,7-dihydro-5-methylpyrazolo[1,5-a]pyrimidin-6-yl]carbonyl]-2,5-bis-(methoxymethyl)pyrrolidine | 465 |
| 243 | 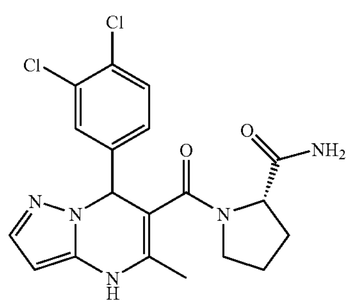 | 1-[[7-(3,4-Dichlorophenyl)-4,7-dihydro-5-methylpyrazolo[1,5-a]pyrimidin-6-yl]carbonyl]-L-prolinamide | 420 |
| 244 | 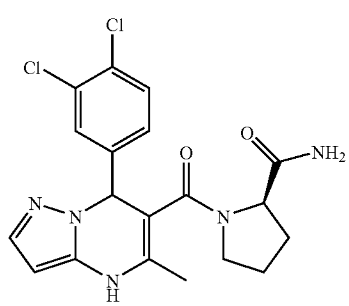 | 1-[[7-(3,4-Dichlorophenyl)-4,7-dihydro-5-methylpyrazolo[1,5-a]pyrimidin-6-yl]carbonyl]-D-prolinamide | 420 |
| 245 | 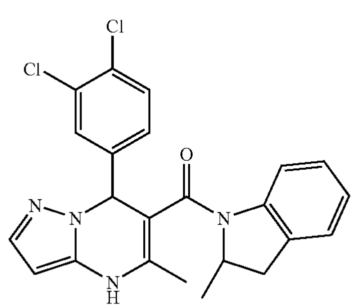 | 1-[[7-(3,4-Dichlorophenyl)-4,7-dihydro-5-methylpyrazolo[1,5-a]pyrimidin-6-yl]carbonyl]-2,3-dihydro-2-methyl-1H-indole | 439 |

-continued

| Example | Structure | Name | (M + H) |
|---|---|---|---|
| 246 | 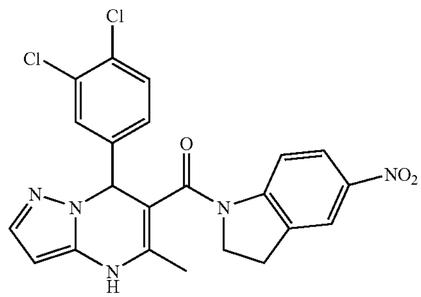 | 1-[[7-(3,4-Dichlorophenyl)-4,7-dihydro-5-methylpyrazolo[1,5-a]pyrimidin-6-yl]carbonyl]-2,3-dihydro-5-nitro-1H-indole | 470 |
| 247 | 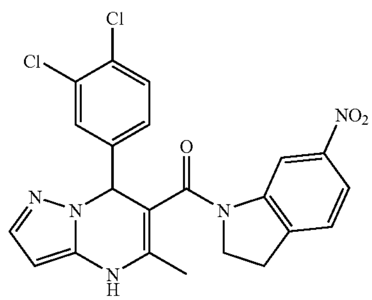 | 1-[[7-(3,4-Dichlorophenyl)-4,7-dihydro-5-methylpyrazolo[1,5-a]-pyrimidin-6-yl]carbonyl]-2,3-dihydro-6-nitro-1H-indole | 470 |
| 248 | 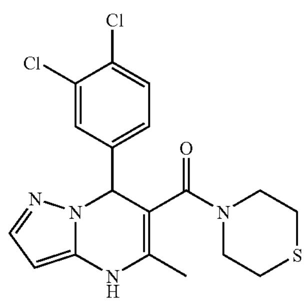 | 4-[[7-(3,4-Dichlorophenyl)-4,7-dihydro-5-methyl-pyrazolo[1,5-a]-pyrimidin-6-yl]carbonyl]-thiomorpholine | 409 |
| 249 | 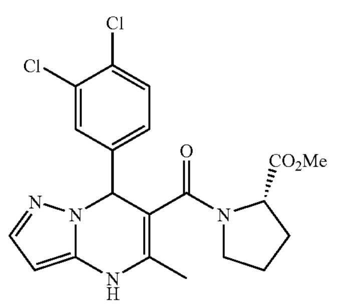 | 1-[[7-(3,4-Dichlorophenyl)-4,7-dihydro-5-methylpyrazolo[1,5-a]pyrimidin-6-yl]carbonyl]-L-proline methyl ester | 435 |
| 250 | 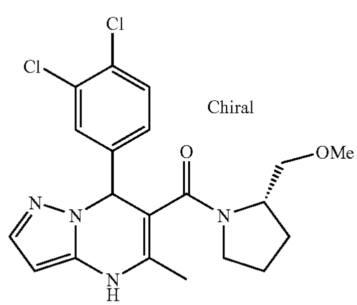 | (2S)-1-[[7-(3,4-Dichlorophenyl)-4,7-dihydro-5-methyl-pyrazolo[1,5-a]pyrimidin-6-yl]carbonyl]-2-(methoxymethyl)pyrrolidine, enantiomer A | 421 |

-continued

| Example | Structure | Name | (M + H) |
|---|---|---|---|
| 251 | 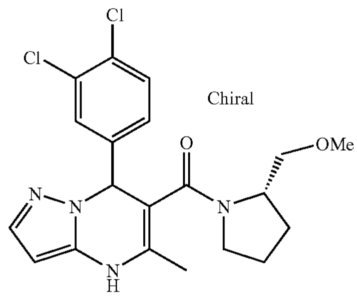 | (2S)-1-[[7-(3,4-Dichlorophenyl)-4,7-dihydro-5-methyl-pyrazolo[1,5-a]pyrimidin-6-yl]carbonyl]-2-(methoxymethyl)-pyrrolidine, enantiomer B | 421 |
| 252 | 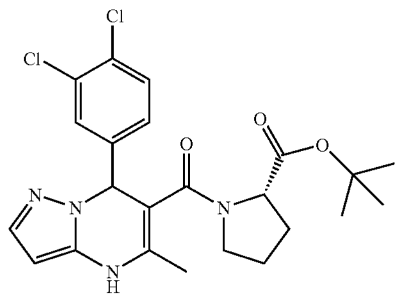 | 1-[[7-(3,4-Dichlorophenyl)-4,7-dihydro-5-methylpyrazolo[1,5-a]-pyrimidin-6-yl]carbonyl]-L-proline-1,1-dimethylethyl ester | 477 |
| 253 | 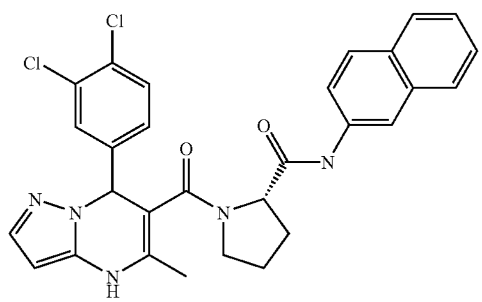 | 1-[[7-(3,4-Dichlorophenyl)-4,7-dihydro-5-methylpyrazolo[1,5-a]pyrimidin-6-yl]carbonyl]-N-(2-naphthalenyl)-L-prolinamide | 560 |
| 254 | 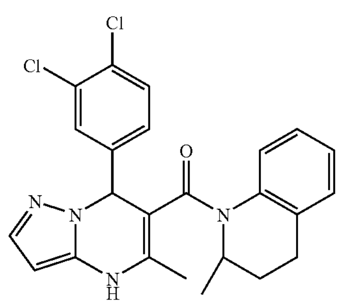 | 1-[[7-(3,4-Dichlorophenyl)-4,7-dihydro-5-methylpyrazolo[1,5-a]pyrimidin-6-yl]carbonyl]-1,2,3,4-tetrahydro-2-methylquinoline | 453 |
| 255 | 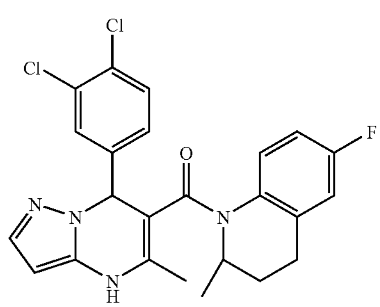 | 1-[[7-(3,4-Dichlorophenyl)-4,7-dihydro-5-methylpyrazolo[1,5-a]pyrimidin-6-yl]carbonyl]-6-fluoro-1,2,3,4-tetrahydro-2-methylquinoline | 471 |

-continued

| Example | Structure | Name | (M + H) |
|---|---|---|---|
| 256 | 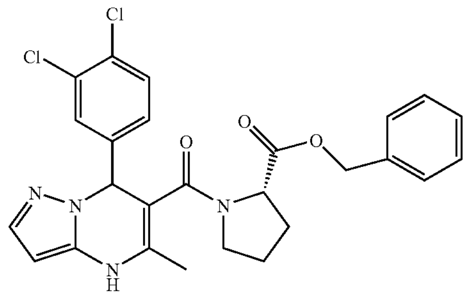 | 1-[[7-(3,4-Dichlorophenyl)-4,7-dihydro-5-methylpyrazolo[1,5-a]pyrimidin-6-yl]carbonyl]-L-proline phenylmethyl ester | 511 |
| 257 | 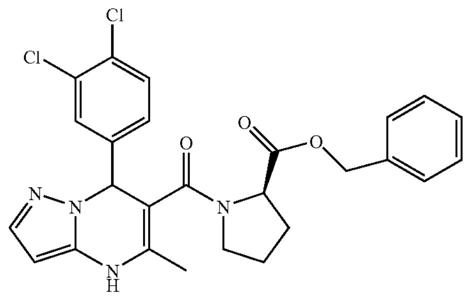 | 1-[[7-(3,4-Dichlorophenyl)-4,7-dihydro-5-methylpyrazolo[1,5-a]pyrimidin-6-yl]carbonyl]-D-proline phenylmethyl ester | 511 |
| 258 | 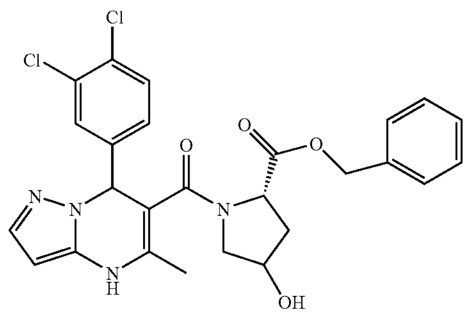 | 1-[[7-(3,4-Dichlorophenyl)-4,7-dihydro-5-methylpyrazolo[1,5-a]pyrimidin-6-yl]carbonyl]-4-hydroxy-L-proline phenylmethyl ester | 527 |
| 259 | 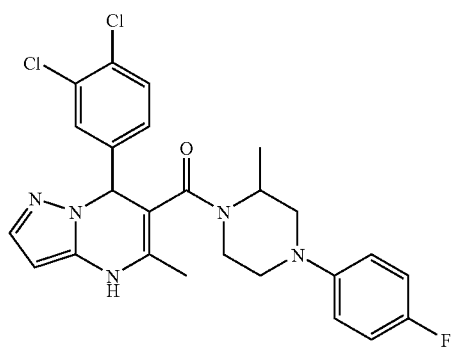 | 1-[[7-(3,4-Dichlorophenyl)-4,7-dihydro-5-methylpyrazolo[1,5-a]pyrimidin-6-yl]carbonyl]-4-(4-fluorophenyl)-2-methylpiperazine | 500 |
| 260 | 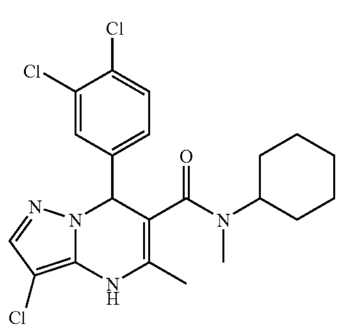 | 3-Chloro-N-cyclohexyl-7-(3,4-dichlorophenyl)-4,7-dihydro-N,5-dimethylpyrazolo[1,5-a]-pyrimidine-6-carboxamide | 453 |

-continued

| Example | Structure | Name | (M + H) |
|---|---|---|---|
| 261 | 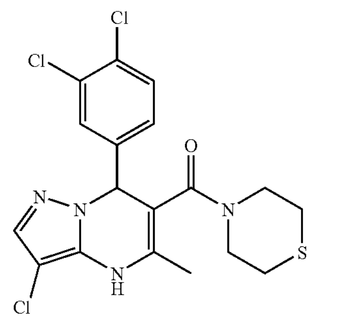 | 4-[[3-Chloro-7-(3,4-dichlorophenyl)-4,7-dihydro-5-methylpyrazolo[1,5-a]pyrimidin-6-yl]carbonyl]thiomorpholine | 443 |
| 262 | 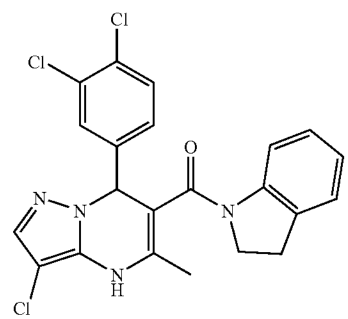 | 1-[[3-Chloro-7-(3,4-dichlorophenyl)-4,7-dihydro-5-methyl-pyrazolo[1,5-a]pyrimidin-6-yl]carbonyl]-2,3-dihydro-1H-indole | 459 |
| 263 | 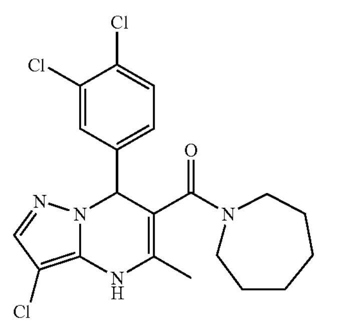 | 1-[[3-Chloro-7-(3,4-dichlorophenyl)-4,7-dihydro-5-methyl-pyrazolo[1,5-a]pyrimidin-6-yl]carbonyl]hexahydro-1H-azepine | 439 |
| 264 | 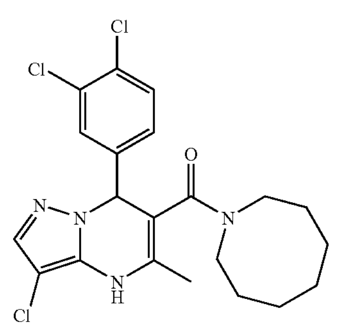 | 1-[[3-Chloro-7-(3,4-dichlorophenyl)-4,7-dihydro-5-methylpyrazolo[1,5-a]pyrimidin-6-yl]carbonyl]octahydroazocine | 453 |

-continued

| Example | Structure | Name | (M + H) |
|---|---|---|---|
| 265 | 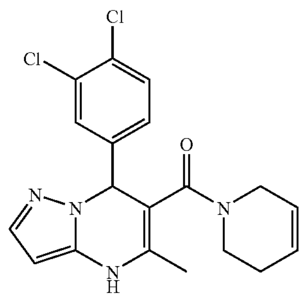 | 1-[[3-Chloro-7-(3,4-dichlorophenyl)-4,7-dihydro-5-methylpyrazolo[1,5-a]pyrimidin-6-yl]carbonyl]-1,2,3,6-tetrahydropyridine | 423 |
| 266 | 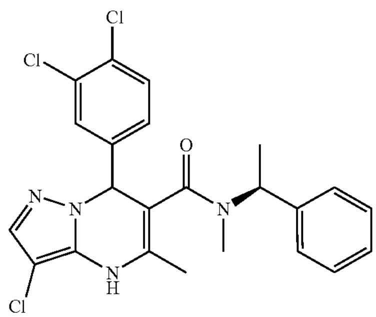 | 3-Chloro-7-(3,4-dichlorophenyl)-4,7-dihydro-N,5-dimethyl-N-[(1S)-1-phenylethyl]-pyrazolo[1,5-a]pyrimidine-6-carboxamide | 475 |
| 267 | 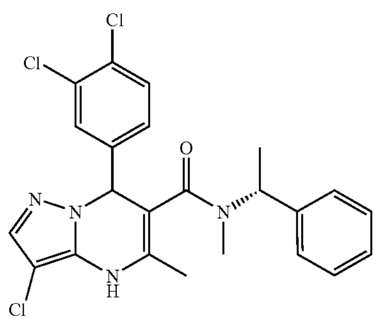 | 3-Chloro-7-(3,4-dichlorophenyl)-4,7-dihydro-N,5-dimethyl-N-[(1R)-1-phenylethyl]-pyrazolo[1,5-a]pyrimidine-6-carboxamide | 475 |
| 268 | 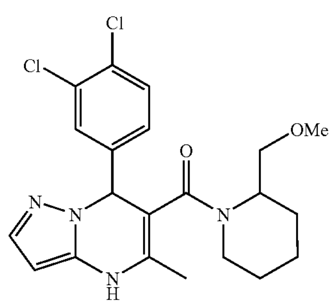 | 1-[[7-(3,4-Dichlorophenyl)-4,7-dihydro-5-methyl-pyrazolo[1,5-a]pyrimidin-6-yl]carbonyl]-2-(methoxymethyl)piperidine | 435 |
| 269 | 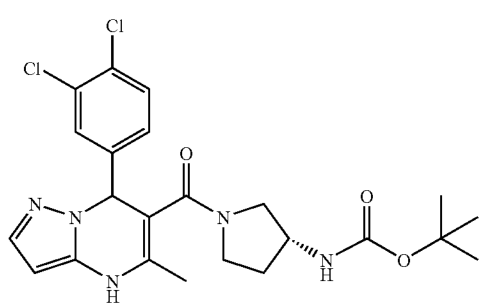 | [(3R)-1-[[7-(3,4-Dichlorophenyl)-4,7-dihydro-5-methylpyrazolo[1,5-a]pyrimidin-6-yl]carbonyl-3-pyrrolidinyl]carbamic acid 1,1-dimethylethyl ester | 492 |

-continued

| Example | Structure | Name | (M + H) |
|---|---|---|---|
| 270 | 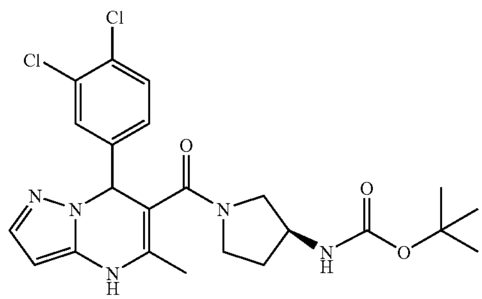 | [(3S)-1-[[7-(3,4-Dichlorophenyl)-4,7-dihydro-5-methylpyrazolo[1,5-a]pyrimidin-6-yl]carbonyl]-3-pyrrolidinyl]-carbamic acid 1,1-dimethylethyl ester | 492 |
| 271 | 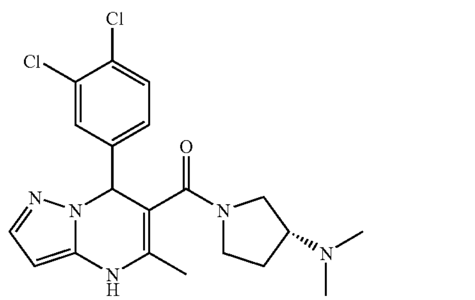 | (3R)-1-[[7-(3,4-Dichlorophenyl)-4,7-dihydro-5-methyl-pyrazolo[1,5-a]pyrimidin-6-yl]carbonyl]-3-(dimethylamino)pyrrolidine | 420 |
| 272 | 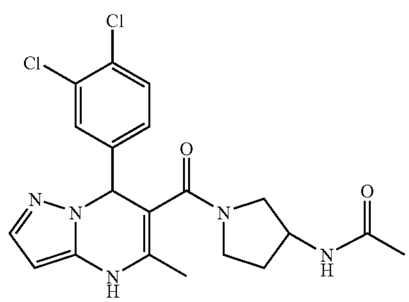 | N-[1-[[7-(3,4-Dichlorophenyl)-4,7-dihydro-5-methyl-pyrazolo[1,5-a]pyrimidin-6-yl]carbonyl]-3-pyrrolidinyl]acetamide | 434 |
| 273 | 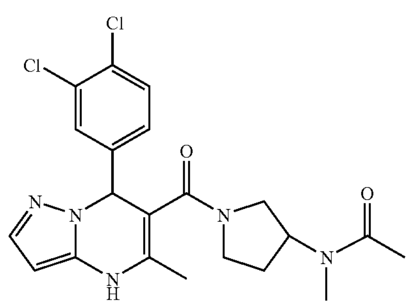 | N-[1-[[7-(3,4-Dichlorophenyl)-4,7-dihydro-5-methylpyrazolo[1,5-a]pyrimidin-6-yl]carbonyl]-3-pyrrolidinyl]-N-methylacetamide | 448 |
| 274 | 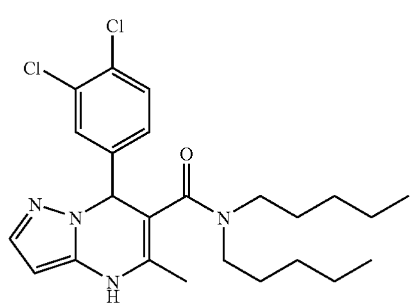 | 7-(3,4-Dichlorophenyl)-4,7-dihydro-5-methyl-N,N-dipentyl-pyrazolo[1,5-a]-pyrimidine-6-carboxamide | 463 |

-continued

| Example | Name | (M + H) |
|---|---|---|
| 275 | 7-(3,4-Dichlorophenyl)-N,N-dihexyl-4,7-dihydro-5-methylpyrazolo[1,5-a]-pyrimidine-6-carboxamide | 491 |
| 276 | 1-[[3-Chloro-7-(3,4-dichlorophenyl)-4,7-dihydro-5-methylpyrazolo[1,5-a]pyrimidin-6-yl]carbonyl]piperidine | 425 |
| 277 | 3-Chloro-7-(3-chlorophenyl)-N-cyclohexyl-4,7-dihydro-N,5-dimethyl-pyrazolo[1,5-a]pyrimidine-6-carboxamide | 419 |
| 278 | (2S)-1-[[3-Chloro-7-(3,4-dichlorophenyl)-4,7-dihydro-5-methyl-pyrazolo[1,5-a]pyrimidin-6-yl]carbonyl]-2-(methoxymethyl)pyrrolidine | 455 |
| 279 | 1-[[3-Chloro-7-(3,4-dichlorophenyl)-4,7-dihydro-5-methylpyrazolo[1,5-a]pyrimidin-6-yl]carbonyl]decahydroquinoline | 479 |

-continued

| Example | Structure | Name | (M + H) |
|---|---|---|---|
| 280 | 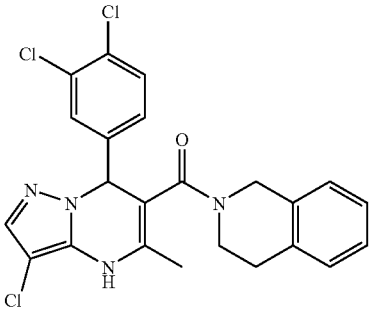 | 2-[[3-Chloro-7-(3,4-dichlorophenyl)-4,7-dihydro-5-methyl-pyrazolo[1,5-a]pyrimidin-6-yl]carbonyl]-1,2,3,4-tetrahydroisoquinoline | 473 |
| 281 | 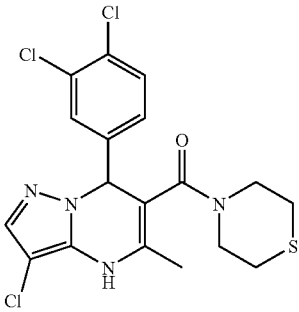 | 4-[[3-Chloro-7-(3-chlorophenyl)-4,7-dihydro-5-methyl-pyrazolo[1,5-a]pyrimidin-6-yl]carbonyl]thiomorpholine | 409 |
| 282 | 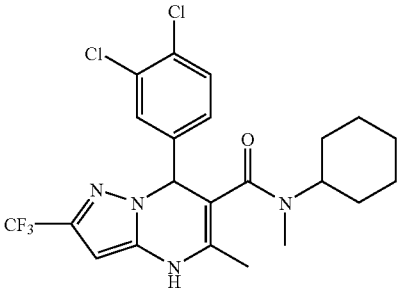 | N-Cyclohexyl-7-(3,4-dichlorophenyl)-4,7-dihydro-N,5-dimethyl-2-(trifluoromethyl)-pyrazolo[1,5-a]pyrimidine-6-carboxamide | 487 |
| 283 | 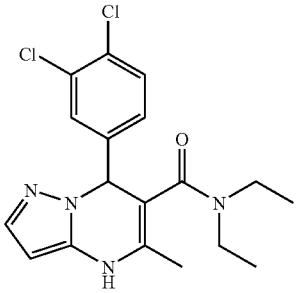 | 7-(3,4-Dichlorophenyl)-N,N-diethyl-4,7-dihydro-5-methylpyrazolo[1,5-a]pyrimidine-6-carboxamide | 379 |
| 284 | 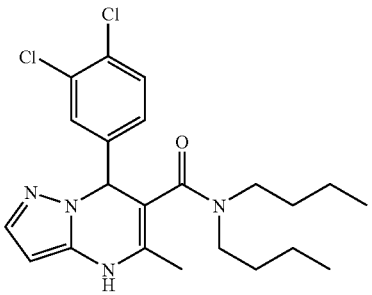 | N,N-Dibutyl-7-(3,4-dichlorophenyl)-4,7-dihydro-5-methylpyrazolo[1,5-a]pyrimidine-6-carboxamide | 435 |

-continued

| Example | Structure | Name | (M + H) |
|---|---|---|---|
| 285 | 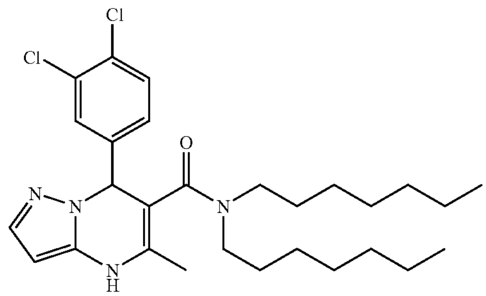 | 7-(3,4-Dichlorophenyl)-N,N-diheptyl-4,7-dihydro-5-methyl-pyrazolo[1,5-a]pyrimidine-6-carboxamide | 519 |
| 286 | 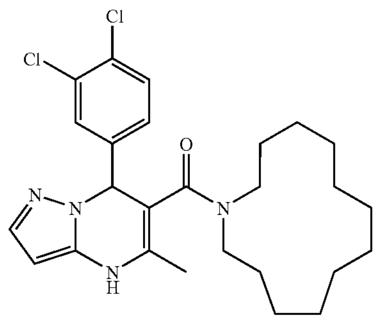 | 1-[[7-(3,4-Dichlorophenyl)-4,7-dihydro-5-methyl-pyrazolo[1,5-a]pyrimidin-6-yl]carbonyl]-azacyclotridecane | 489 |
| 287 | 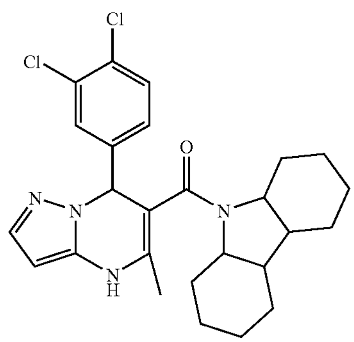 | 9-[[7-(3,4-Dichlorophenyl)-4,7-dihydro-5-methylpyrazolo[1,5-a]-pyrimidin-6-yl]carbonyl]-dodecahydro-1H-fluorene | 485 |
| 288 | 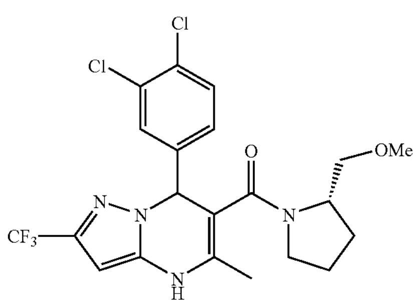 | (2S)-1-[[7-(3,4-Dichlorophenyl)-4,7-dihydro-5-methyl-2-(trifluoromethyl)pyrazolo[1,5-a]pyrimidin-6-yl]carbonyl]-2-(methoxy-methyl)pyrrolidine | 489 |
| 289 | 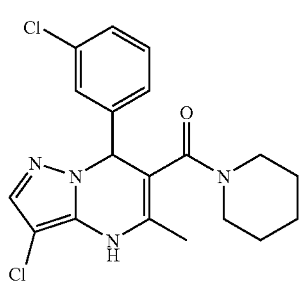 | 1-[[3-Chloro-7-(3-chlorophenyl)-4,7-dihydro-5-methylpyrazolo[1,5-a]pyrimidin-6-yl]carbonyl]piperidine | 391 |

-continued

| Example | Structure | Name | (M + H) |
|---|---|---|---|
| 290 | 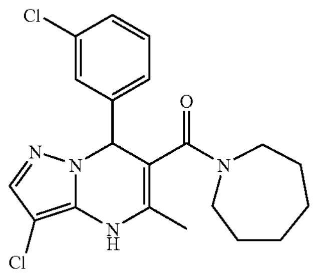 | 1-[[3-Chloro-7-(3-chlorophenyl)-4,7-dihydro-5-methylpyrazolo[1,5-a]pyrimidin-6-yl]carbonyl]hexahydro-1H-azepine | 405 |
| 291 | 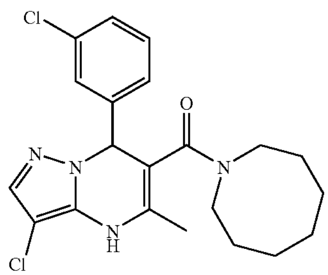 | 1-[[3-Chloro-7-(3-chlorophenyl)-4,7-dihydro-5-methylpyrazolo[1,5-a]pyrimidin-6-yl]carbonyl]octahydroazocine | 419 |
| 292 | 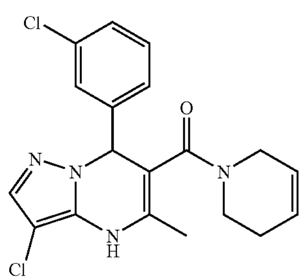 | 1-[[3-Chloro-7-(3-chlorophenyl)-4,7-dihydro-5-methylpyrazolo[1,5-a]pyrimidin-6-yl]carbonyl]-1,2,3,6-tetrahydropyridine | 389 |
| 293 | 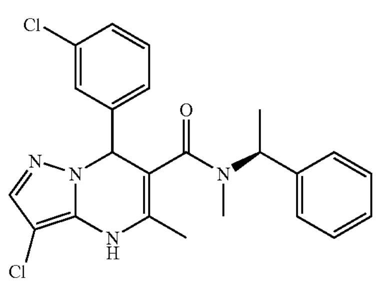 | 3-Chloro-7-(3-chlorophenyl)-4,7-dihydro-N,5-dimethyl-N-[(1S)-1-phenyl-ethyl]pyrazolo[1,5-a]pyrimidine-6-carboxamide | 441 |
| 294 | 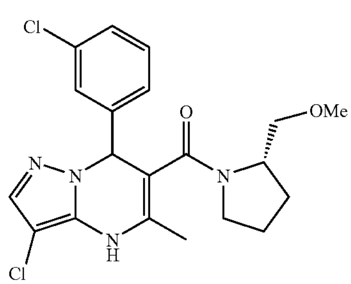 | (2S)-1-[[3-Chloro-7-(3-chlorophenyl)-4,7-dihydro-5-methylpyrazolo[1,5-a]pyrimidin-6-yl]carbonyl]-2-(methoxymethyl)pyrrolidine | 421 |

| Example | Structure | Name | (M + H) |
|---|---|---|---|
| 295 | 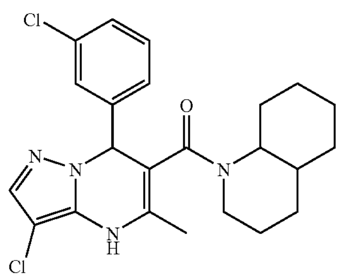 | 1-[[3-Chloro-7-(3-chlorophenyl)-4,7-dihydro-5-methylpyrazolo[1,5-a]pyrimidin-6-yl]carbonyl]decahydroquinoline | 445 |
| 296 | 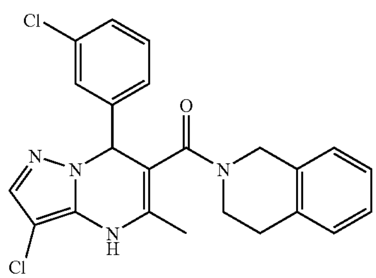 | 2-[[3-Chloro-7-(3-chlorophenyl)-4,7-dihydro-5-methylpyrazolo[1,5-a]pyrimidin-6-yl]carbonyl]-1,2,3,4-tetrahydroisoquinoline | 439 |
| 297 | 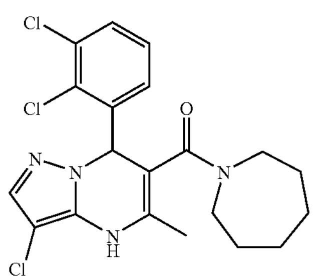 | 1-[[3-Chloro-7-(2,3-dichlorophenyl)-4,7-dihydro-5-methylpyrazolo[1,5-a]pyrimidin-6-yl]carbonyl]hexahydro-1H-azepine | 439 |
| 298 | 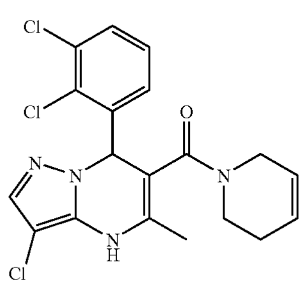 | 1-[[3-Chloro-7-(2,3-dichlorophenyl)-4,7-dihydro-5-methylpyrazolo[1,5-a]pyrimidin-6-yl]carbonyl]-1,2,3,6-tetrahydropyridine | 423 |
| 299 | 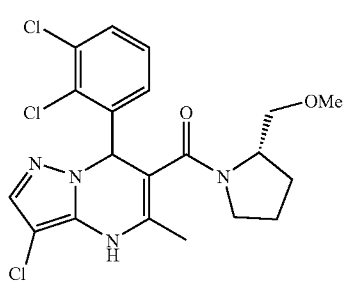 | (2S)-1-[[3-Chloro-7-(2,3-dichlorophenyl)-4,7-dihydro-5-methyl-pyrazolo[1,5-a]pyrimidin-6-yl]carbonyl]-2-(methoxymethyl)pyrrolidine | 455 |

| Example | Structure | Name | (M + H) |
|---|---|---|---|
| 300 | 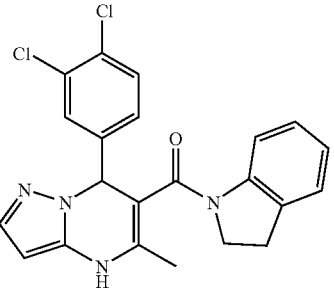 | 1-[[7-(3,4-Dichloro-phenyl)-4,7-dihydro-5-methyl-2-(trifluoromethyl)-pyrazolo[1,5-a]pyrimidin-6-yl]carbonyl]-2,3-dihydro-1H-indole | 493 |
| 301 | 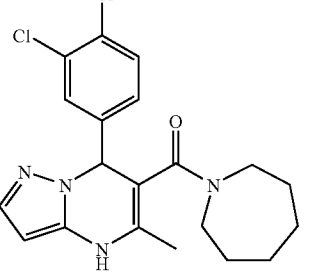 | 1-[[7-(3,4-Dichloro-phenyl)-4,7-dihydro-5-methyl-2-(trifluoromethyl)pyrazolo-[1,5-a]pyrimidin-6-yl]carbonyl]-hexahydro-1H-azepine | 473 |
| 302 | 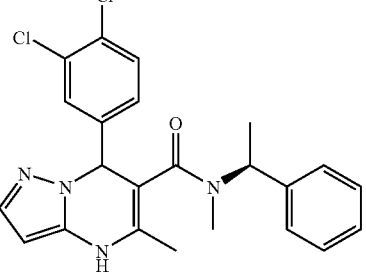 | 7-(3,4-Dichlorophenyl)-4,7-dihydro-N,5-dimethyl-N-[(1S)-1-phenylethyl]-2-(trifluoromethyl)pyrazolo[1,5-a]-pyrimidine-6-carboxamide | 509 |
| 303 | 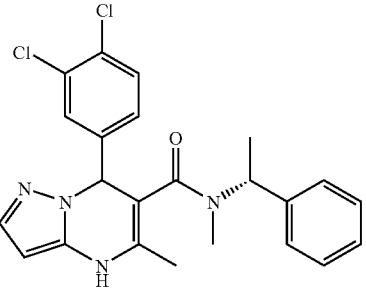 | 7-(3,4-Dichlorophenyl)-4,7-dihydro-N,5-dimethyl-N-[(1R)-1-phenylethyl]-2-(trifluoromethyl)pyrazolo[1,5-a]-pyrimidine-6-carboxamide | 509 |
| 304 | 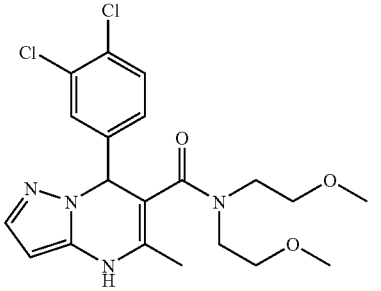 | 7-(3,4-Dichlorophenyl)-4,7-dihydro-N,N-bis(2-methoxyethyl)-5-methylpyrazolo-[1,5-a]pyrimidine-6-carboxamide | 439 |

-continued

| Example | Structure | Name | (M + H) |
|---|---|---|---|
| 305 | 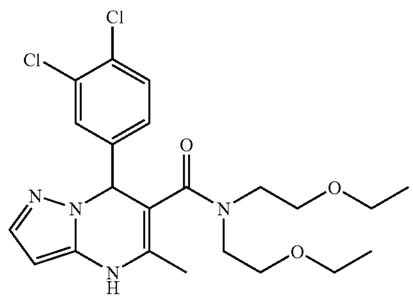 | 7-(3,4-Dichlorophenyl)-N,N-bis(2-ethoxyethyl)-4,7-dihydro-5-methylpyrazolo[1,5-a]-pyrimidine-6-carboxamide | 467 |
| 306 | 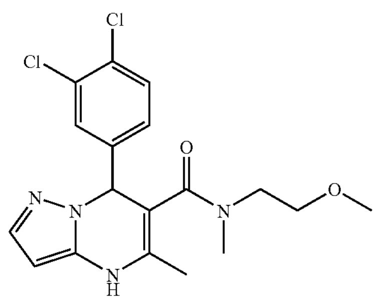 | 7-(3,4-Dichlorophenyl)-4,7-dihydro-N-(2-methoxyethyl)-N,5-dimethylpyrazolo[1,5-a]-pyrimidine-6-carboxamide | 395 |
| 307 | 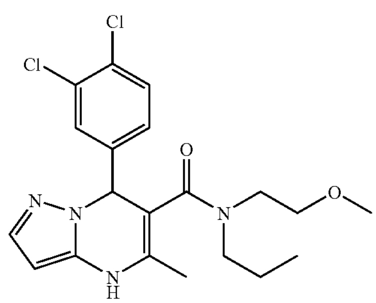 | 7-(3,4-Dichlorophenyl)-4,7-dihydro-N-(2-methoxyethyl)-5-methyl-N-propylpyrazolo[1,5-a]-pyrimidine-6-carboxamide | 423 |
| 308 | 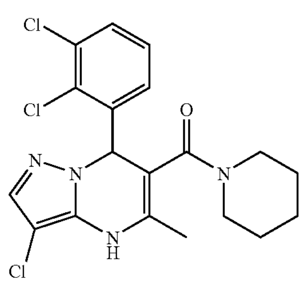 | 1-[[3-Chloro-7-(2,3-dichlorophenyl)-4,7-dihydro-5-methylpyrazolo[1,5-a]pyrimidin-6-yl]carbonyl]piperidine | 425 |
| 309 | 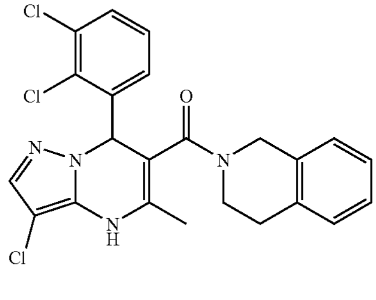 | 2-[[3-Chloro-7-(2,3-dichlorophenyl)-4,7-dihydro-5-methylpyrazolo[1,5-a]pyrimidin-6-yl]carbonyl]-1,2,3,4-tetrahydroisoquinoline | 473 |

-continued

| Example | Structure | Name | (M + H) |
|---|---|---|---|
| 310 | 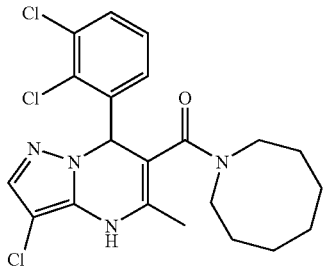 | 1-[[3-Chloro-7-(2,3-dichlorophenyl)-4,7-dihydro-5-methylpyrazolo[1,5-a]pyrimidin-6-yl]carbonyl]-octahydroazocine | 453 |
| 311 | 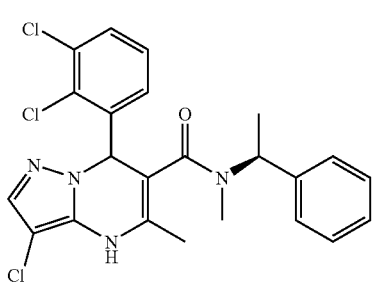 | 3-Chloro-7-(2,3-dichlorophenyl)-4,7-dihydro-N,5-dimethyl-N-[(1S)-1-phenylethyl]-pyrazolo[1,5-a]pyrimidine-6-carboxamide | 475 |
| 312 | 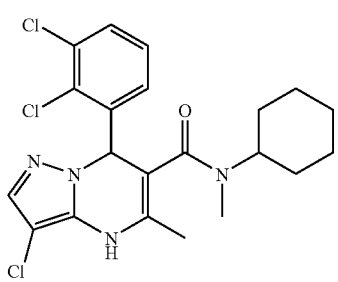 | 3-Chloro-N-cyclohexyl-7-(2,3-dichlorophenyl)-4,7-dihydro-N,5-dimethylpyrazolo[1,5-a]-pyrimidin-6-carboxamide | 453 |
| 313 | 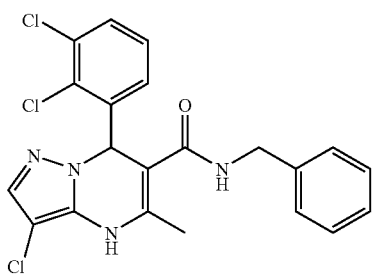 | 3-Chloro-7-(2,3-dichlorophenyl)-4,7-dihydro-5-methyl-N-(phenylmethyl)pyrazolo-[1,5-a]pyrimidine-6-carboxamide | 447 |
| 314 | 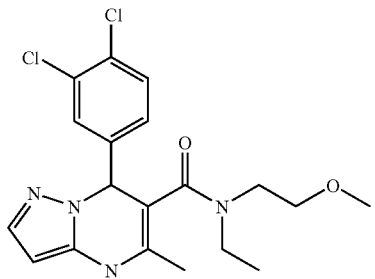 | 7-(3,4-Dichlorophenyl)-N-ethyl-4,7-dihydro-N-(2-methoxyethyl)-5-methylpyrazolo-[1,5-a]pyrimidine-6-carboxamide | 409 |

-continued

| Example | Structure | Name | (M + H) |
|---|---|---|---|
| 315 | 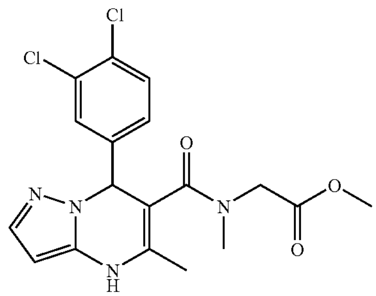 | N-[[7-(3,4-Dichloro-phenyl)-4,7-dihydro-5-methylpyrazolo[1,5-a]pyrimidin-6-yl]carbonyl]-N-methylglycine ethyl ester | 423 |
| 316 | 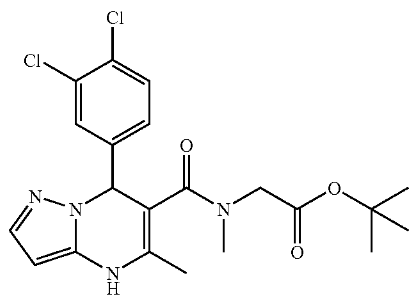 | N-[[7-(3,4-Dichloro-phenyl)-4,7-dihydro-5-methylpyrazolo[1,5-a]pyrimidin-6-yl]carbonyl]-N-methylglycine 1,1-dimethylethyl ester | 451 |
| 317 | 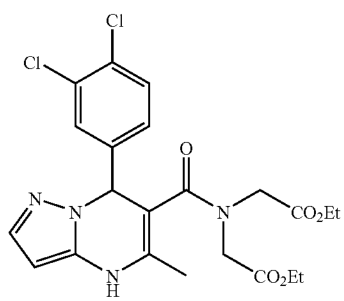 | N-[[7-(3,4-Dichloro-phenyl)-4,7-dihydro-5-methylpyrazolo[1,5-a]pyrimidin-6-yl]carbonyl]-N-(2-ethoxy-2-oxoethyl)glycine ethyl ester | 495 |
| 318 | 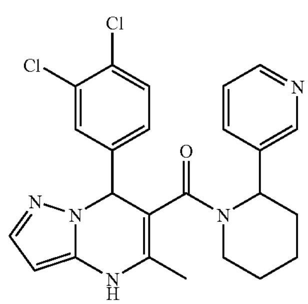 | 1-[[7-(3,4-Dichloro-phenyl)-4,7-dihydro-5-methylpyrazolo[1,5-a]pyrimidin-6-yl]carbonyl]-2-(3-pyridinyl)piperidine | 468 |
| 319 | 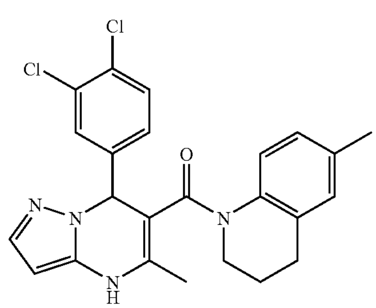 | 1-[[7-(3,4-Dichloro-phenyl)-4,7-dihydro-5-methylpyrazolo[1,5-a]pyrimidin-6-yl]carbonyl]-1,2,3,4-tetrahydro-6-methylquinoline | 453 |

-continued

| Example | Structure | Name | (M + H) |
|---|---|---|---|
| 320 | 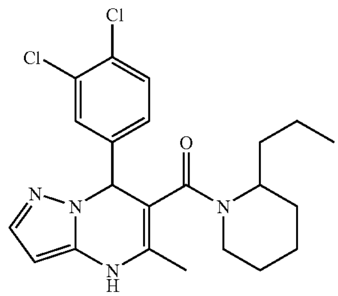 | 1-[[7-(3,4-Dichloro-phenyl)-4,7-dihydro-5-methylpyrazolo[1,5-a]pyrimidin-6-yl]carbonyl]-2-propylpiperidine | 433 |
| 321 | 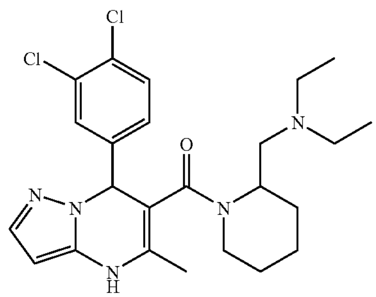 | 1-[[7-(3,4-Dichloro-phenyl)-4,7-dihydro-5-methylpyrazolo[1,5-a]pyrimidin-6-yl]carbonyl]-2-[(diethylamino)-methyl]piperidine | 476 |
| 322 | 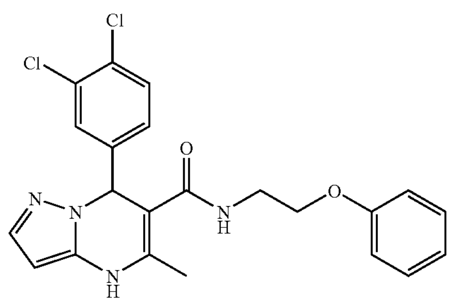 | 7-(3,4-Dichlorophenyl)-4,7-dihydro-5-methyl-N-(2-phenoxyethyl)-pyrazolo[1,5-a]-pyrimidine-6-carboxamide | 443 |
| 323 | 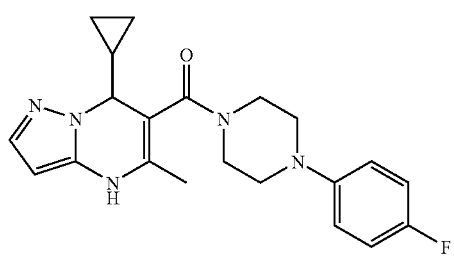 | 1-[(7-Cyclopropyl-4,7-dihydro-5-methylpyrazolo[1,5-a]pyrimidin-6-yl)carbonyl]-4-(4-fluorophenyl)-piperazine | 381 |
| 324 | 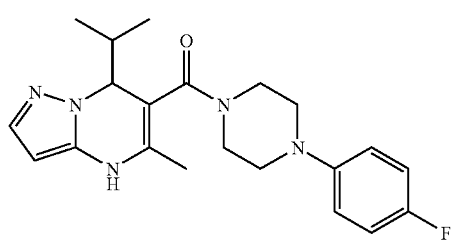 | 1-[[4,7-Dihydro-5-methyl-7-(1-methylethyl)-pyrazolo[1,5-a]pyrimidin-6-yl]carbonyl]-4-(4-fluorophenyl)-piperazine | 383 |

-continued

| Example | Structure | Name | (M + H) |
|---|---|---|---|
| 325 | 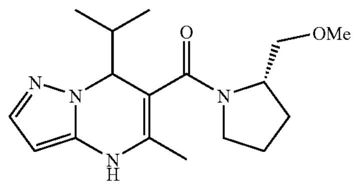 | (2S)-1-[[4,7-Dihydro-5-methyl-7-(1-methylethyl)-pyrazolo[1,5-a]pyrimidin-6-yl]carbonyl]-2-(methoxymethyl)-pyrrolidine | 318 |
| 326 | 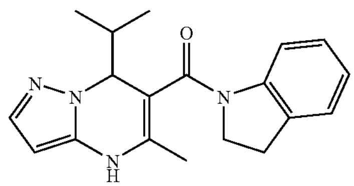 | 1-[[4,7-Dihydro-5-methyl-7-(1-methylethyl)-pyrazolo[1,5-a]pyrimidin-6-yl]carbonyl]-2,3-dihydro-1H-indole | 322 |
| 327 | 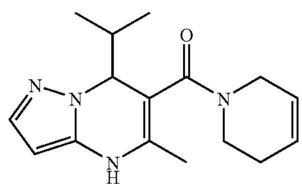 | 1-[[4,7-Dihydro-5-methyl-7-(1-methylethyl)-pyrazolo[1,5-a]pyrimidin-6-yl]carbonyl]-1,2,3,6-tetrahydropyridine | 286 |
| 328 | Chiral | 3-[[7-(3,4-Dichloro-phenyl)-4,7-dihydro-5-methyl-pyrazolo[1,5-a]pyrimidin-6-yl]carbonyl]thiazolidine, enantiomer A | 395 |
| 329 | Chiral | 3-[[7-(3,4-Dichloro-phenyl)-4,7-dihydro-5-methylpyrazolo[1,5-a]-pyrimidin-6-yl]carbonyl]-thiazolidine, enantiomer B | 395 |
| 330 | 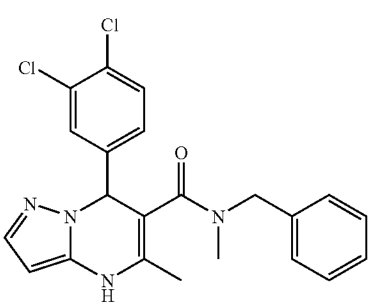 | 7-(3,4-Dichlorophenyl)-4,7-dihydro-N,5-dimethyl-N-(phenyl-methyl)pyrazolo[1,5-a]pyrimidine-6-carboxamide | 427 |

-continued

| Example | Structure | Name | (M + H) |
|---|---|---|---|
| 331 | 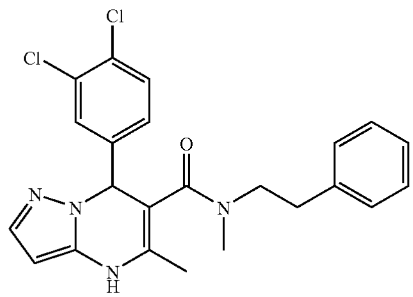 | 7-(3,4-Dichlorophenyl)-4,7-dihydro-N,5-dimethyl-N-(2-phenyl-ethyl)pyrazolo[1,5-a]pyrimidine-6-carboxamide | 441 |
| 332 | 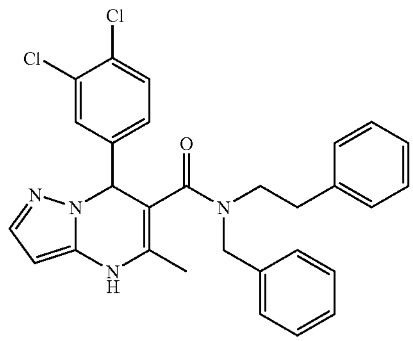 | 7-(3,4-Dichlorophenyl)-4,7-dihydro-5-methyl-N-(2-phenyl-ethyl)-N-(phenylmethyl)pyrazolo-[1,5-a]pyrimidine-6-carboxamide | 517 |
| 333 | 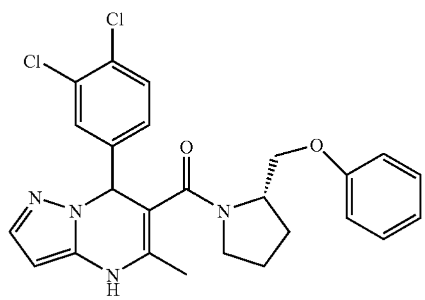 | (2S)-1-[[7-(3,4-Dichlorophenyl)-4,7-dihydro-5-methylpyrazolo[1,5-a]pyrimidin-6-yl]carbonyl]-2-(phenoxymethyl)pyrrolidine | 483 |
| 334 | 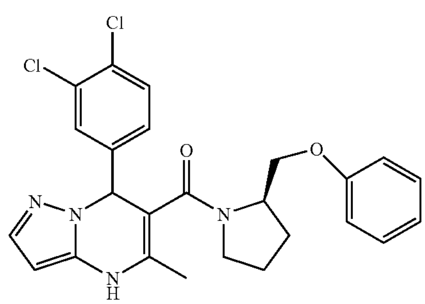 | (2R)-1-[[7-(3,4-Dichlorophenyl)-4,7-dihydro-5-methylpyrazolo[1,5-a]pyrimidin-6-yl]carbonyl]-2-(phenoxymethyl)pyrrolidine | 483 |
| 335 | 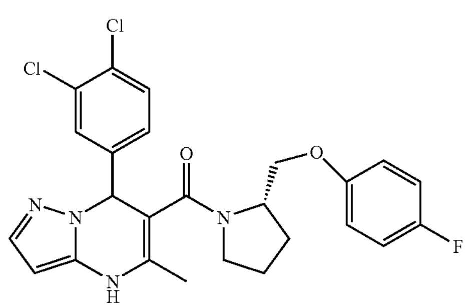 | (2S)-1-[[7-(3,4-Dichlorophenyl)-4,7-dihydro-5-methylpyrazolo[1,5-a]pyrimidin-6-yl]carbonyl]-2-[(4-fluorophenoxy)methyl]pyrrolidine | 501 |

-continued

| Example | Structure | Name | (M + H) |
|---|---|---|---|
| 336 | 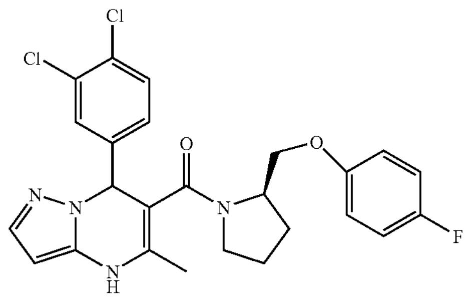 | (2R)-1-[[7-(3,4-Dichlorophenyl)-4,7-dihydro-5-methylpyrazolo[1,5-a]pyrimidin-6-yl]carbonyl]-2-[(4-fluorophenoxy)methyl]pyrrolidine | 501 |
| 337 | 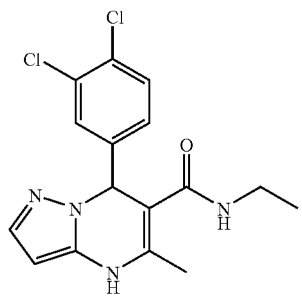 | 7-(3,4-Dichlorophenyl)-N-ethyl-4,7-dihydro-5-methyl-pyrazolo[1,5-a]pyrimidine-6-carboxamide | 351 |
| 338 | 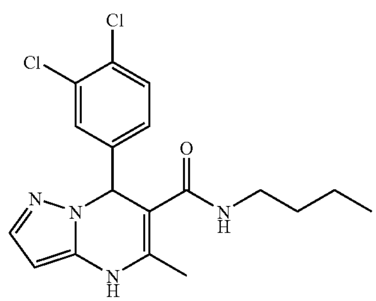 | N-Butyl-7-(3,4-dichlorophenyl)-4,7-dihydro-5-methylpyrazolo[1,5-a]pyrimidine-6-carboxamide | 379 |
| 339 | 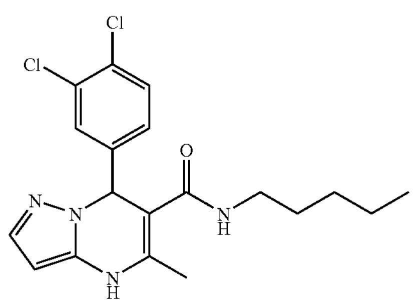 | 7-(3,4-Dichlorophenyl)-4,7-dihydro-5-methyl-N-pentyl-pyrazolo[1,5-a]pyrimidine-6-carboxamide | 393 |
| 340 | 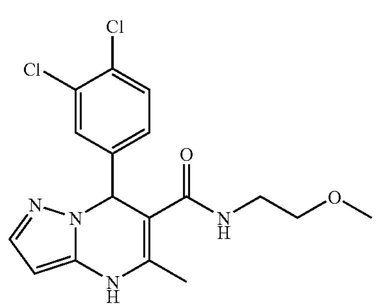 | 7-(3,4-Dichlorophenyl)-4,7-dihydro-N-(2-methoxyethyl)-5-methylpyrazolo[1,5-a]pyrimidine-6-carboxamide | 381 |

-continued

| Example | Name | (M + H) |
|---|---|---|
| 341 | (2S)-1-[[7-(3,4-Dichlorophenyl)-4,7-dihydro-5-methylpyrazolo[1,5-a]pyrimidin-6-yl]carbonyl]-2-(hydroxydiphenylmethyl)pyrrolidine | 559 |
| 342 | (2R)-1-[[7-(3,4-Dichlorophenyl)-4,7-dihydro-5-methylpyrazolo[1,5-a]pyrimidin-6-yl]carbonyl]-2-(hydroxydiphenylmethyl)pyrrolidine | 559 |
| 343 | 1-[[7-(3,4-Dichlorophenyl)-4,7-dihydro-5-methyl-pyrazolo[1,5-a]pyrimidin-6-yl]carbonyl]-2-(3-pyridinyl)pyrrolidine | 454 |
| 344 | (2S)-1-[[7-(2,3-Dichlorophenyl)-4,7-dihydro-5-methylpyrazolo[1,5-a]pyrimidin-6-yl]carbonyl]-2-(methoxymethyl)pyrrolidine | 421 |
| 345 | 1-[[7-(3,4-Dichlorophenyl)-4,7-dihydro-5-methylpyrazolo[1,5-a]pyrimidin-6-yl]carbonyl]-2-phenylpyrrolidine | 453 |

-continued

| Example | Structure | Name | (M + H) |
|---|---|---|---|
| 346 | 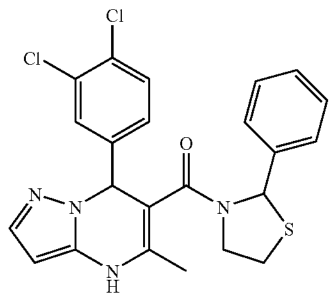 | 3-[[7-(3,4-Dichloro-phenyl)-4,7-dihydro-5-methyl-pyrazolo[1,5-a]pyrimidin-6-yl]carbonyl]-2-phenylthiazolidine | 471 |
| 347 | 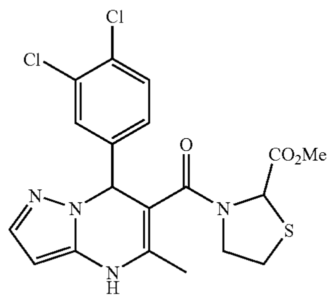 | 3-[[7-(3,4-Dichloro-phenyl)-4,7-dihydro-5-methyl-pyrazolo[1,5-a]pyrimidin-6-yl]carbonyl]-2-thiazolidinecarboxylic acid methyl ester | 453 |
| 348 | 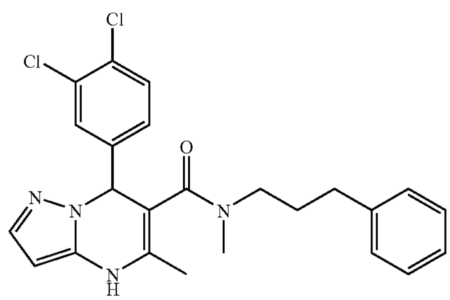 | 7-(3,4-Dichlorophenyl)-4,7-dihydro-N,5-dimethyl-N-(3-phenylpropyl)pyrazolo[1,5-a]-pyrimidine-6-carboxamide | 455 |
| 349 | 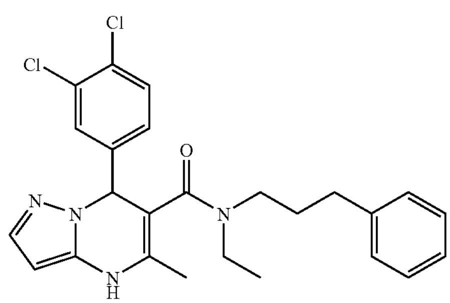 | 7-(3,4-Dichlorophenyl)-N-ethyl-4,7-dihydro-5-methyl-N-(3-phenylpropyl)pyrazolo[1,5-a]-pyrimidine-6-carboxamide | 469 |
| 350 | 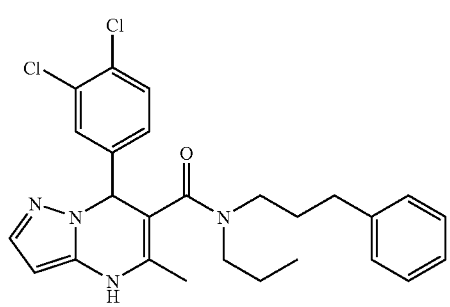 | 7-(3,4-Dichlorophenyl)-4,7-dihydro-5-methyl-N-(3-phenylpropyl)-N-propylpyrazolo[1,5-a]-pyrimidine-6-carboxamide | 483 |

-continued

| Example | Structure | Name | (M + H) |
|---|---|---|---|
| 351 | 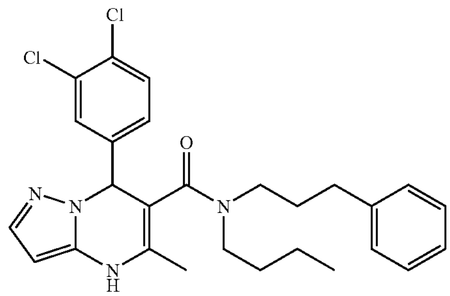 | N-Butyl-7-(3,4-dichloro-phenyl)-4,7-dihydro-5-methyl-N-(3-phenylpropyl)pyrazolo[1,5-a]-pyrimidine-6-carboxamide | 497 |
| 352 | 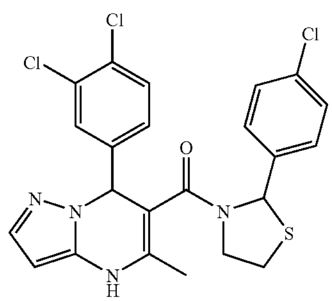 | 2-(4-Chlorophenyl)-3-[[7-(3,4-dichlorophenyl)-4,7-dihydro-5-methylpyrazolo[1,5-a]pyrimidin-6-yl]carbonyl]thiazolidine | 505 |
| 353 | 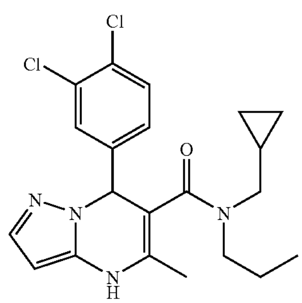 | N-(Cyclopropylmethyl)-7-(3,4-dichlorophenyl)-4,7-dihydro-5-methyl-N-propylpyrazolo[1,5-a]-pyrimidine-6-carboxamide | 419 |
| 354 | 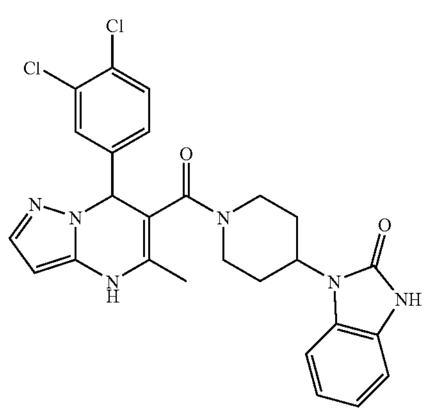 | 1-[[7-(3,4-Dichloro-phenyl)-4,7-dihydro-5-methyl-pyrazolo[1,5-a]pyrimidin-6-yl]-carbonyl]-4-(2,3-dihydro-2-oxo-1H-benzimidazol-1-yl)piperidine | 523 |

-continued

| Example | Structure | Name | (M + H) |
|---|---|---|---|
| 355 | 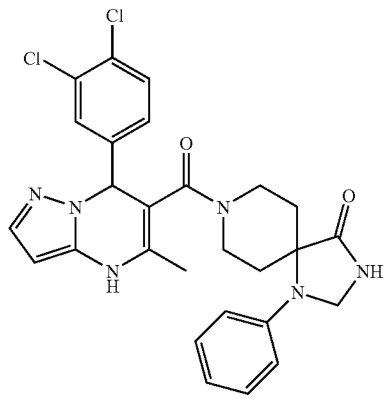 | 8-[[7-(2,3-Dichloro-phenyl)-4,7-dihydro-5-methyl-pyrazolo[1,5-a]pyrimidin-6-yl]-carbonyl]-1-phenyl-1,3,8-triazaspiro-[4.5]decan-4-one | 537 |
| 356 | 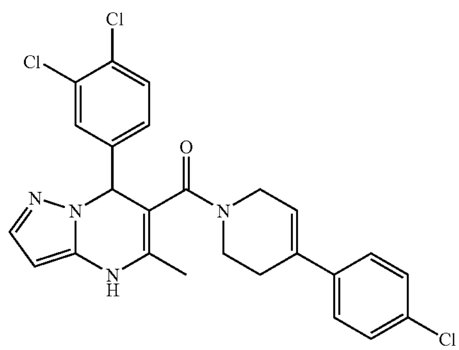 | 4-(4-Chlorophenyl)-1-[[7-(3,4-dichlorophenyl)-4,7-dihydro-5-methylpyrazolo[1,5-a]pyrimidin-6-yl]carbonyl]-1,2,3,6-tetrahydropyridine | 499 |
| 357 | 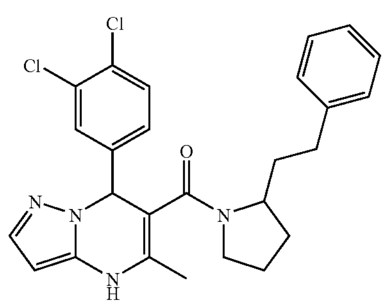 | 1-[[7-(3,4-Dichloro-phenyl)-4,7-dihydro-5-methyl-pyrazolo[1,5-a]pyrimidin-6-yl]carbonyl]-2-(2-phenyl-ethyl)pyrrolidine | 481 |
| 358 | 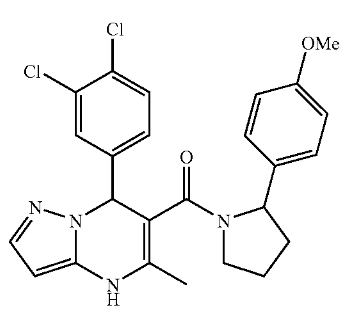 | 1-[[7-(3,4-Dichloro-phenyl)-4,7-dihydro-5-methyl-pyrazolo[1,5-a]pyrimidin-6-yl]carbonyl]-2-(4-methoxy-phenyl)pyrrolidine | 483 |

-continued

| Example | Structure | Name | (M + H) |
|---|---|---|---|
| 359 | 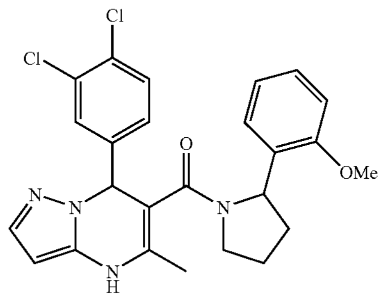 | 1-[[7-(3,4-Dichlorophenyl)-4,7-dihydro-5-methyl-pyrazolo[1,5-a]pyrimidin-6-yl]carbonyl]-2-(2-methoxyphenyl)pyrrolidine | 483 |
| 360 | 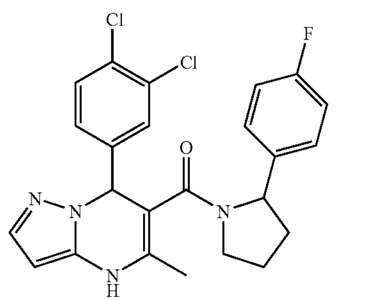 | 1-[[7-(3,4-Dichlorophenyl)-4,7-dihydro-5-methyl-pyrazolo[1,5-a]pyrimidin-6-yl]carbonyl]-2-(4-fluorophenyl)pyrrolidine | 471 |
| 361 | 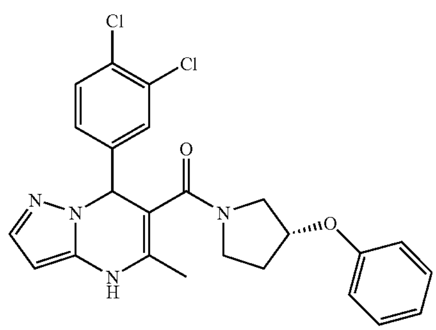 | (3R)-1-[[7-(3,4-Dichlorophenyl)-4,7-dihydro-5-methylpyrazolo[1,5-a]pyrimidin-6-yl]carbonyl]-3-phenoxypyrrolidine | 469 |
| 362 | 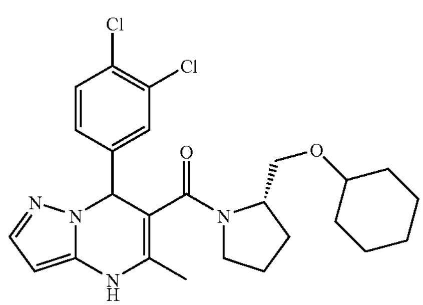 | (2S)-2-[(Cyclohexyloxy)methyl]-1-[[7-(3,4-dichlorophenyl)-4,7-dihydro-5-methylpyrazolo[1,5-a]pyrimidin-6-yl]carbonyl]pyrrolidine | 489 |
| 363 | 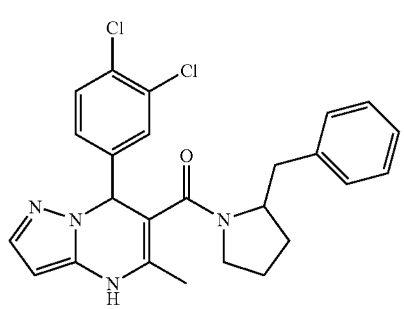 | 1-[[7-(3,4-Dichlorophenyl)-4,7-dihydro-5-methyl-pyrazolo[1,5-a]pyrimidin-6-yl]carbonyl]-2-(phenylmethyl)pyrrolidine | 467 |

| Example | Structure | Name | (M + H) |
|---|---|---|---|
| 364 | 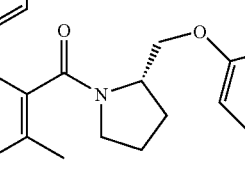 Chiral | (2S)-1-[[7-(3,4-Dichlorophenyl)-4,7-dihydro-5-methylpyrazolo[1,5-a]pyrimidin-6-yl]carbonyl]-2-(phenoxymethyl)pyrrolidine, diastereomer A | 483 |
| 365 | 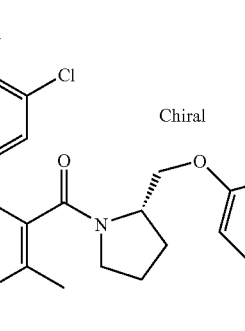 Chiral | (2S)-1-[[7-(3,4-Dichlorophenyl)-4,7-dihydro-5-methylpyrazolo[1,5-a]pyrimidin-6-yl]carbonyl]-2-(phenoxymethyl)pyrrolidine, diastereomer B | 483 |
| 366 | 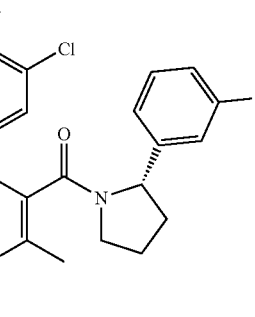 | 1-[[7-(3,4-Dichlorophenyl)-4,7-dihydro-5-methylpyrazolo[1,5-a]pyrimidin-6-yl]carbonyl]-2-(3-methoxyphenyl)pyrrolidine | 483 |
| 367 | 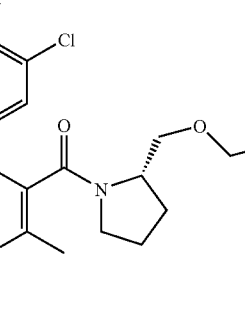 | (2S)-2-(Butoxymethyl)-1-[[7-(3,4-dichlorophenyl)-4,7-dihydro-5-methylpyrazolo[1,5-a]pyrimidin-6-yl]carbonyl]pyrrolidine | 463 |
| 368 | 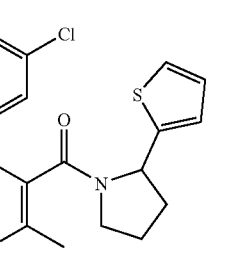 | 1-[[7-(3,4-Dichlorophenyl)-4,7-dihydro-5-methylpyrazolo[1,5-a]pyrimidin-6-yl]carbonyl]-2-(2-thienyl)pyrrolidine | 459 |

-continued

| Example | Structure | Name | (M + H) |
|---|---|---|---|
| 369 | 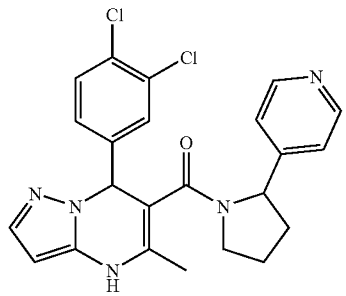 | 1-[[7-(3,4-Dichloro-phenyl)-4,7-dihydro-5-methyl-pyrazolo[1,5-a]pyrimidin-6-yl]carbonyl]-2-(4-pyridinyl)pyrrolidine | 454 |
| 370 | 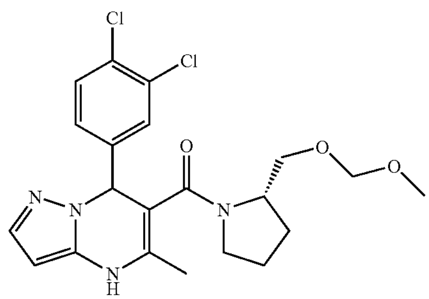 | (2S)-1-[[7-(3,4-Dichlorophenyl)-4,7-dihydro-5-methylpyrazolo[1,5-a]pyrimidin-6-yl]carbonyl]-2-[(methoxymethoxy)-methyl]pyrrolidine | 451 |
| 371 | 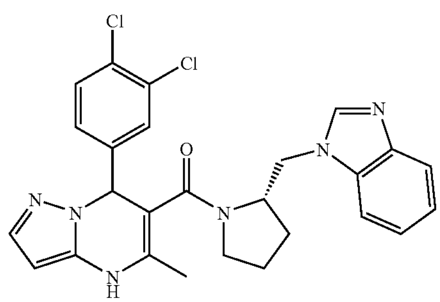 | (2S)-2-(1H-Benzimidazol-1-ylmethyl)-1-[[7-(3,4-dichlorophenyl)-4,7-dihydro-5-methylpyrazolo[1,5-a]pyrimidin-6-yl]carbonyl]pyrrolidine | 507 |
| 372 | 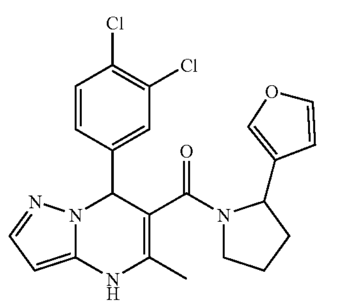 | 1-[[7-(3,4-Dichloro-phenyl)-4,7-dihydro-5-methyl-pyrazolo[1,5-a]pyrimidin-6-yl]carbonyl]-2-(3-furanyl)pyrrolidine | 443 |
| 373 | 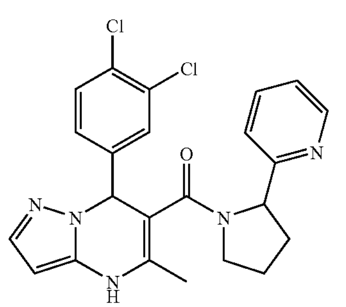 | 1-[[7-(3,4-Dichloro-phenyl)-4,7-dihydro-5-methyl-pyrazolo[1,5-a]pyrimidin-6-yl]carbonyl]-2-(2-pyridinyl)pyrrolidine | 454 |

-continued

| Example | Structure | Name | (M + H) |
|---|---|---|---|
| 374 | 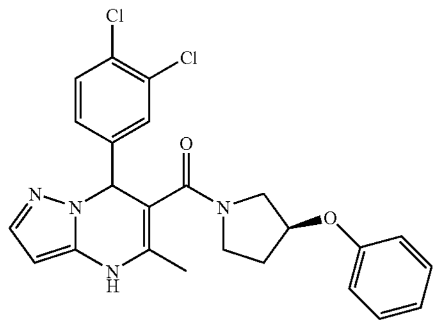 | (3S)-1-[[7-(3,4-Dichlorophenyl)-4,7-dihydro-5-methylpyrazolo[1,5-a]pyrimidin-6-yl]carbonyl]-3-phenoxypyrrolidine | 469 |
| 375 | 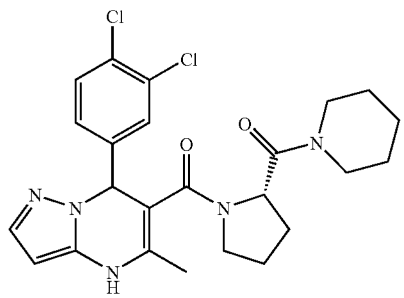 | (3S)-1-[[7-(3,4-Dichlorophenyl)-4,7-dihydro-5-methylpyrazolo[1,5-a]pyrimidin-6-yl]carbonyl]-3-phenoxypyrrolidine | 488 |
| 376 | 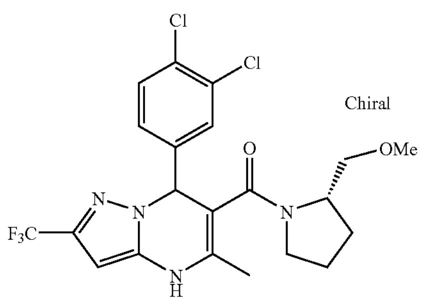 | (2S)-1-[[7-(3,4-Dichlorophenyl)-4,7-dihydro-5-methyl-2-(trifluoromethyl)pyrazolo[1,5-a]-pyrimidin-6-yl]carbonyl]-2-(methoxymethyl)pyrrolidine, enantiomer A | 489 |
| 377 | 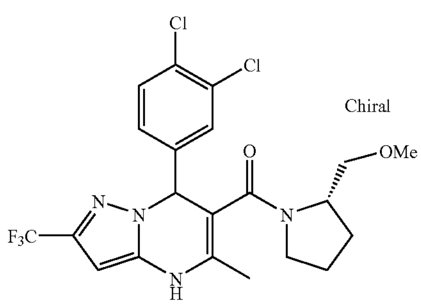 | (2S)-1-[[7-(3,4-Dichlorophenyl)-4,7-dihydro-5-methyl-2-(trifluoromethyl)pyrazolo[1,5-a]-pyrimidin-6-yl]carbonyl]-2-(methoxymethyl)pyrrolidine, enantiomer B | 489 |

EXAMPLE 378

1-[[7-(3,4-Dichlorophenyl)-4,7-dihydro-5-methylpyrazolo[1,5-a]pyrimidin-6-yl]carbonyl]-L-proline

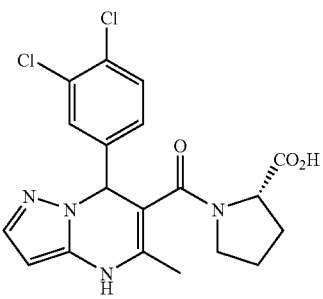

Method:

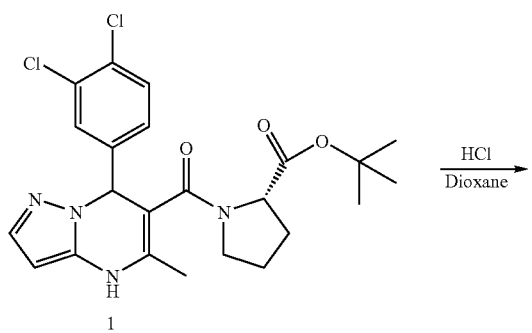

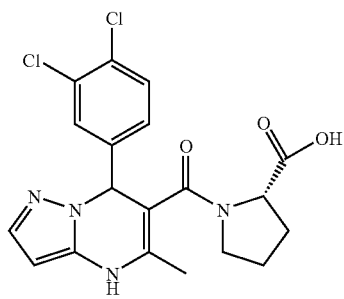

Compound 1: Compound 1 (the compound of Example 252) was prepared in a manner similar to that described in Example 170.

Title Compound: Hydrochloric acid (5 mL, 4M in Dioxane) was added to compound 1 (0.05 g, 0.1 mmol). The resulting mixture was stirred at room temperature. After 3 h the mixture was concentrated in vacuo. LC/MS analysis of the residue indicated that starting material remained. Additional Hydrochloric acid (5 mL, 4M in Dioxane) was added. The resulting mixture was stirred at room temperature for 7 h. TLC analysis indicated that compound 1 was consumed. The mixture was concentrated in vacuo. The residue was purified by preparative reverse phase HPLC to give the title compound as a mixture of diastereomers. LC/MS indicated that the compound was still impure (50% pure). Reverse Phase LC/MS: YMC S5 ODS 4.6×50 mm Ballistic, UV detection at 220 λ, 4 min. gradient, 0–100% Solvent B/A (Solvent A: 10% MeOH/H20 with 0.1% TFA, Solvent B: 90% MeOH/H$_2$O with 0.1% TFA), 4 mL/min. Diastereomer A Rt=3.34, Diastereomer B Rt=3.49 min. MS (M+H: 421). The product was triturated with dichlormethane to give 0.014 g (32% yield) of the title compound (85% pure by HPLC). Reverse Phase LC/MS: YMC S5 4.6×50 mm combiscreen, UV detection at 220 λ, 4 min. gradient, 0–100% Solvent B/A (Solvent A: 10% MeOH/H20 with 0.2% H$_3$PO$_4$, Solvent B: 90% MeOH/H$_2$O with 0.2% H$_3$PO$_4$), 4 mL/min. Diastereomer A Rt=2.82, Diastereomer B Rt=2.97 min.

EXAMPLE 379

7-(3,4-Dichlorophenyl)-4,7-dihydro-N-[(1R)-2,3-dihydro-1H-inden-1-yl]-5-methyl-2-(triflouromethyl)pyrazolo[1,5-a]pyrimidine-6-carboxamide

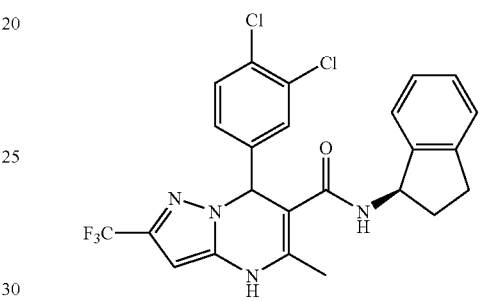

Method:

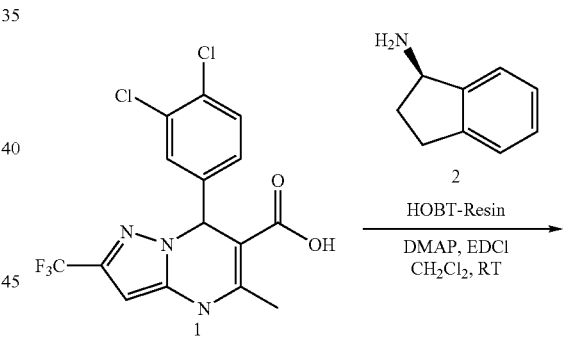

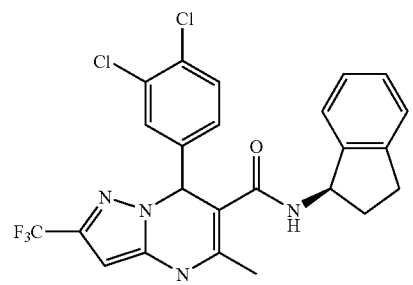

Compound 1: Compound 1 was prepared as described in Example 17.

Title Compound: To a suspension of polystyrene-supported HOBt resin (NovaBiochem, >1.2 mmol/g, 50 mg, 1.0 eq) in anhydrous CH$_2$Cl$_2$ (1.0 mL) was added Compound 1 (47 mg, 2.0 eq), EDCI (23 mg, 2.0 eq), and DMAP (0.7 mg, 0.1 eq). The suspension was shaken vigorously using a VORTEX-GENIE2 for 1 hr. Solvent was then drained and the resin was washed sequentially with DMF (3×2 mL), THF (3×2 mL), and CH$_2$Cl$_2$ (3×2 mL) with vigorous shaking. The resin was resuspended in CH$_2$Cl$_2$ (1 mL) and to which was added (R)-(−)-Aminoindan 2 (0.006 mL, 0.8 eq). The mixture was shaken for 2 hr. Solvent was drained and the resin was washed with CH$_2$Cl$_2$ (3×1 mL) with vigorous shaking. All the washing solutions were combined and the solvent was removed under reduced pressure. The residue was purified through a silica gel cartridge eluting with 100% EtOAc to give the title compound as a white solid Reverse Phase LC/MS: YMC S5 ODS 4.6×50 mm Ballistic column, UV detection at 220 λ, 4 min. gradient 0–100% Solvent B/A (Solvent A: 10% MeOH/H20 with 0.2% H$_3$PO$_4$, Solvent B: 90% MeOH/H$_2$O with 0.2% H$_3$PO$_4$), 4 mL/min. Rt=2.96 min, (diastereomers, 96% pure). MS (M+H): 507.

EXAMPLES 380–391

The compounds of Examples 380–391, shown in the table provided below, were prepared in a manner similar to that described in Example 379.

| Example | Structure | Name | (M + H) |
|---|---|---|---|
| 380 | 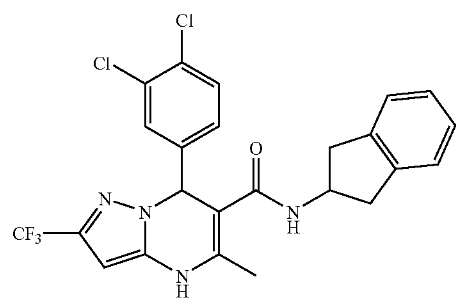 | 7-(3,4-Dichlorophenyl)-N-(2,3-dihydro-1H-inden-2-yl)-4,7-dihydro-5-methyl-2-(trifluoromethyl)-pyrazolo[1,5-a]pyrimidine-6-carboxamide | 507 |
| 381 | 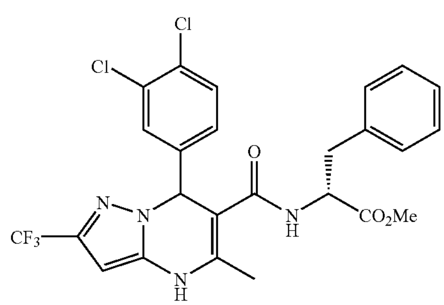 | N-[[7-(3,4-Dichloro-phenyl)-4,7-dihydro-5-methyl-2-(trifluoromethyl)-pyrazolo[1,5-a]pyrimidin-6-yl]carbonyl]-D-phenylalanine methyl ester | 553 |
| 382 | 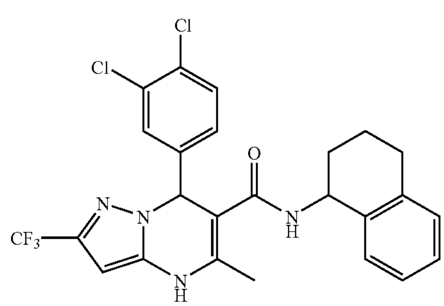 | 7-(3,4-Dichlorophenyl)-4,7-dihydro-5-methyl-N-(1,2,3,4-tetrahydro-1-naphthalenyl)-2-(trifluoro-methyl)pyrazolo[1,5-a]pyrimidine-6-carboxamide | 521 |
| 383 | 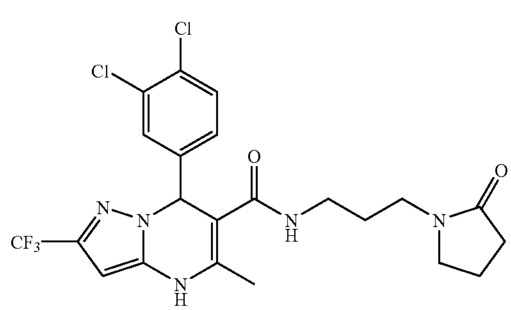 | 7-(3,4-Dichlorophenyl)-4,7-dihydro-5-methyl-N-[3-(2-oxo-1-pyrrolidinyl)propyl]-2-(trifluoro-methyl)pyrazolo[1,5-a]pyrimidine-6-carboxamide | 516 |

-continued

| Example | Structure | Name | (M + H) |
|---|---|---|---|
| 384 | 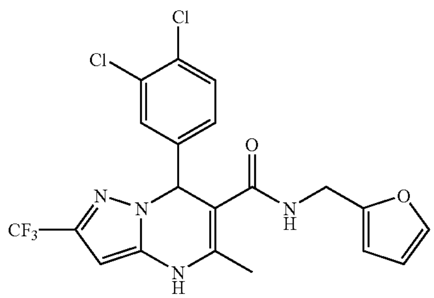 | 7-(3,4-Dichlorophenyl)-N-(2-furanylmethyl)-4,7-dihydro-5-methyl-2-(trifluoromethyl)pyrazolo[1,5-a]pyrimidine-6-carboxamide | 471 |
| 385 | 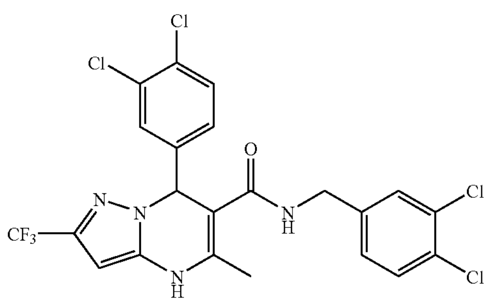 | 7-(3,4-Dichlorophenyl)-N-[(3,4-dichloro-phenyl)methyl]-4,7-dihydro-5-methyl-2-(trifluoromethyl)pyrazolo[1,5-a]pyrimidine-6-carboxamide | 550 |
| 386 | 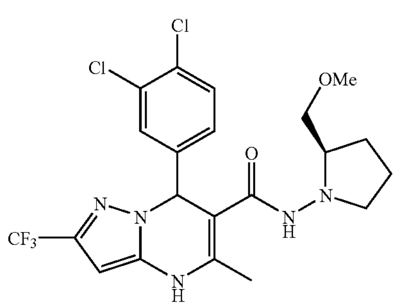 | 7-(3,4-Dichlorophenyl)-4,7-dihydro-N-[(2R)-2-(methoxymethyl)-1-pyrrolidinyl]-5-methyl-2-(trifluoromethyl)pyrazolo[1,5-a]pyrimidine-6-carboxamide | 504 |
| 387 | 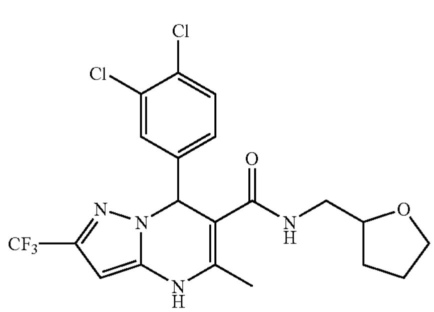 | 7-(3,4-Dichlorophenyl)-4,7-dihydro-5-methyl-N-[(tetrahydro-2-furanyl)methyl]-2-(trifluoromethyl)pyrazolo[1,5-a]pyrimidine-6-carboxamide | 475 |

-continued

| Example | Name | (M + H) |
|---|---|---|
| 388 | 7-(3,4-Dichlorophenyl)-4,7-dihydro-N-[(1S)-2,3-dihydro-1H-inden-1-yl]-5-methyl-2-(trifluoromethyl)pyrazolo[1,5-a]pyrimidine-6-carboxamide | 507 |
| 389 | 7-(3,4-Dichlorophenyl)-N-[2-(3,4-dichlorophenyl)ethyl]-4,7-dihydro-5-methyl-2-(trifluoromethyl)pyrazolo[1,5-a]pyrimidine-6-carboxamide | 564 |
| 390 | 7-(3,4-Dichlorophenyl)-4,7-dihydro-5-methyl-2-(trifluoromethyl)-N-[[4-[(trifluoromethyl)thio]-phenyl]methyl]pyrazolo-[1,5-a]pyrimidine-6-carboxamide | 581 |
| 391 | (2S)-1-[[7-(3,4-Dichloro-phenyl)-4,7dihydro-5-methyl-2-(trifluoro-methyl)pyrazolo[1,5-a]pyrimidin-6-yl]carbonyl]-2-(1-pyrrolidinyl-methyl)-pyrrolidine | 666 |

EXAMPLE 392

1-[[7-(3,4-Dichlorophenyl)-4,7-dihydro-5-methylpyrazolo[1,5-a]pyrimidin-6-yl]carbonyl]-4-(1-naphthalenylsulfonyl)piperazine

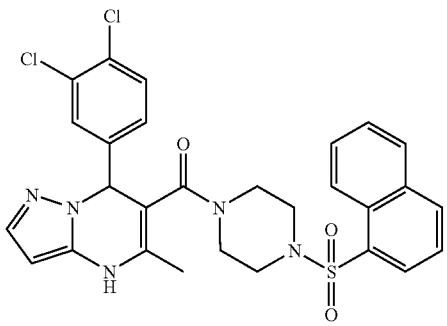

Method:

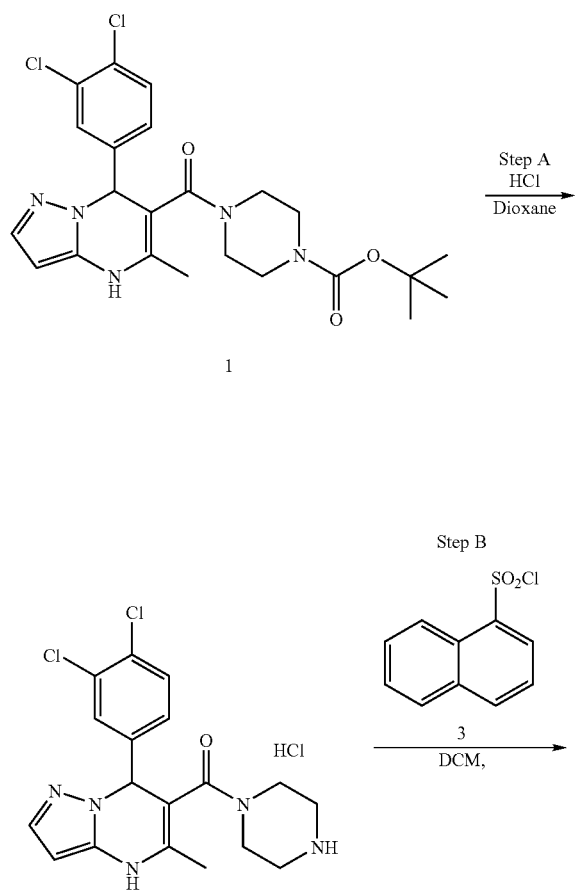

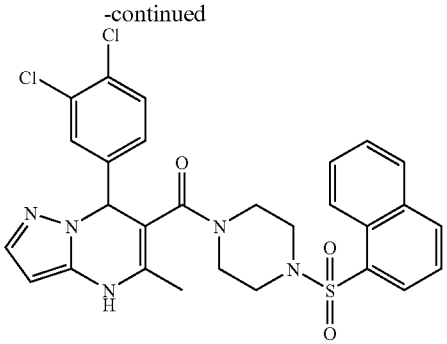

Compound 1: Compound 1 (the compound of Example 60) was prepared in a manner similar to that described in Example 18, Method 2.

Step A: HCl (4M in dioxane) was added to solid compound 1 (0.53 g, 1.1 mmol). A gummy precipitate forms immediately. Dichloromethane was added, the gummy precipitate remained. The solvent was decanted and the residue was triturated with ethyl acetate (3×), concentrated to give 0.63 g (130% contains residual dioxane) of the hydrochloride salt compound 2 as a light yellow powder. Reverse Phase LC/MS: YMC S5 ODS 4.6×50 mm Ballistic column, UV detection at 220 λ, 4 min. gradient 40–100% Solvent B/A (Solvent A: 10% MeOH/H20 with 0.1% TFA, Solvent B: 90% MeOH/$H_2O$ with 0.1% TFA), 4 mL/min. Rt=0.57 min, (92% pure). MS (M+H): 392. Compound 2 was used without purification.

Step B: Compound 2 (0.077 g, 0.18 mmol) and compound 3 (0.049 g, 0.22 mmol) were suspended in dichloromethane (1 mL). Triethylamine (0.05 mL, 0.36 mmol) was added. A clear solution results. TLC after 30 min indicated consumption of starting material. The mixture was loaded directly onto a Worldwide Monitoring CLEAN-UP CARTRIDGE (silica, CUSIL12M6) which had been equilibrated with 100% hexanes. Elution with 100% hexanes (40 mL), followed by 50% Ethyl acetate/hexanes (40 mL) and 100% ethyl acetate (40 mL). The purest fractions (TLC analysis) were combined to give 0.068 g (65% yield) of the title compound as a white solid. Reverse Phase LC/MS: YMC S5 ODS 4.6×50 mm Ballistic column, UV detection at 220 λ, 4 min. gradient 40–100% Solvent B/A (Solvent A: 10% MeOH/H20 with 0.1% TFA, Solvent B: 90% MeOH/$H_2O$ with 0.1% TFA), 4 mL/min. Rt=3.46 min, (90% pure). MS (M+H: 582). HMR (CDCl$_3$, 400 MHz): 8.60(1H, d, J=8), 8.05(2H, m), 7.95(1H, m), 7.62(4H, m), 7.35(1H, d, J=2 Hz), 7.17(1H, d, J=8 Hz), 7.06(1H, d, J=2 Hz), 6.81(1H, d, J=6 Hz), 6.17(1H, m), 5.54(1H, d, J=2 Hz), 3.23(8H,m), 1.86(3H, s).

EXAMPLES 393–396

The compounds of Examples 393–396, shown in the table provided below, were prepared in a manner similar to that described in Example 392.

| Example | Structure | Name | (M + H) |
|---|---|---|---|
| 393 | 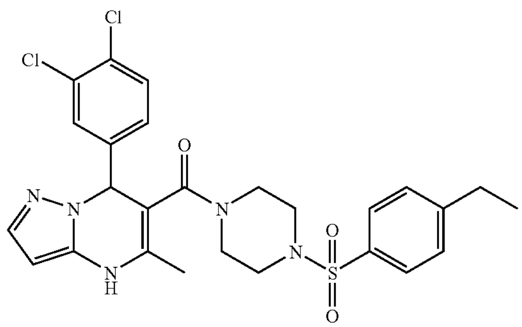 | 1-[[7-(3,4-Dichloro-phenyl)-4,7-dihydro-5-methylpyrazolo[1,5-a]pyrimidin-6-yl]carbonyl]-4-[(4-ethylphenyl)sulfonyl]-piperazine | 560 |
| 394 | 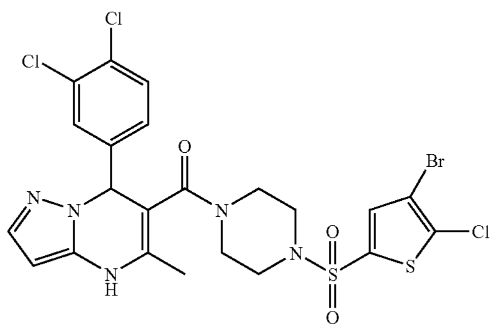 | 1-[(4-Bromo-5-chloro-2-thienyl)sulfonyl]-4-[[7-(3,4-dichlorophenyl)-4,7-dihydro-5-methyl-pyrazolo[1,5-a]pyrimidin-6-yl]carbonyl]-piperazine | 651 |
| 395 | 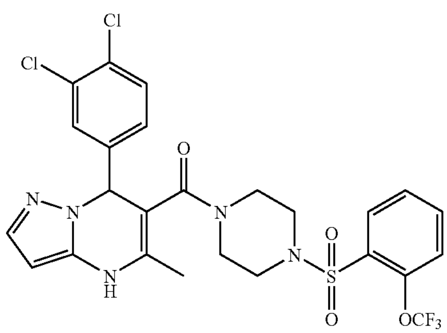 | 1-[[7-(3,4-Dichloro-phenyl)-4,7-dihydro-5-methyl-pyrazolo[1,5-a]pyrimidin-6-yl]carbonyl]-4-[[2-(trifluoromethoxy)phenyl]sulfonyl]piperazine | 616 |
| 396 | 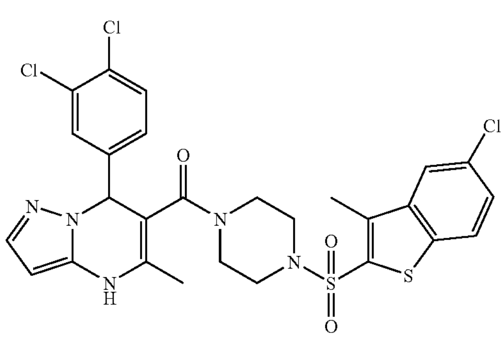 | 1-[(5-Chloro-3-methyl-benzo[b]thiophen-2-yl)-sulfonyl]-4-[[7-(3,4-dichlorophenyl)-4,7-dihydro-5-methylpyrazolo[1,5-a]pyrimidin-6-yl]carbonyl]piperazine | 637 |

EXAMPLE 397

1-[[7-(3,4-Dichlorophenyl)-4,7-dihydro-5-methylpyrazolo[1,5-a]pyrimidin-6-yl]carbonyl]-4-[(3-methoxyphenyl)carbonyl]piperazine

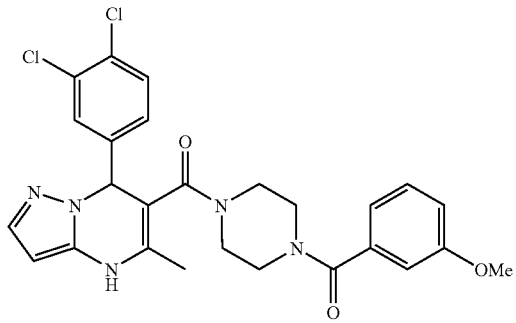

Method:

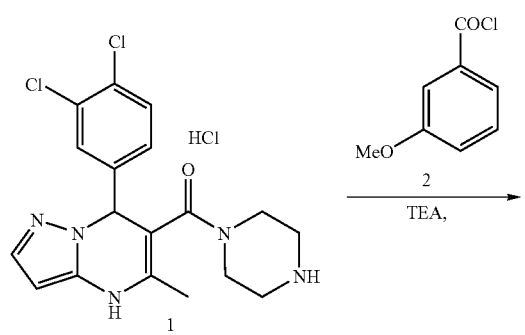

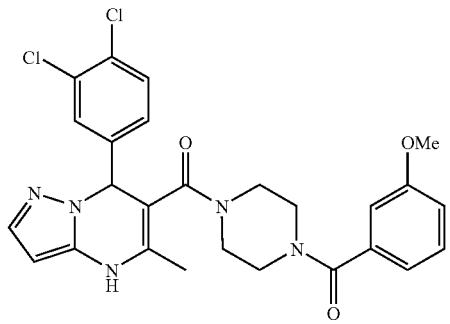

Compound 1: Compound 1 was prepared as described in Step A of Example 392.

Title Compound: Compound 1 (0.062 g, 0.15 mmol) and compound 2 (0.025 mL, 0.17 mmol) were suspended in dichloromethane (1 mL). Triethylamine (0.040, 0.29 mmol) was added. A clear solution results. TLC after 30 min indicated consumption of starting material. The mixture was loaded directly onto a Worldwide Monitoring CLEAN-UP CARTRIDGE (CUSIL12M6) which had been equilibrated with 100% hexanes. Elution with 100% hexanes (40 mL), followed by 50% Ethyl acetate/hexanes (100 mL) and 100% ethyl acetate (100 mL). The purest fractions (TLC analysis) were combined to give 0.022 g (29% yield) of the title compound as a white solid. Reverse Phase LC/MS: YMC S5 ODS 4.6×50 mm Ballistic column, UV detection at 220 λ, 4 min. gradient 40–100% Solvent B/A (Solvent A: 10% MeOH/H20 with 0.1% TFA, Solvent B: 90% MeOH/H$_2$O with 0.1% TFA), 4 mL/min. Rt=2.69 min, (90% pure). MS (M+H: 526).

EXAMPLES 398 AND 399

The compounds of Examples 398 and 399, shown in the table provided below, were prepared in a manner similar to that described in Example 397.

| Example | Structure | Name | (M + H) |
|---|---|---|---|
| 398 | 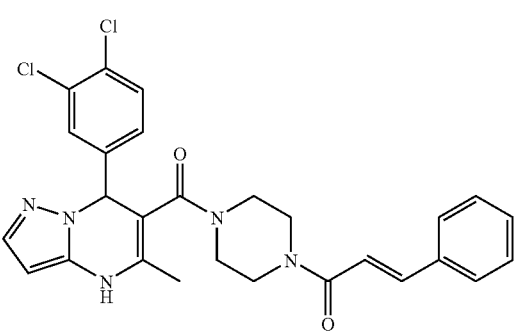 | 1-[[7-(3,4-Dichlorophenyl)-4,7-dihydro-5-methyl-pyrazolo[1,5-a]pyrimidin-6-yl]carbonyl]-4-(1-oxo-3-phenyl-2-propenyl)-piperazine | 522 |

| Example | Structure | Name | (M + H) |
| --- | --- | --- | --- |
| 399 | 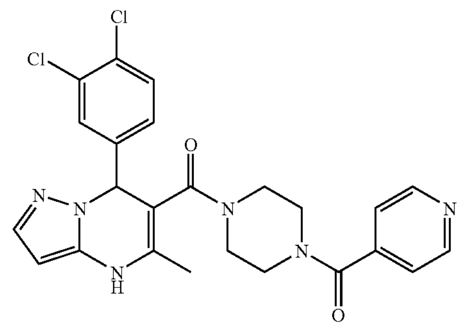 | 1-[[7-(3,4-Dichloro-phenyl)-4,7-dihydro-5-methyl-pyrazolo[1,5-a]pyrimidin-6-yl]carbonyl]-4-(4-pyridinylcarbonyl)piperazine | 497 |

EXAMPLE 400

1-[[7-(2,3-Dichlorophenyl)-4,7-dihydro-4,5-dimethylpyrazolo[1,5-a]pyrimidin-6-yl]carbonyl]-4-phenylpiperazine

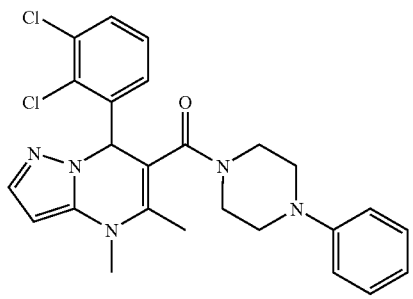

Method:

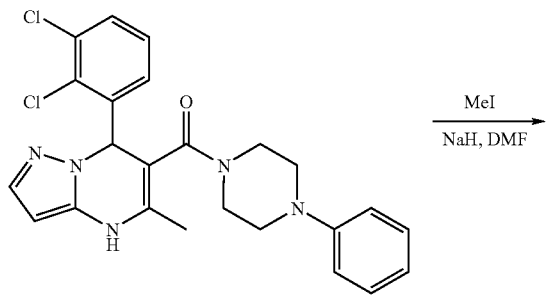

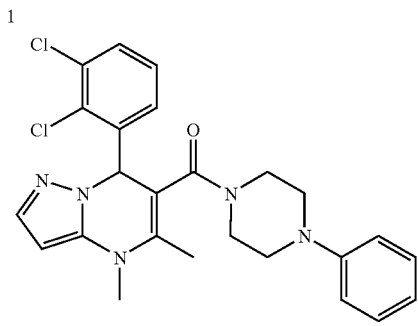

Compound 1: Compound 1 was prepared as described in Example 18.

Title Compound: Compound 1 (0.08 g, 0.17 mmol) was dissolved in dimethylformamide (1.0 mL). NaH (0.005 g, 0.22 mmol, 60% in oil) was added and the mixture was stirred for 5 min. Iodomethane (0.012 mL, 0.18 mmol) was added. When TLC (5% methanol/dichloromethane) analysis indicated consumption of starting material the reaction was quenched with water, diluted with ethyl acetate, transferred to a separatory funnel, washed with saturated water and brine, dried over anhydrous sodium sulfate and concentrated. The residue was purified by silica gel chromatography eluting with 100% dichloromethane followed by 3% methanol/dichloromethane to provide 0.06 g (75%) of the title compound as a amber oil. Reverse Phase LC/MS: YMC S5 ODS 4.6×50 mm Ballistic column, UV detection at 220 λ, 4 min. gradient 40–100% Solvent B/A (Solvent A: 10% MeOH/H20 with 0.1% TFA, Solvent B: 90% MeOH/$H_2O$ with 0.1% TFA), 4 mL/min. Rt=2.99 min, (96% pure). MS (M+H: 482).

EXAMPLES 401–406

The compounds of Examples 401–406, shown in the table provided below, were prepared in a manner similar to that described in Example 400.

HPLC resolution of Example 403, Chiralpak AD column (50×500 mm), eluting with 35% isopropanol/hexanes containing 0.1% triethylamine at 50 mL/min), UV detection at 254λ provided enantiomers A (Example 405) and B (Example 404). Chiralpak AD column (4.6×250 mm) eluting with 30% isopropanol/hexanes containing 0.1% triethylamine at 1 mL/min), UV detection at 254λ, enantiomer A Rt=14.4 min, >99% ee. Enantiomer B Rt=28.7 min, >99% ee.

| Example | Structure | Name | (M + H) |
|---|---|---|---|
| 401 | 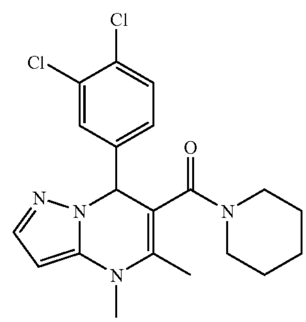 | 1-[[7-(3,4-Dichloro-phenyl)-4,7-dihydro-4,5-dimethyl-pyrazolo[1,5-a]pyrimidin-6-yl]carbonyl]piperidine | 405 |
| 402 | 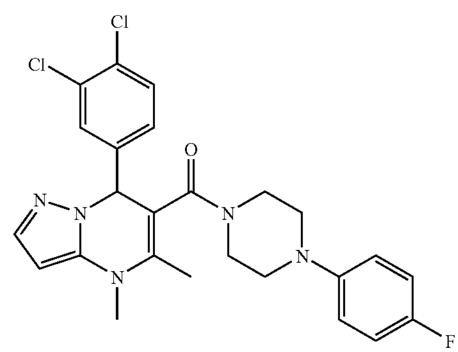 | 1-[[7-(3,4-Dichloro-phenyl)-4,7-dihydro-4,5-dimethyl-pyrazolo[1,5-a]pyrimidin-6-yl]carbonyl]-4-(4-fluoro-phenyl) piperazine | 500 |
| 403 | 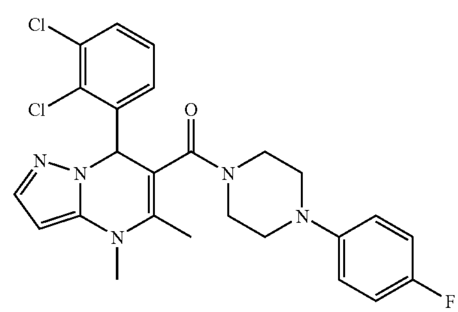 | 1-[[7-(2,3-Dichloro-phenyl)-4,7-dihydro-4,5-dimethyl-pyrazolo[1,5-a]pyrimidin-6-yl]carbonyl]-4-(4-fluoro-phenyl) piperazine | 500 |
| 404 | 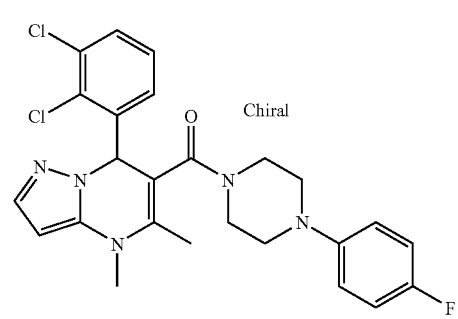 | 1-[[7-(2,3-Dichloro-phenyl)-4,7-dihydro-4,5-dimethyl-pyrazolo[1,5-a]pyrimidin-6-yl]carbonyl]-4-(4-fluoro-phenyl) piperazine, enantiomer B | 500 |

-continued

| Example | Structure | Name | (M + H) |
|---|---|---|---|
| 405 | *Chiral* | 1-[[7-(2,3-Dichloro-phenyl)-4,7-dihydro-4,5-dimethylpyrazolo[1,5-a]pyrimidin-6-yl]carbonyl]-4-(4-fluoro-phenyl)piperazine, enantiomer A | 500 |
| 406 | 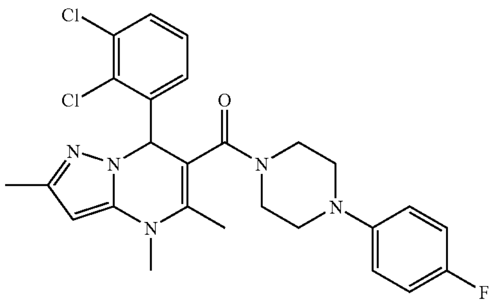 | 1-[[7-(2,3-Dichlorophenyl)-4,7-dihydro-2,4,5-trimethylpyrazolo[1,5-a]pyrimidin-6-yl]carbonyl]-4-(4-fluoro-phenyl)piperazine | 514 |

EXAMPLE 407

1-[[7-(2,3-Dichlorophenyl)-4-[(4-fluorophenyl)methyl]-4,7-dihydro-2,5-dimethylpyrazolo[1,5-a]pyrimidin-6-yl]carbonyl]-4-(4-fluorophenyl)piperazine

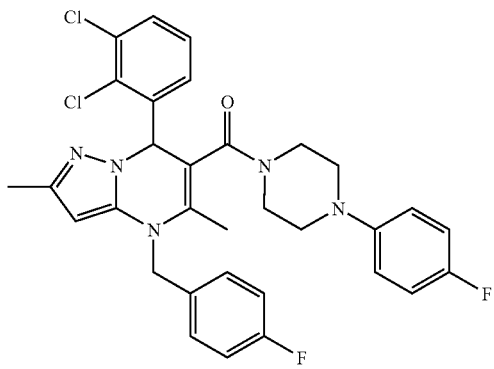

Method:

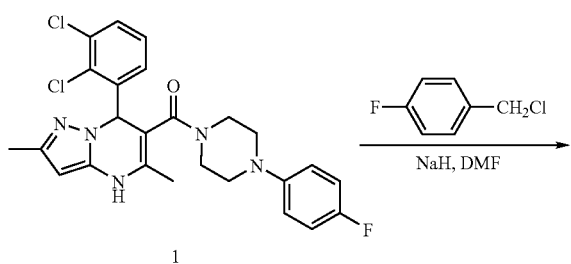

-continued

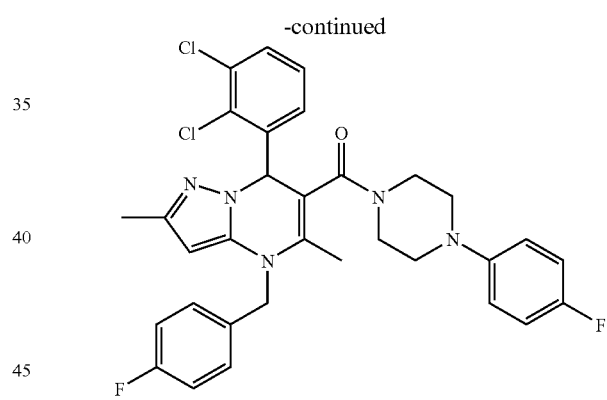

Compound 1: Compound 1 was prepared in a manner similar to that described in Example 18, Method 2.

Title Compound: Compound 1 (0.10 g, 0.21 mmol) was dissolved in dimethylformamide (1.0 mL). NaH (0.007 g, 0.27 mmol, 60% in oil) was added and the mixture was stirred for 5 min. 4-Fluorobenzyl chloride (0.028 mL, 0.23 mmol) was added. When TLC (5% methanol/dichloromethane) analysis indicated consumption of starting material the reaction was quenched with water, diluted with ethyl acetate, transferred to a separatory funnel, washed with saturated water and brine, dried over anhydrous sodium sulfate and concentrated. The residue was purified by silica gel chromatography eluting with 100% dichloromethane followed by 3% methanol/dichloromethane to provide 0.09 g (69%) of the title compound as a amber oil. Reverse Phase LC/MS: YMC S5 ODS 4.6×50 mm Ballistic column, UV detection at 220 λ, 4 min. gradient 40–100% Solvent B/A (Solvent A: 10% MeOH/H20 with 0.1% TFA, Solvent B: 90% MeOH/H$_2$O with 0.1% TFA), 4 mL/min. Rt=3.20 min, (93% pure). MS (M+H: 608).

EXAMPLE 408

7-(2,3-Dichlorophenyl)-6-[[4-(4-fluorophenyl)-1-piperazinyl]carbonyl]-2,5-dimethylpyrazolo[1,5-a]pyrimidine-4-(7H)-acetic acid ethyl ester

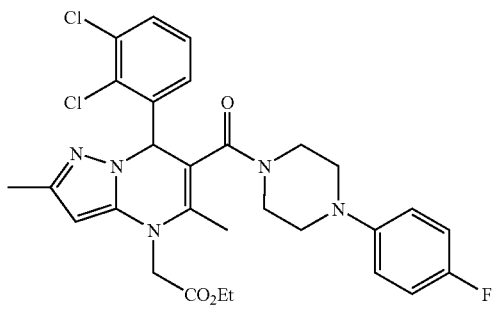

Method:

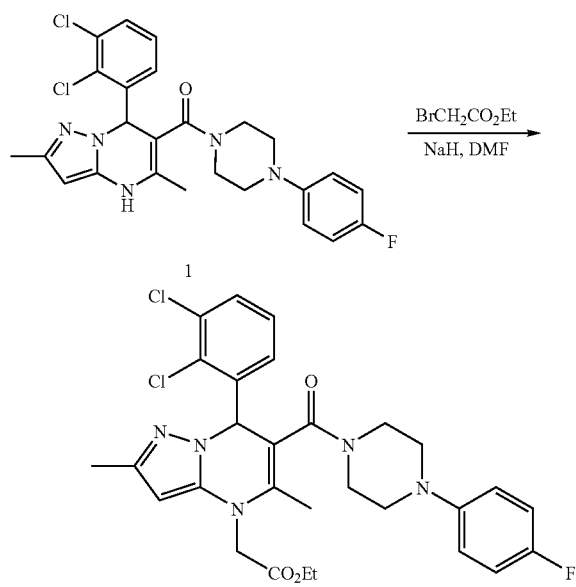

Compound 1: Compound 1 was prepared in a manner similar to that described in Example 18, Method 2.

Title Compound: Compound 1 (0.10 g, 0.21 mmol) was dissolved in dimethylformamide (1.0 mL). NaH (0.006 g, 0.24 mmol, 60% in oil) was added and the mixture was stirred for 5 min. Ethyl bromoacetate (0.029 mL, 0.26 mmol) was added. When TLC (5% methanol/dichloromethane) analysis indicated consumption of starting material the reaction was quenched with water, diluted with ethyl acetate, transferred to a separatory funnel, washed with saturated water and brine, dried over anhydrous sodium sulfate and concentrated. The residue was purified by silica gel chromatography eluting with 100% dichloromethane followed by 3% methanol/dichloromethane to provide 0.086 g (74%) of the title compound as a yellow glass. Reverse Phase LC/MS: YMC S5 ODS 4.6×50 mm Ballistic column, UV detection at 220 λ, 4 min. gradient 40–100% Solvent B/A (Solvent A: 10% MeOH/H20 with 0.1% TFA, Solvent B: 90% MeOH/H$_2$O with 0.1% TFA), 4 mL/min. Rt=3.22 min, (97% pure). MS (M+H: 586).

EXAMPLE 409

7-(2,3-Dichlorophenyl)-6-[[4-(4-fluorophenyl)-1-piperazinyl]carbonyl]-N,N,2,5-tetramethylpyrazolo[1,5-a]pyrimidine-4(7H)-acetamide

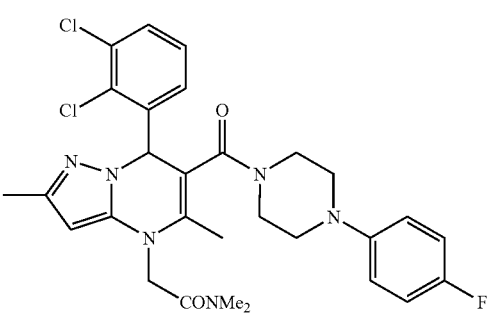

Method:

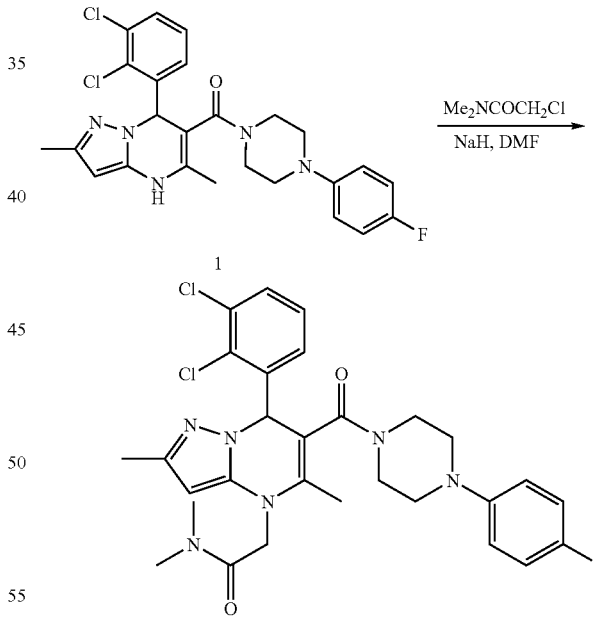

Compound 1: Compound 1 was prepared in a manner similar to that described in Example 18, Method 2.

Title Compound: Compound 1 (0.08 g, 0.16 mmol) was dissolved in dimethylformamide (0.8 mL). NaH (0.005 g, 0.19 mmol, 60% in oil) was added and the mixture was stirred for 5 min. 2-chloro-N,N-dimethylacetamide (0.021 mL, 0.21 mmol) was added. When TLC (5% methanol/dichloromethane) analysis indicated consumption of starting material the reaction was quenched with water, diluted with ethyl acetate, transferred to a separatory funnel, washed with water and saturated brine, dried over anhydrous sodium sulfate and concentrated. The residue was purified by silica gel chromatography eluting with 100% dichloromethane followed by 3% methanol/dichloromethane to provide 0.058 g (62%) of the title compound as a yellow oil. Reverse Phase LC/MS: YMC S5 ODS 4.6×50 mm Ballistic column, UV detection at 220 λ, 4 min. gradient 40–100% Solvent B/A (Solvent A: 10% MeOH/H20 with 0.1% TFA, Solvent B: 90% MeOH/H$_2$O with 0.1% TFA), 4 mL/min. Rt=2.63 min, (93% pure). MS (M+H: 585).

EXAMPLE 410

1-[[7-(2,3-Dichlorophenyl)-4-[2-(dimethylamino)ethyl]-4,7-dihydro-2,5-dimethylpyrazolo[1,5-a]pyrimidin-6-yl]carbonyl]-4-(4-fluorophenyl)piperazine

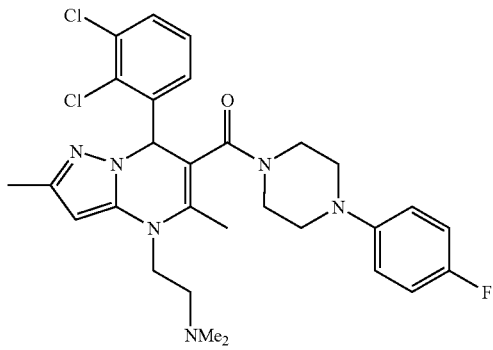

Method:

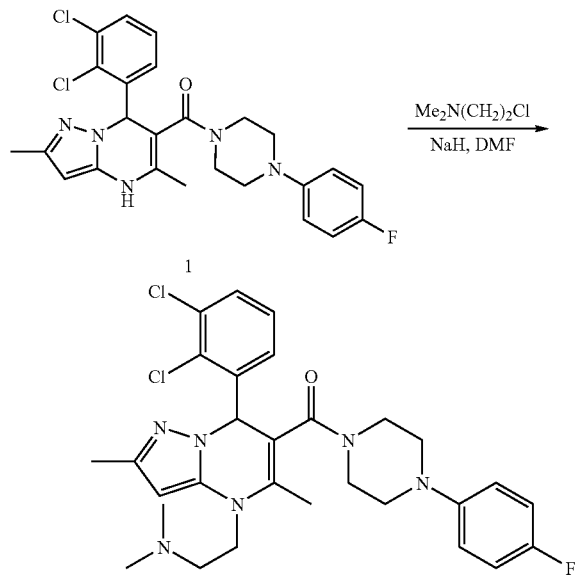

Compound 1: Compound 1 was prepared in a manner similar to that described in Example 18, Method 2.

Title Compound: Compound 1 (0.11 g, 0.21 mmol) was dissolved in dimethylformamide (1.0 mL). Sodium hydride (0.054 g, 0.47 mmol, 60% in oil) was added and the mixture was stirred for 5 min. 1-Chloro-2-dimethylaminoethane hydrochloride (0.040 g, 0.27 mmol) was added. After 25 min the reaction was quenched with water, diluted with ethyl acetate, transferred to a separatory funnel, washed with saturated water and brine, dried over anhydrous sodium sulfate and concentrated. LC/MS analysis of the residue indicated mostly unreacted starting material. The residue was redissolved in dimethylformamide (1.0 mL), Sodium hydride (0.10 g, 4.2 mmol) was added and the mixture was stirred for 5 min. 1-Chloro-2-dimethylaminoethane hydrochloride (0.15 g, 1.05 mmol) was added. When TLC (5% methanol/dichloromethane) analysis indicated consumption of starting material the reaction was quenched with water, diluted with ethyl acetate, transferred sodium sulfate and concentrated. The residue was purified by silica gel chromatography eluting with 100% dichloromethane followed by 3% methanol/dichloromethane to provide 0.030 g (25%) of the title compound as a yellow glass. Reverse Phase LC/MS: YMC S5 ODS 4.6×50 mm Ballistic column, UV detection at 220 λ, 4 min. gradient 40–100% Solvent B/A (Solvent A: 10% MeOH/H20 with 0.1% TFA, Solvent B: 90% MeOH/H$_2$O with 0.1% TFA), 4 mL/min. Rt=1.72 min, (92% pure). MS (M+H: 571).

EXAMPLE 411

1-[[4-(Cyclopropylmethyl)-7-(2,3-dichlorophenyl)-4,7-dihydro-2,5dimethylpyrazolo[1,5-a]pyrimidin-6-yl]carbonyl]-4-(4-fluorophenyl)piperazine

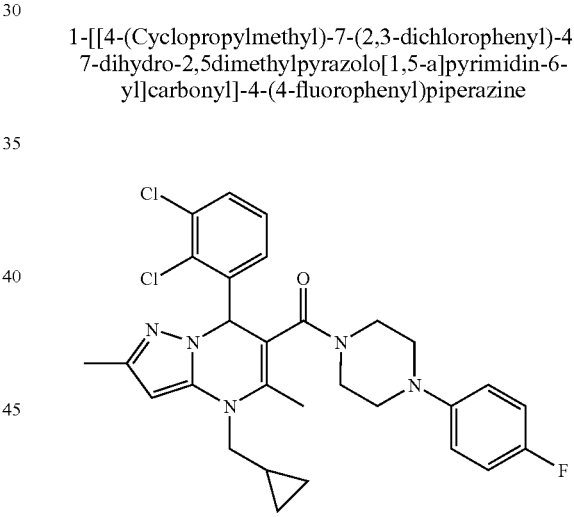

Method:

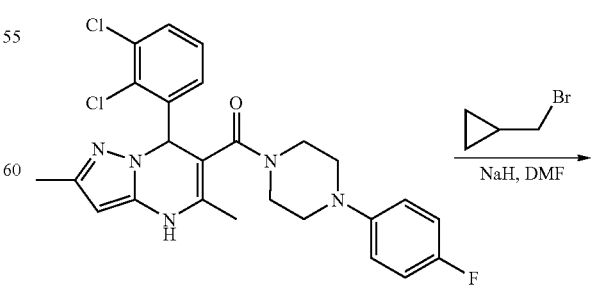

-continued

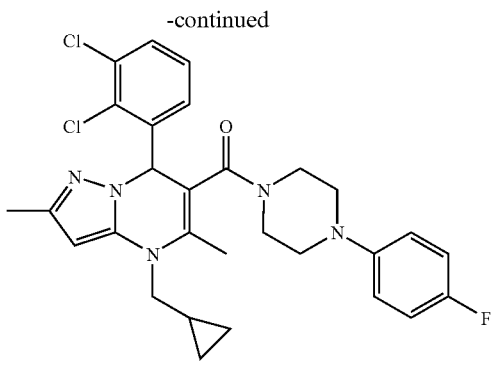

Compound 1: Compound 1 was prepared in a manner similar to that described in Example 18, Method 2.

Title Compound: Compound 1 (0.11 g, 0.21 mmol) was dissolved in dimethylformamide (1.0 mL). Sodium hydride (0.006 g, 0.25 mmol, 60% in oil) was added and the mixture was stirred for 5 min. (Bromomethyl)cylcopropane (0.0251 mL, 0.27 mmol) was added. When TLC (5% methanol/dichloromethane) analysis indicated consumption of starting material the reaction was quenched with water, diluted with ethyl acetate, transferred to a separatory funnel, washed with saturated water and brine, dried over anhydrous sodium sulfate and concentrated. The residue was purified by silica gel chromatography eluting with 100% dichloromethane followed by 3% methanol/dichloromethane to provide 0.104 g (89%) of the title compound as a yellow glass. Reverse Phase LC/MS: YMC S5 ODS 4.6×50 mm Ballistic column, UV detection at 220 λ, 4 min. gradient 40–100% Solvent B/A (Solvent A: 10% MeOH/H20 with 0.1% TFA, Solvent B: 90% MeOH/H$_2$O with 0.1% TFA), 4 mL/min. Rt=2.99 min, (95% pure). MS (M+H: 554).

EXAMPLE 412

7-(2,3-Dichlorophenyl)-6-[[4-(4-fluorophenyl)-1-piperazinyl]carbonyl]-N, N,2,5-tetramethylpyrazolo[1,5-a]pyrimidine-4(7H)-carboxamide

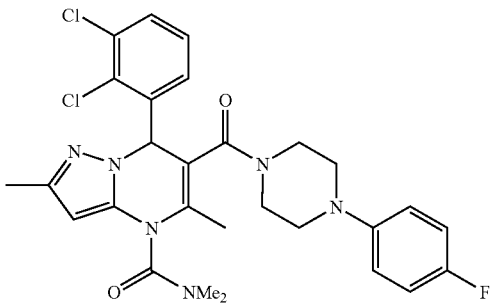

Method:

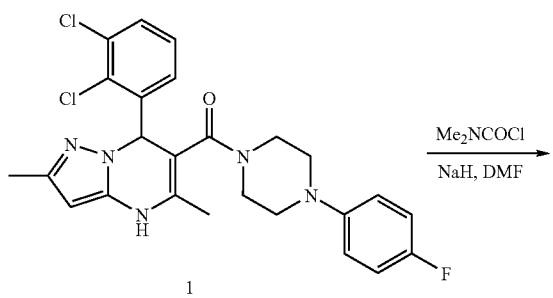

-continued

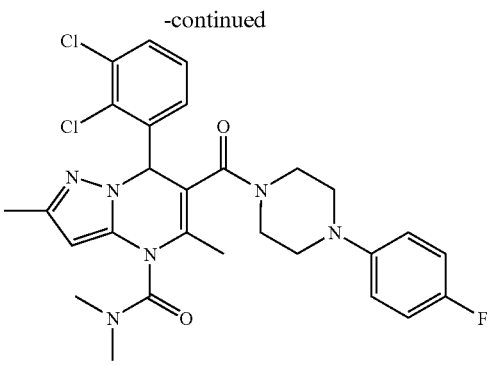

Compound 1: Compound 1 was prepared in a manner similar to that described in Example 18, Method 2.

Title Compound: Compound 1 (0.22 g, 0.44 mmol) was dissolved in tetrahydrofuran (3.0 mL). Sodium hydride (0.106 g, 4.44 mmol, 60% in oil) was added and the mixture was stirred for 5 min. N,N-Dimethylcarbamoyl chloride (0.12 mL, 1.33 mmol) was added. The mixture was stirred overnight. TLC (5% methanol/dichloromethane) analysis indicated consumption of starting material the reaction was quenched with water, diluted with ethyl acetate, transferred to a separatory funnel, washed with saturated water and brine, dried over anhydrous sodium sulfate and concentrated. The residue was purified by silica gel chromatography eluting with 100% dichloromethane followed by 3% methanol/dichloromethane to provide 0.22 g (87% yield) of the title compound. LC/MS indicated that the compound was impure. The title compound was further purified by silica gel chromatoagraphy eluting with 10% ethyl acetate/hexanes, followed by 50% ethyl acetate/hexanes and 100% ethyl acetate to afford 0.118 g (47% yield) of the title compound as a white glass. Reverse Phase LC/MS: YMC S5 ODS 4.6×50 mm Ballistic column, UV detection at 220 λ, 4 min. gradient 40–100% Solvent B/A (Solvent A: 10% MeOH/H20 with 0.1% TFA, Solvent B: 90% MeOH/H$_2$O with 0.1% TFA), 4 mL/min. Rt=2.45 min, (95% pure). MS (M+H: 571).

EXAMPLE 413

1-[[7-(2,3-Dichlorophenyl)-4,7-dihydro-4-methyl-5 (trifluoromethyl)pyrazolo[1,5-a]pyrimidin-6-yl]carbonyl]-4-(4fluorophenyl)piperazine

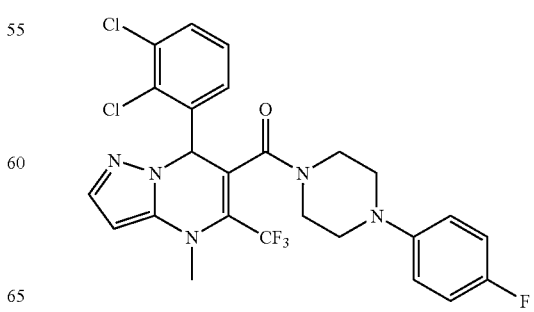

Method:

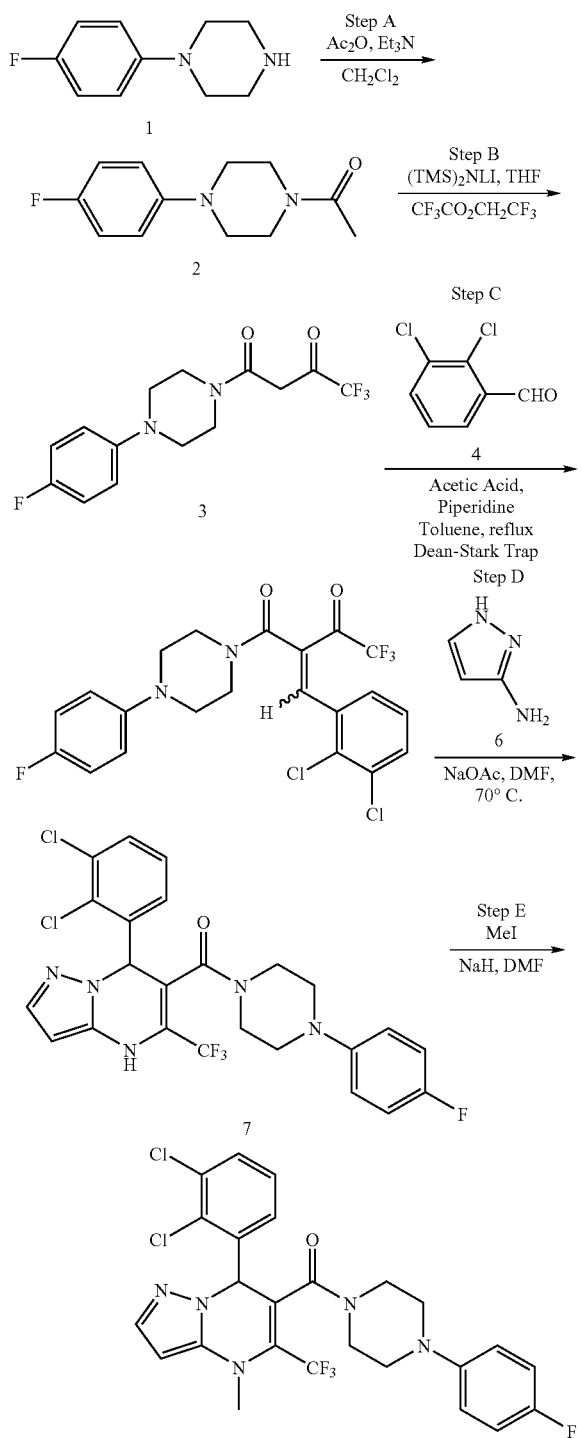

Step A: Acetic anhydride (0.77 mL, 8.14 mmol) was dropwise added to a solution of 4-(4-fluorophenyl)piperazine 1 (1.17 g, 6.49 mmol) in dichloromethane (10 mL). TLC after 30 min. indicated reaction was complete. The mixture was transferred to a separatory funnel, washed with water and brine, dried over anhydrous sodium sulfate and concentrated to give 1.28 g (89% yield) of compound 2 as a clear solid. Reverse Phase LC/MS: YMC S5 ODS 4.6×50 mm Ballistic column, UV detection at 220 λ, 4 min. gradient 0–100% Solvent B/A (Solvent A: 10% MeOH/H20 with 0.1% TFA, Solvent B: 90% MeOH/$H_2O$ with 0.1% TFA), 4 mL/min. Rt=1.58 min, (92% pure). MS (M+H: 223). HMR ($CDCl_3$, 400 MHz): 6.96(2H, m), 6.89(2H, m), 3.77(2H, m), 3.62(2H, m), 3.07(4H, m), 2.14(3H, s). Compound 2 was used without further purification in the next step.

Step B: Lithium hexamethyldisilylazide (6.1 mL, 6.1 mmol, 1M in tetrahydrofuran) was dropwise added to a −78° C. solution of compound 2 (1.22 g, 5.5 mmol) in tetrahydrofuran (25 mL). After 40 min. 2,2,2-trifluoroethyl trifluoroacetate (0.9 mL, 6.6 mmol) was added to the yellow solution. The reaction turned from yellow to clear. After an additional 10 min. the cooling bath was removed and the mixture was allowed to warm to room temperature. After 30 min. more the reaction was quenched with saturated ammonium chloride, diluted with ethyl acetate, transferred to a separatory funnel, washed with saturated ammonium chloride, water and brine, dried over anhydrous sodium sulfate and concentrated onto enough silica gel such that a free flowing powder was obtained. The resulting powder was loaded onto a chromatography column prepacked with silica gel and 30% ethylacetate/hexanes. Elution with 30% ethyl acetate/hexanes gave 0.998 g (57% yield) of compound 3 as a yellow solid. Reverse Phase LC/MS: YMC S5 ODS 4.6×50 mm Ballistic column, UV detection at 220 λ, 4 min. gradient 40–100% Solvent B/A (Solvent A: 10% MeOH/H20 with 0.1% TFA, Solvent B: 90% MeOH/$H_2O$ with 0.1% TFA), 4 mL/min. Rt=2.87 min, (90% pure). MS (M+H: 319). HMR ($CDCl_3$, 400 MHz): (note compound exists in the enol form) 7.00(2H, m), 6.90(2H, m), 5.80(1H, s), 3.79 (4H, m), 3.13(4H, m).

Step C: Compound 3 and compound 4 were condensed as described in Example 18, Method 2 Step B, to provide compound 5. Compound 5 was used in the next step without further purification.

Step D: Compound 5 and compound 6 were condensed as described in Example 18, Method 2 Step C1, to afford compound 7. Reverse Phase LC/MS of crude 6: YMC S5 ODS 4.6×50 mm Ballistic column, UV detection at 220 λ, 4 min. gradient 0–100% Solvent B/A (Solvent A: 10% MeOH/H20 with 0.1% TFA, Solvent B: 90% MeOH/$H_2O$ with 0.1% TFA), 4 mL/min. Rt=4.12 min, (58% pure). MS (M+H: 540). Compound 7 was purified by silica gel chromatography eluting with 20–50% ethyl acetate/hexanes followed by recrystallization from ethyl acetate/hexanes to give 0.084 g (6% yield) of compound 7 as a white solid. Reverse Phase LC: YMC S5 ODS 4.6×50 mm Ballistic column, UV detection at 220 λ, 4 min. gradient 0–100% Solvent B/A (Solvent A: 10% MeOH/H20 with 0.2% $H_3PO_4$, Solvent B: 90% MeOH/$H_2O$ with 0.2% $H_3PO_4$), 4 mL/min. Rt=4.15 min, (92% pure).

Step E: Compound 7 (0.08 g, 0.14 mmol) was dissolved in dimethylformamide (1.0 mL). NaH (0.005 g, 0.19 mmol, 60% in oil) was added and the mixture was stirred for 305 min. Iodomethane (0.010 mL, 0.16 mmol) was added. The mixture was stirred for 2 h and then quenched with saturated ammonium chloride, diluted with ethyl acetate, transferred to a separatory funnel, washed with saturated water and brine, dried over anhydrous sodium sulfate and concentrated. The residue was purified by preparative reverse phase HPLC:YMC S5 ODS 20×100 mm Ballistic column, UV detection at 220 λ, 10 min. gradient 30–100% Solvent B/A (Solvent A: 10% MeOH/H20 with 0.1% TFA, Solvent B: 90% MeOH/$H_2O$ with 0.1% TFA), 20 mL/min. Rt=10.6 min, to provide 0.037 g (45%) of the title compound. Reverse Phase LC/MS: YMC S5 ODS 4.6×50 mm Ballistic column, UV detection at 220 λ, 4 min. gradient 0–100% Solvent B/A (Solvent A: 10% MeOH/H20 with 0.1% TFA, Solvent B: 90% MeOH/H$_2$O with 0.1% TFA), 4 mL/min. Rt=3.83 min. MS (M+H: 568). Reverse Phase LC: YMC S5 ODS 4.6×50 mm Ballistic column, UV detection at 220 λ, 4 min. gradient 0–100% Solvent B/A (Solvent A: 10% MeOH/H20 with 0.2% H$_3$PO$_4$, Solvent B: 90% MeOH/H$_2$O with 0.2% H$_3$PO$_4$), 4 mL/min. Rt=4.37 min., 89% pure.

EXAMPLES 414–421

The compounds of Examples 414–421, shown in the table provided below, were prepared in a manner similar to that described in Example 413.

HPLC resolution of Example 416, Chiralpak AD column (50×500 mm), eluting with 50% isopropanol/hexanes containing 0.1% triethylamine at 50 mL/min), UV detection at 254λ, provided enantiomers A (Example 418) and B (Example 417). Chiralpak AD column (4.6×250 mm) eluting with 50% isopropanol/hexanes containing 0.1% triethylamine at 1 mL/min), UV detection at 254λ, enantiomer A Rt=14.4 min, 89% ee. Enantiomer B Rt=28.7 min, 87% ee.

| Example | Structure | Name | (M + H) |
|---|---|---|---|
| 414 | 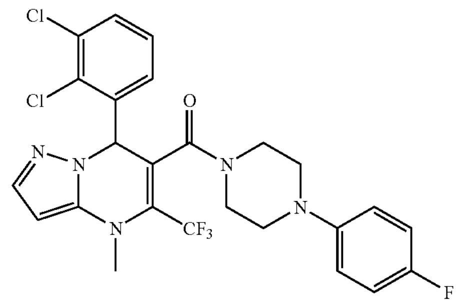 | 1-[[7-(2,3-Dichlorophenyl)-4,7-dihydro-5-(trifluoromethyl)pyrazolo[1,5-a]pyrimidin-6-yl]carbonyl]-4-(4-fluorophenyl)piperazine | 554 |
| 415 | 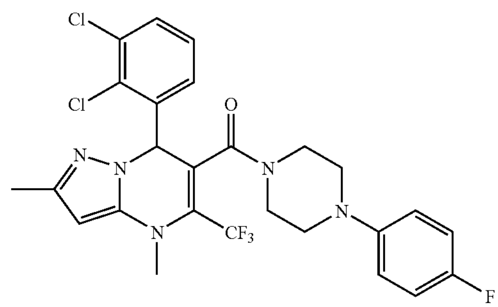 | 1-[[7-(2,3-Dichlorophenyl)-4,7-dihydro-2-methyl-5-(trifluoromethyl)pyrazolo[1,5-a]pyrimidin-6-yl]carbonyl]-4-(4-fluorophenyl)piperazine | 554 |
| 416 | 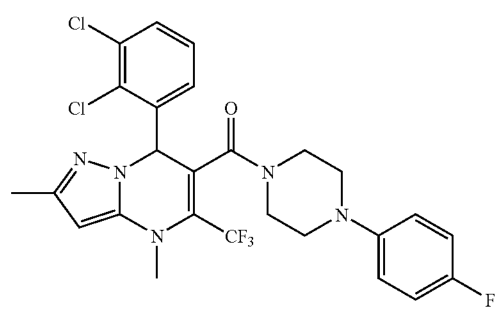 | 1-[[7-(2,3-Dichlorophenyl)-4,7-dihydro-2,4-dimethyl-5-(trifluoromethyl)pyrazolo[1,5-a]pyrimidin-6-yl]carbonyl]-4-(4-fluorophenyl)piperazine | 568 |
| 417 | 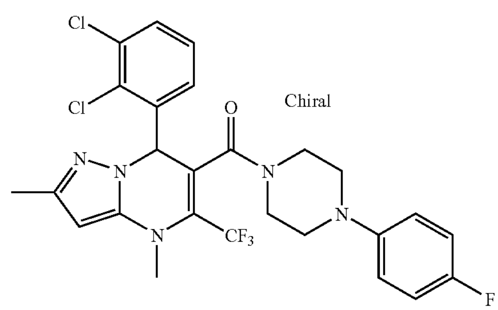 | 1-[[7-(2,3-Dichlorophenyl)-4,7-dihydro-2,4-dimethyl-5-(trifluoromethyl)pyrazolo[1,5-a]pyrimidin-6-yl]carbonyl]-4-(4-fluorophenyl)piperazine, enantiomer B | 568 |

-continued

| Example | Structure | Name | (M + H) |
|---|---|---|---|
| 418 | Chiral | 1-[[7-(2,3-Dichloro-phenyl)-4,7-dihydro-2,4-di-methyl-5-(trifluoro-methyl)pyrazolo[1,5-a]py-rimidin-6-yl]car-bonyl]-4-(4-fluoro-phenyl)piperazine, enantiomer A | 568 |
| 419 | 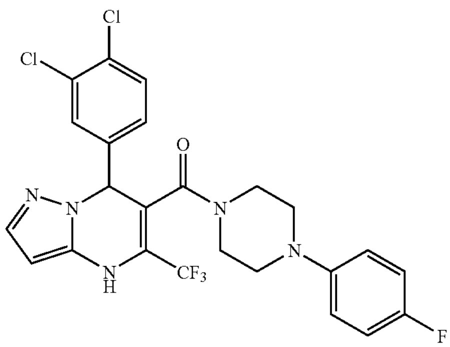 | 1-[[7-(3,4-Dichloro-phenyl)-4,7-dihydro-5-(tri-fluoromethyl)pyrazolo[1,5-a]py-rimidin-6-yl]car-bonyl]-4-(4-fluoro-phenyl)piperazine | 540 |
| 420 | 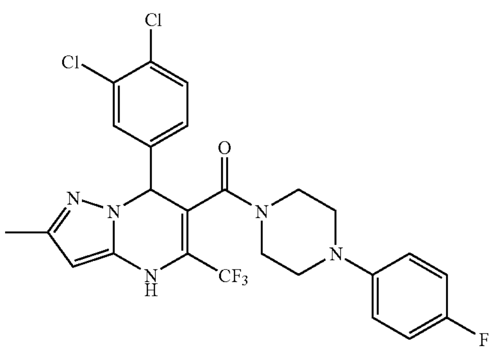 | 1-[[7-(3,4-Dichloro-phenyl)-4,7-dihydro-2-meth-yl-5-(trifluoro-methyl)pyrazolo[1,5-a]py-rimidin-6-yl]car-bonyl]-4-(4-fluoro-phenyl)piperazine | 554 |

EXAMPLE 421

1-[[1-Benzoyl-7-(2,3-dichlorophenyl)-1,2,4,7-tet-rahydro-5-methyl-2-oxopyrazolo[1,5-a]pyrimidin-6-yl]carbonyl]-4-phenylpiperazine Method:

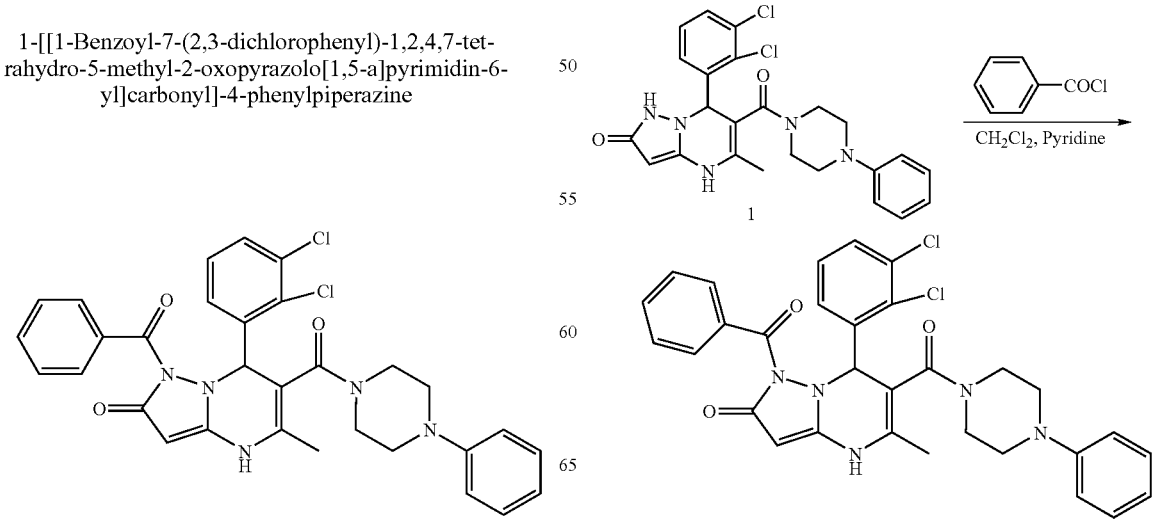

Compound 1: Compound 1 was prepared in manner similar to that described in Example 18, Method 2.

Title Compound: Benzoyl chloride (0.007 mL, 0.06 mmol) and pyridine (0.008 mL, 0.10 mmol) were added to a 0° C. solution of compound 1 (0.08 g, 0.17 mmol) in dichloromethane (5 mL). After 1 h, TLC indicated the reaction was complete. The reaction was quenched with methanol and concentrated. The residue was purified by silica gel chromatography eluting with 80% ethyl acetate/ hexanes to afford 0.024 g (81%) of the title compound as a white solid. Reverse Phase LC/MS: YMC S5 ODS 4.6×50 mm Ballistic column, UV detection at 220 λ, 4 min. gradient 0–100% Solvent B/A (Solvent A: 10% MeOH/H20 with 0.1% TFA, Solvent B: 90% MeOH/H$_2$O with 0.1% TFA), 4 mL/min. Rt=4.05 min, (86% pure). (M+H: 588). HMR (CDCl$_3$, 400 MHz): 8.08(1H, s), 8.06(1H, s), 7.51(1H, m), 7.37(2H, t, J=8 Hz), 7.28(1H, m), 7.18(2H, m), 7.08(1H, m), 6.9–6.7(3H, m), 6.45 (1H, bs), 5.60(1H, bs), 4.15–2.8 (6H, m), 2.20(1H, bs), 1.88(3H, s), 1.45(1H, bs).

EXAMPLES 422–431

The compounds of Examples 422–431, shown in the table provided below, were prepared in a manner similar to that described in Example 421.

| Example | Structure | Name | (M + H) |
| --- | --- | --- | --- |
| 422 | 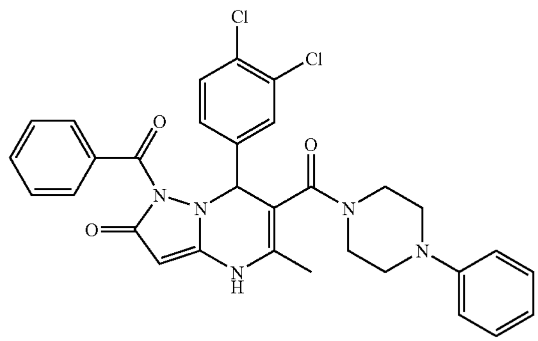 | 1-[[1-Benzoyl-7-(3,4-di-chlorophenyl)-1,2,4,7-tetra-hydro-5-methyl-2-oxo-pyrazolo[1,5-a]pyrimidin-6-yl]carbonyl]-4-phenyl-piperazine | 588 |
| 423 | 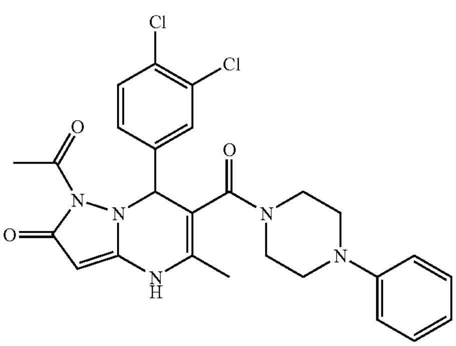 | 1-[[1-Acetyl-7-(3,4-di-chlorophenyl)-1,2,4,7-tetra-hydro-5-methyl-2-oxo-pyrazolo[1,5-a]pyrimidin-6-yl]carbonyl]-4-phenyl-piperazine | 526 |
| 424 | 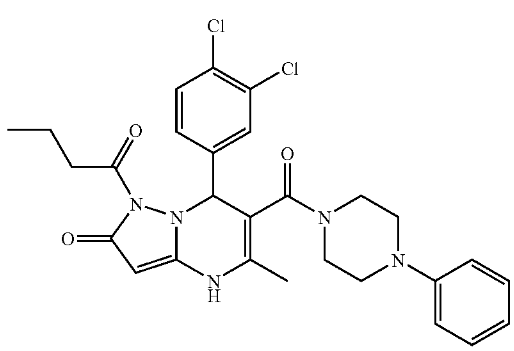 | 1-[[7-(3,4-Dichloro-phenyl)-1,2,4,7-tetra-hydro-5-methyl-2-oxo-1-(1-oxo-butyl)-pyrazolo[1,5-a]pyrimidin-6-yl]carbonyl]-4-phenylpiperazine | 554 |

-continued

| Example | Structure | Name | (M + H) |
|---|---|---|---|
| 425 | 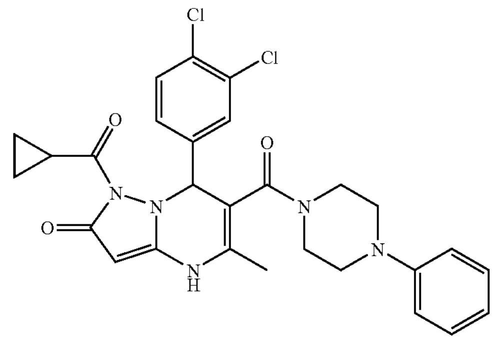 | 1-[[1-(Cyclopropyl-carbonyl)-7-(3,4-di-chlorophenyl)-1,2,4,7-tetra-hydro-5-methyl-2-oxo-pyrazolo[1,5-a]py-rimidin-6-yl]car-bonyl]-4-phenyl-piperazine | 552 |
| 426 | 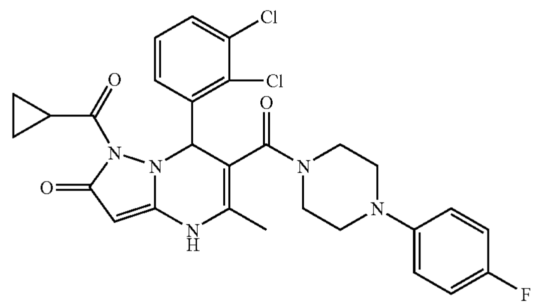 | 1-[[1-(Cyclopropyl-carbonyl)-7-(2,3-di-chlorophenyl)-1,2,4,7-tetra-hydro-5-methyl-2-oxo-pyrazolo[1,5-a]py-rimidin-6-yl]car-bonyl]-4-(4-fluoro-phenyl)piperazine | 570 |
| 427 | 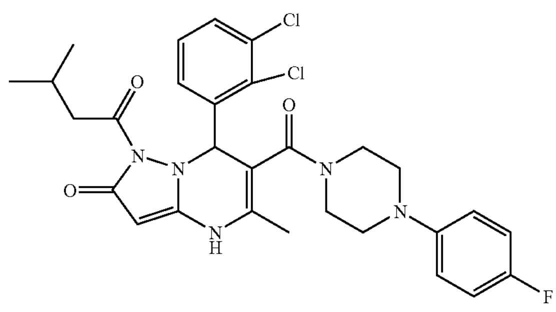 | 1-[[7-(2,3-Dichloro-phenyl)-1,2,4,7-tetra-hydro-5-methyl-1-(3-methyl-1-oxo-butyl)-2-oxopyra-zolo[1,5-a]pyri-midin-6-yl]carbo-nyl]-4-(4-fluorophenyl)-piperazine | 586 |
| 428 | 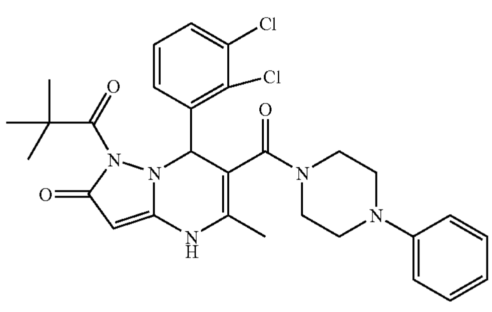 | 1-[[7-(2,3-Dichloro-phenyl)-(2,2,-dimethyl-1-oxo-propyl)-1,2,4,7-tetra-hydro-5-methyl-2-oxo-pyrazolo[1,5-a]py-rimidin-6-yl]car-bonyl]-4-phenyl-piperazine | 568 |

-continued

| Example | Structure | Name | (M + H) |
|---|---|---|---|
| 429 | 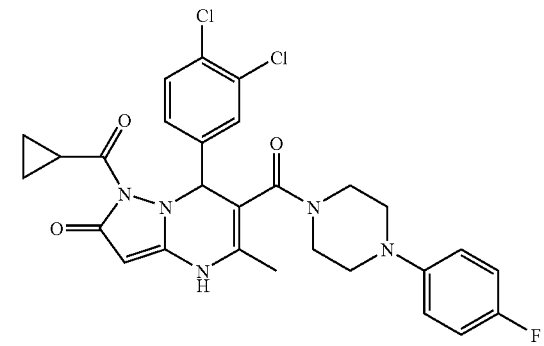 | 1-[[1-(Cyclopropyl-carbonyl)-7-(3,4-di-chlorophenyl)-1,2,4,7-tetra-hydro-5-methyl-2-oxo-pyrazolo[1,5-a]py-rimidin-6-yl]car-bonyl]-4-(4-fluoro-phenyl)piperazine | 570 |
| 430 | 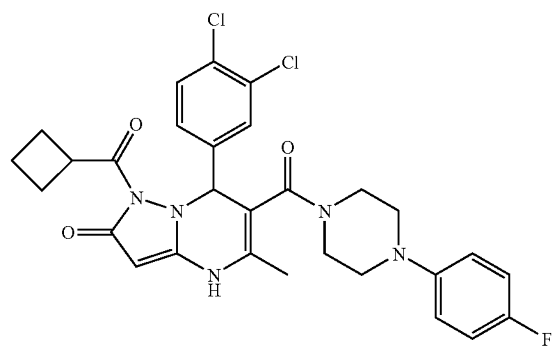 | 1-[[1-(Cyclobutyl-carbonyl)-7-(3,4-di-chlorophenyl)-1,2,4,7-tetra-hydro-5-methyl-2-oxo-pyrazolo[1,5-a]py-rimidin-6-yl]car-bonyl]-4-(4-fluoro-phenyl)piperazine | 584 |
| 431 | 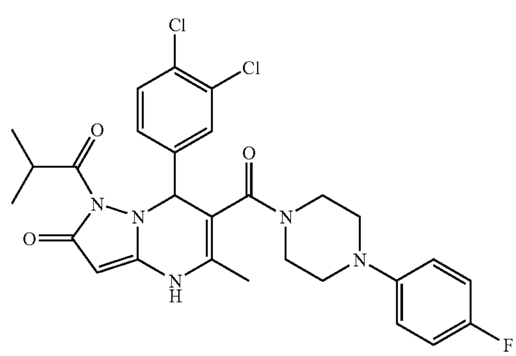 | 1-[[7-(3,4-Dichloro-phenyl)-1,2,4,7-tetra-hydro-5-methyl-1-(2-meth-yl-1-oxopropyl)-2-oxo-pyrazolo[1,5-a]py-rimidin-6-yl]car-bonyl]-4-(4-fluoro-phenyl)piperazine | 572 |

EXAMPLE 432

1-[[7-(2,3-Dichlorophenyl)-1,2,4,7-tetrahydro-5-methyl-1-[(1-methylethyl)sulfonyl]-2-oxopyrazolo[1,5-a]pyrimidin-6-yl]carbonyl]-4-phenylpiperazine

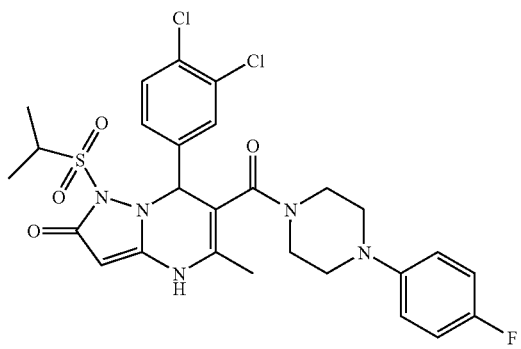

EXAMPLE 433

1-[[7-(3,4-Dichlorophenyl)-1,2,4,7-tetrahydro-5-methyl-1-[(1-methylethyl)sulfonyl]-2-oxopryazolo[1,5-a]pyrimidin-6-yl]carbonyl]-4-(4-fluorophenyl)piperazine

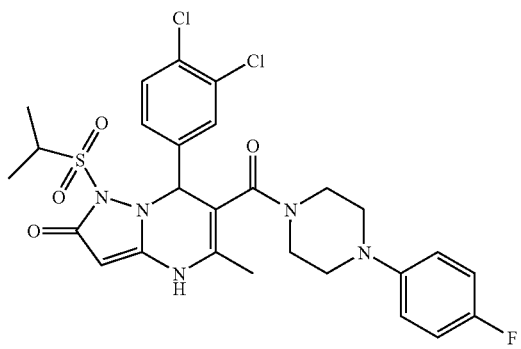

The title compound was prepared in a manner similar to that described in Example 432. (M+H) 608.

EXAMPLE 434

7-(2,3-Dichlorophenyl)-4,7-dihydro-5-methyl-N-(1-methylethyl)-2-oxo-6-[(4-phenyl-1-piperazinyl)carbonyl]pyrazolo[1,5-a]pyrimidine-1(2H)-carboxamide

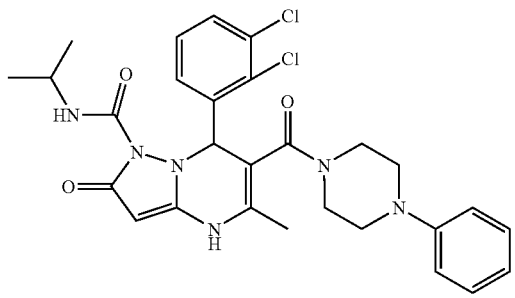

Method:

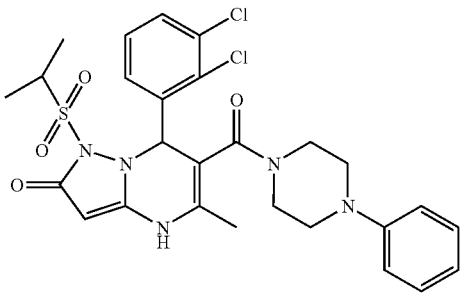

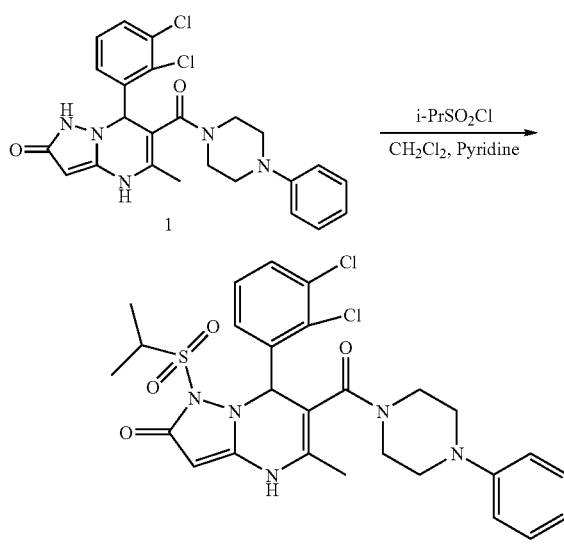

Compound 1: Compound 1 was prepared in a manner similar to that described in Example 18, Method 2.

Title Compound: Isopropylsulfonyl chloride (0.11 mL, 0.97 mmol) and pyridine (0.12 mL, 1.46 mmol) were added to a 0° C. solution of compound 1 (0.234 g, 0.487 mmol) in dichloromethane (10 mL). The resulting mixture was allowed to warm to room temperature. After 5 h, TLC indicated the reaction was complete. The reaction was quenched with methanol and concentrated. The residue was purified by silica gel chromatography eluting with 5% methanol/ethyl acetate to afford 0.095 g (33%) of the title compound as a pale yellow solid. Reverse Phase LC/MS: YMC S5 ODS 4.6×50 mm Ballistic column, UV detection at 220 λ, 4 min. gradient 0–100% Solvent B/A (Solvent A: 10% MeOH/H20 with 0.1% TFA, Solvent B: 90% MeOH/H$_2$O with 0.1% TFA), 4 mL/min. Rt=3.57 min, (92% pure). (M+H: 590).

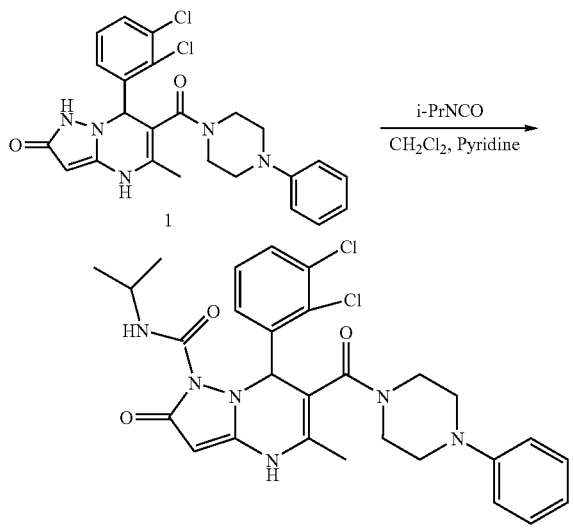

Compound 1: Compound 1 was prepared in a manner similar to that described in Example 18, Method 2.

Title Compound: Isopropyl isocyanate (0.034 mL, 0.35 mmol) and pyridine (0.057 mL, 0.706 mmol) were added to a 0° C. solution of compound 1 (0.170 g, 0.350 mmol) in dichloromethane (50 mL). The resulting mixture was allowed to warm to room temperature. After 5 h, TLC indicated the reaction was complete. The reaction was quenched with methanol and concentrated. The residue was purified by silica gel chromatography eluting with 75% ethyl acetate/hexanes to afford 0.027 g (13%) of the title compound as a white solid. Reverse Phase LC/MS: YMC S5 ODS 4.6×50 mm Ballistic column, UV detection at 220 λ, 4 min. gradient 0–100% Solvent B/A (Solvent A: 10% MeOH/H20 with 0.1% TFA, Solvent B: 90% MeOH/H$_2$O with 0.1% TFA), 4 mL/min. Rt=3.68 min, (95% pure). (M+H: 569).

EXAMPLES 435 and 436

The compounds of Examples 435 and 436, shown in the table provided below, were prepared in a manner similar to that described in Example 434.

EXAMPLE 437

7-(3,4-Dichlorophenyl)-6-[[4-(4-fluorophenyl)-1-piperazinyl]carbonyl]-4,7-dihydro-N,N,5-trimethyl-2-oxopyrazolo[1,5-a]pyrimidine-1(2H)-carboxamide

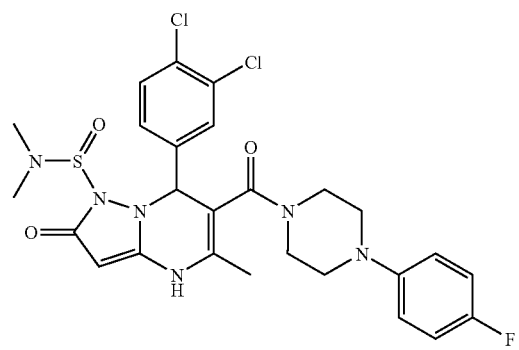

| Example | Structure | Name | (M + H) |
|---|---|---|---|
| 435 | ![structure] | 7-(2,3-Dichlorophenyl)-4,7-dihydro-N,5-dimethyl-2-oxo-6-[(4-phenyl-1-piperazinyl)-carbonyl]pyrazolo[1,5-a]pyrimidine-1(2H)-carboxamide | 541 |
| 436 | ![structure] | 7-(2,3-Dichlorophenyl)-4,7-dihydro-5-methyl-2-oxo-6-[(4-phenyl-1-piperazinyl)carbonyl]-pyrazolo[1,5-a]pyrimidine-1(2H)-carboxamide | 527 |

Method:

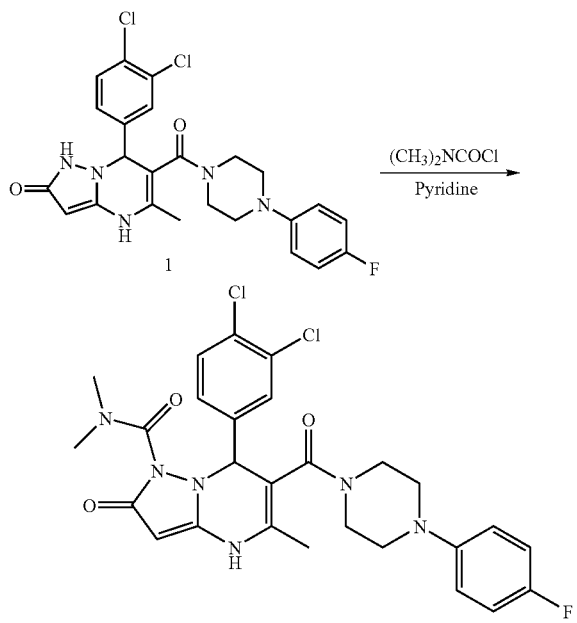

Compound 1: Compound 1 was prepared in a manner similar to that described in Example 18, Method 2.

Title Compound: Dimethylcarbamoyl chloride (0.10 mL, 1.1 mmol) was added to a 0° C. solution of compound 1 (0.52 g, 1.0 mmol) in pyridine (5 mL). The resulting mixture was stirred at 0° C. for 30 min., the cooling bath was removed, and the mixture was concentrated. The residue was dissolved in ethyl acetate and washed with water and brine, dried over anhydrous sodium sulfate and concentrated. The residue was purified by silica gel chromatography eluting with 5% methanol/ethyl acetate to afford 0.038 g (6%) of the title compound as a white solid. Reverse phase LC/MS: YMC S5 TurboPack Pro 4.6×33 column, UV detection at 220 λ, 2 min gradient 0–100% Solvent B/A (Solvent A: 10% MeOH/H$_2$O with 0.1% TFA, Solvent B: 90% MeOH/H$_2$O with 0.1% TFA), 4 mL/min. Rt=1.97 min, 92% pure). MS (M+H: 573).

EXAMPLE 438

1-[[(3-Butenyl)-7-(3,4-dichlorophenyl)-1,2,4,7-tetrahydro-5-methyl-2-oxopyrazolo[1,5-a]pyrimidin-6-yl]carbonyl]-4-(4-fluorophenyl)piperazine

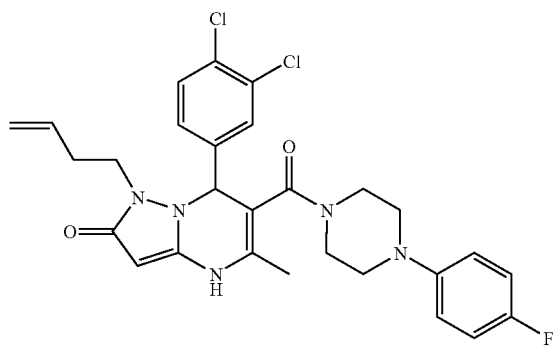

Method:

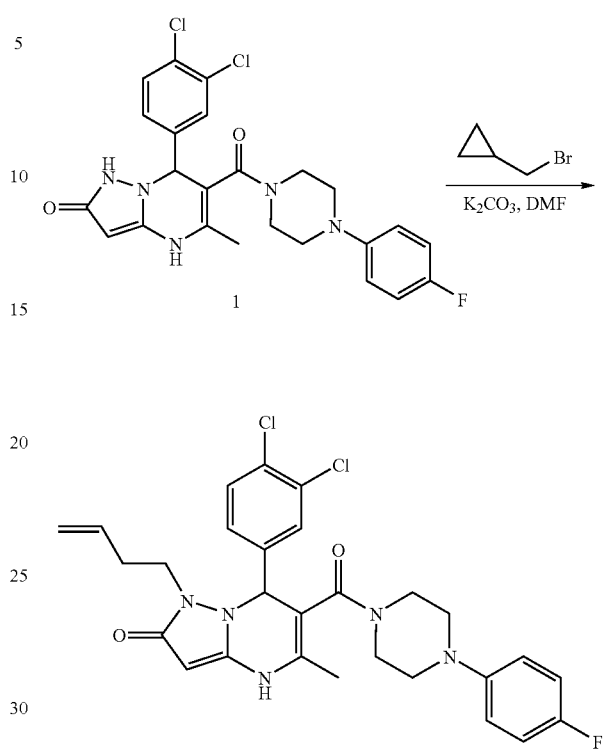

Compound 1: Compound 1 was prepared in a manner similar to that described in Example 18, Method 2.

Title Compound: (Bromomethyl)cyclopropane (0.246 mL, 1.82 mmol) was added to a mixture of compound 1 (0.831 g, 1.66 mmol) and potassium carbonate (g, mmol) in dimethylformamide (10 mL). The resulting mixture was allowed to stir at room temperature for 4 h. The reaction was diluted with ethyl acetate, transferred to a separatory funnel, washed with water and brine, dried over anhydrous sodium sulfate and concentrated. The residue was purified by silica gel chromatography eluting with 5% methanol/ethyl acetate to afford 0.030 g (3%) of the title compound. Reverse Phase LC/MS: YMC S5 ODS 4.6×50 mm Ballistic column, UV detection at 220 λ, 4 min. gradient 0–100% Solvent B/A (Solvent A: 10% MeOH/H20 with 0.1% TFA, Solvent B: 90% MeOH/H$_2$O with 0.1% TFA), 4 mL/min. Rt=2.99 min, (87% pure). (M+H): 556).

EXAMPLES 439 and 440

1-[[7-(3,4-Dichlorophenyl)-1,2,4,7-tetrahydro-5-methyl-2-oxo-1-(2,2,2-trifluoroethyl)pyrazolo-[1,5-a]pyrimidin-6-yl]carbonyl]-4-(4-fluoro- -continued phenyl)piperazine

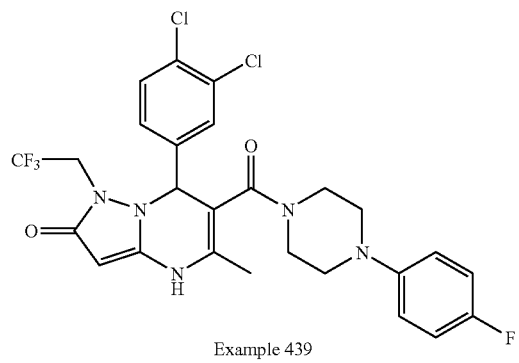

Example 439

1-[[7-(3,4-Dichlorophenyl)-1,2,4,7-tetrahydro-5-methyl-2-oxo-1,4-bis(2,2,2-trifluoroethyl)pyrazolo[1,5-a]pyrimidin-6-yl]carbonyl]-4-(4-fluorophenyl)piperazine

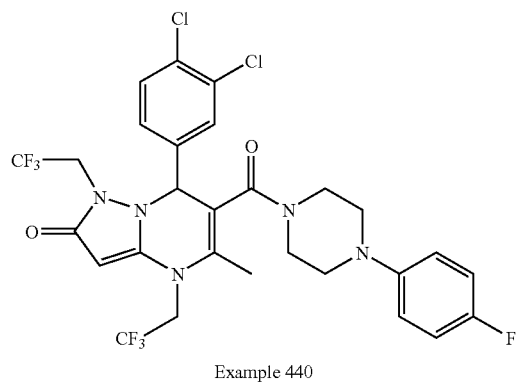

Example 440

Method:

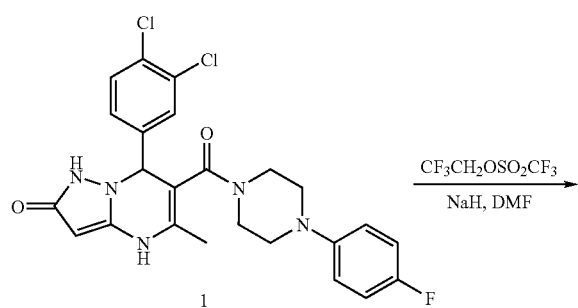

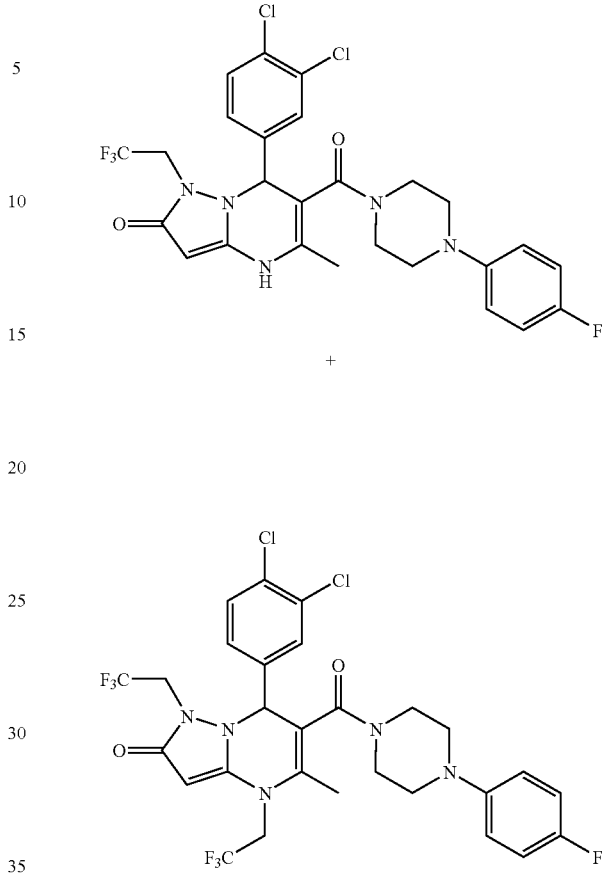

Compound 1: Compound 1 was prepared in a manner similar to that described in Example 18, Method 2.

Title Compounds: 2,2,2-trifluoroethyl trifluormethanesulfonate (0.49 g, 2.1 mmol) was added to a solution of compound 1 (0.967 g, 1.93 mmol) in dimethylformamide (10 mL). Sodium hydride (0.12 g, 2.89 mmol) was added. TLC (10% methanol/ethyl acetate) indicated consumption of compound 1. The resulting mixture was diluted with ethyl acetate, transferred to a separatory funnel, washed with water and brine, dried over anhydrous sodium sulfate and concentrated. The residue was purified by silica gel chromatography eluting with 100% ethyl acetate followed by 10% methanol/ethyl acetate to give a mixture of the title compounds. The title compounds were separated by preparative reverse phase HPLC YMC S5 ODS 20×100 mm column, 25 mL/min, 15 minute gradient eluting with 50%–100% solvent B/A (Solvent A: 10% MeOH/H20 with 0.1% TFA, Solvent B: 90% MeOH/$H_2O$ with 0.1% TFA). Compound of Example 439 Rt=11.05 min, Compound of Example 440 Rt=11.88 min. Compound of Example 439: Reverse phase LC/MS: YMC S5 4.6×50 Ballistic column, UV detection at 220 λ, 4 min gradient 0–100% Solvent B/A (Solvent A: 10% MeOH/$H_2O$ with 0.1% TFA, Solvent B: 90% MeOH/$H_2O$ with 0.1% TFA), 4 mL/min. Rt=2.87 min, 95% pure). MS (M+H: 584). Compound of Example 440: Reverse phase LC/MS: YMC S5 4.6×50 Ballistic column, UV detection at 220 λ, 4 min gradient 0–100% Solvent B/A (Solvent A: 10% MeOH/$H_2O$ with 0.1% TFA, Solvent B: 90% MeOH/$H_2O$ with 0.1% TFA), 4 mL/min. Rt=3.25 min, 85% pure). MS (M+H: 666).

EXAMPLE 441

7-(3,4-Dichlorophenyl)-6-[[4-(4-fluorophenyl)-1-piperazinyl]carbonyl]-4,7dihydro-5-methyl-2-oxopyrazolo[1,5-a]pyrimidine-1 (2H)-carboxylic Acid 1-methylethyl ester

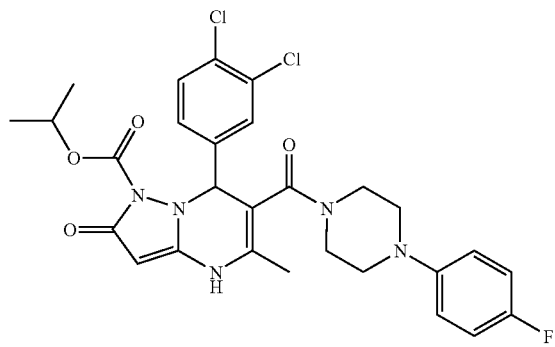

Method:

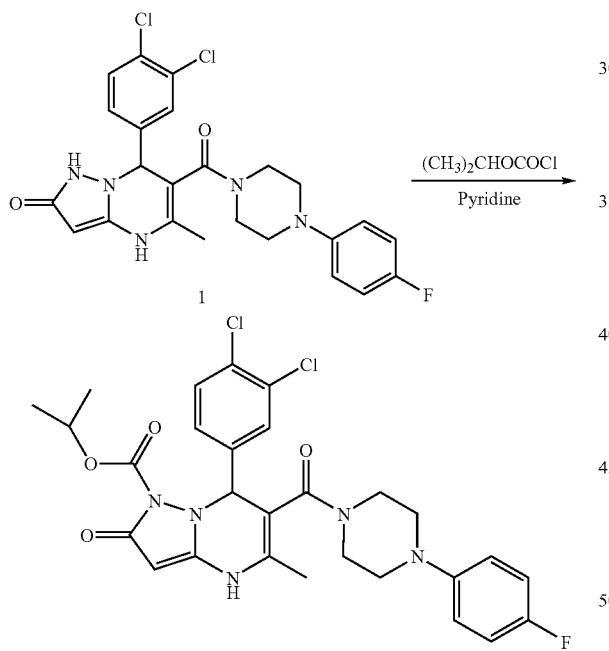

Compound 1: Compound 1 was prepared in a manner similar to that described in Example 18, Method 2.

Title Compound: Isopropyl chloroformate (1.0 mL, 1.0 mmol, 1M in toluene) was added to a 0° C. solution of compound 1 (0.46 g, 0.92 mmol) in pyridine (5 mL). The resulting mixture was stirred at 0° C. for 30 min., the cooling bath was removed. After 2 h methanol was added to quench the reaction and the mixture was concentrated. The residue was purified by silica gel chromatography eluting with 5% methanol/ethyl acetate to afford 0.057 g (11%) of the title compound as a light pink solid. Reverse phase LC/MS: YMC S5 ODS 4.6×50 column, UV detection at 220 λ, 4 min gradient 0–100% Solvent B/A (Solvent A: 10% MeOH/H$_2$O with 0.1% TFA, Solvent B: 90% MeOH/H$_2$O with 0.1% TFA), 4 mL/min. Rt=3.67 min, 95% pure). (M+H: 573).

EXAMPLE 442

1-[(4,7-Dihydro-5-methylpyrazolo[1,5-a]pyrimidin-6-yl)carbonyl]-4-phenylpiperazine

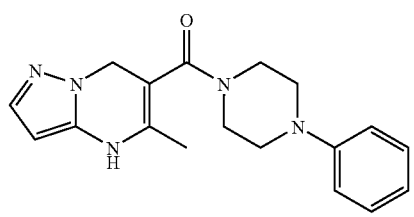

Method:

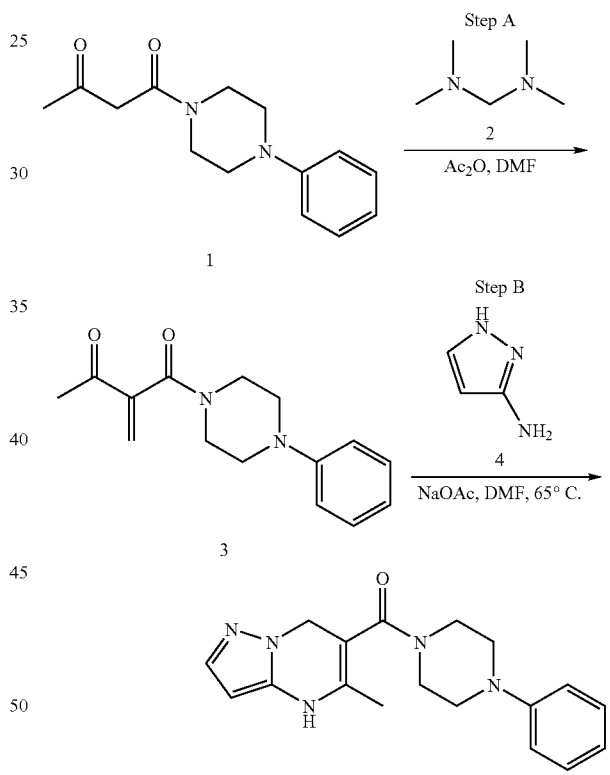

Compound 1: Compound 1 was prepared in a manner similar to that described in Example 18, Method 2.

Step A: Compound 2 (0.6 mL, 4.4 mmol) and acetic anhydride (0.83 mL, 8.8 mmol) were added to a solution of compound 1 (0.72 g, 2.9 mmol) in dimethylformamide (10 mL). The mixture was allowed to stir overnight, poured into water, extracted with dichloromethane. The extracts were combined, dried over anhydrous sodium sulfate and concentrated. The residue was purified by silica gel chromatography eluting with 50% ethyl acetate/hexanes to 100% ethyl acetate/hexanes to give 0.290 g (38% yield) of compound 3 as a colorless syrup. (M+H: 259).

Step B: Condensation of compound 3 and compound 4 as described in Example 18, Method 2 Step C provided the title compound. Reverse Phase LC/MS: YMC S5 ODS 4.6×50 mm Ballistic column, UV detection at 220 λ, 4 min. gradient 0–100% Solvent B/A (Solvent A: 10% MeOH/H20 with 0.1% TFA, Solvent B: 90% MeOH/H₂O with 0.1% TFA), 4 mL/min. Rt=1.96 min, (87% pure). (M+H: 323).

EXAMPLE 443

7-(3,4-Dichlorophenyl)-6-[[4-(4-fluorophenyl)-1-piperazinyl]carbonyl]-4,7-dihydro-5-methylpyrazolo[1,5-a]pyrimidine-2-carboxylic acid

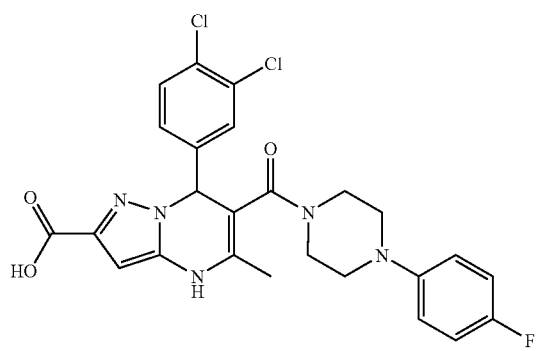

Method:

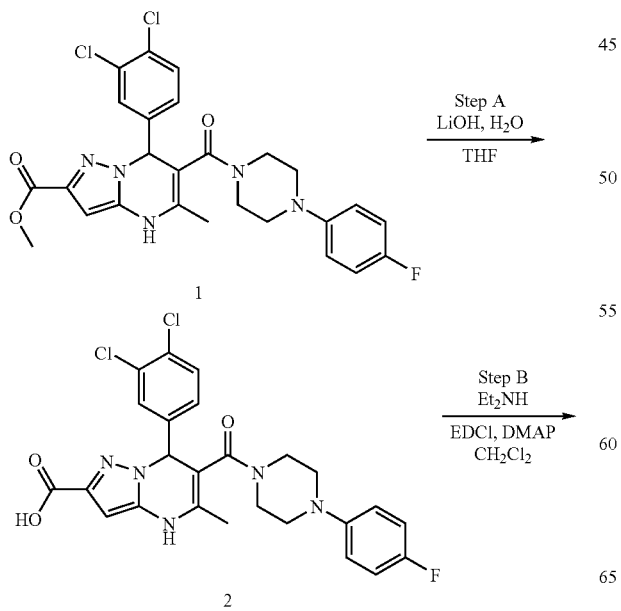

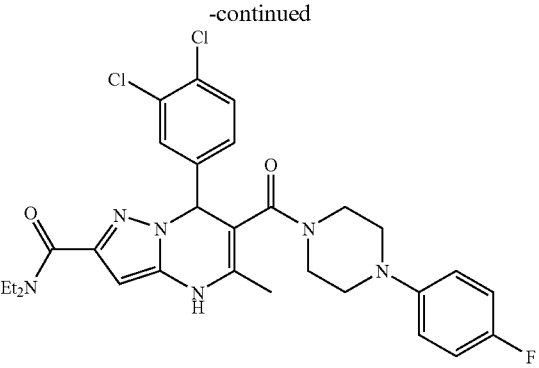

Compound 1: Compound 1 was prepared in a manner similar to that described in Example 18, Method 2.

Step A: Lithium hydroxide (0.43 g, 1.8 mmol) was dissolved in water (3 mL) and added slowly to a room temperature solution of compound 1 in tetrahydofuran (9 mL). The resulting mixture was stirred at room temperature for 3 h. TLC indicated that all of compound 1 had been consumed. The mixture was quenched by the addition of acidic Dowex resin. The resin was filtered off. The filtrate was diluted with ethyl acetate, washed with water and brine, dried over anhydrous sodium sulfate and concentrated to give 0.41 g (86% yield) of compound 2 as a light yellow solid. Reverse phase LC/MS: YMC S5 ODS 4.6×50 column, UV detection at 220 λ, 4 min gradient 0–100% Solvent B/A (Solvent A: 10% MeOH/H₂O with 0.1% TFA, Solvent B: 90% MeOH/H₂O with 0.1% TFA), 4 mL/min. Rt=3.37 min, 96% pure). MS (M+H: 530).

Step B: EDCI (0.025 g, 0.13 mmol), DMAP (0.003 g, 0.02 mmol) were added to a solution of compound 2 (0.0508 g, 0.1 mmol) and diethylamine (0.014 mL, 0.13 mmol) in dichloromethane (3 mL). The mixture was stirred overnight. TLC indicated some starting material remained. The solvent was removed under reduced pressure. The resulting residue was purified by silica gel chromatography eluting with 5% methanol/ethyl acetate to give the title compound as a white solid. Reverse phase LC/MS: YMC S5 4.6×50 Ballistic column, UV detection at 220 λ, 4 min gradient 0–100% Solvent B/A (Solvent A: 10% MeOH/H₂O with 0.1% TFA, Solvent B: 90% MeOH/H₂O with 0.1% TFA), 4 mL/min. Rt=3.74 min, 91% pure). MS (M+H: 585).

Examples 444–449

The compounds of Examples 445–450, shown in the table provided below, were prepared in a manner similar to that described in Example 443.

| Example | Structure | Name | (M + H) |
|---------|-----------|------|---------|
| 444 | 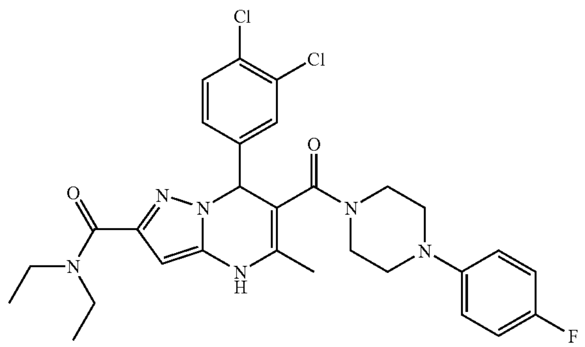 | 7-(3,4-Dichlorophenyl)-N,N-diethyl-6-[[4-(4-fluorophenyl)-1-piperazinyl]carbonyl]-4,7-dihydro-5-methyl-pyrazolo[1,5-a]pyrimidine-2-carboxamide | 585 |
| 445 | 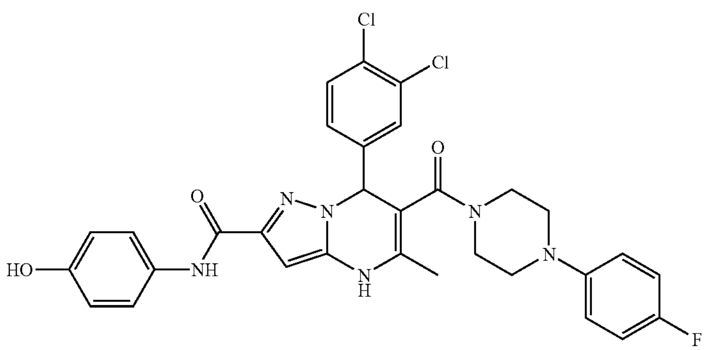 | 7-(3,4-Dichlorophenyl)-6-[[4-(4-fluorophenyl)-1-piperazinyl]carbonyl]-4,7-dihydro-N-(4-hydroxy-phenyl)-5-methyl-pyrazolo[1,5-a]pyrimidin-2-carboxamide | 621 |
| 446 | 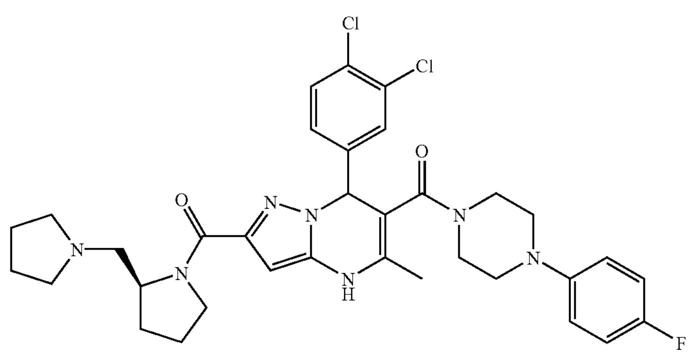 | 1-[[7-(3,4-Dichlorophenyl)-4,7dihydro-5-methyl-2-[[(2S)-2-(1-pyrrolidinylmethyl)-1-pyrrolidinyl]carbonyl]-pyrazolo[1,5-a]pyrimidin-6-yl]carbonyl]-4-(4-fluorophenyl)piperazine | 666 |
| 447 | 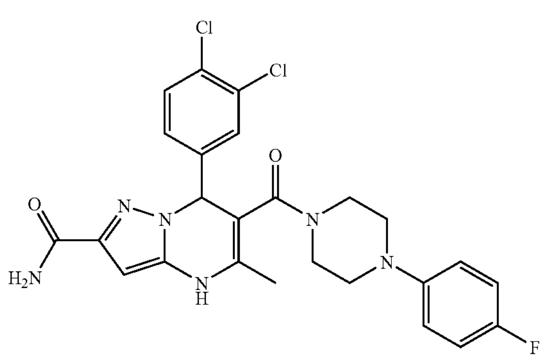 | 7-(3,4-Dichlorophenyl)-6-[[4-(4-fluorophenyl)-1-piperazinyl]carbonyl]-4,7-dihydro-5-methyl-pyrazolo[1,5-a]pyrimidine-2-carboxamide | 529 |

-continued

| Example | Structure | Name | (M + H) |
|---|---|---|---|
| 448 | 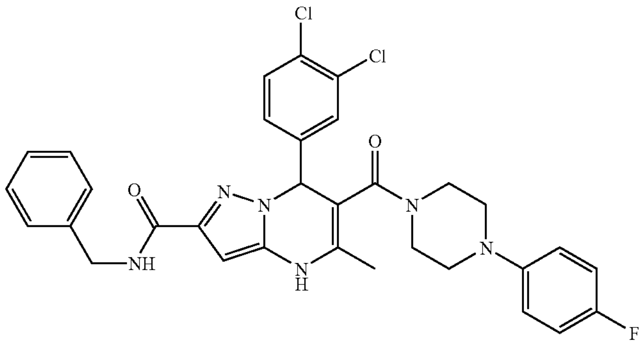 | 7-(3,4-Dichlorophenyl)-6-[[4-(4-fluorophenyl)-1-piperazinyl]carbonyl]-4,7-dihydro-5-methyl-N-(phenylmethyl)pyrazolo-[1,5-a]pyrimidine-2-carboxamide | 619 |
| 449 | 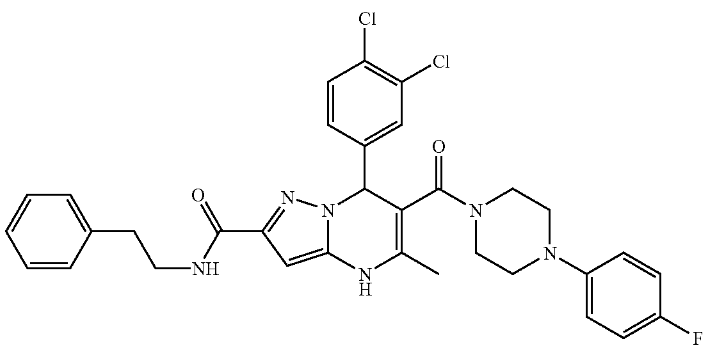 | 7-(3,4-Dichlorophenyl)-6-[[4-(4-fluorophenyl)-1-piperazinyl]carbonyl]-4,7-dihydro-5-methyl-N-(2-phenylethyl)-pyrazolo[1,5-a]pyrimidine-2-carboxamide | 633 |

EXAMPLE 450

1-[[2-Cyano-7-(3,4-dichlorophenyl)-4,7-dihydro-5-methylpyrazolo[1,5-a]pyrimidin-6-yl]carbonyl]-4-(4-fluorophenyl)piperazine Method:

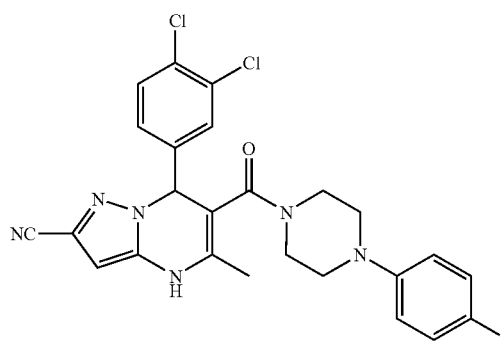

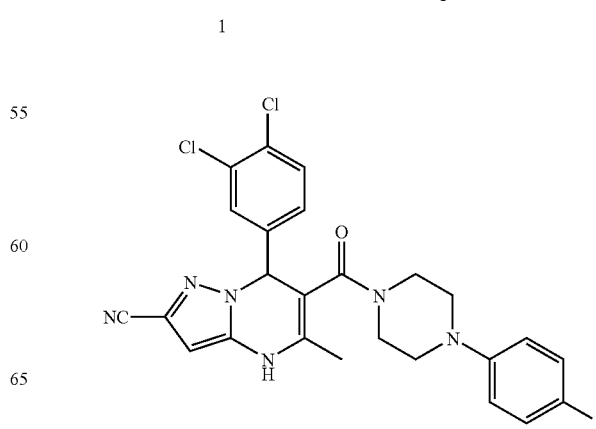

Compound 1: Compound 1 (the compound of Example 447) was prepared in a manner similar to that described in Example 443.

Title Compound: Triflic anhydride (0.036 mL, 0.21 mmol) was added to a 0° C. solution of compound 1 (0.103 g, 0.19 mmol) and triethylamine (0.054 mL, 0.39 mmol) in dichloromethane (5 mL). After 10 min., TLC (5% methanol/ethyl acetate) indicated that compound 1 remained. Additional Triflic anhydride (0.036 mL, 0.21 mmol) and triethylamine (0.054 mL, 0.39 mmol) were added. After 10 min., TLC (5% methanol/ethyl acetate) indicated that compound 1 remained. The mixture was warmed to room temperature and stirred for an additional 30 min. The reaction was poured into saturated sodium bicarbonate, extracted with dichloromethane. The extracts were combined, dried over anhydrous sodium sulfate and concentrated. The resulting residue was purified by silica gel chromatography eluting with 2% methanol/ethyl acetate to 0.018 g (19% yield) of the title compound as a white solid. Reverse phase LC/MS: YMC S5 4.6×33 column, UV detection at 220 λ, 2 min gradient 0–100% Solvent B/A (Solvent A: 10% MeOH/H$_2$O with 0.1% TFA, Solvent B: 90% MeOH/H$_2$O with 0.1% TFA), 4 mL/min. Rt=3.60 min, 81% pure). MS (M+H: 511).

EXAMPLE 451

3-Bromo-7-(3,4-dichlorophenyl)-4,7-dihydro-5-methylpyrazolo[1,5-a]pyrimidine-6-carboxylic acid 1,1-dimethylethyl ester

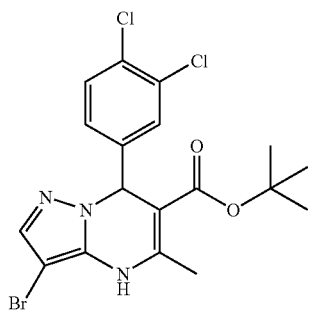

Method:

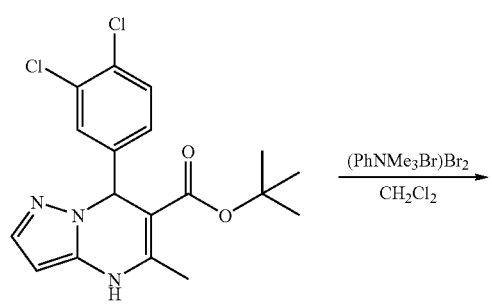

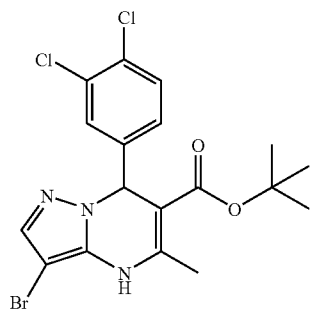

Compound 1: Compound 1 was prepared as described in Example 4.

Title Compound: Phenyltrimethylammonium tribromide (0.057 g, 0.14 mmol) was added to a 0° C. solution of compound 1 (0.05 g, 0.13 mmol) in dichloromethane (2 mL). The mixture was allowed to warm to room temperature over 4 h. The solvent was removed under reduced pressure. The resulting residue was purified by preparative TLC (Analtech, silica gel, 20×20 cm, 1000μ). Elution with 25% acetone/hexane provided 0.047 g (79% yield) of the title compound as a white solid. Reverse Phase HPLC: YMC S5 ODS 4.6×50 mm Ballistic column, UV detection at 220 λ, 4 min. gradient 0–100% Solvent B/A (Solvent A: 10% MeOH/H$_2$O with 0.2% H$_3$PO$_4$, Solvent B: 90% MeOH/H$_2$O with 0.2% H$_3$PO$_4$), 4 mL/min. Rt=4.67 min, (95% pure). Reverse Phase LC/MS: YMC S5 ODS 4.6×50 mm Ballistic column, UV detection at 220 λ, 4 min. gradient 0–100% Solvent B/A (Solvent A: 10% MeOH/H$_2$O with 0.1% TFA, Solvent B: 90% MeOH/H$_2$O with 0.1% TFA), 4 mL/min. Rt=4.19 min. MS (EM, M+1: 458) HMR (CDCl$_3$, 400 MHz): 7.37, (1H,d,J=2.0 Hz), 7.36(1H,d,J=8.0 Hz), 7.33 (1H,s), 7.12(1H,dd,J=2.2 and 8.4 Hz), 6.38(1H,s), 6.27(1H, s), 2.53(3H,s), 1.36(9H,s).

EXAMPLE 452

1-[[3-Bromo-7-(2,3-dichlorophenyl)-4,7-dihydro-5-methylpyrazolo[1,5-a]pyrimidin-6-yl]carbonyl]-4-phenylpiperazine

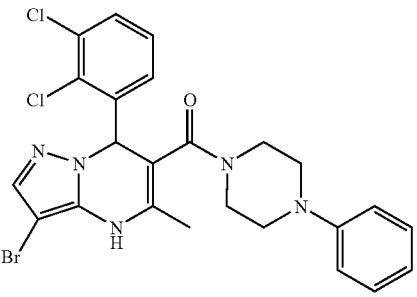

The compound of Example 452 was prepared in a manner similar to that described in Example 451. (M+H) 547.

EXAMPLE 453

1-[[3-Chloro-7-(2,3-dichlorophenyl)-4,7-dihydro-5-methylpyrazolo[1,5-a]pyrimidin-6-yl]carbonyl]-4-phenylpiperazine

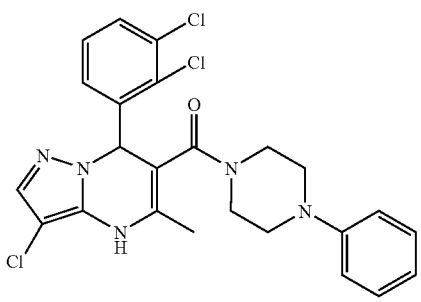

Method:

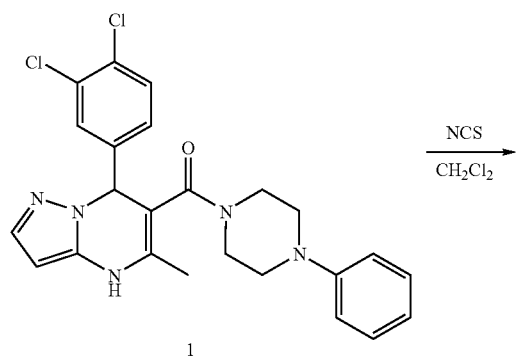

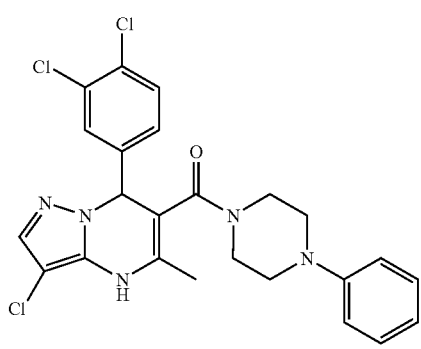

Compound 1: Compound 1 was prepared in a manner similar to that described in Example 18, Method 2.

Title Compound: N-chlorosuccinimide (0.0102 g, 0.076 mmol) was added to a 0° C. solution of compound 1 (0.0343 g, 0.073 mmol) in dichloromethane (4 mL). The mixture was allowed to warm to room temperature over 2 h. The solvent was removed under reduced pressure. The resulting residue was purified by preparative TLC (Analtech, silica gel, 20×20 cm, 1000μ). Elution with 50% acetone/hexane provided 0.0287 g (77% yield) of the title compound as a yellow oil which solidified upon standing. Reverse Phase HPLC: YMC S5 ODS 4.6×50 mm Ballistic column, UV detection at 220 λ, 4 min. gradient 0–100% Solvent B/A (Solvent A: 10% MeOH/H$_2$O with 0.2% PPA, Solvent B: 90% MeOH/H$_2$O with 0.2% PPA), 4 mL/min. Rt=4.21 min, (91% pure). Reverse Phase LC/MS: YMC S5 ODS 4.6×50 mm Ballistic column, UV detection at 220 λ, 4 min. gradient 0–100% Solvent B/A (Solvent A: 10% MeOH/H$_2$O with 0.1% TFA, Solvent B: 90% MeOH/H$_2$O with 0.1% TFA), 4 mL/min. Rt=3.72 min. MS (EM, M+1: 501)

EXAMPLE 454–463

The compounds of Examples 454–463, shown in the table provided below, were prepared in a manner similar to that described in Example 453.

Example 456 was obtained from the single enantiomer B of Example 30, and Example 457 was obtained from the single enantiomer A of Example 29. Chiralpak AD column (4.6×250 mm) eluting with 30% isopropanol/hexanes containing 0.1% triethylamine at 1 mL/min), UV detection at 254λ, Example 456 Rt=5.9 min, >99% ee. Example 457 Rt=6.3 min, >99% ee.

Example 458 was obtained from the single enantiomer A of Example 51, and Example 459 was obtained from the single enantiomer B of Example 52. Chiralcel OD column (4.6×250 mm) eluting with 30% isopropanol/hexanes containing 0.1% triethylamine at 1 mL/min), UV detection at 254λ, Example 458 Rt=7.8 min, >99% ee. Example 459 Rt=8.4 min, >99% ee.

Example 460 was obtained from the single enantiomer A of Example 169, and Example 461 was obtained from the single enantiomer B of Example 168. Chiralpak AD column (4.6×250 mm) eluting with 20% isopropanol/hexanes containing 0.1% triethylamine at 1 mL/min), UV detection at 254λ, Example 461 Rt=9.2 min, >99% ee. Example 460 Rt=9.4 min, >99% ee.

Example 462 was obtained from the single enantiomer A of Example 81, and Example 463 was obtained from the single enantiomer B of Example 82. Chiralpak AD column (4.6×250 mm) eluting with 20% isopropanol/hexanes containing 0.1% triethylamine at 1 mL/min), UV detection at 254λ, Example 462 Rt=8.25 min, >99% ee. Example 463 Rt=8.28 min, >99% ee.

| Example | Structure | Name | (M + H) |
| --- | --- | --- | --- |
| 454 | 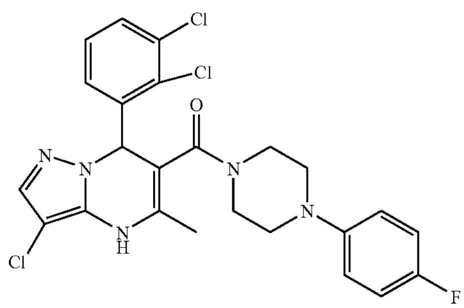 | 1-[[3-Chloro-7-(2,3-di-chlorophenyl)-4,7-di-hydro-5-methyl-pyrazolo[1,5-a]pyrimidin-6-yl]carbonyl]-4-(4-fluoro-phenyl)piperazine | 520 |
| 455 | 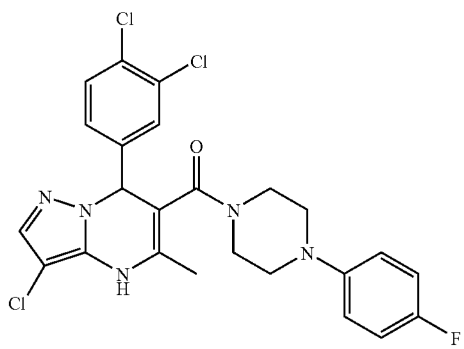 | 1-[[3-Chloro-7-(3,4-di-chlorophenyl)-4,7-di-hydro-5-methyl-pyrazolo[1,5-a]pyrimidin-6-yl]carbonyl]-4-(4-fluoro-phenyl)piperazine | 520 |
| 456 | Chiral | 1-[[3-Chloro-7-(2,3-di-chlorophenyl)-4,7-di-hydro-5-methyl-pyrazolo[1,5-a]pyrimidin-6-yl]carbonyl]-4-phenyl-piperazine, enantiomer B | 502 |
| 457 | Chiral | 1-[[3-Chloro-7-(2,3-di-chlorophenyl)-4,7-di-hydro-5-methyl-pyrazolo[1,5-a]pyrimidin-6-yl]carbonyl]-4-phenyl-piperazine, enantiomer A | 502 |
| 458 | Chiral | 1-[[3-Chloro-7-(2,3-di-chlorophenyl)-4,7-di-hydro-5-methyl-pyrazolo[1,5-a]pyrimidin-6-yl]carbonyl]-4-(4-fluoro-phenyl)piperazine, enantiomer A | 520 |

-continued

| Example | Structure | Name | (M + H) |
|---|---|---|---|
| 459 | 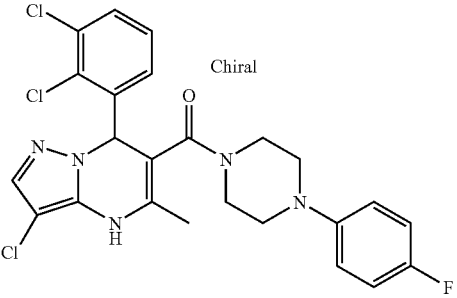 | 1-[[3-Chloro-7-(2,3-dichlorophenyl)-4,7-dihydro-5-methyl-pyrazolo[1,5-a]pyrimidin-6-yl]carbonyl]-4-(4-fluorophenyl)piperazine, enantiomer B | 520 |
| 460 | 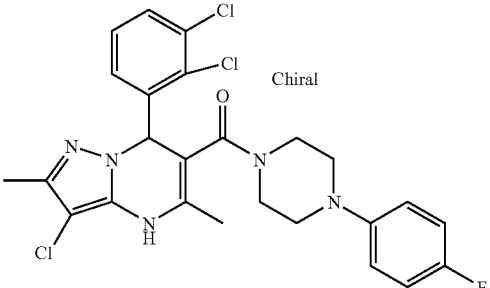 | 1-[[3-Chloro-7-(2,3-dichlorophenyl)-4,7-dihydro-2,5-dimethyl-pyrazolo[1,5-a]pyrimidin-6-yl]carbonyl]-4-(4-fluorophenyl)piperazine, enantiomer A | 534 |
| 461 | 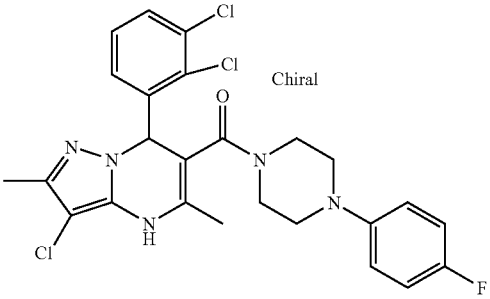 | 1-[[3-Chloro-7-(2,3-dichlorophenyl)-4,7-dihydro-2,5-dimethyl-pyrazolo[1,5-a]pyrimidin-6-yl]carbonyl]-4-(4-fluorophenyl)piperazine, enantiomer B | 534 |
| 462 | 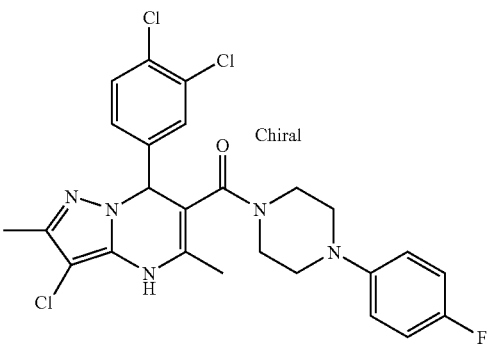 | 1-[[3-Chloro-7-(3,4-dichlorophenyl)-4,7-dihydro-2,5-dimethyl-pyrazolo[1,5-a]pyrimidin-6-yl]carbonyl]-4-(4-fluorophenyl)piperazine, enantiomer A | 534 |

| Example | Structure | Name | (M + H) |
|---|---|---|---|
| 463 | 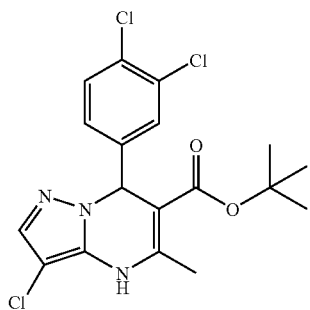 | 1-[[3-Chloro-7-(3,4-dichlorophenyl)-4,7-dihydro-2,5-dimethylpyrazolo[1,5-a]pyrimidin-6-yl]carbonyl]-4-(4-fluorophenyl)piperazine, enantiomer B | 534 |

Example 464

3-Chloro-7-(3,4-dichlorophenyl)-4,7-dihydro-5-methylpyrazolo[1,5-a]pyrimidine-6-carboxylic acid 1,1-dimethylethyl ester Method:

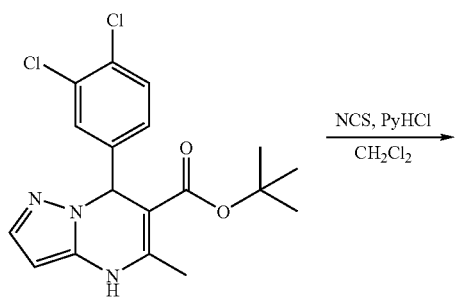

Compound 1: Compound 1 was prepared as described in Example 4.

Title Compound: Pyridine hydrochloride (0.020 g, 0.173 mmol) was added to a 0° C. solution of compound 1 (0.060 g, 0.158 mmol) in dichloromethane (4 mL). After 2 min, N-chlorosuccinimide (0.0231 g, 0.174 mmol) was added. The mixture was allowed to warm to room temperature and was stirred for 13 h. The solvent was removed under reduced pressure. The resulting residue was purified by preparative TLC (Analtech, silica gel, 20×20 cm, 1000μ). Elution with 20% acetone/hexane provided 0.0092 g (14% yield) of the title compound as a yellow oil. Reverse Phase HPLC: YMC S5 ODS 4.6×50 mm Ballistic column, UV detection at 220 λ, 4 min. gradient 0–100% Solvent B/A (Solvent A: 10% MeOH/$H_2O$ with 0.2% PPA, Solvent B: 90% MeOH/$H_2O$ with 0.2% PPA), 4 mL/min. Rt=4.61 min, (94% pure). Reverse Phase LC/MS: YMC S5 ODS 4.6×50 mm Ballistic column, UV detection at 220 λ, 4 min. gradient 0–100% Solvent B/A (Solvent A: 10% MeOH/$H_2O$ with 0.1% TFA, Solvent B: 90% MeOH/$H_2O$ with 0.1% TFA), 4 mL/min. Rt=4.71 min. MS (EM, M+1: 414). HMR (CDCl$_3$, 400 MHz): 7.37(1H,s), 7.36(1H,d,J=1.7 Hz), 7.36(1H,d,J=8.4 Hz), 7.12(1H,dd,J=2.0 and 8.4 Hz), 6.45(1H,brs), 6.24(1H, s), 2.52(3H,s), 1.36(9H,s).

EXAMPLE 465

7-(3,4-Dichlorophenyl)-4,7-dihydro-5-methyl-6-(5-phenyl-2-oxazolyl)pyrazolo[1,5-a]pyrimidine

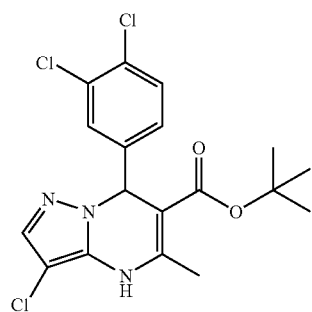
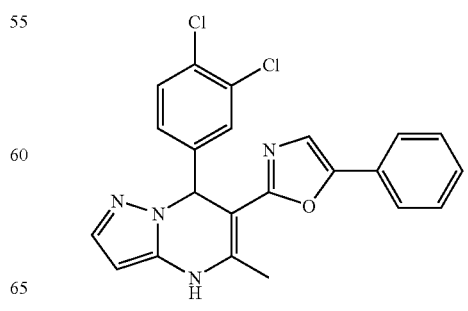

Method:

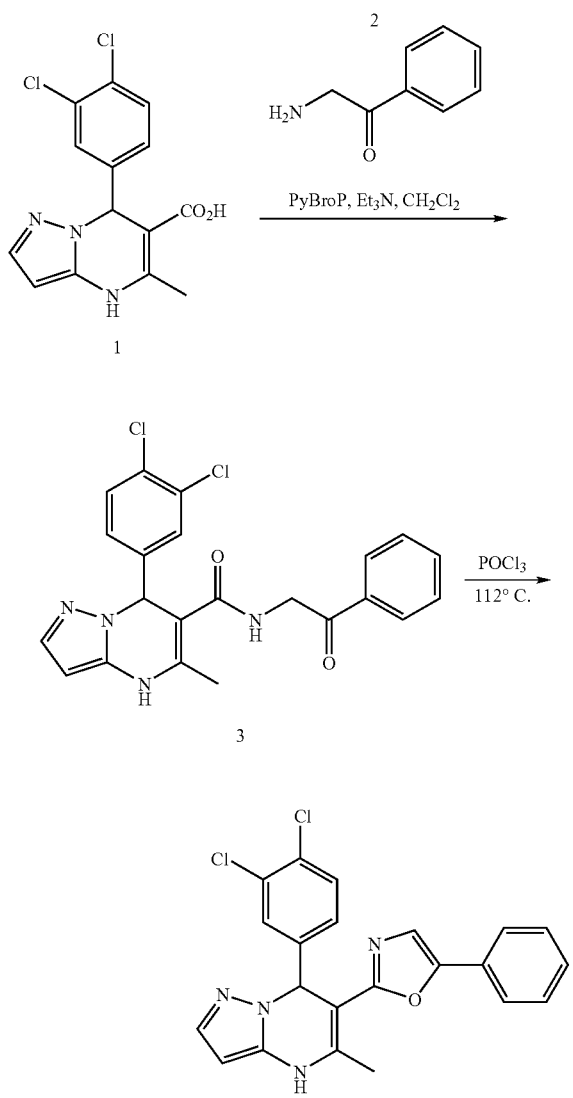

Compound 1: Compound 1 was synthesized as described in Example 16.

Compound 3: Compound 1 (200 mg, 0.62 mmol) was suspended in 2 mL of dichloromethane. Triethylamine (300 µL, 2.2 mmol) and 2-aminoacetophenone 2 (116 mg, 0.68 mmol) were added followed by bromo-tris-pyrrolidino-phosphonium hexafluorophosphate (PyBrOP) (312 mg, 0.68 mmol). All the solid dissolved upon addition of PyBrOP and the reaction was stirred for 4 hrs. The mixture was loaded onto silica gel and purified by flash chromatography on silica gel eluted with 40% acetone, hexane to yield 106 mg (39%) of a pink solid. $^1$H NMR (400 MHz, CDCl3) 44180-148-16; $^1$H COSY (400 MHz, CD3OD); $^{13}$C NMR (100 MHz, CDCl$_3$); HPLC>99% at 4.0 min (YMC S5 ODS 4.6×50 mm column; 10–90% methanol, water with 0.2% phosphoric acid gradient over 4 min.; 4 mL/min.; uv detection at 220 nm).

Title Compound: The amide 3 (100 mg, 0.22 mmol) was dissolved in 2 mL phosphorus oxychloride and heated to 112° for 2 h. The mixture was then quenched onto ice and extracted with ethylacetate. The extracts were dried over magnesium sulfate, filtered and the solvent removed to provide 339 mg of a brown oil. The oil was purified by flash chromatography on silica gel eluted with 20–40% acetone, hexane to yield 50 mg (51%) of the title compound as a white powder. mp 229–231°; $^1$H NMR (400 MHz, CD3OD); MS (ESI) m/z 423 (MH$^+$); HPLC>99% at 4.7 min (YMC S5 ODS 4.6×50 mm column; 10–90% methanol, water with 0.2% phosphoric acid gradient over 4 min. then hold at 90% methanol, water; 4 mL/min.; uv detection at 220 nm).

EXAMPLES 466–469

The compounds of Examples 466–473, shown in the table provided below, were prepared in a manner similar to that described in Example 465.

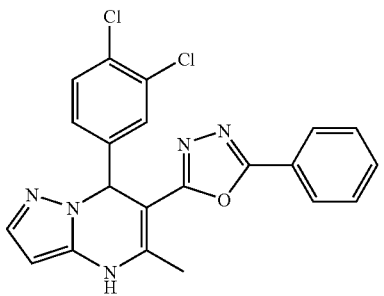

| Example | Structure | Name | (M + H) |
| --- | --- | --- | --- |
| 466 | ![structure] | 7-(3,4-Dichlorophenyl)-4,7-dihydro-5-methyl-6-(5-phenyl-1,3,4-oxadiazol-2-yl)pyrazolo[1,5-a]pyrimidine | 424 |

-continued

| Example | Structure | Name | (M + H) |
|---|---|---|---|
| 467 | 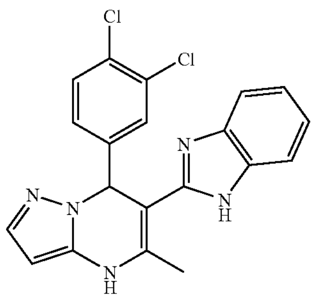 | 6-(1H-Benzimidazol-2-yl)-7-(3,4-di-chloro-phenyl)-4,7-di-hydro-5-methylpyrazolo[1,5-a]pyrimidine | 396 |
| 468 | 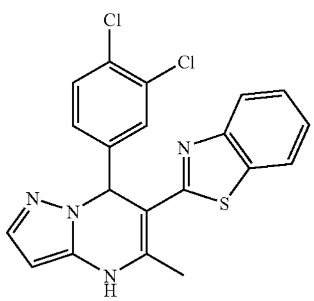 | 6-(2-Benzothiazolyl)-7-(3,4-di-chlorophenyl)-4,7-di-hydro-5-methyl-pyrazolo[1,5-a]pyrimidine | 413 |
| 469 | 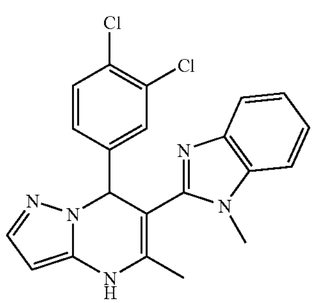 | 7-(3,4-Dichlorophenyl)-4,7-di-hydro-5-methyl-6-(1-methyl-1H-benzimi-dazol-2-yl)pyrazolo[1,5-a]pyrimidine | 410 |

EXAMPLE 470

7-(3,4-Dichlorophenyl)-4,7-dihydro-5-methyl-6-[5-(trifluoromethyl)-1-propyl-1H-benzimidazol-2-yl]pyrazolo[1,5-a]pyrimidine

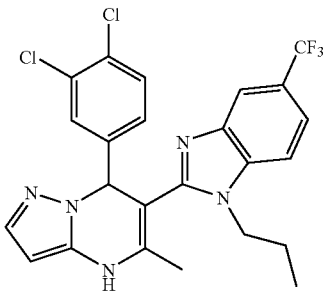

Method:

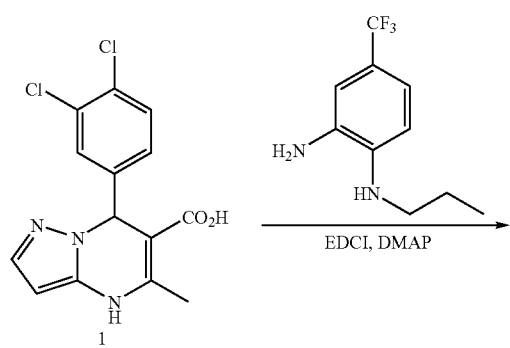

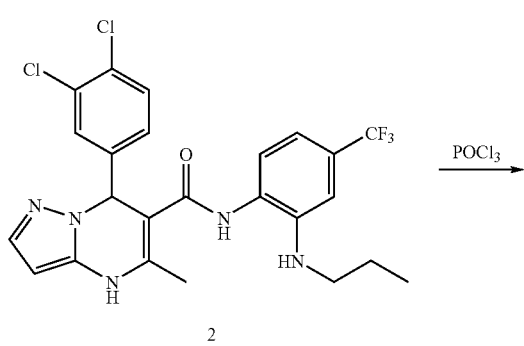

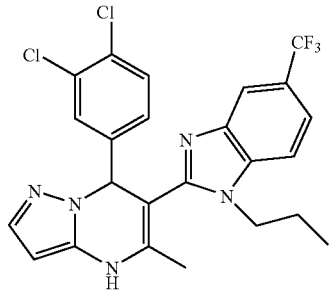

Compound 2: To a solution of acid 1, prepared as described in Example 16, (0.15 g, 0.463 mmol), 2-(n-propylamino)-5-trifluromethylaniline (0.141 g, 0.648 mmol) and DMAP (5 mg, cat.) EDCI (0.124 g, 0.0648 mmol) was added and the solution was stirred at room temperature for 2 hours. The reaction was treated with saturated sodium bicarbonate, the organic solution was dried with magnesium sulfate and the solvent was evaporated. The crude product 2 was used without further purification.

Title Compound: Compound 2 was dissolved in phosphorus oxychloride (4 mL) and heated to 80° C. for 4 h. TLC indicated the reaction was not complete. Additional phosphorus oxychloride (2 mL) was added and the mixture was heated for 2 h and then left to stand at room temperature overnight. The mixture was then quenched onto ice, made basic with ammonium hydroxide, and extracted with ethyl acetate. The extracts were dried over magnesium sulfate and concentrated. The crude product was purified by preparative reversed phase chromatography (YMC PACK ODSA S3 20×100 mm column 50–100 methanol, water with 0.1% TFA gradient over 10 min.; 20 mL/min.; uv detection at 220 nm.) The appropriate fractions were evaporated, the residue was partitioned between saturated sodium bicarbonate and ethyl acetate, the organic solution was dried and the solvent was removed under vacuum giving the product (27 mg, 11.5%) as a tan glass. [M+H]$^+$ m/z 506; HPLC 91.1% at 4.6 min (YMC S5 ODS 4.6×50 mm column; 10–90% methanol, water with 0.2% phosphoric acid gradient over 4 min.; 4 mL/min.; uv detection at 220 nm).

EXAMPLES 471–482

The compounds of Examples 471–482, shown in the table provided below, were prepared in a manner similar to that described in Example 470.

HPLC resolution of Example 480, Chiralcel OD column (50×500 mm), eluting with 25% isopropanol/hexanes containing 0.1% triethylamine at 50 mL/min), UV detection at 254λ provided enantiomers A (Example 481) and B (Example 482). Analytical Chiralcel OD column (4.6×250 mm) eluting with 25% isopropanol/hexanes containing 0.1% triethylamine at 1 mL/min), UV detection at 254λ, enantiomer A Rt=7.2 min, >99% ee. Enantiomer B Rt=10.0 min, >99% ee.

| Example | Structure | Name | (M + H) |
|---|---|---|---|
| 471 | 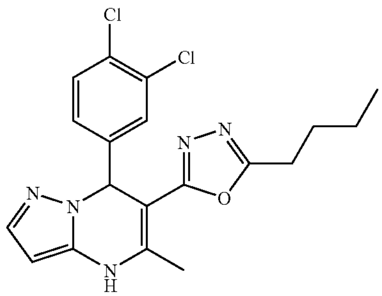 | 6-(5-Butyl-1,3,4-oxa-diazol-2-yl)-7-(3,4-di-chlorophenyl)-4,7di-hydro-5-methyl-pyrazolo[1,5-a]pyrimidine | 404 |
| 472 | 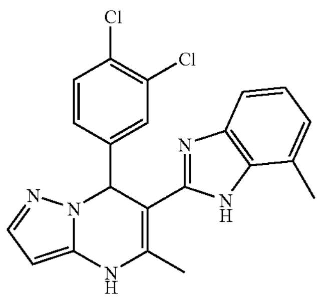 | 1-[[7-(3,4-Dichloro-phenyl)-4,7-dihydro-5-meth-yl-6-(4-methyl-1H-benzimi-dazol-2-yl)pyra-zolo[1,5-a]pyrimidine | 410 |
| 473 | 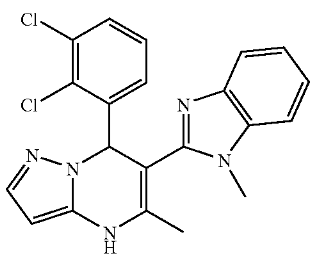 | 1-[[7-(2,3-Dichloro-phenyl)-4,7-dihydro-5-meth-yl-6-(1-methyl-1H-benzimi-dazol-2-yl)pyra-zolo[1,5-a]pyrimidine | 410 |
| 474 | 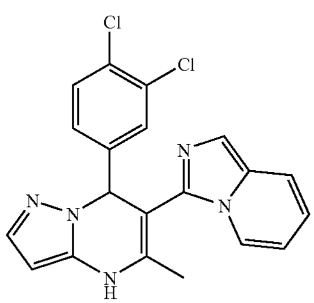 | 7-(3,4-Dichlorophenyl)-4,7-di-hydro-6-(imida-zo[1,5-a]pyridin-3-yl)-5-methyl-pyrazolo[1,5-a]pyrimidine | 510 |
| 475 | 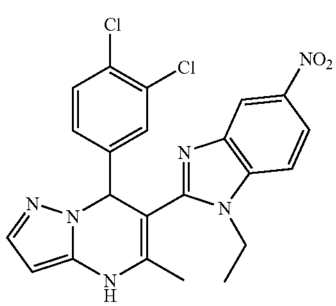 | 7-(3,4-Dichlorophenyl)-6-(1-eth-yl-5-nitro-1H-benzimi-dazol-2-yl)-4,7-di-hydro-5-methyl-pyrazolo[1,5-a]pyri-midine | 469 |

-continued

| Example | Structure | Name | (M + H) |
|---|---|---|---|
| 476 | 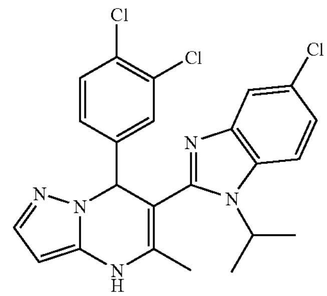 | 6-[5-Chloro-1-(1-methylethyl)-1H-benzimidazol-2-yl]-7-(3,4-dichlorophenyl)-4,7-dihydro-5-methylpyrazolo[1,5-a]pyrimidine | 472 |
| 477 | 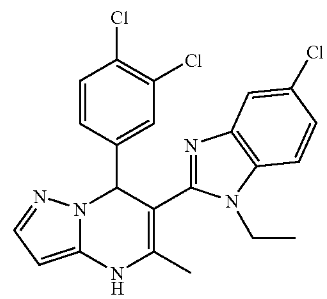 | 6-(5-Chloro-1-ethyl-1H-benzimidazol-2-yl)-7-(3,4-dichlorophenyl)-4,7-dihydro-5-methylpyrazolo[1,5-a]pyrimidine | 458 |
| 478 | 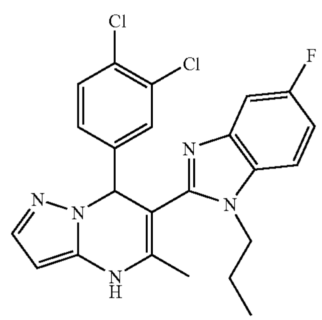 | 7-(3,4-Dichlorophenyl)-6-(5-fluoro-1-propyl-1H-benzimidazol-2-yl)-4,7-dihydro-5-methylpyrazolo[1,5-a]pyrimidine | 456.35 |
| 479 | 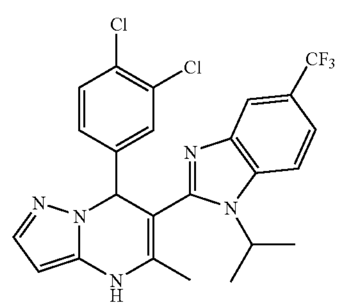 | 7-(3,4-Dichlorophenyl)-4,7-dihydro-5-methyl-6-[1-(1-methylethyl)-5-(trifluoromethyl)-1H-benzimidazol-2-yl]pyrazolo[1,5-a]pyrimidine | 506 |

| Example | Structure | Name | (M + H) |
|---|---|---|---|
| 480 | 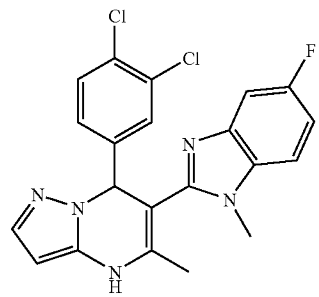 | 7-(3,4-Dichlorophenyl)-6-(5-fluoro-1-methyl-1H-benzimidazol-2-yl)-4,7-dihydro-5-methyl-pyrazolo[1,5-a]pyrimidine | 428 |
| 481 | Chiral | 7-(3,4-Dichlorophenyl)-6-(5-fluoro-1-methyl-1H-benzimidazol-2-yl)-4,7-dihydro-5-methyl-pyrazolo[1,5-a]pyrimidine, enantiomer A | 428 |
| 482 | Chiral | 7-(3,4-Dichlorophenyl)-6-(5-fluoro-1-methyl-1H-benzimidazol-2-yl)-4,7-dihydro-5-methyl-pyrazolo[1,5-a]pyrimidine, enantiomer B | 428 |

EXAMPLE 483

7-(3,4-Dichlorophenyl)-4,7-dihydro-5-methyl-6-[1-(phenylmethyl)-1H-benzimidazol-2-yl]pyrazolo[1,5-a]pyrimidine

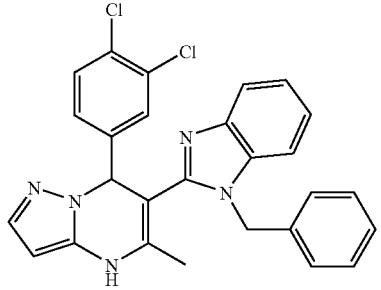

Method:

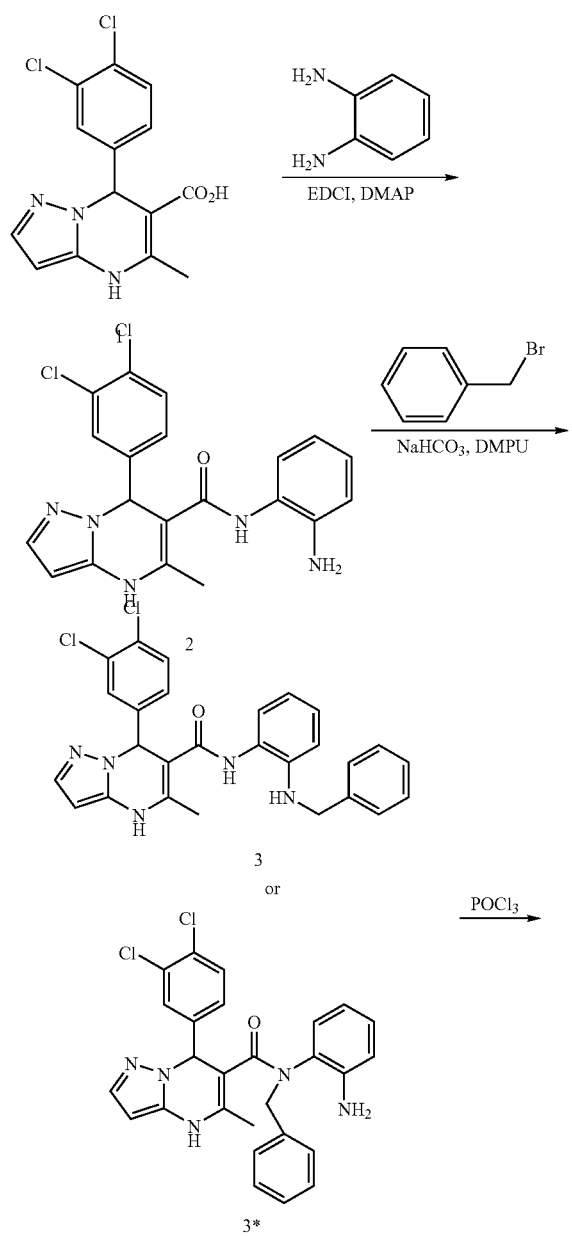

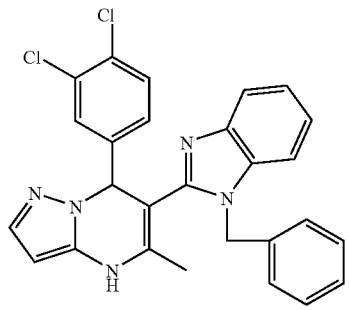

Compound 1: Prepared as described in Example 16.

Compound 2: Prepared from compound 1 and phenylenediamine in a manner similar to that described in Example 470.

Compound 3: A suspension of 2 (50 mg 0.121 mmol), NaHCO$_3$ (50 mg, 0.6 mmol) and benzyl bromide (20 mg, 0.121 mmol) in DMPU (0.5 mL) was stirred at room temp. overnight. Another equivalent of benzyl bromide was added completing the reaction. The suspension was partitioned between water and ethyl acetate, the organic phase was dried (MgSO$_4$), and the solvent was evaporated. The residue was flash chromatographed through silica eluting with hexane-acetone 2:1 to provide either or both of compounds 3 and 3* (exact structure was not determined) (24.8 mg, 41%) as a white solid. Mp 135–140; [M+H]$^+$ m/z 504; HPLC 100% at 4.4 min (YMC S5 ODS 4.6×50 mm column; 10–90% methanol, water with 0.2% phosphoric acid gradient over 4 min.; 4 mL/min.; uv detection at 220 nm).

Title Compound: Compound(s) 3/3* was dissolved in phosphorus oxychloride (1.5 mL) and heated to 80° C. for 5 h. Heating was discontinued and the mixture was left to stand at room temperature overnight. The mixture was quenched onto ice, made basic with ammonium hydroxide, and extracted with ethyl acetate. The extracts were dried over magnesium sulfate and concentrated. The residue was purified by flash chromatography (silica gel, 50% acetone/hexanes) to give 6.6 mg of the title compound as a tan solid. Mp 225–230; [M+H]$^+$ m/z 486; HPLC 100% at 3.8 min (YMC S5 ODS 4.6×50 mm column; 10–90% methanol, water with 0.2% phosphoric acid gradient over 4 min.; 4 mL/min.; uv detection at 220 nm).

EXAMPLE 484

7-(3,4-Dichlorophenyl)-4,7-dihydro-5-(methoxymethyl)-N-(2-pyridinylmethyl)pyrazolo[1,5-a]pyrimidine-6-carboxamide

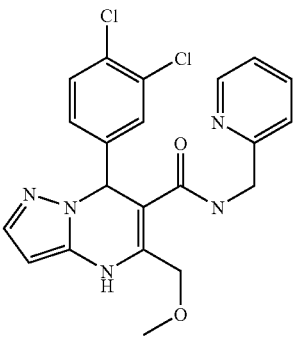

Scheme:

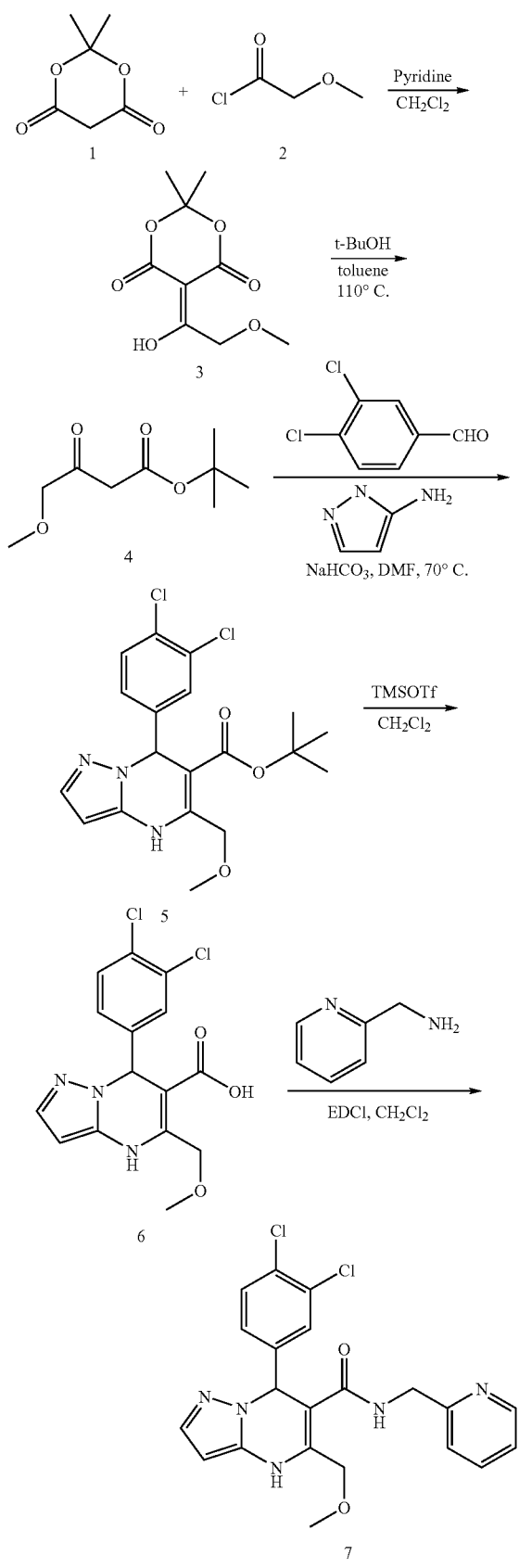

Synthesis of 3: A solution of recrystalized (acetone, hexane) 2,2-Dimethyl-1,3-dioxane-4,6-dione (1, 25.0 g, 173.5 mmol) in dichloromethane (350 mL) was treated with pyridine (27.4 g, 346.9 mmol). The reaction mixture was cooled to −5.1° C. To this stirred solution was added a solution of methoxyacetyl chloride (2, 20.7 g, 190.8 mmol) in dichloromethane (150 mL) over 50 mins., maintaining the reaction temperature below 1.5° C. The reaction mixture turned orange and a precipitate formed. The reaction mixture was allowed to warm to 17.5° C. over 40 mins. The reaction mixture turned maroon and the solids dissolved. After TLC (100% ethyl acetate) showed the reaction was complete, the reaction was quenched with 3.7% aqueous hydrochloric acid (500 mL) and the aqueous layer was extracted with dichloromethane). The organic extracts were combined and washed with saturated aqueous sodium chloride, dried over anhydrous magnesium sulfate, and filtered. The solvent was removed. The resulting oil was dried on high vacuum to constant weight to give 3 (33.11 g) in 88.3% yield.

Synthesis of 4: To a solution of 3 (33.1 g, 153 mmol) in 100 mL of toluene was added 2-methyl-2-propanol (100 mL, 1.05 mol) and the reaction was heated to reflux. After 1.5 h the reaction was concentrated to give 4 (30.2 g) in 100% yield.

Synthesis of 5: To the solution of β-ketoester 4 (30.2 g, 160.6 mmol) in dimethylformamide (120 mL) was added 3,4 dichlorobenzaldehyde (28.13 g, 160.6 mmol), followed by 3-aminopyrazole (14.7 g, 176.7 mmol), then sodium hydrogen carbonate (54 g, 642.6 mmol). The reaction mixture was heated at 70° C. for 48 hrs. The reaction mixture was then cooled to 35° C. and transferred into rapidly stirring water (1.5 L) at RT. The resulting off-white solid was filtered. The filtered solid was slurried in water (1 L) and filtered again. The wet cake (165 g) was dissolved into ethyl acetate (1 L), giving a two-phase mixture. The mixture was washed with saturated aqueous sodium chloride (500 mL). The organic layer was dried over anhydrous magnesium sulfate and filtered. The solvent was removed. The resulting crude material was purified by column chromatography using 40% ethyl acetate in hexane as eluent to give 5 (22.6 g, 34.3%) as a white powder.

Synthesis of 6: To a solution of dihydropyrimidine tert-butyl ester 5 (10.13 g, 24.7 mmol) in dichloromethane (150 mL) was added a solution of trimethylsilyltrifluoromethanesulfonate (11 g, 49.5 mmol) in dichloromethane (11 mL). After 1 hr, hexane (300 mL) was added slowly and the reaction was concentrated to 250 mL. The product formed a gum and supernatant was decanted. Hexane (250 mL) was added and the mixture was allowed to stir for 1 hr. The gum had solidified and fromed a powder. The supernatant was decanted again and another 250 mL of hexane was added. The mixture was stirred for 10 min and filtered. The resulting wet cake was washed with hexane (250 mL)) and a fine off-white powder 6 resulted which was allowed to suction dry.

Synthesis of 7: To a suspension of dihydropyrimidine acid 6 (100 mg, 0.28 mmol) in dichloromethane (10 mL) was added EDCI (76 mg, 0.39 mmol), followed by a solution of 2-pyridylmethylamine (32.4 mg, 0.39 mmol) in dichloromethane (1 mL). After 2.5 hrs, the reaction was concentrated to dryness and the crude mixture was purified by silica gel chromatograhy using 10% methanol in dichlormethane as eluent to give the title compound (90 mg, 72.4%) as an off-white powder. Mass Spec m/z (M+Na)$^+$ 466.

EXAMPLES 485–496

The following compounds were prepared by the methods described in example 484.

| Ex. # | Structure | Name | Mass Spec (m/z) |
|---|---|---|---|
| 485 | 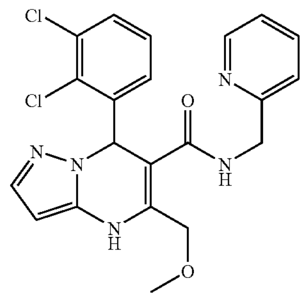 | 7-(2,3-Dichlorophenyl)-4,7-dihydro-5-(methoxymethyl)-N-(2-pyridinylmethyl)pyrazolo[1,5-a]pyrimidine-6-carboxamide | 444(M + H)$^+$ |
| 486 | 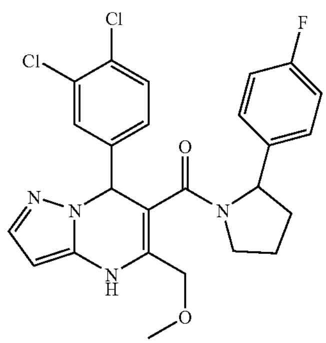 | 1-[[7-(3,4-Dichlorophenyl)-4,7-dihydro-5-(methoxymethyl)pyrazolo[1,5-a]pyrimidin-6-yl]carbonyl]-2-(4-fluorophenyl)pyrrolidine | 501(M + H)$^+$ |
| 487 | 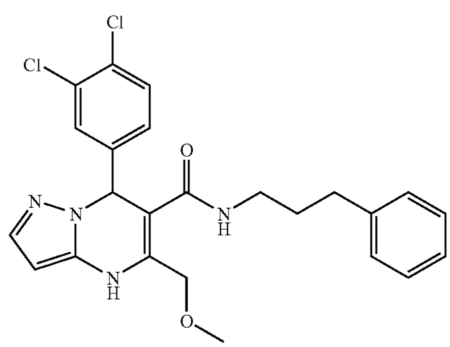 | 7-(3,4-Dichlorophenyl)-4,7-dihydro-5-(methoxymethyl)-N-(3-phenylpropyl)pyrazolo[1,5-a]pyrimidine-6-carboxamide | 471(M + H)$^+$ |
| 488 | 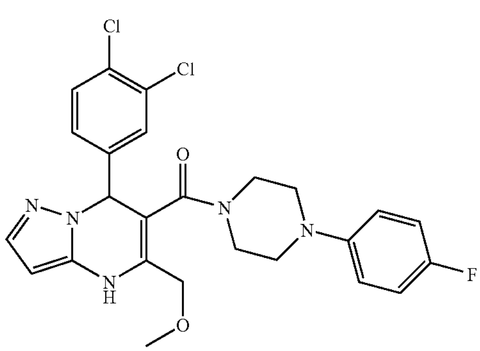 | 1-[[7-(3,4-Dichlorophenyl)-4,7-dihydro-5-(methoxymethyl)pyrazolo[1,5-a]pyrimidin-6-yl]carbonyl]-4-(4-fluorophenyl)piperazine | 516(M + H)$^+$ |

-continued

| Ex. # | Structure | Name | Mass Spec (m/z) |
|---|---|---|---|
| 489 | 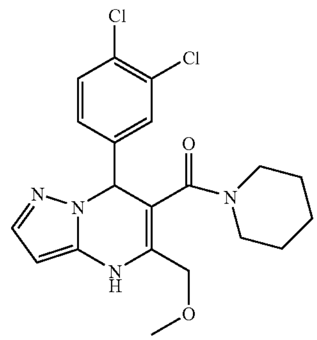 | 1-[[7-(3,4-Dichlorophenyl)-4,7-dihydro-5-(methoxymethyl)pyrazolo[1,5-a]pyrimidin-6-yl]carbonyl]piperidine | 421(M + H)+ |
| 490 | 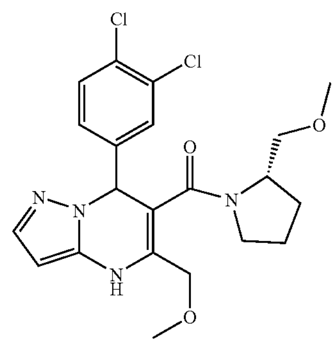 | (2S)-1-[[7-(3,4-Dichlorophenyl)-4,7-dihydro-5-(methoxymethyl)pyrazolo[1,5-a]pyrimidin-6-yl]carbonyl]-2-(methoxymethyl)pyrrolidine | 451(M + H)+ |
| 491 | 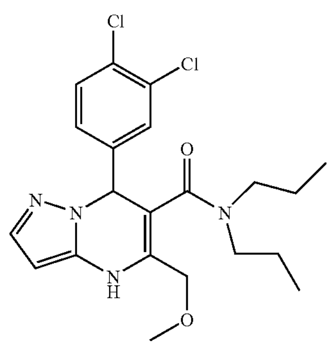 | 7-(3,4-Dichlorophenyl)-4,7-dihydro-5-(methoxymethyl)-N,N-dipropylpyrazolo[1,5-a]pyrimidine-6-carboxamide | 437(M + H)+ |
| 492 | 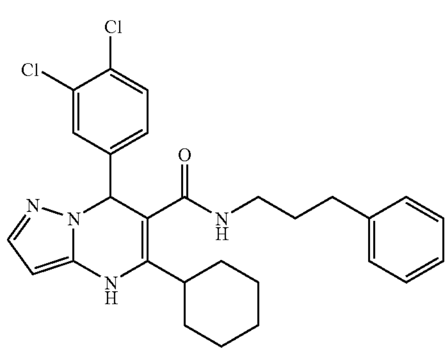 | 5-Cyclohexyl-7-(3,4-dichlorophenyl)-4,7-dihydro-N-(3-phenylpropyl)pyrazolo[1,5-a]pyrimidine-6-carboxamide | 509(M + H) |

-continued

| Ex. # | Structure | Name | Mass Spec (m/z) |
|---|---|---|---|
| 493 | 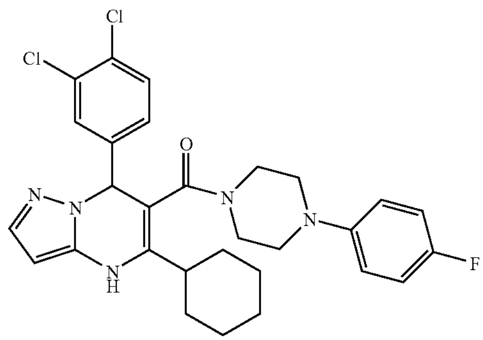 | 1-[[5-Cyclohexyl-7-(3,4-di-chlorophenyl)-4,7-di-hydropyrazolo[1,5-a]pyrimidin-6-yl]carbo-nyl]-4-(4-fluorophenyl)piperazine | 554(M + H) |
| 494 | 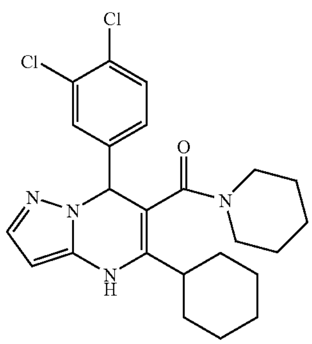 | 1-[[5-Cyclohexyl-7-(3,4-di-chlorophenyl)-4,7-di-hydropyrazolo[1,5-a]pyrimidin-6-yl]carbo-nyl]piperidine | 459(M + H) |
| 495 | 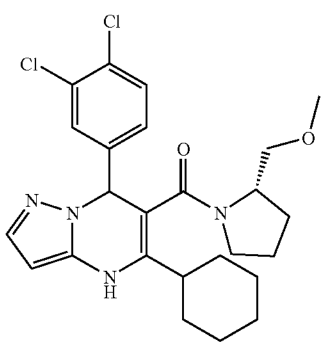 | (2S)-1-[[5-Cyclohexyl-7-(3,4-di-chlorophenyl)-4,7-di-hydropyrazolo[1,5-a]pyrimidin-6-yl]car-bonyl]-2-(methoxymethyl)pyrrolidine | 489(M + H) |
| 496 | 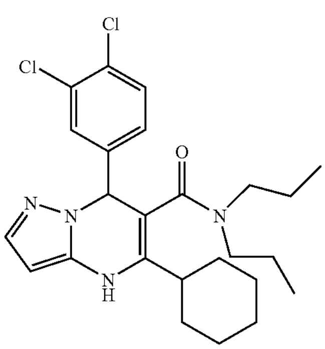 | 5-Cyclohexyl-7-(3,4-di-chlorophenyl)-4,7-dihydro-N,N-di-propylpyrazolo[1,5-a]pyrimidine-6-carboxamide | 475(M + H) |

EXAMPLE 497

7-(3,4-Dichlorophenyl)-4,7-dihydro-6-(imidazo[1,5-a]pyridin-3-yl)-5(methoxymethyl)pyrazolo[1,5-a]pyrimidine

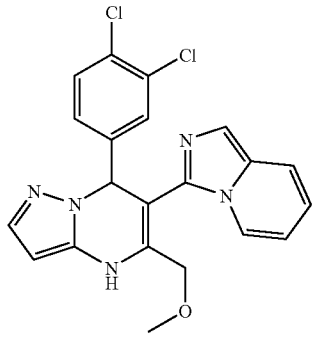

Scheme

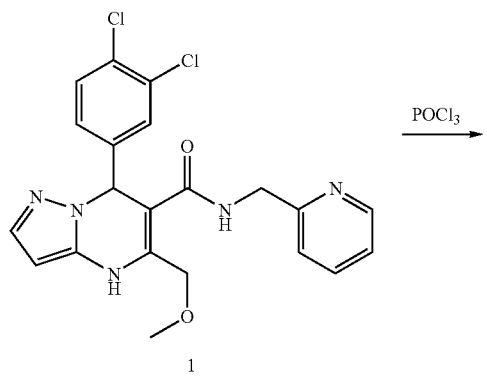

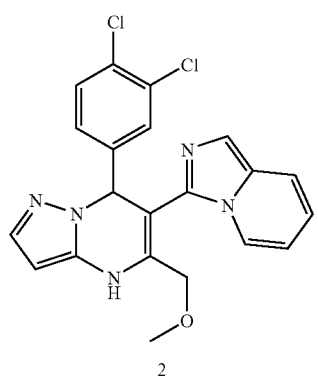

Synthesis of 1: The synthesis 1 was described in Example 484.

Synthesis of 2: The title compound was synthesized in a manner described in Example 465. The product was purified by preparative TLC in 10% methanol in dichloromethane. Mass Spec m/z (M+H)+ 426.

EXAMPLE 498

7-(2,3-Dichlorophenyl)-4,7-dihydro-6-(imidazo[1,5-a]pyridin-3-yl)-5-(methoxymethyl)pyrazolo[1,5-a]pyrimidine

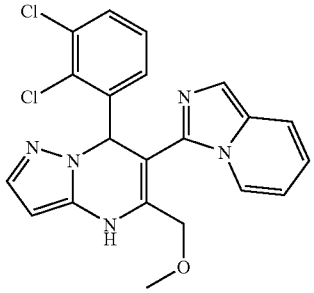

The title compound was synthesized in a manner similar to that described in Example 497. Mass Spec m/z (M+H)+ 426

EXAMPLE 499

7-(3,4-Dichlorophenyl)-6-(5-fluoro-1-methyl-1H-benzimidazol-2-yl)-4,7-dihydro-5-(methoxymethyl)pyrazolo[1,5-a]pyrimidine

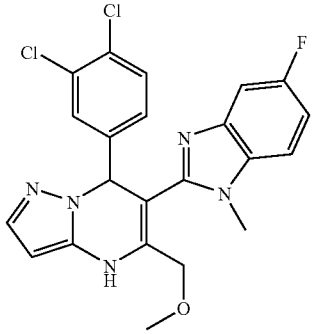

Starting with compound 6 from Example 484, the title compound was synthesized in a manner similar to that described in Example 470. Mass Spec m/z (M+H)+ 458. The title compound can be separated into pure chiral form via preparative chiral HPLC (Chiralpak AD 5 cm×50 cm column eluted with 25% isopropanol in hexane with 0.1% TEA at 50 mL/min with UV detection at 254 nM). The faster eluting isomer (example 503) is enantiomer A (HPLC retention time 6.8 min, 4.6×250 mm Chiralpak AD column eluted with 25% isopropanol, hexane with 0.1% triethylamine at 1 mL/min with UV detection at 220 nm) and the slower eluting isomer (example 504) is enantiomer B (HPLC retention time 12.0 min, 4.6×250 mm Chiralpak AD column eluted with 25% isopropanol, hexane with 0.1% triethylamine at 1 mL/min with UV detection at 254 nm).

EXAMPLES 500–504

The following examples were synthesized by methods described in Example 499:

| Ex. | Structure | Name | Mass Spec |
|---|---|---|---|
| 500 | 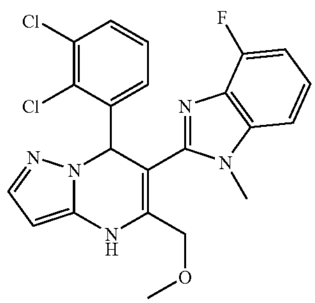 | 7-(2,3-Dichlorophenyl)-6-(4-fluoro-1-methyl-1H-benzimidazol-2-yl)-4,7-dihydro-5-(methoxymethyl)pyrazolo[1,5-a]pyrimidine | 458(M + H)+ |
| 501 | 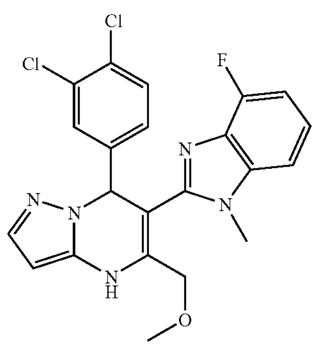 | 7-(3,4-Dichlorophenyl)-6-(4-fluoro-1-methyl-1H-benzimidazol-2-yl)-4,7-dihydro-5-(methoxymethyl)pyrazolo[1,5-a]pyrimidine | 458(M + H)+ |
| 502 | 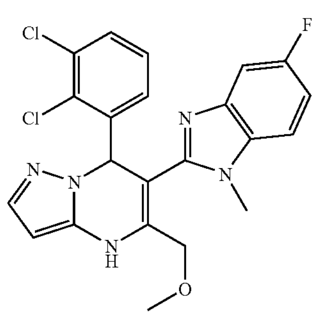 | 7-(2,3-Dichlorophenyl)-6-(5-fluoro-1-methyl-1H-benzimidazol-2-yl)-4,7-dihydro-5-(methoxymethyl)pyrazolo[1,5-a]pyrimidine | 458(M + H)+ |
| 503 | 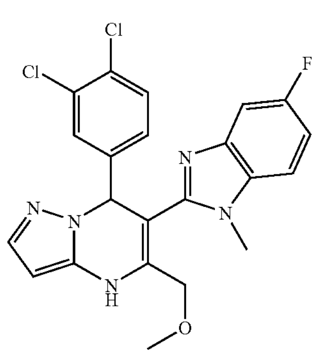 | 7-(3,4-Dichlorophenyl)-6-(5-fluoro-1-methyl-1H-benzimidazol-2-yl)-4,7-dihydro-5-(methoxymethyl)pyrazolo[1,5-a]pyrimidine enantiomer A | 458(M + H) |

| Ex. | Structure | Name | Mass Spec |
|---|---|---|---|
| 504 | 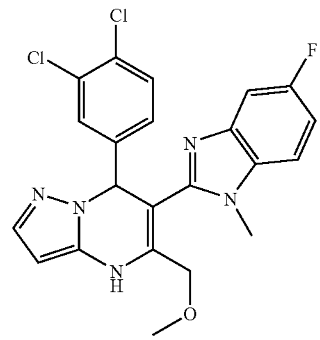 | 7-(3,4-Dichlorophenyl)-6-(5-fluoro-1-methyl-1H-benzimidazol-2-yl)-4,7-dihydro-5-(methoxymethyl)pyrazolo[1,5-a]pyrimidine enantiomer B | 458(M + H) |
EXAMPLE 505
7-(3,4-Dichlorophenyl)-4,7-dihydro-5-phenyl-N-(3-phenylpropyl)pyrazolo[1,5-a]pyrimidine-6-carboxamide
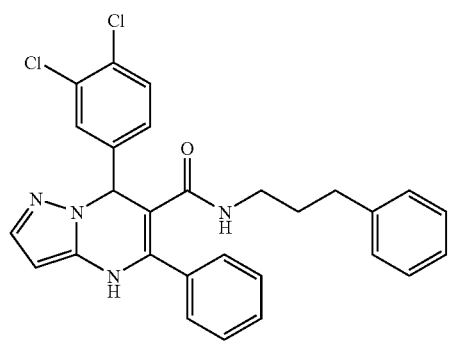
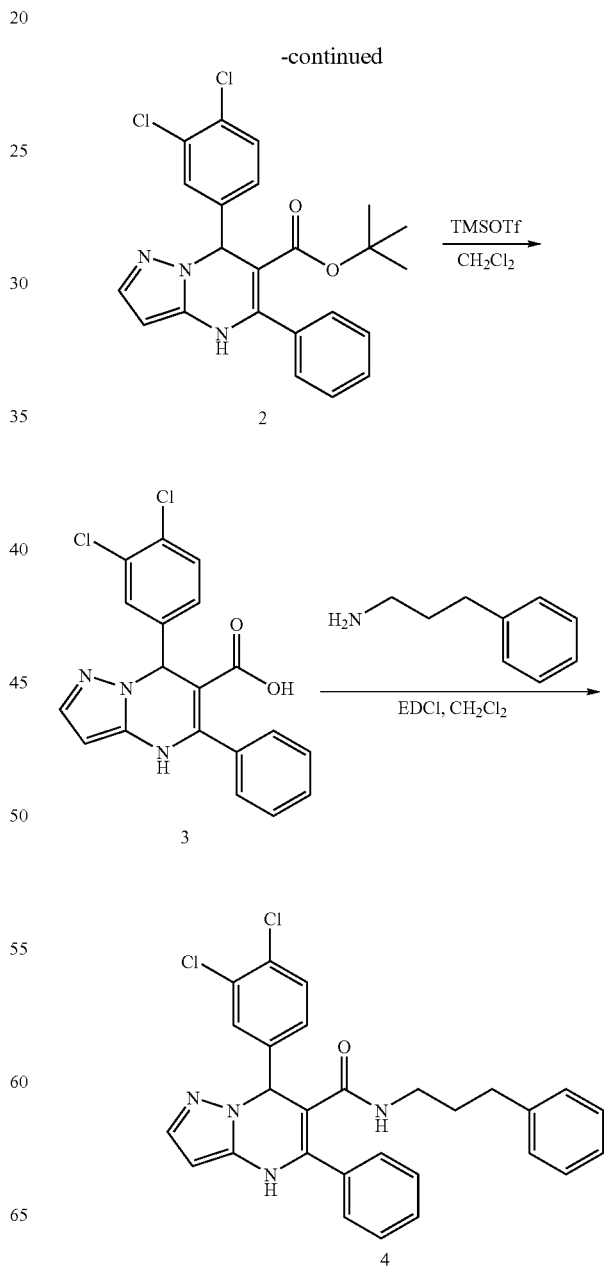

Synthesis of 1: A solution of benzoic acid (3.05 g, 25 mmol) in tetrahydrofuran (25 mL) was treated with CDI (4.05 g, 25 mmol) at ambient temperature. In a separate flask lithiumdiisopropylamide was generated at −78° C. by treatment of a tetrahydrofuran solution (40 mL) of diisopropyl amine (10.6 mL, 76.0 mmol) with 2.5 M n-butyl lithium in hexanes (30 mL, 75.0 mmol). Tert-butyl acetate was added dropwise and the reaction was stirred at −78° C. for 1 hr. The enolate was transferred at −78° C. to a stirred solution of the imidazoylbenzoate prepared previously. The resulting solution was cooled to −78° C. After the addition of the enolate was complete, a thick slurry resulted, which was broken up by shaking the reaction. The reaction mixture was allowed to stir for 1 h at −78° C. A 1N aqueous solution of hydrochloric acid was added until the pH was 4. The reaction mixture was allowed to warm to ambient temperature with stirring. The reaction mixture was extracted with diethyl ether. The combined organic layer was washed with aqueous 1N hydrochloric acid, aqueous 10% sodium hydrogen carbonate, saturated aqueous sodium chloride, dried over magnesium sulfate, and filtered. The solvent was removed to give 1 (5.0 g, 91%) as an oil.

Synthesis of 2: Compound 2 was synthesized in a manner similar to that of compound 5 in example 484.

Synthesis of 3: Compound 3 was synthesized in a manner similar to that of compound 6 in example 484.

Synthesis of 4: The title compund was synthesized in a manner similar to that of compound 7 in example 484. Mass Spec m/z (M+H)$^+$ 503.

EXAMPLES 506–509

The following Examples 506–509 were synthesized in a manner similar to that described in Example 505:

| Ex. | Structure | Name | Mass Spec |
|---|---|---|---|
| 506 | 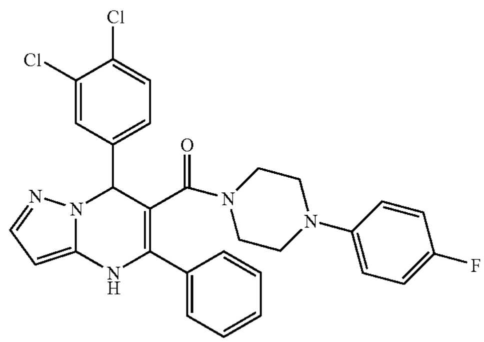 | 1-[[7-(3,4-Dichlorophenyl)-4,7-dihydro-5-phenylpyrazolo[1,5-a]pyrimidin-6-yl]carbonyl]-4-(4-fluorophenyl)piperazine | 448(M + H)$^+$ |
| 507 | 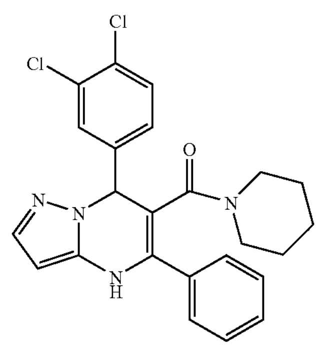 | 1-[[7-(3,4-Dichlorophenyl)-4,7-dihydro-5-phenylpyrazolo[1,5-a]pyrimidin-6-yl]carbonyl]piperidine | 459(M + H)$^+$ |
| 508 | 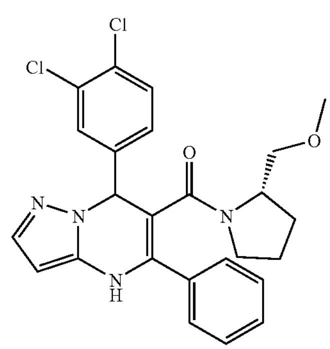 | (2S)-1-[[7-(3,4-Dichlorophenyl)-4,7-dihydro-5-phenylpyrazolo[1,5-a]pyrimidin-6-yl]carbonyl]-2-(methoxymethyl)pyrrolidine | 483(M + H)$^+$ |

| Ex. | Structure | Name | Mass Spec |
|---|---|---|---|
| 509 | 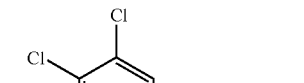 | 7-(3,4-Dichlorophenyl)-4,7-di-hydro-5-phenyl-N,N-di-propylpyrazolo[1,5-a]py-rimidine-6-carboxamide | 475(M + H) |

EXAMPLE 510

1-[[7-(3,4-Dichlorophenyl)-4,7-dihydro-5-methylpyrazolo[1,5-a]pyrimidin-6-yl]carbonyl]-2-phenylpyrazolidine

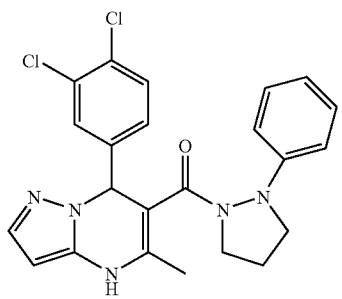

Preparation of 3: To a solution of dihydropyrimidine acid 1 (0.336 g, 1 mmol) in dichloromethane (10 mL) was added 1-phenylpyrazolidine 2 (0.215 g, 1.5 mmol, prepared using the procedure described in *Tetrahedron*, 1973, 29, 4045) followed by 1-[3-(dimethylamino)propyl]-3-ethylcarbodiimide hydrochloride (0.278 g, 1.5 mmol) and the mixture stirred at room temperature for 2 hours. The solvent was evaporated and the residue purified by silica gel chromatography, eluting with ethyl acetate, to give the title compound 3 (0.184 g, 39%) as a white powder. $(M+H)^+=455$.

EXAMPLE 511

6-(1-Chloro-6,7-dihydro-5H-pyrrolo[1,2-c]imidazol-3-yl)-7-(3,4-dichlorophenyl)-4,7-dihydro-5-methylpyrazolo[1,5-a]pyrimidine

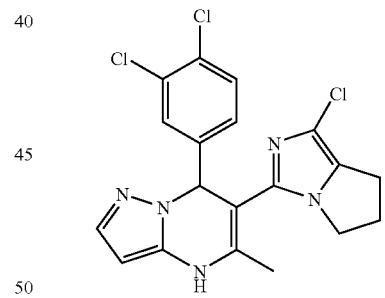

Scheme:

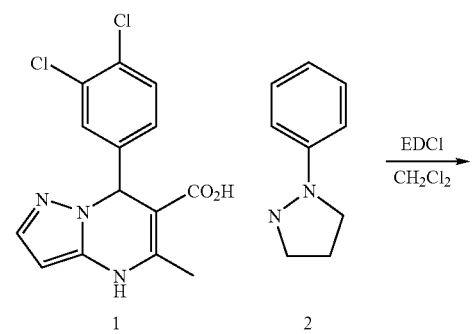

Scheme

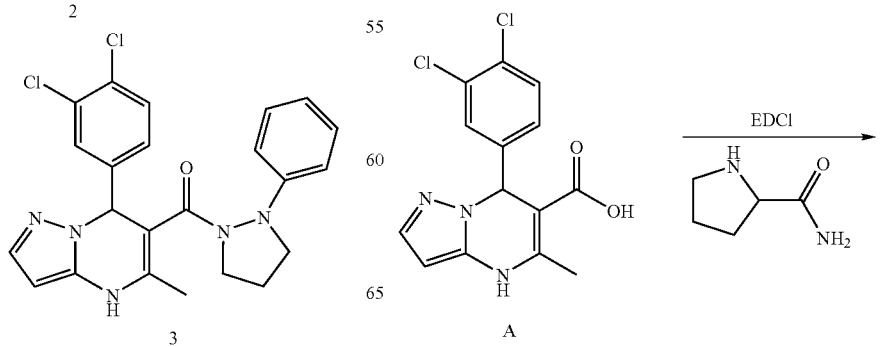

-continued

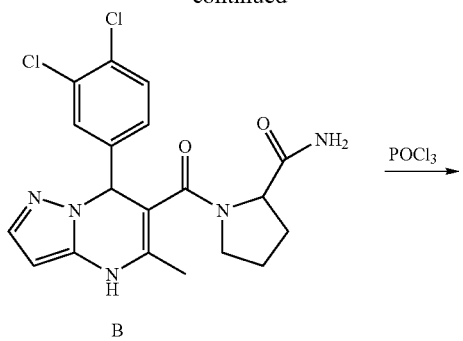

B

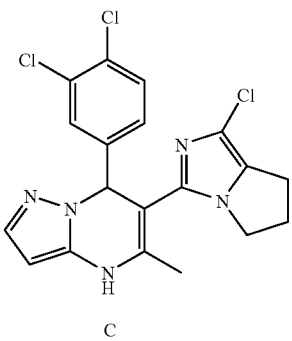

C

Preparation of B: At 20° C., EDCI (100 mg, 0.52 mmol) was added to a stirred slurry of carboxylic acid A (120 mg, 0.37 mmol) in CH$_2$Cl$_2$. After 5 mins, proline amide was added (60 mg, 0.52 mmol) and the reaction mixture was stirred at ambient temperature for 3 h. The resulting yellow slurry was concentrated under reduced pressure, dissolved in 2 mL acetone and applied directly to a preparative silica gel TLC plate, (20×20 cm, 1 mm thickness, 254 nm UV indicator) eluting with 10% MeOH in CH$_2$Cl$_2$. The product B was isolated as a 1:1 ratio of diastereomers (79 mg, 50% yield as a pale yellow glass.) HPLC: R$_T$ 2.61 and 2.80 min (YMC S5 ODS 4.6×50 mm Ballistic column) 10–90% MeOH/water with 0.2% PPA linear gradient over 4 min, 4 mL/min, UV Detection at 220 nm. LCMS: R$_T$ 2.63 and 2.81 min (YMC S5 ODS 4.6×50 mm Ballistic column) 10–90% MeOH/water with 0.1% TFA linear gradient over 4 min, 4 mL/min, UV Detection at 220 nm, Mass Spec m/z (M+H)$^+$ 420.

Preparation of C: Phosphorus oxychloride (4 mL) was added to diastereomers B (190 mg, 0.46 mmol). The slurry was heated to 100° C. for 12 h whereupon the precipitate dissolved furnishing an orange colored solution. The cooled reaction mixture was poured cautiously into saturated K$_2$CO$_3$ (ca. 20 mL) and extracted with EtOAc (3×30 mL). The combined organic portions were dried over Na$_2$SO$_4$, decanted and concentrated yielding an orange oil which was purified directly by preparative HPLC: R$_T$ 28.40 min (YMC S5 ODS 30×250 mm Reversed phase C18 column) 30–90% MeOH/water with 0.1% TFA linear gradient over 30 min, 25 mL/min, UV Detection at 220 nm. Product C (96 mg, 51% yield) was obtained as a free base after removal of MeOH from the HPLC fractions, addition of 1.0M NaOH and extraction into CH$_2$Cl$_2$ (3×30 mL). The enantiomers were separated by chiral preparative HPLC: R$_T$ 42.4 and 59.0 min (ChiralPak OD 50×500 mm Normal phase column) 15% EtOH/hexane Isocratic, 50 mL/min, Uv Detection at 220 nm. Both enantiomers were isolated as pale yellow powders, (34 mg of enantiomer A and 38 mg enantiomer B). Chiral-HPLC Enantiomer B: R$_T$ 7.36 min (ChiralPak OD 4.6×250 mm Normal phase column) 15% EtOH/hexane Isocratic, 2 mL/min, UV Detection at 220 nm 100% ee. ChiralHPLC Enantiomer A: R$_T$ 4.94 min (ChiralPak OD 4.6×250 mm Normal phase column) 15% EtOH/hexane Isocratic, 2 mL/min, UV Detection at 220 nm 100% ee.

EXAMPLE 512

7-(3,4-Dichlorophenyl)-4,7-dihydro-5-methyl-6-(1-methyl-1H-thieno[3,4-d]imidazol-2-yl)pyrazolo[1,5-a]pyrimidine

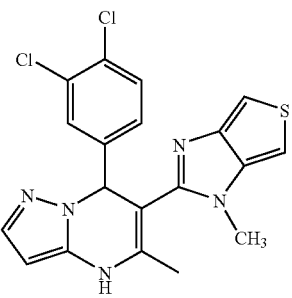

Scheme

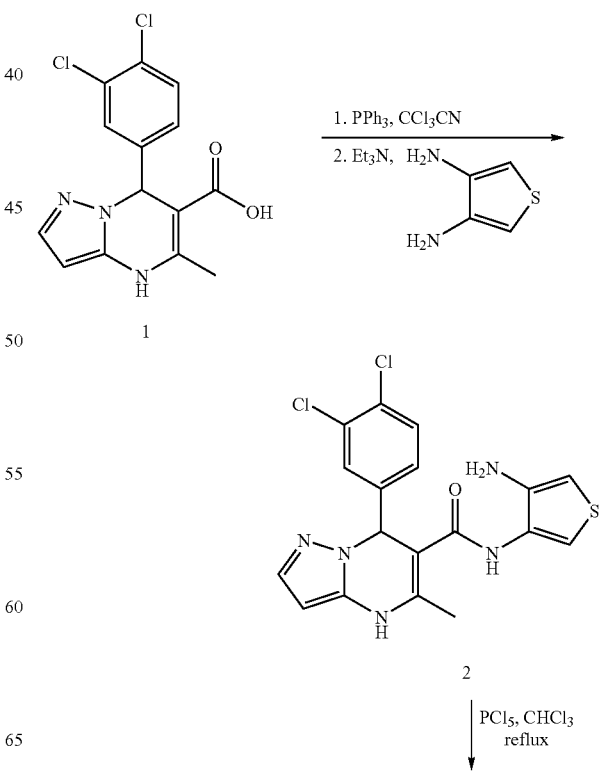

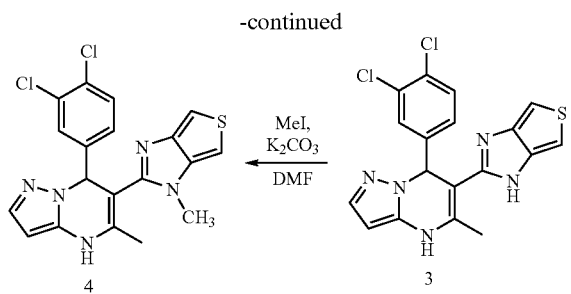

Preparation of compound 1: as described in example 16.

Preparation of compound 2: To a suspension of the acid (152.9 mg, 0.47 mmol) in 5 mL of anhydrous dichloromethane were added trichloroacetonitrile (57.0 µL, 0.67 mmol) and triphenylphosphine (186.2 mg, 0.71 mmol). The mixture became clear and was allowed to stir at room temperature for 1 hour. The reaction mixture was transferred into a solution of 3,4-diaminothiophene hydrochloride (88.5 mg, 0.47 mmol) and triethylamine (198.0 µL, 1.42 mmol) in 5 mL of dichloromethane. The reaction was monitored using TLC or LC/MS. Upon completion of the coupling, the reaction mixture was loaded directly onto silica gel and eluted with 5% methanol/dichloromethane to yield the desired amide as a white solid (132.3 mg, 67%).

Preparation of compound 3: A suspension of the resulting amide (107 mg, 0.25 mmol) and phosphorus pentachloride (53.1 mg, 0.25 mmol) in chloroform (20 mL) was heated to reflux under anhydrous argon for 5 hours and the mixture was allowed to cool down to room temperature and stir overnight. Solvent was removed under reduced pressure, and the residue was redissolved in ethyl acetate and briefly washed with saturated aqueous sodium bicarbonate solution. The organic layer was separated, dried over sodium sulfate, and concentrated to give the crude thienoimidazole, which was purified by flash chromatograph using 100% ethyl acetate to give a brown solid (73 mg, 71%).

Preparation of compound 4: To a solution of the thienoimidazole (22.4 mg, 0.06 mmol) in 2 mL of anhydrous DMF was added iodomethane (4.5 µL, 0.07 mmol) and potassium carbonate (15.4 mg, 0.11 mmol). The mixture was allowed to stir at room temperature overnight. The reaction was quenched using methanol. The mixture was diluted with ethyl acetate and washed with 10% LiCl (3×10 mL) and brine (10 mL). The organic layer was separated and dried over sodium sulfate and concentrated to give a residue, which was further purified using flash chromatograph (5% MeOH/ethyl acetate) and (6% MeOH/chloroform) to give the titled compound as a white solid (4.5 mg, 20%).

EXAMPLE 513

7-(3,4-Dichlorophenyl)-4,7-dihydro-5-methyl-6-(4-methyl-4H-imidazo[3,4d][1,2,5]thiadiazol-5-yl)pyrazolo[1,5-a]pyrimidine

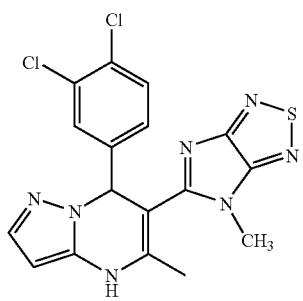

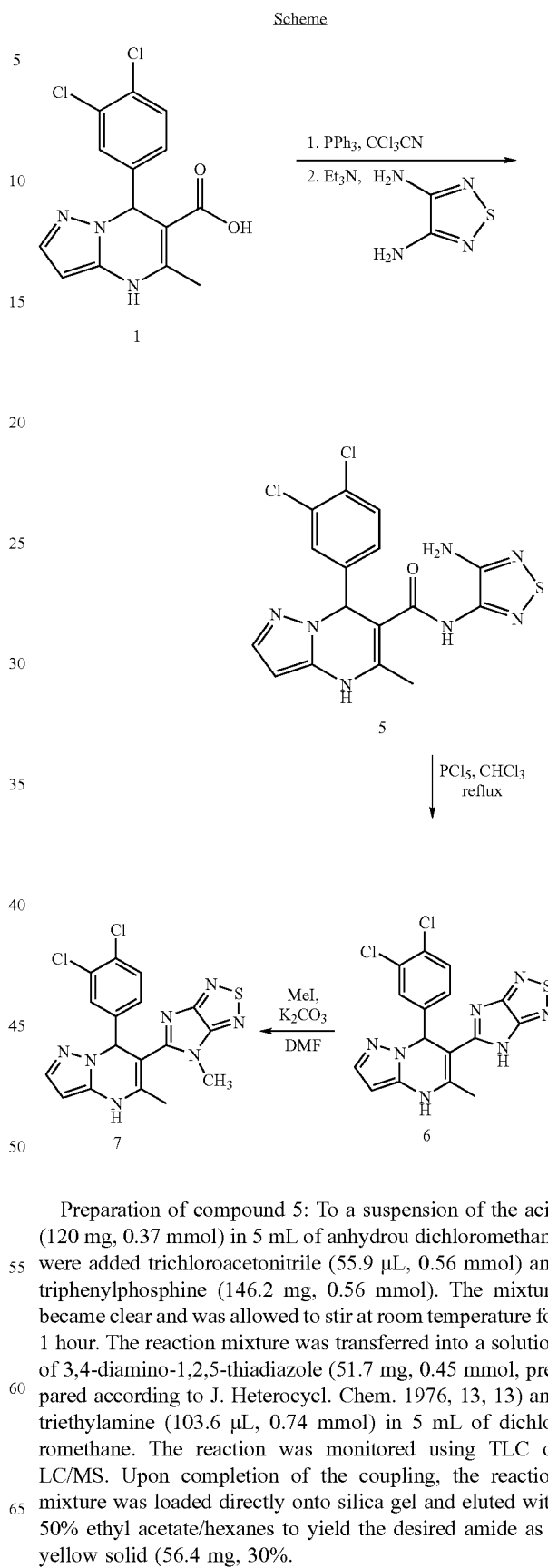

Preparation of compound 5: To a suspension of the acid (120 mg, 0.37 mmol) in 5 mL of anhydrou dichloromethane were added trichloroacetonitrile (55.9 µL, 0.56 mmol) and triphenylphosphine (146.2 mg, 0.56 mmol). The mixture became clear and was allowed to stir at room temperature for 1 hour. The reaction mixture was transferred into a solution of 3,4-diamino-1,2,5-thiadiazole (51.7 mg, 0.45 mmol, prepared according to J. Heterocycl. Chem. 1976, 13, 13) and triethylamine (103.6 µL, 0.74 mmol) in 5 mL of dichloromethane. The reaction was monitored using TLC or LC/MS. Upon completion of the coupling, the reaction mixture was loaded directly onto silica gel and eluted with 50% ethyl acetate/hexanes to yield the desired amide as a yellow solid (56.4 mg, 30%.

Preparation of compound 6: A suspension of the resulting amide (80 mg, 0.19 mmol) and phosphorus pentachloride (79 mg, 0.38 mmol) in chloroform (10 mL) was stirred at room temperature under anhydrous argon for one hour and then heated to reflux for 2 hours. The mixture was allowed to cool down to room temperature and solvent was removed under reduced pressure. The residue was redissolved in ethyl acetate and briefly washed with saturated aqueous sodium bicarbonate solution. The organic layer was separated, dried over sodium sulfate, and concentrated to give the crude thiodiazoimidazole, which was purified by flash chromatograph using 80% ethyl acetate/hexanes to give a yellow solid (29 mg, 38%).

Preparation of compound 7: To a solution of the thiadiazoimidazole (29 mg, 0.07 mmol) in 2 mL of anhydrous DMF was added iodomethane (4.9 μL, 0.08 mmol) and potassium carbonate (19.9 mg, 0.14 mmol). The mixture was allowed to stir at room temperature under dry argon for 3 hours. The reaction was quenched using methanol and diluted with ethyl acetate and washed with 10% LiCl (3×10 mL) and brine (10 mL). The organic layer was separated and dried over sodium sulfate and concentrated to give a residue, which was purified using HPLC to give the titled compound as a white solid (1.6 mg, 5%).

EXAMPLE 514

7-(3,4-Dichlorophenyl)-6-(1,6-dihydro-1,3,6-trimethylimidazo[4,5-c]pyrazol-5-yl)-4,7-dihydro-5-methylpyrazolo[1,5-a]pyrimidine

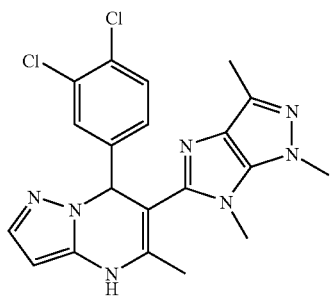

Scheme

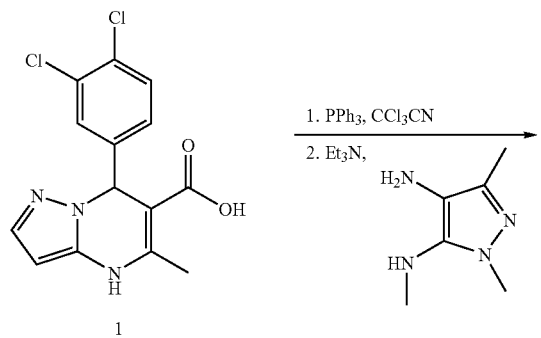

-continued

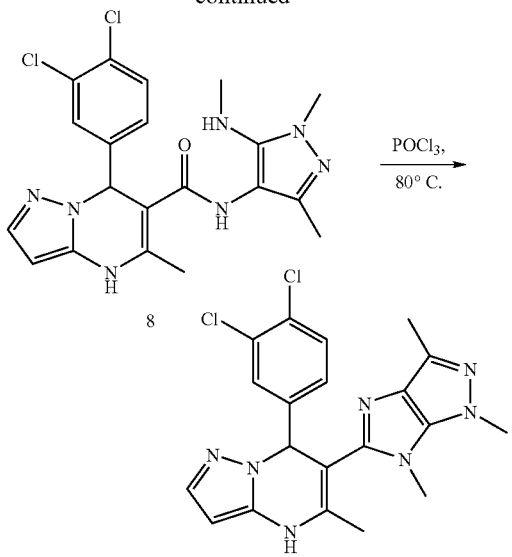

Preparation of compound 8: To a suspension of the acid (150 mg, 0.46 mmol) in 5 mL of anhydrou dichloromethane were added trichloroacetonitrile (69.8 μL, 0.70 mmol) and triphenylphosphine (182.7 mg, 0.70 mmol). The mixture became clear and was allowed to stir at room temperature for 1 hour. The reaction mixture was transferred into a solution of the diaminopyrazole (prepared according to *J. Med. Chem.* 1995, 38, 3524) and triethylamine (129.5 μL, 0.93 mmol) in 5 mL of dichloromethane. The reaction was monitored using TLC or LC/MS. Upon completion of the coupling, the reaction mixture was loaded directly onto silica gel and eluted with 10% methanol/ethyl acetate to yield the desired amide as a white solid.

Preparation of compound 9: A suspension of the resulting amide (39.5 mg, 0.09 mmol) in phosphorus oxychloride (10 mL) was stirred at 80° C. under anhydrous argon overnight. The mixture was allowed to cool down to room temperature and solvent was removed under reduced pressure. The residue was redissolved in ethyl acetate and briefly washed with saturated aqueous sodium bicarbonate solution. The organic layer was separated, dried over sodium sulfate, and concentrated to give a residue, which was purified by flash chromatograph using 10% methanol/dichloromethane to give the desired product as a light brown solid (13.9 mg, 37%).

EXAMPLE 515

1-[[7-(3,4-Dichlorophenyl)-4,7-dihydro-5-methyl-2-(trifluoromethyl)pyrazolo[1,5-a]pyrimidin-6-yl]carbonyl]-2-(2-thienyl)pyrrolidine

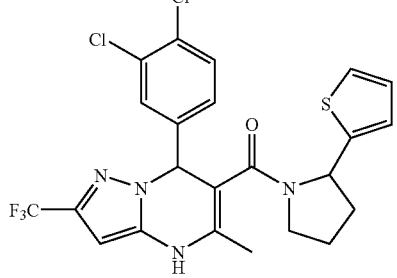

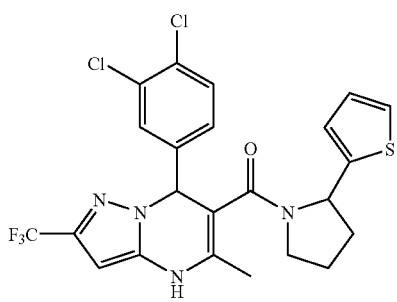

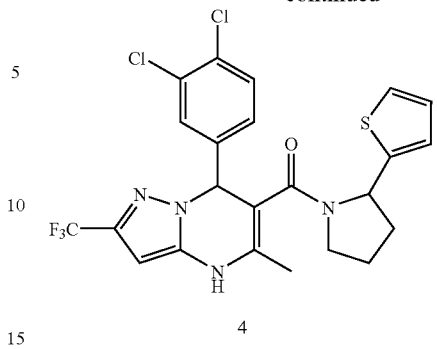

Scheme

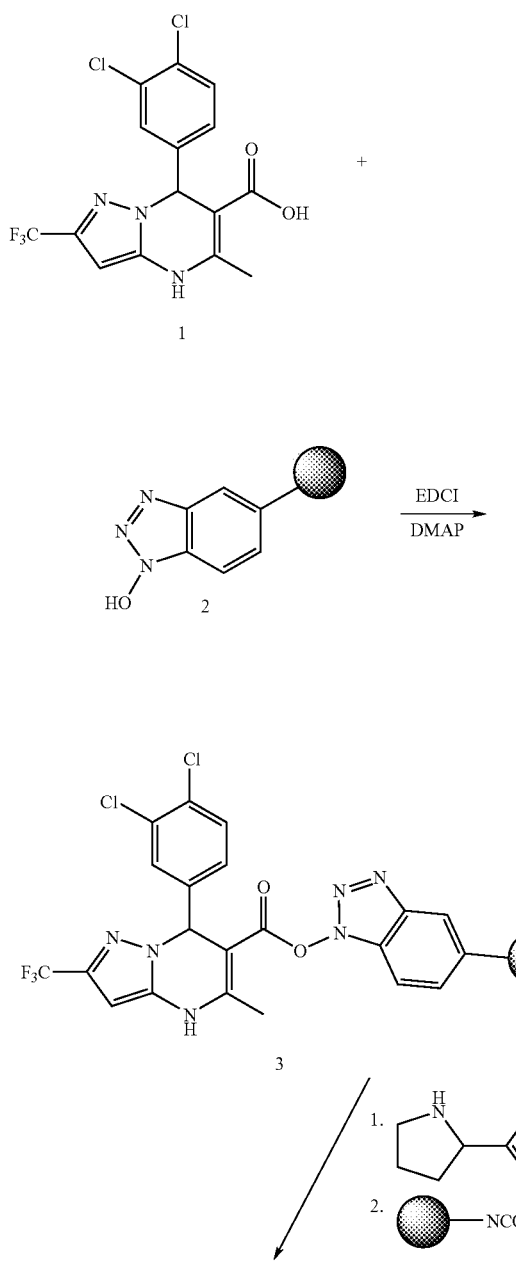

Preparation of compound 1: as described in example 17.

Preparation of compound 3: To a suspension of polystyrene supported HOBt reagent (5.2 g, 8.0 mmol) in 100 mL of anhydrous dichloromethane in a reaction vessel that has a fritted glass filter at the bottom was added the acid (4.7 g, 12.0 mmol), 1-[3-(dimethylamino)propyl]-3-ethylcarbodiimide hydrochloride (2.3 g, 12.0 mmol), and 4-dimethylaminopyridine (98 mg, 0.8 mmol). The mixture was shook using an orbital shaker for 3 hours at room temperature. Solvent was drained through filtration, and the resin washed with anhydrous DMF (3×30 mL), anhydrous TF (3×30 mL), and anhydrous dichloromethane (3×30 mL). The resin that contains activated ester was allowed to dry in vacuo overnight. The coupling yield was estimated based on the weight gain to be 84%.

Preparation of compound 4: Resin containing the HOBt-activated ester (58 mg, 0.05 mmol) was distributed into a well, to which 2-(2'-thienyl)-pyrrolidine (80 μL of 0.5 M, 0.04 mmol) was dispensed. The suspension was allowed to shake at room temperature for 3 hours, and then polystyrene-supported isocyanate reagent was added (83 mg, 0.08 mmol) and the suspension was shook for 2 hours. Solvent was collected through filtration, and the resin was washed with dichloromethane (2×0.5 mL). All filtrates were combined and concentrated under reduced pressure to give the desired product as a white solid (18 mg). The purity of the product was checked using LC/MS to be 100%, and m/z is 527.

EXAMPLES 516–587

The following compounds were synthesized using the procedure as described in Example 515. Those compounds that have low purity were purified using preparative HPLC to give the corresponding desired products.

| Ex. | Structure | Name | Mass Spec |
|---|---|---|---|
| 516 | 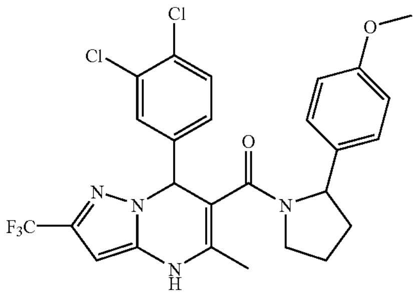 | 1-[[7-(3,4-Dichlorophenyl)-4,7-dihydro-5-methyl-2-(trifluoromethyl)pyrazolo[1,5-a]pyrimidin-6-yl]carbonyl]-2-(4-methoxyphenyl)pyrrolidine | 551(M + H)+ |
| 517 | 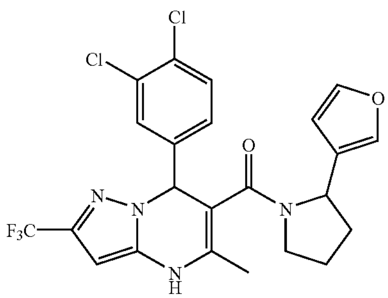 | 1-[[7-(3,4-Dichlorophenyl)-4,7-dihydro-5-methyl-2-(trifluoromethyl)pyrazolo[1,5-a]pyrimidin-6-yl]carbonyl]-2-(3-furanyl)pyrrolidine | 511(M + H)+ |
| 518 | 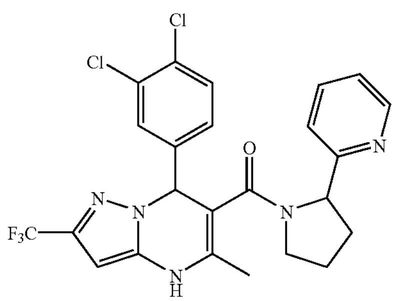 | 1-[[7-(3,4-Dichlorophenyl)-4,7-dihydro-5-methyl-2-(trifluoromethyl)pyrazolo[1,5-a]pyrimidin-6-yl]carbonyl]-2-(2-pyridinyl)pyrrolidine | 522(M + H)+ |
| 519 | 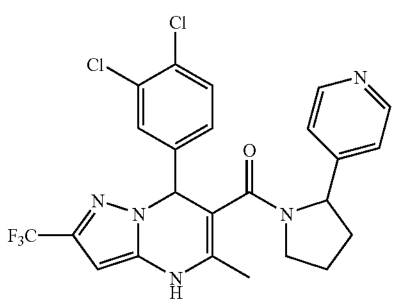 | 1-[[7-(3,4-Dichlorophenyl)-4,7-dihydro-5-methyl-2-(trifluoromethyl)pyrazolo[1,5-a]pyrimidin-6-yl]carbonyl]-2-(4-pyridinyl)pyrrolidine | 522(M + H) |
| 520 | 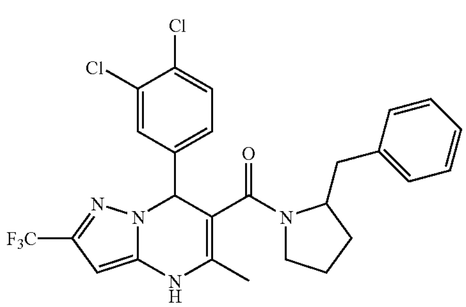 | 1-[[7-(3,4-Dichlorophenyl)-4,7-dihydro-5-methyl-2-(trifluoromethyl)pyrazolo[1,5-a]pyrimidin-6-yl]carbonyl]-2-(phenylmethyl)pyrrolidine | 535(M + H) |

| Ex. | Structure | Name | Mass Spec |
|---|---|---|---|
| 521 | 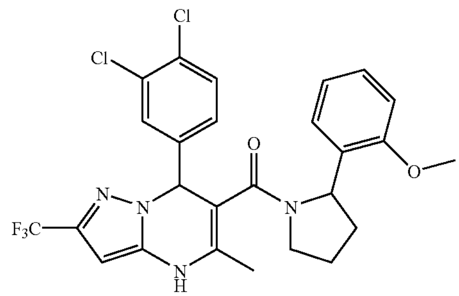 | 1-[[7-(3,4-Dichlorophenyl)-4,7-di-hydro-5-methyl-2-(tri-fluoromethyl)pyrazolo[1,5-a]py-rimidin-6-yl]carbonyl]-2-(2-methoxy-phenyl)pyrrolidine | 551(M + H) |
| 522 | 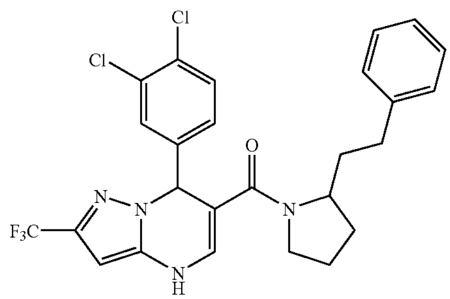 | 1-[[7-(3,4-Dichlorophenyl)-4,7-di-hydro-5-methyl-2-(tri-fluoromethyl)pyrazolo[1,5-a]py-rimidin-6-yl]carbonyl]-2-(2-phenyl-ethyl)pyrrolidine | 549(M + H) |
| 523 | 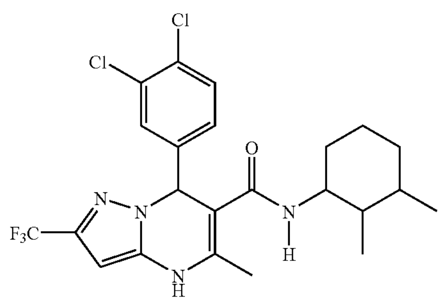 | 7-(3,4-Dichlorophenyl)-N-(2,3-di-methylcyclohexyl)-4,7-dihydro-5-meth-yl-2-(tri-fluoromethyl)pyrazolo[1,5-a]py-rimidine-6-carboxamide | 501(M + H) |
| 524 | 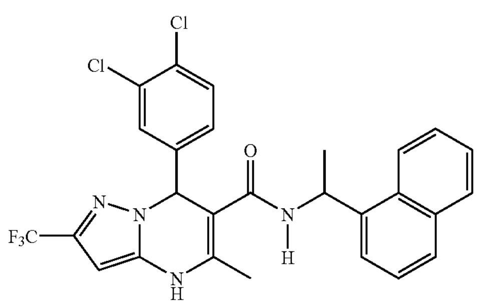 | 7-(3,4-Dichlorophenyl)-4,7-dihydro-5-meth-yl-N-[1-(1-naph-thalenyl)ethyl]-2-(tri-fluoromethyl)pyrazolo[1,5-a]py-rimidine-6-carboxamide | 545(M + H) |
| 525 | 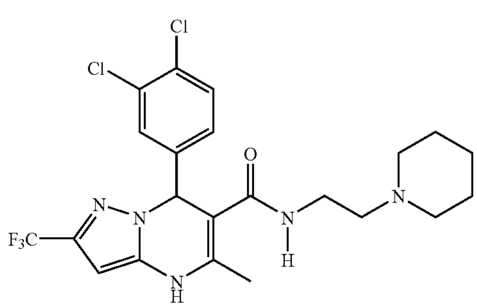 | 7-(3,4-Dichlorophenyl)-4,7-dihydro-5-meth-yl-N-[2-(1-piperidinyl)ethyl]-2-(tri-fluoromethyl)pyrazolo[1,5-a]py-rimidine-6-carboxamide | 502(M + H) |

-continued

| Ex. | Structure | Name | Mass Spec |
|---|---|---|---|
| 526 | 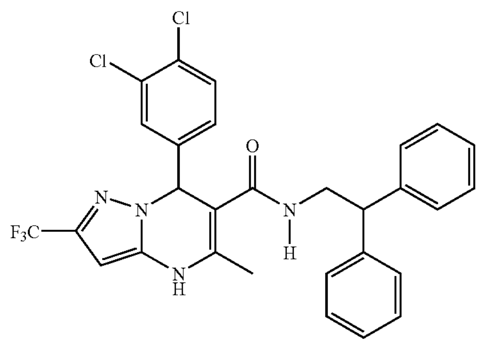 | 7-(3,4-Dichlorophenyl)-N-(2,2-diphenylethyl)-4,7-dihydro-5-methyl-2-(trifluoromethyl)pyrazolo[1,5-a]pyrimidine-6-carboxamide | 571(M + H) |
| 527 | 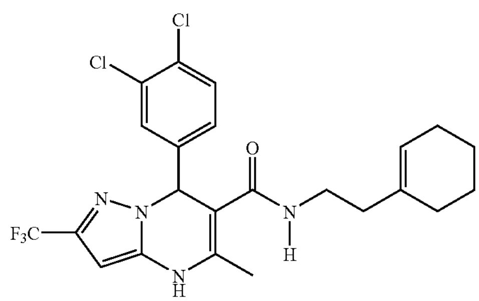 | N-[2-(1-Cyclohexen-1-yl)ethyl]-7-(3,4-dichlorophenyl)-4,7-dihydro-5-methyl-2-(trifluoromethyl)pyrazolo[1,5-a]pyrimidine-6-carboxamide | 499(M + H) |
| 528 | 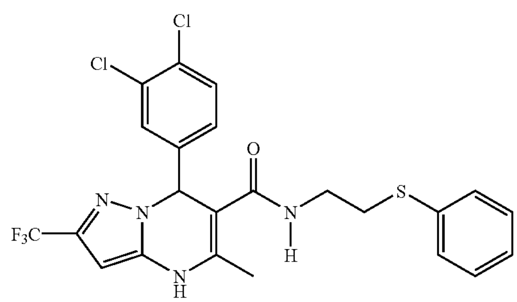 | 7-(3,4-Dichlorophenyl)-4,7-dihydro-5-methyl-N-[2-(phenylthio)ethyl]-2-(trifluoromethyl)pyrazolo[1,5-a]pyrimidine-6-carboxamide | 527(M + H) |
| 529 | 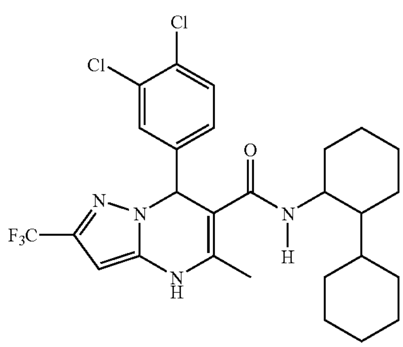 | N-([1,1'-Bicyclohexyl]-2-yl)-7-(3,4-dichlorophenyl)-4,7-dihydro-5-methyl-2-(trifluoromethyl)pyrazolo[1,5-a]pyrimidine-6-carboxamide | 555(M + H) |
| 530 | 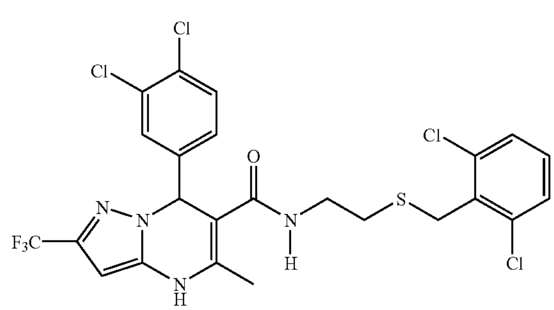 | 7-(3,4-Dichlorophenyl)-N-[2-[[(2,6-dichlorophenyl)methyl]thio]ethyl]-4,7-dihydro-5-methyl-2-(trifluoromethyl)pyrazolo[1,5-a]pyrimidine-6-carboxamide | 610(M + H) |

-continued

| Ex. | Structure | Name | Mass Spec |
|---|---|---|---|
| 531 | 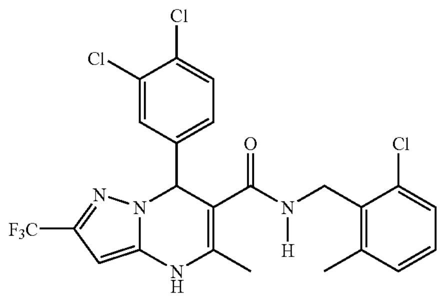 | N-[(2-Chloro-6-methyl-phenyl)methyl]-7-(3,4-di-chlorophenyl)-4,7-dihydro-5-methyl-2-(tri-fluoromethyl)pyrazolo[1,5-a]pyrimidine-6-carboxamide | 529(M + H) |
| 532 | 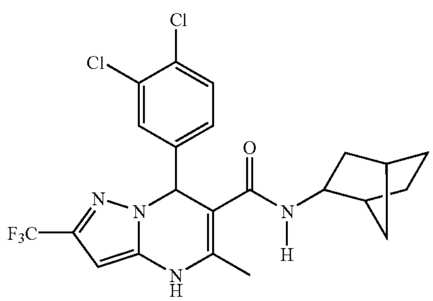 | N-(Bicyclo[2.2.1]heptan-2-yl)-7-(3,4-di-chlorophenyl)-4,7-dihydro-5-methyl-2-(tri-fluoromethyl)pyrazolo[1,5-a]pyrimidine-6-carboxamide | 485(M + H) |
| 533 | 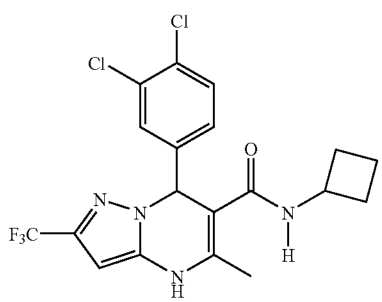 | N-Cyclobutyl-7-(3,4-di-chlorophenyl)-4,7-dihydro-5-methyl-2-(tri-fluoromethyl)pyrazolo[1,5-a]pyrimidine-6-carboxamide | 445(M + H) |
| 534 | 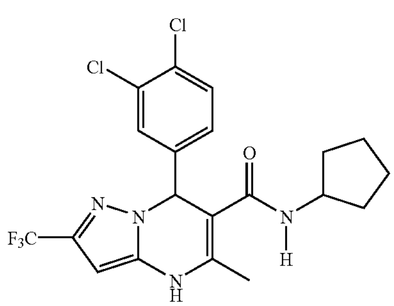 | N-Cyclopentyl-7-(3,4-di-chlorophenyl)-4,7-dihydro-5-methyl-2-(tri-fluoromethyl)pyrazolo[1,5-a]pyrimidine-6-carboxamide | 458(M + H) |
| 535 | 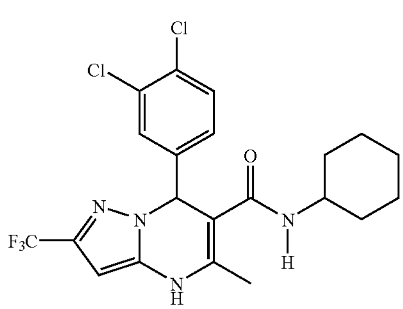 | N-Cyclohexyl-7-(3,4-di-chlorophenyl)-4,7-dihydro-5-methyl-2-(tri-fluoromethyl)pyrazolo[1,5-a]pyrimidine-6-carboxamide | 473(M + H) |

-continued

| Ex. | Structure | Name | Mass Spec |
|---|---|---|---|
| 536 | 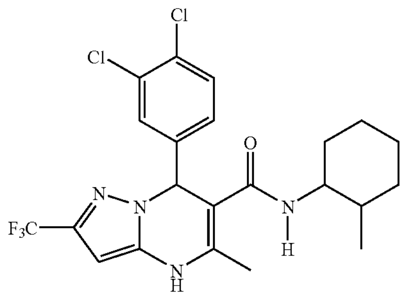 | 7-(3,4-Dichlorophenyl)-4,7-dihydro-5-methyl-N-(2-methylcyclohexyl)-2-(trifluoromethyl)pyrazolo[1,5-a]pyrimidine-6-carboxamide | 487(M + H) |
| 537 | 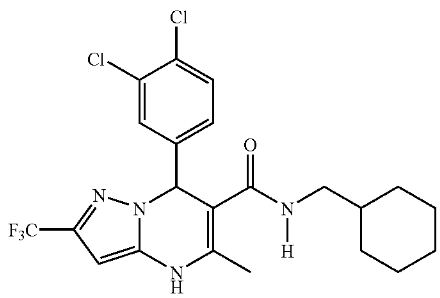 | N-(Cyclohexylmethyl)-7-(3,4-dichlorophenyl)-4,7-dihydro-5-methyl-2-(trifluoromethyl)pyrazolo[1,5-a]pyrimidine-6-carboxamide | 487(M + H) |
| 538 | 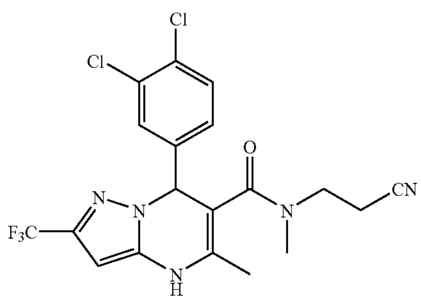 | N-(2-Cyanoethyl)-7-(3,4-dichlorophenyl)-4,7-dihydro-N,5-dimethyl-2-(trifluoromethyl)pyrazolo[1,5-a]pyrimidine-6-carboxamide | 458(M + H) |
| 539 | 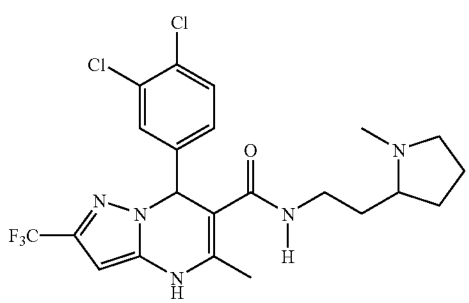 | 7-(3,4-Dichlorophenyl)-4,7-dihydro-5-methyl-N-[2-(1-methyl-2-pyrrolidinyl)ethyl]-2-(trifluoromethyl)pyrazolo[1,5-a]pyrimidine-6-carboxamide | 502(M + H) |
| 540 | 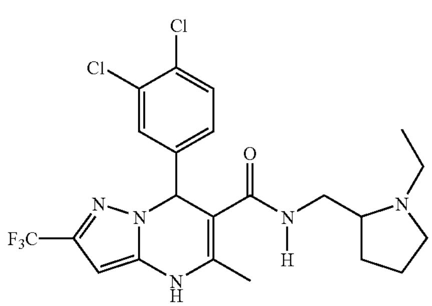 | 7-(3,4-Dichlorophenyl)-N-[(1-ethyl-2-pyrrolidinyl)methyl]-4,7-dihydro-5-methyl-2-(trifluoromethyl)pyrazolo[1,5-a]pyrimidine-6-carboxamide | 502(M + H) |

-continued

| Ex. | Structure | Name | Mass Spec |
|---|---|---|---|
| 541 | 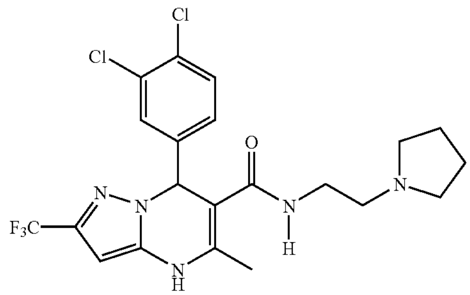 | 7-(3,4-Dichlorophenyl)-4,7-dihydro-5-methyl-N-[2-(1-pyrrolidinyl)ethyl]-2-(trifluoromethyl)pyrazolo[1,5-a]pyrimidine-6-carboxamide | 488(M + H) |
| 542 | 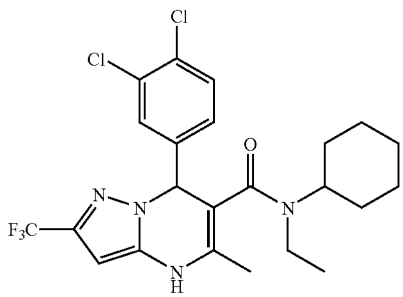 | N-Cyclohexyl-7-(3,4-dichlorophenyl)-N-ethyl-4,7-dihydro-5-methyl-2-(trifluoromethyl)pyrazolo[1,5-a]pyrimidine-6-carboxamide | 501(M + H) |
| 543 | 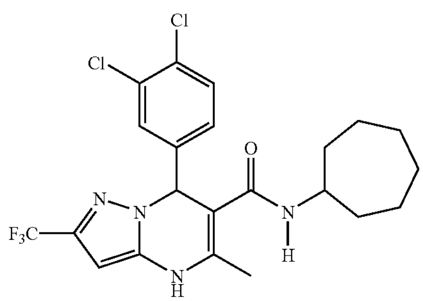 | N-Cycloheptyl-7-(3,4-dichlorophenyl)-4,7-dihydro-5-methyl-2-(trifluoromethyl)pyrazolo[1,5-a]pyrimidine-6-carboxamide | 487(M + H) |
| 544 | 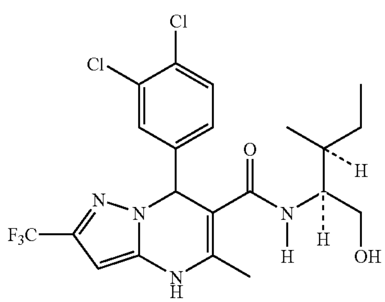 | 7-(3,4-Dichlorophenyl)-4,7-dihydro-[(1S,2S)-1-(hydroxymethyl)-2-methylbutyl]-5-methyl-2-(trifluoromethyl)pyrazolo[1,5-a]pyrimidine-6-carboxamide | 491(M + H) |
| 545 | 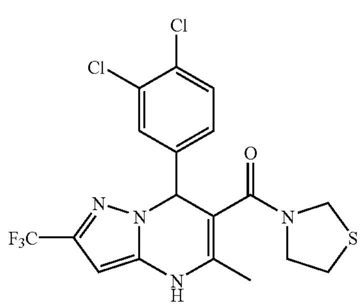 | 3-[[7-(3,4-Dichlorophenyl)-4,7dihydro-5-methyl-2-(trifluoromethyl)pyrazolo[1,5-a]pyrimidin-6-yl]carbonyl]thiazolidine | 463(M + H) |

| Ex. | Structure | Name | Mass Spec |
|---|---|---|---|
| 546 | 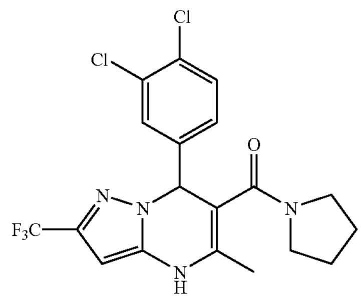 | 1-[[7-(3,4-Dichlorophenyl)-4,7di-hydro-5-methyl-2-(tri-fluoromethyl)pyrazolo[1,5-a]py-rimidin-6-yl]carbo-nyl]pyrrolidine | 445(M + H) |
| 547 | 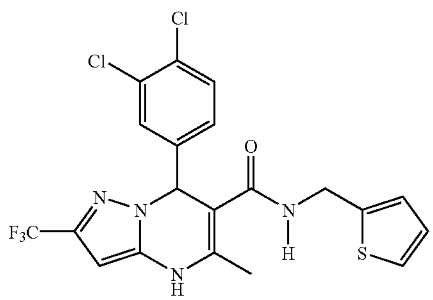 | 7-(3,4-Dichlorophenyl)-4,7-dihydro-5-meth-yl-N-(2-thienylmethyl)-2-(tri-fluoromethyl)pyrazolo[1,5-a]py-rimidine-6-carboxamide | 487(M + H) |
| 548 | 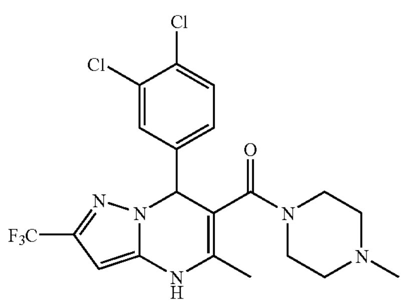 | 1-[[7-(3,4-Dichlorophenyl)-4,7di-hydro-5-methyl-2-(tri-fluoromethyl)pyrazolo[1,5-a]py-rimidin-6-yl]carbonyl]-4-methyl-piperazine | 474(M + H) |
| 549 | 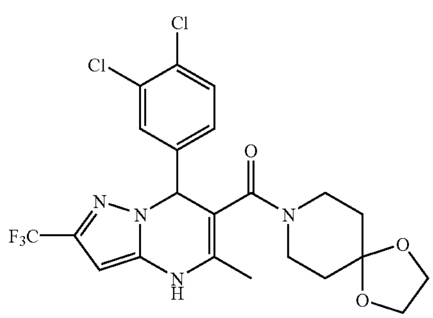 | 8-[[7-(3,4-Dichlorophenyl)-4,7di-hydro-5-methyl-2-(tri-fluoromethyl)pyrazolo[1,5-a]py-rimidin-6-yl]carbonyl]-1,4-di-oxa-8-azaspiro[4.5]decane | 517(M + H) |
| 550 | 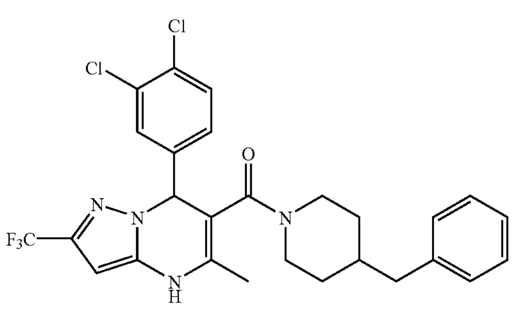 | 1-[[7-(3,4-Dichlorophenyl)-4,7-di-hydro-5-methyl-2-(tri-fluoromethyl)pyrazolo[1,5-a]py-rimidin-6-yl]carbonyl]-4-(phenyl-methyl)piperidine | 549(M + H) |

-continued

| Ex. | Structure | Name | Mass Spec |
|---|---|---|---|
| 551 | 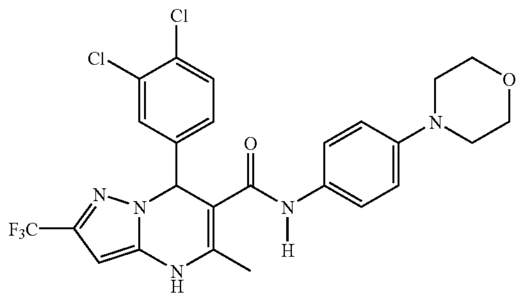 | 7-(3,4-Dichlorophenyl)-4,7-dihydro-5-methyl-N-[4-(4-morpholinyl)phenyl]-2-(trifluoromethyl)pyrazolo[1,5-a]pyrimidine-6-carboxamide | 552(M + H) |
| 552 | 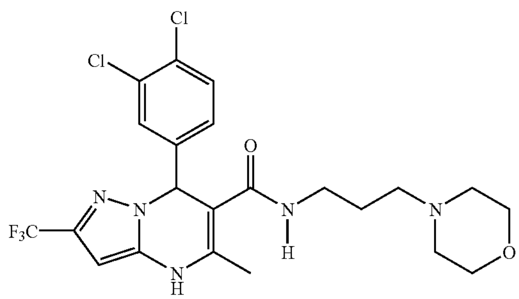 | 7-(3,4-Dichlorophenyl)-4,7-dihydro-5-methyl-N-[3-(4-morpholinyl)propyl]-2-(trifuoromethyl)pyrazolo[1,5-a]pyrimidine-6-carboxamide | 518(M + H) |
| 553 | 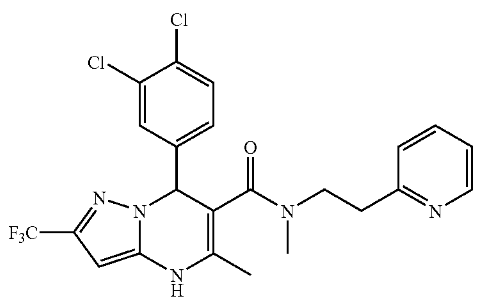 | 7-(3,4-Dichlorophenyl)-4,7-dihydro-N,5-dimethyl-N-[2-(2-pyridinyl)ethyl]-2-(trifluoromethyl)pyrazolo[1,5-a]pyrimidine-6-carboxamide | 510(M + H) |
| 554 | 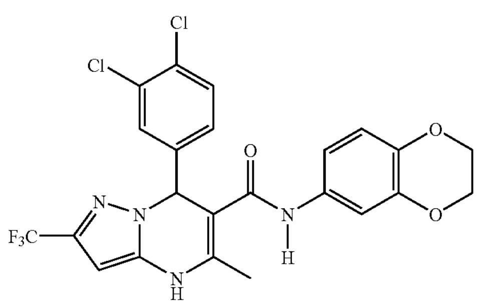 | 7-(3,4-Dichlorophenyl)-N-(2,3-dihydro-1,4-benzodioxin-6-yl)-4,7-dihydro-5-methyl-2-(trifluoromethyl)pyrazolo[1,5-a]pyrimidine-6-carboxamide | 525(M + H) |
| 555 | 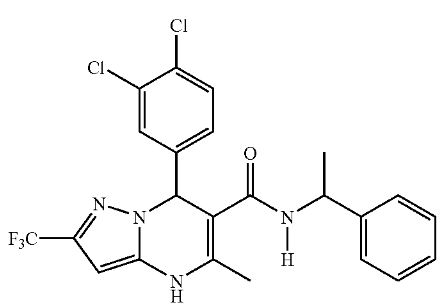 | 7-(3,4-Dichlorophenyl)-4,7-dihydro-5-methyl-N-(1-phenylethyl)-2-(trifluoromethyl)pyrazolo[1,5-a]pyrimidine-6-carboxamide | 495(M + H) |

| Ex. | Structure | Name | Mass Spec |
|---|---|---|---|
| 556 | 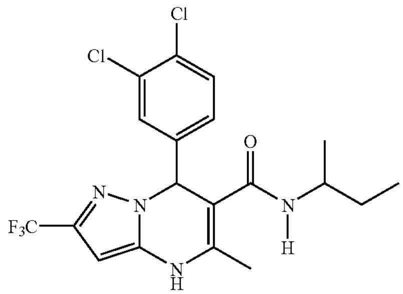 | 7-(3,4-Dichlorophenyl)-4,7-dihydro-5-methyl-N-(1-methylpropyl)-2-(trifluoromethyl)pyrazolo[1,5-a]pyrimidine-6-carboxamide | 447(M + H) |
| 557 | 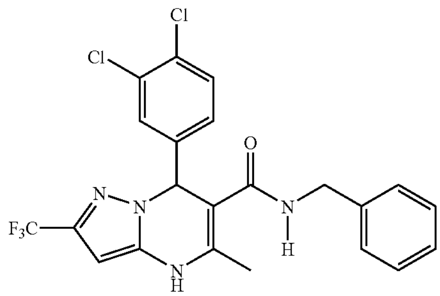 | 7-(3,4-Dichlorophenyl)-4,7-dihydro-5-methyl-N-(phenylmethyl)-2-(trifluoromethyl)pyrazolo[1,5-a]pyrimidine-6-carboxamide | 481(M + H) |
| 558 | 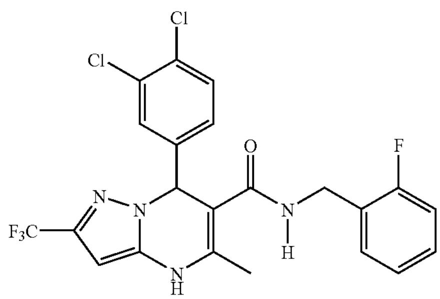 | 7-(3,4-Dichlorophenyl)-N-[(2-fluorophenyl)methyl]-4,7-dihydro-5-methyl-2-(trifluoromethyl)pyrazolo[1,5-a]pyrimidine-6-carboxamide | 499(M + H) |
| 559 | 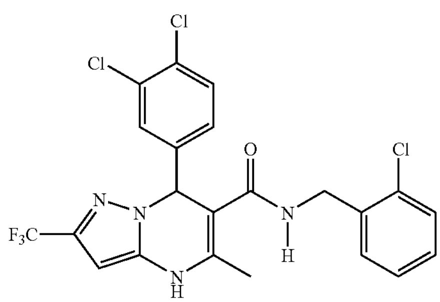 | N-[(2-Chlorophenyl)methyl]-7-(3,4-dichlorophenyl)-4,7-dihydro-5-methyl-2-(trifluoromethyl)pyrazolo[1,5-a]pyrimidine-6-carboxamide | 515(M + H) |
| 560 | 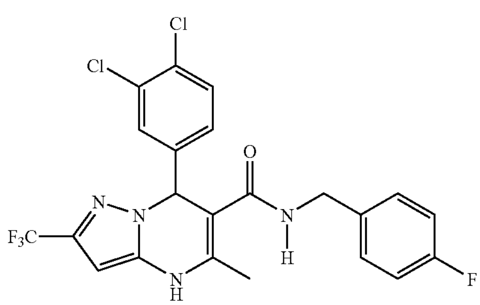 | 7-(3,4-Dichlorophenyl)-N-[(4-fluorophenyl)methyl]-4,7-dihydro-5-methyl-2-(trifluoromethyl)pyrazolo[1,5-a]pyrimidine-6-carboxamide | 499(M + H) |

-continued

| Ex. | Structure | Name | Mass Spec |
|---|---|---|---|
| 561 | 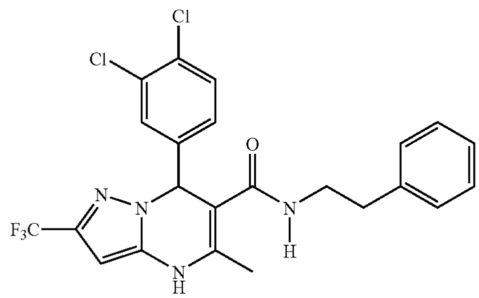 | 7-(3,4-Dichlorophenyl)-4,7-dihydro-5-methyl-N-(2-phenylethyl)-2-(trifluoromethyl)pyrazolo[1,5-a]pyrimidine-6-carboxamide | 495(M + H) |
| 562 | 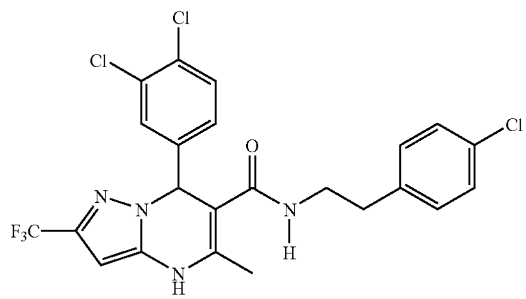 | N-[2-(4-Chlorophenyl)ethyl]-7-(3,4-dichlorophenyl)-4,7-dihydro-5-methyl-2-(trifluoromethyl)pyrazolo[1,5-a]pyrimidine-6-carboxamide | 530(M + H) |
| 563 | 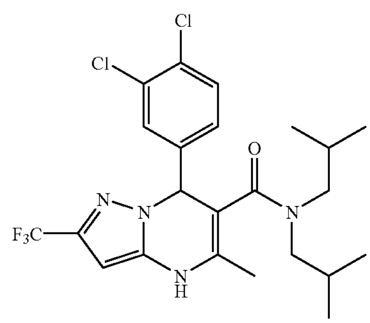 | 7-(3,4-Dichlorophenyl)-4,7-dihydro-5-methyl-N,N-bis(2-methylpropyl)-2-(trifluoromethyl)pyrazolo[1,5-a]pyrimidine-6-carboxamide | 503(M + H) |
| 564 | 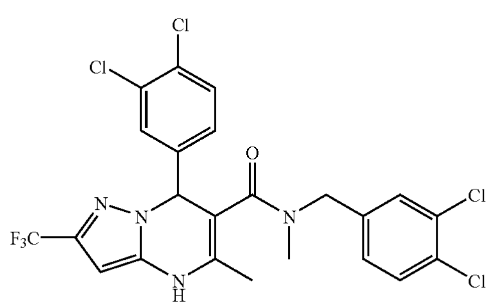 | 7-(3,4-Dichlorophenyl)-N-[(3,4-dichlorophenyl)methyl]-4,7-dihydro-N,5-dimethyl-2-(trifluoromethyl)pyrazolo[1,5-a]pyrimidine-6-carboxamide | 564(M + H) |
| 565 | 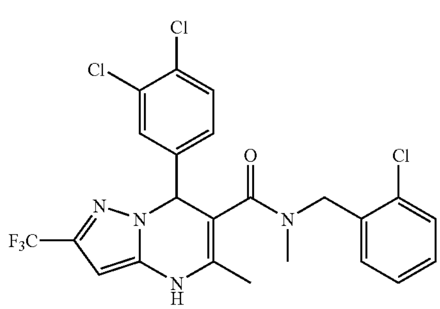 | N-[(2-Chlorophenyl)methyl]-7-(3,4-dichlorophenyl)-4,7-dihydro-N,5-dimethyl-2-(trifluoromethyl)pyrazolo[1,5-a]pyrimidine-6-carboxamide | 530(M + H) |

-continued

| Ex. | Structure | Name | Mass Spec |
|---|---|---|---|
| 566 | 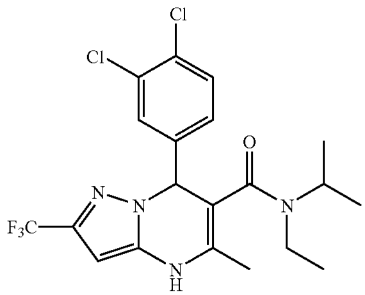 | 7-(3,4-Dichlorophenyl)-N-ethyl-4,7-dihydro-5-methyl-N-(1-methylethyl)-2-(trifluoromethyl)pyrazolo[1,5-a]pyrimidine-6-carboxamide | 461(M + H) |
| 567 | 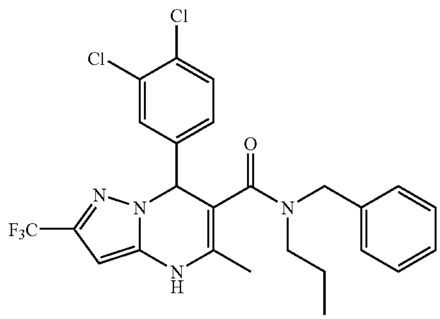 | 7-(3,4-Dichlorophenyl)-4,7-dihydro-5-methyl-N-(phenylmethyl)-N-propyl-2-(trifluoromethyl)pyrazolo[1,5-a]pyrimidine-6-carboxamide | 523(M + H) |
| 568 | 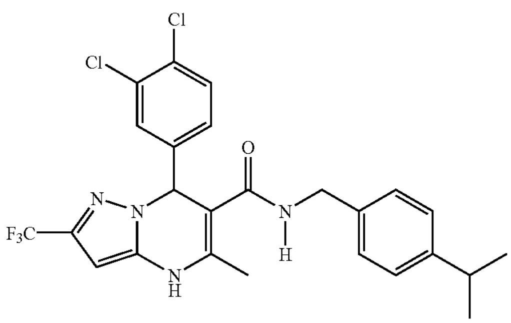 | 7-(3,4-Dichlorophenyl)-4,7-dihydro-5-methyl-N-[[4-(1-methylethyl)phenyl]methyl]-2-(trifluoromethyl)pyrazolo[1,5-a]pyrimidine-6-carboxamide | 523(M + H) |
| 569 | 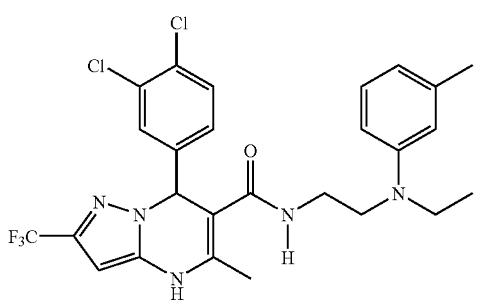 | 7-(3,4-Dichlorophenyl)-N-[2-[ethyl(3-methylphenyl)amino]ethyl]-4,7-dihydro-5-methyl-2-(trifluoromethyl)pyrazolo[1,5-a]pyrimidine-6-carboxamide | 552(M + H) |
| 570 | 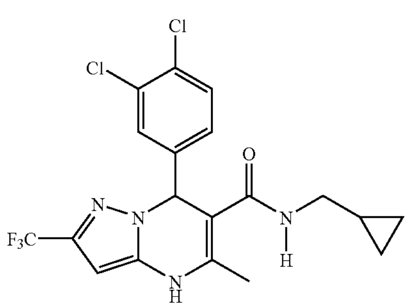 | N-(Cyclopropylmethyl)-7-(3,4-dichlorophenyl)-4,7-dihydro-5-methyl-2-(trifluoromethyl)pyrazolo[1,5-a]pyrimidine-6-carboxamide | 445(M + H) |

-continued

| Ex. | Structure | Name | Mass Spec |
|---|---|---|---|
| 571 | 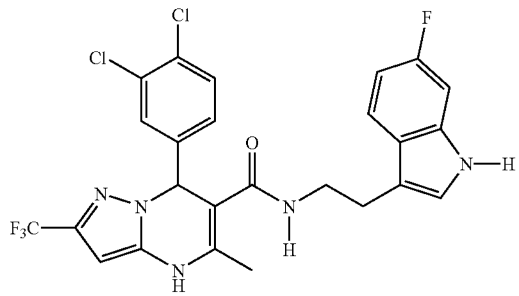 | 7-(3,4-Dichlorophenyl)-N-[2-(6-fluoro-1H-indol-3-yl)ethyl]-4,7-dihydro-5-methyl-2-(trifluoromethyl)pyrazolo[1,5-a]pyrimidine-6-carboxamide | 552(M + H) |
| 572 | 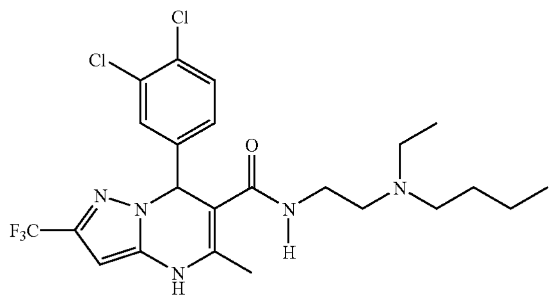 | N-[2-(Butylethylamino)ethyl]-7-(3,4-dichlorophenyl)-4,7-dihydro-5-methyl-2-(trifluoromethyl)pyrazolo[1,5-a]pyrimidine-6-carboxamide | 518(M + H) |
| 573 | 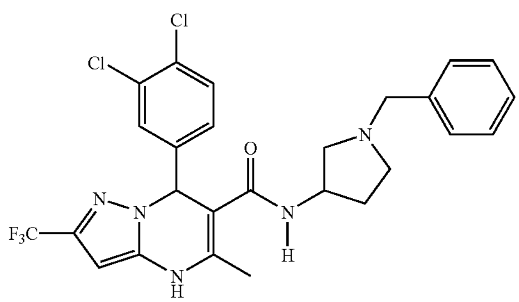 | 7-(3,4-Dichlorophenyl)-4,7-dihydro-5-methyl-N-[1-(phenylmethyl)-3-pyrrolidinyl]-2-(trifluoromethyl)pyrazolo[1,5-a]pyrimidine-6-carboxamide | 550(M + H) |
| 574 | 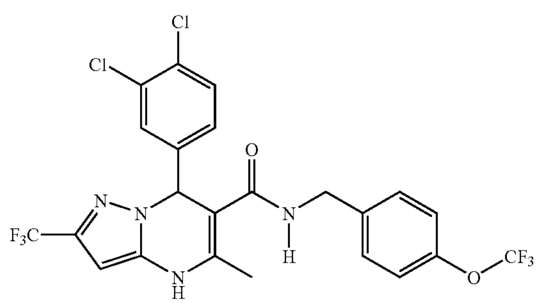 | 7-(3,4-Dichlorophenyl)-4,7-dihydro-5-methyl-N-[[4-(trifluoromethoxy)phenyl]methyl]-2-(trifluoromethyl)pyrazolo[1,5-a]pyrimidin-6-carboxamide | 565(M + H) |
| 575 | 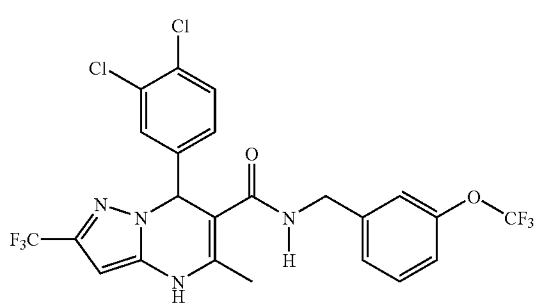 | 7-(3,4-Dichlorophenyl)-4,7-dihydro-5-methyl-N-[[3-(trifluoromethoxy)phenyl]methyl]-2-(trifluoromethyl)pyrazolo[1,5-a]pyrimidine-6-carboxamide | 565(M + H) |

| Ex. | Structure | Name | Mass Spec |
|---|---|---|---|
| 576 | 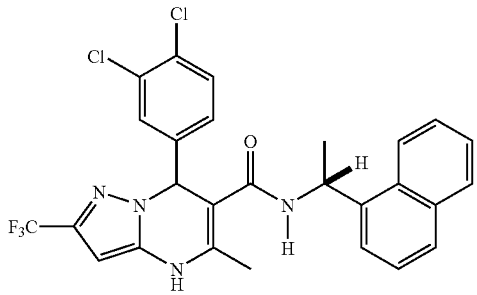 | 7-(3,4-Dichlorophenyl)-4,7-dihydro-5-methyl-N-[(1R)-1-(1-naphthalenyl)ethyl]-2-(trifluoromethyl)pyrazolo[1,5-a]pyrimidine-6-carboxamide | 545(M + H) |
| 577 | 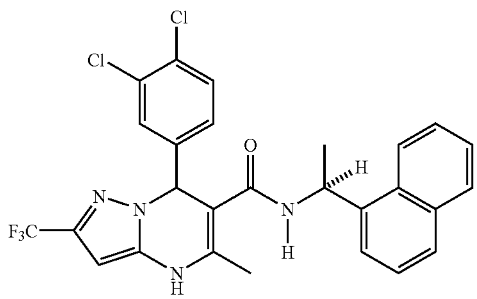 | 7-(3,4-Dichlorophenyl)-4,7-dihydro-5-methyl-N-[(1S)-1-(1-naphthalenyl)ethyl]-2-(trifluoromethyl)pyrazolo[1,5-a]pyrimidine-6-carboxamide | 545(M + H) |
| 578 | 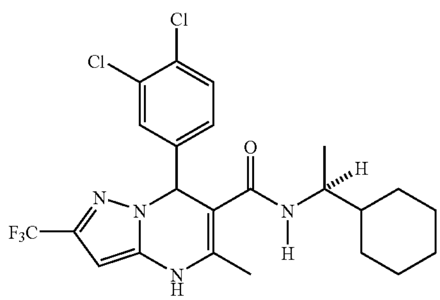 | N-[(1S)-1-Cyclohexylethyl]-7-(3,4-dichlorophenyl)-4,7-dihydro-5-methyl-2-(trifluoromethyl)pyrazolo[1,5-a]pyrimidine-6-carboxamide | 501(M + H) |
| 579 | 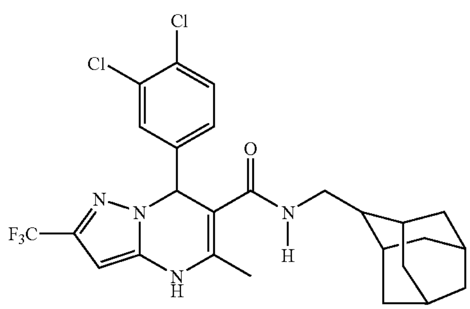 | 7-(3,4-Dichlorophenyl)-4,7-dihydro-5-methyl-N-(tricyclo[3.3.1.1<3,7]decan-1-ylmethyl)-2-(trifluoromethyl)pyrazolo[1,5-a]pyrimidine-6-carboxamide | 539(M + H) |
| 580 | 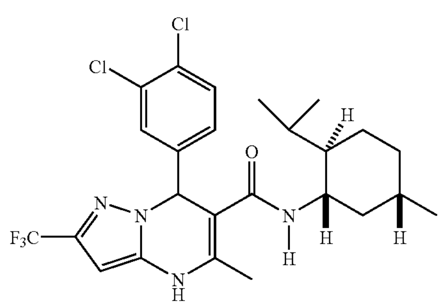 | 7-(3,4-Dichlorophenyl)-4,7-dihydro-5-methyl-N-[(1R,2S,5R)-5-methyl-2-(1-methylethyl)cyclohexyl]-2-(trifluoromethyl)pyrazolo[1,5-a]pyrimidine-6-carboxamide | 529(M + H) |

| Ex. | Structure | Name | Mass Spec |
|---|---|---|---|
| 581 | 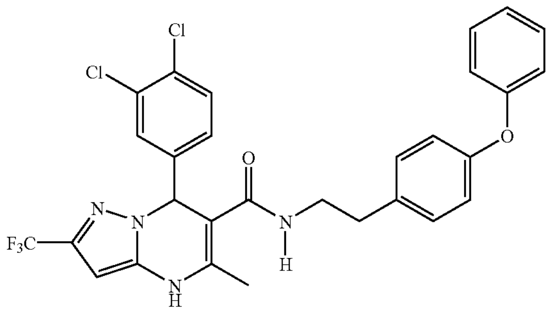 | 7-(3,4-Dichlorophenyl)-4,7-dihydro-5-methyl-N-[2-(4-phenoxyphenyl)ethyl]-2-(trifluoromethyl)pyrazolo[1,5-a]pyrimidine-6-carboxamide | 587(M + H) |
| 582 | 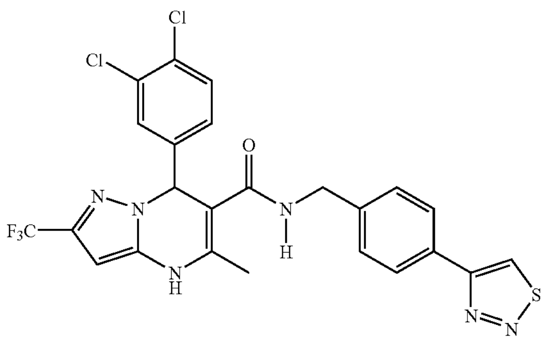 | 7-(3,4-Dichlorophenyl)-4,7-dihydro-5-methyl-N-[[4-(1,2,3-thiadiazol-4-yl)phenyl]methyl]-2-(trifluoromethyl)pyrazolo[1,5-a]pyrimidine-6-carboxamide | 565(M + H) |
| 583 | 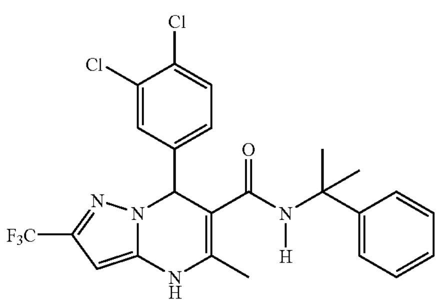 | 7-(3,4-Dichlorophenyl)-4,7-dihydro-5-methyl-N-(1-methyl-1-phenylethyl)-2-(trifluoromethyl)pyrazolo[1,5-a]pyrimidine-6-carboxamide | 509(M + H) |
| 584 | 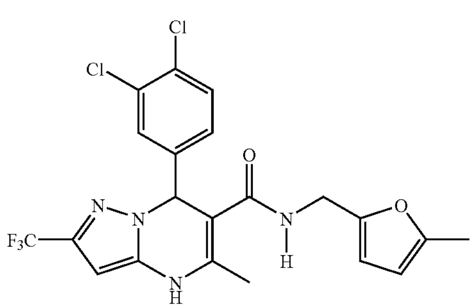 | 7-(3,4-Dichlorophenyl)-4,7-dihydro-5-methyl-N-[(5-methyl-2-furanyl)methyl]-2-(trifluoromethyl)pyrazolo[1,5-a]pyrimidine-6-carboxamide | 584(M + H) |

| Ex. | Structure | Name | Mass Spec |
|---|---|---|---|
| 585 | 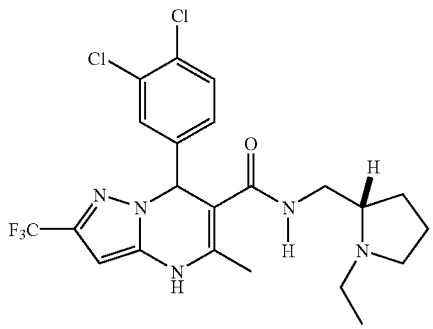 | 7-(3,4-Dichlorophenyl)-N-[[(2S)-1-ethyl-2-pyrrolidinyl]methyl]-4,7-dihydro-5-methyl-2-(trifluoromethyl)pyrazolo[1,5-a]pyrimidine-6-carboxamide | 502(M + H) |
| 586 | 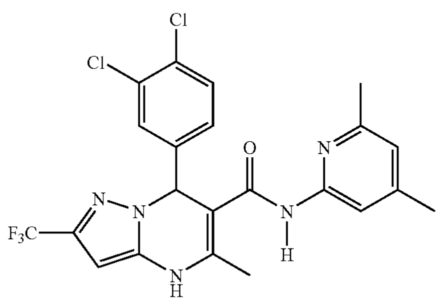 | 7-(3,4-Dichlorophenyl)-N-(4,6-dimethyl-2-pyridinyl)-4,7-dihydro-5-methyl-2-(trifluoromethyl)pyrazolo[1,5-a]pyrimidine-6-carboxamide | 596(M + H) |
| 587 | 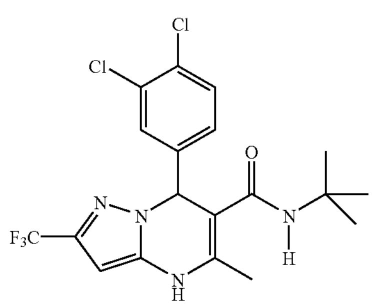 | 7-(3,4-Dichlorophenyl)-N-(1,1-dimethylethyl)-4,7-dihydro-5-methyl-2-(trifluoromethyl)pyrazolo[1,5-a]pyrimidine-6-carboxamide | 447(M + H) |

EXAMPLE 588

1-[[7-(3,4-Dichlorophenyl)-4,7-dihydro-5-methylpyrazolo[1,5-a]pyrimidin-6-yl]carbonyl]-2-(3-methyl-1,2,4-oxadiazol-5-yl)pyrrolidine

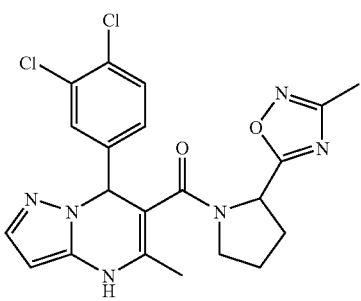

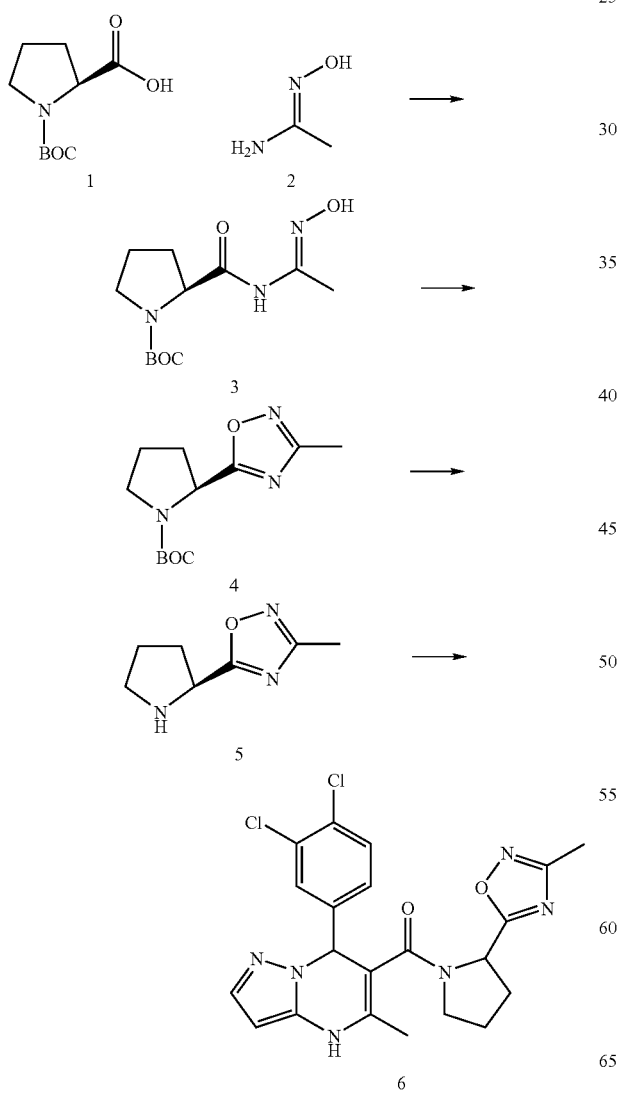

Synthesis of 3: A mixture of N-(tert-butoxycarbonyl)-L-proline 1 (0.5 g, 2.3 mmol), hydroxyamidine 2 (0.172 g, 2.3 mmol, prepared using the procedure outlined in *J. Fluor. Chem.* 1999, 95, 127) and 1-hydroxybenzotriazole hydrate (0.323 g, 2.4 mmol) in 22% dimethyl formamide in dichloromethane (9 mL) was stirred at room temperature for 0.5 hours. Then 1-[3-(dimethylamino)propyl]-3-ethylcarbodiimide hydrochloride (0.757 g, 3.9 mmol) was added and the mixture stirred further at room temperature for 2 hours when HPLC indicated completion of the reaction. The reaction mixture was diluted with water and extracted with dichloromethane. The organic layers were washed successively with saturated aqueous sodium bicarbonate solution, saturated aqueous sodium chloride solution and dried over magnesium sulfate. Evaporation of the solvent provided a white solid with an $(M+H)^+$ of 272 consistent for the coupled product 3.

Preparation of 4: The solid 3 was dissolved in tetrahydrofuran (17 mL), cesium carbonate (1.6 g) added and the mixture heated at 50–70° C. for 18 hours after which HPLC indicated the complete consumption of 3. The reaction was diluted with water and extracted with ethyl acetate. The organic layers were dried over magnesium sulfate and evaporated to give a light-green colored oil that had an $(M+H)^+$ of 254 consistent with the desired oxadiazole 4 which was used without any further purification.

Synthesis of 5: To a solution of 4 (0.288 g, 1.1 mmol) in dichloromethane (9 mL) was added 0.9 mL of trifluoroacetic acid and the solution stirred at room temperature for 18 hours when HPLC indicated the absence of 4. The reaction mixture was concentrated and the residue purified by ion-exchange chromatography (using BioRad AG-50W-X2 resin, 200–400 mesh, hydrogen form) eluting with 2N ammonia in methanol to give the deprotected pyrrolidine 5 as an oil (0.122 g, 70%). $(M+H)^+=154$ Synthesis of 6: To a solution of dihydropyrimidine acid (0.21 gram, 0.65 mmol) in dichloromethane (10 mL) was added pyrrolidine 5 (0.139 gram, 0.9 mmol) followed by 1-[3-(dimethylamino)propyl]-3-ethylcarbodiimide hydrochloride (0.174 gram, 0.9 mmol) and the reaction stirred at room temperature for 1.5 hours. The solvent was evaporated and the residue purified by silica gel chromatography, eluting with ethyl acetate, to give two diastereomers—a fast moving, less polar diastereomer-1 and a slow moving, more polar diastereomer-2, both as white amorphous solids with an $(M+H)^+$ of 460.

EXAMPLE 589

1-[[7-(3,4-Dichlorophenyl)-4,7-dihydro-5-methylpyrazolo[1,5-a]pyrimidin-6-yl]carbonyl]-2-(3-methyl-1,2,4-oxadiazol-5-yl)piperidine

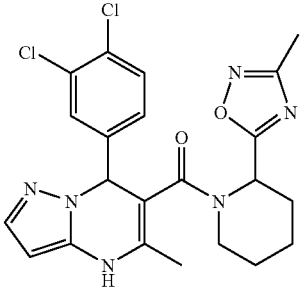

Scheme:

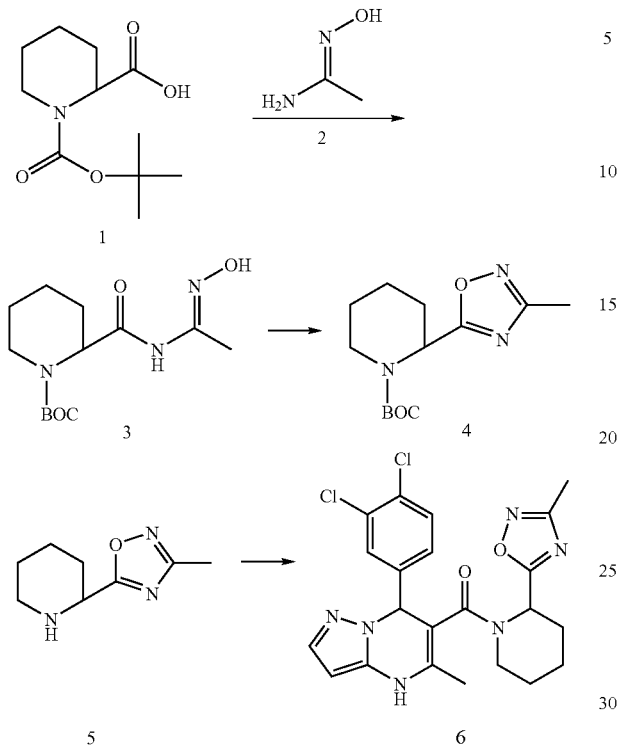

Synthesis of 4: A mixture of (+/−)N-(tert-butoxycarbonyl)-pipecolinic acid 1 (0.8 gram, 3.5 mmol), 1-hydroxybenzotriazole hydrate (1.14 gram, 5.9 mmol) and 1-[3-(dimethylamino)propyl]-3-ethylcarbodiimide hydrochloride (0.49 gram, 3.6 mmol) in 22% dimethyl formamide in dichloromethane (20 mL) was stirred at room temperature for 0.5 hours. Then hydroxyamidine 2 (0.26 gram, 3.5 mmol, prepared using the procedure outlined in J. Fluor. Chem. 1999, 95, 127) was added and the mixture stirred further at room temperature for 18 hours when HPLC indicated completion of the reaction. The reaction mixture was diluted with water and extracted with dichloromethane. The organic layers were washed successively with saturated aqueous sodium bicarbonate solution, saturated aqueous sodium chloride solution and dried over magnesium sulfate. Evaporation of the solvent provided a clear oil with an (M+H)+ of 285 consistent for the coupled product 3. The oil 3 was dissolved in tetrahydrofuran (25 mL), cesium carbonate (2.5 g) added and the mixture heated at 50–70° C. for 18 hours after which HPLC indicated the complete consumption of 3. The reaction was diluted with water and extracted with ethyl acetate. The organic layers were dried over magnesium sulfate and evaporated to give a clear oil that had an (M+H)+ of 267 consistent with the desired oxadiazole 4 which was used without any further purification.

Synthesis of 5: To a solution of 4 (0.82 gram, 3.1 mmol) in dichloromethane (20 mL) was added 2 mL of trifluoroacetic acid and the solution stirred at room temperature for 18 hours when HPLC indicated the absence of 4. The reaction mixture was concentrated and the residue purified by ion-exchange chromatography (using BioRad AG-50W-X2 resin, 200–400 mesh, hydrogen form) eluting with 2N ammonia in methanol to give the deprotected pyrrolidine 5 as an oil (0.46 gram, 89%). (M+H)+=167

Synthesis of title compound: To a solution of dihydropyrimidine acid (0.64 gram, 2.0 mmol) in dichloromethane (30 mL) was added pyrrolidine 5 (0.462 gram, 2.8 mmol) followed by 1-[3-(dimethylamino)propyl]-3-ethylcarbodiimide hydrochloride (0.53 gram, 2.8 mmol) and the reaction stirred at room temperature for 2.5 hours. The solvent was evaporated and the residue purified by silica gel chromatography, eluting with ethyl acetate, to give two diastereomers—a minor and less polar diastereomer (diastereomer 1) and a major more polar diastereomer (diastereomer 2), both as white amorphous solids with an (M+H)+ of 473.

We claim:
1. A compound of the formula I*

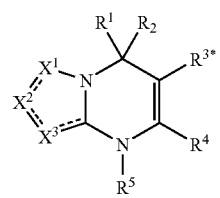

(I*)

enantiomers, diasteriomers and pharmaceutically acceptable salts thereof, wherein
$X^1$, $X^2$ and $X^3$, together with the atoms to which they are bonded, form a ring selected from:

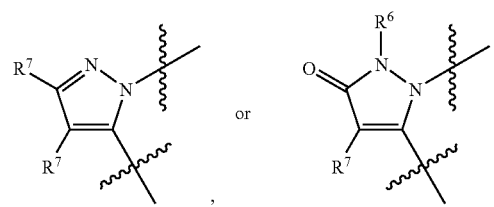

, $R^1$, $R^5$, $R^6$ and $R^7$ are independently selected from groups of the formula —$(CH_2)_n$-$(Z^1)_m$-$(CH_2)_p$-$Z^2$;
$R^2$ is phenyl or substituted phenyl;
$R^4$ is alkyl or substituted alkyl;
$Z^1$ is —$CZ^3Z^4$—, —O—, —$NZ^3$—, —S—, —SO—, —$SO_2$—, —C(O)—, —C(O)$Z^3$—, —C(O)$NZ^4$, —C(S)—, —C(=$NOZ^3$)—, alkyl, substituted alkyl, alkenyl, substituted alkenyl, alkynyl, substituted alkynyl, carbocyclo, substituted carbocyclo, aryl, substituted aryl, heterocyclo, or substituted heterocyclo;
$Z^2$ is hydrogen; —$OZ^5$, —OC(O)$Z^5$, —$NZ^5$-C(O)-$Z^6$, —$NZ^5$-$CO_2$-$Z^6$, —$NZ^5$(C=O)—$NZ^6Z^7$, —$NZ^5Z^6$, —$NO_2$, halo, —CN, —C(O)$Z^5$, —$CO_2Z^5$, —C(S)$Z^5$, —(C=$NOZ^5$)$Z^6$, —C(O)$NZ^5Z^6$, —C(S)$NZ^5Z^6$, —$SZ^5$, —$SOZ^5$, —$SO_2Z^5$, —$SO_2NZ^5Z^6$, —$CF_3$, alkyl, substituted alkyl, alkenyl, substituted alkenyl, alkynyl, substituted alkynyl, carbocyclo, substituted carbocyclo, aryl, substituted aryl, heterocyclo, or substituted heterocyclo;
$Z^3$, $Z^4$, $Z^5$, $Z^6$ and $Z^7$ are independently hydrogen, halo, alkyl, substituted alkyl, alkenyl, substituted alkenyl, alkynyl, substituted alkynyl, carbocyclo, substituted carbocyclo, aryl, substituted aryl, heterocyclo, or substituted heterocyclo; or
$Z^3$, $Z^4$, $Z^5$, $Z^6$ and $Z^7$ may, in one or more pairs of two, together with the atoms to which they are bonded, form a carbocyclic, substituted carbocyclic, heterocyclic or substituted heterocyclic group;

$R^{3*}$ is $-C(O)NZ^{5*}Z^{6*}$;

$Z^{5*}$ and $Z^{6*}$ together with the nitrogen atom to which they are bonded form a heterocyclic group or substituted heterocyclic group, provided that $Z^{5*}$ and $Z^{6*}$ do not together form unsubstituted piperidinyl, substituted piperidinyl, unsubstituted pyrrolidinyl, or unsubstituted morpholinyl;

n and p are independently selected from integers from 0 to 10 wherein, when m is 0, p is also 0;

m is an integer selected from 0 or 1; and q is an integer selected from 1 to 3.

2. A compound of claim 1 wherein $R^1$ is H.

3. A compound of claim 1 wherein $R^{3*}$ is selected from

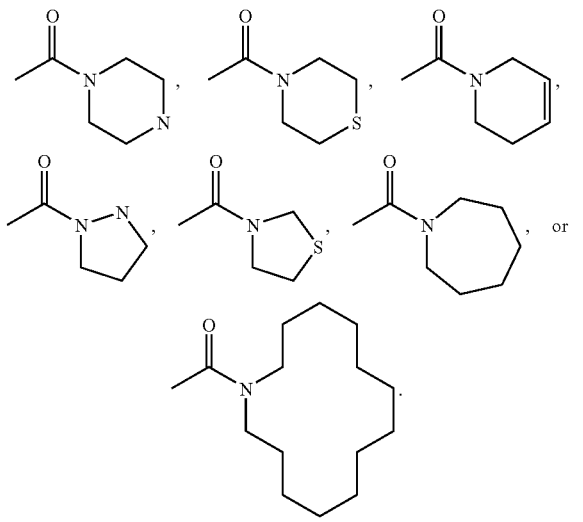

4. A compound of claim 1 wherein $R^7$ is selected from alkyl, $-CO_2$alkyl, $-CF_3$, $-CN$, F or Cl.

5. A compound of claim 1 wherein:
$R^1$ is H;
$R^2$ is phenyl or substituted phenyl;
$R^4$ alkyl or substituted alkyl;
$R^5$ is hydrogen, $-(CH_2)_n-Z^2$ wherein $Z^2$ is selected from $-C(O)NZ^5Z^6$, $-CO_2Z^5$, $-NZ^5Z^6$, aryl, substituted aryl, alkyl, or substituted alkyl; and
$R^7$ is selected from alkyl, $-CO_2$alkyl, $-CF_3$, $-CN$, F or Cl.

6. A compound of claim 1 wherein:
$R^1$ is H;
$R^2$ is phenyl or substituted phenyl;
$R^4$ is lower alkyl, halo-substituted alkyl, or alkoxy-substituted alkyl;
$R^5$ is hydrogen, alkyl or substituted alkyl; and
$R^7$ is selected from alkyl, $-CO_2$alkyl, $-CF_3$, $-CN$, F or Cl.

7. A compound of claim 1 wherein:
$R^1$ is H;
$R^2$ is phenyl or substituted phenyl;
$R^4$ is lower alkyl, halo-substituted alkyl, or alkoxy-substituted alkyl;
$R^5$ is hydrogen, alkyl or substituted alkyl; and
$R^7$ is selected from alkyl, $-CO_2$alkyl, $-CF_3$, $-CN$, F or Cl.

8. A compound of claim 1 wherein:
$R^1$ is H;
$R^2$ is substituted phenyl;
$R^4$ is lower alkyl, or alkoxy-substituted alkyl;
$R^5$ is hydrogen, alkyl or substituted alkyl; and
$R^7$ is selected from alkyl, $-CO_2$alkyl, $-CF_3$, $-CN$, F or Cl.

9. A compound selected from the group consisting of:

1-[[7-(2,3-Dichlorophenyl)-4,7-dihydro-5-methylpyrazolo[1,5-a]pyrimidin-6-yl]carbonyl]-4-phenylpiperazine;

1-[[7-(3,4-Dichlorophenyl)-4,7-dihydro-5-methylpyrazolo[1,5-a]pyrimidin-6-yl]carbonyl]-4phenylpiperazine;

1-[[(7-(2,3-Dichlorophenyl)-4,7-dihydro-5-methyl-pyrazolo[1,5-a]pyrimidin-6-yl]carbonyl]-4-phenylpiperazine, enantiomer A;

1-[[7-(2,3-Dichlorophenyl)-4,7-dihydro-5-methyl-pyrazolo[1,5-a]pyrimidin-6-yl]carbonyl]-4phenylpiperazine, enantiomer B;

1-[[7-(4-Chlorophenyl)-4,7-dihydro-5-methylpyrazolo[1,5-a]pyrimidin-6-yl]carbonyl]-4phenylpiperazine;

1-[[7-(3,4-Dichlorophenyl)-4,7-dihydro-5-methyl-pyrazolo[1,5-a]pyrimidin-6-yl]carbonyl]-4-methylpiperazine;

1-[[7-(3,4-Dichlorophenyl)-4,7-dihydro-5-methyl-pyrazolo[1,5-a]pyrimidin-6-yl]carbonyl]-4-(phenylmethyl)piperazine;

1-[[7-(3-Chlorophenyl)-4,7-dihydro-5-methylpyrazolo[1,5-a]pyrimidin-6-yl]carbonyl]-4-(4-fluorophenyl)piperazine;

1-[[7-(3,4-Difluorophenyl)-4,7-dihydro-5-methylpyrazolo[1,5-a]pyrimidin-6-yl]carbonyl]-4-(4-fluorophenyl)piperazine;

1-[[7-(2,3-Dichlorophenyl)-4,7-dihydro-5-methyl-pyrazolo[1,5-a]pyrimidin-6-yl]carbonyl]-4-(4-fluorophenyl)piperazine;

1-(4-Fluorophenyl)-4-[(4,7-dihydro-5-methyl-7-phenylpyrazolo[1,5-a]pyrimidin-6-yl)carbonyl]piperazine;

1-[[7-(3,4-Dichlorophenyl)-1,2,4,7-tetrahydro-5-methyl-2-oxopyrazolo[1,5-a]pyrimidin-6-yl]carbonyl]-4-phenylpiperazine;

1-[[7-(2,3-Dichlorophenyl)-4,7-dihydro-5-methyl-pyrazolo[1,5-a]pyrimidin-6-yl]carbonyl]-4-(4-fluorophenyl)piperazine, enantiomer A;

1-[[7-(2,3-Dichlorophenyl)-4,7-dihydro-5-methyl-pyrazolo[1,5-a]pyrimidin-6-yl]carbonyl]-4-(4-fluorophenyl)piperazine, enantiomer B;

1-(4-Fluorophenyl)-4-[[7-(3-fluorophenyl)-4,7-dihydro-5-methylpyrazolo[1,5-a]pyrimidin-6-yl]carbonyl]-piperazine;

1-[[7-(3,5-Dichlorophenyl)-4,7-dihydro-5-methyl-pyrazolo[1,5-a]pyrimidin-6-yl]carbonyl]-4-(4-fluorophenyl)piperazine;

1-[(7-Cyclohexyl-4,7-dihydro-5-methylpyrazolo[1,5-a]pyrimidin-6-yl)carbonyl]-4-phenylpiperazine;

1-[[7-(2,3-Dichlorophenyl)-4,7-dihydro-2,5-dimethylpyrazolo[1,5-a]pyrimidin-6-yl]carbonyl]-4-phenylpiperazine;

7-(2,3-Dichlorophenyl)-4,7-dihydro-5-methyl-6-[(4-phenyl-1-piperazinyl)-carbonyl]pyrazolo[1,5-a]pyrimidine-3-carboxylic acid ethyl ester;

4-[[7-(3,4-Dichlorophenyl)-4,7-dihydro-5-methyl-pyrazolo[1,5-a]pyrimidin-6-yl]carbonyl]-1-pipera-zinecarboxylic acid 1,1-dimethylethyl ester;

1-[[7-(3,4-Dichlorophenyl)-4,7-dihydro-2,5-dimethylpyrazolo[1,5-a]pyrimidin-6-yl]carbonyl]4-phenylpiperazine;
1-[[7-(3,4-Dichlorophenyl)-4,7-dihydro-5-methyl-2-phenylpyrazolo[1,5-a]pyrimidin-6-yl]carbonyl]-4-phenylpiperazine;
1-[[7(2,3-Dichlorophenyl)-2-(1,1-dimethylethyl)-4,7-dihydro-5-methylpyrazolo[1,5-a]pyrimidin-6-yl]carbonyl]-4-phenylpiperazine;
7-(2,3-Dichlorophenyl)-4,7-dihydro-5-methyl-6-[(4-phenyl-1-piperazinyl)-carbonyl]pyrazolo[1,5-a]pyrimidine-2-carboxylic acid ethyl ester;
1-[[3Cyano-7(2,3-dichlorophenyl)-4,7-dihydro-5-methylpyrazolo[1,5-a]pyrimidin-6-yl]carbonyl]-4(4-fluorophenyl)piperazine;
1-[[7-(3,4-Dichlorophenyl)-4,7-dihydro-5-methyl-2-(trifluoromethyl)pyrazolo[1,5-a]pyrimidin-6-yl]carbonyl]-4-(4-fluorophenyl)piperazine;
1-[[7-(2,3-Dichlorophenyl)-4,7-dihydro-5-methyl-2-(trifluoromethyl)pyrazolo[1,5-a]pyrimidin-6-yl]carbonyl]-4-(4-fluorophenyl)piperazine;
1-[[7-(2,3-Dichlorophenyl)-4,7-dihydro-5-methyl-2-(trifluoromethyl)pyrazolo[1,5-a]pyrimidin-6-yl]carbonyl]-4-(4-fluorophenyl)piperazine, enantiomer B;
1-[[7-(2,3-Dichlorophenyl)-4,7-dihydro-2,5-dimethylpyrazolo[1,5-a]pyrimidin-6-yl]carbonyl]-4-(4-fluorophenyl)piperazine, enantiomer B;
7-(3,4-Dichlorophenyl-6-[[4-(4-fluorophenyl)-1-piperazinyl]carbonyl]-4,7-dihydro-5-methylpyrazolo[1,5-a]pyrimidine-2-carboxylic acid methyl ester;
(2S)-1-[[7-(2,3-Dichlorophenyl)-4,7-dihydro-5-methyl-2-(trifluoro-methyl)pyrazolo[1,5-a]pyrimidin-6-yl]carbonyl]-2-(methoxymethyl)pyrrolidine;
1-[[7-(2,3-Dichlorophenyl)-2-fluoro-4,7-dihydro-5-methylpyrazolo[1,5-a]pyrimidin-6-yl]carbonyl]-4-(4-fluorophenyl)piperazine;
(2S)-1-[[2-Chloro-7-(2,3-dichlorophenyl)-4,7-dihydro-5-methyl-pyrazolo[1,5-a]pyrimidin-6-yl]carbonyl]-2-(methoxymethyl)pyrrolidine;
(2S)-1-[[2-Chloro-7-(3,4-dichlorophenyl)-4,7-dihydro-5-methyl-pyrazolo[1,5-a]pyrimidin-6-yl]carbonyl]-2(methoxymethyl)pyrrolidine;
(2S)-1-[[7-(2,3-Dichloro-phenyl)-2-fluoro-4,7-dihydro-5-methyl-pyrazolo[1,5-a]pyrimidin-6-yl]carbonyl]-2(methoxymethyl)pyrrolidine;
1-[[7-(3,4-Dichlorophenyl)-4,7-dihydro-2,5-dimethylpyrazolo[1,5-a]pyrimidin-6-yl]carbonyl]-4-(fluorophenyl)piperazine;
1-[[7-(3,4-Dichlorophenyl)-4,7-dihydro-2,5-dimethylpyrazolo[1,5-a]pyrimidin-6-yl]carbonyl]4-(4-fluorophenyl)piperazine, enantiomer A;
1-[[7-(3,4-Dichlorophenyl)-4,7-dihydro-2,5-dimethylpyrazolo[1,5-a]pyrimidin-6-yl]carbonyl]-4-(4-fluorophenyl)piperazine, enantiomer B;
1-[[7-(3,4-Dichlorophenyl)-4,7-dihydro-5-methylpyrazolo[1,5-a]pyrimidin-6-yl]carbonyl]-4-(4-fluorophenyl)piperazine;
1-[[7-(2,3-Difluorophenyl)-4,7-dihydro-5-methylpyrazolo[1,5-a]pyrimidin-6-yl]carbonyl]-4-(4-fluorophenyl)piperazine;
4-6-[[4-(4-Fluorophenyl)-1-piperazinyl]carbonyl]-4,7-dihydro-5-methylpyrazolo[1,5-a]pyrimidin-7-yl]benzoic acid methyl ester;
1-(4-Fluorophenyl)-4-[[7-(2-fluorophenyl)-4,7-dihydro-5-methylpyrazolo[1,5-a]pyrimidin-6-yl]carbonyl]piperazine;
1-[[7-(2-Chlorophenyl)-4,7-dihydro-5-methylpyrazolo[1,5-a]pyrimidin-6-yl]carbonyl]-4-(4-fluorophenyl)piperazine;
1-[[7-(2,4-Dichlorophenyl)-4,7-dihydro-5-methyl-pyrazolo[1,5-a]pyrimidin-6-yl]carbonyl]-4-(4-fluorophenyl)piperazine;
1-[[4,7-Dihydro-7-(2-methoxyphenyl)-5-methylpyrazolo[1,5-a]pyrimidin-6-yl]carbonyl]-4-(4-fluorophenyl)piperazine;
1-[[7-(2,3-Dimethoxyphenyl)-4,7-dihydro-5-methyl-pyrazolo[1,5-a]pyrimidin-6-yl]carbonyl]-4-(4-fluorophenyl)piperazine;
1-[[7-(2,4-Dimethoxyphenyl)-4,7-dihydro-5-methyl-pyrazolo[1,5-a]pyrimidin-6-yl]carbonyl]-4-(4-fluorophenyl)piperazine;
1-[[7-(2,5-Dimethoxyphenyl)-4,7-dihydro-5-methyl-pyrazolo[1,5-a]pyrimidin-6-yl]carbonyl]-4-(4-fluorophenyl)piperazine;
1-[[4,7-Dihydro-5-methyl-7-[2-(trifluoromethyl)phenyl]pyrazolo[1,5-a]pyrimidin-6-yl]carbonyl]-4-(4-fluorophenyl)piperazine;
1-[[4,7-Dihydro-5-methyl-7-(2-methylphenyl)pyrazolo[1,5-a]pyrimidin-6-yl]carbonyl]-4-(4-fluorophenyl)piperazine;
1-[[4,7-Dihydro-5-methyl-7-(3-phenoxyphenyl)pyrazolo[1,5-a]pyrimidin-6-yl]carbonyl]-4-(4-fluorophenyl)piperazine;
1-[[7-(3,4-Dimethoxyphenyl)-4,7-dihydro-5-methyl-pyrazolo[1,5-a]pyrimidin-6-yl]carbonyl]-4-(4-fluorophenyl)piperazine;
1-[[7-(3,5-Dimethoxyphenyl)-4,7-dihydro-5-methyl-pyrazolo[1,5-a]pyrimidin-6-yl]carbonyl]-4-(4-fluorophenyl)piperazine;
1-[[4,7-Dihydro-5-methyl-7-[3-(phenylmethoxy)phenyl]pyrazolo[1,5-a]pyrimidin-6-yl]carbonyl]-4-(4-fluorophenyl)piperazine;
1-[[4,7-Dihydro-7-(3-hydroxyphenyl)-5-methyl-pyrazolo[1,5-a]pyrimidin-6-yl]carbonyl]-4-(4-fluorophenyl)piperazine;
1-[[4,7-Dihydro-5-methyl-7-[3(trifluoromethyl)phenyl]pyrazolo[1,5-a]pyrimidin-6-yl]carbonyl]-4-(4-fluorophenyl)piperazine;
1-[[4,7-Dihydro-5-methyl-7-(3-methylphenyl)pyrazolo[1,5-a]pyrimidin-6-yl]carbonyl]-4-(4-fluorophenyl)piperazine;
1-[[7-(4-Cyanophenyl)-4,7-dihydro-5-methylpyrazolo[1,5-a]pyrimidin-6-yl]carbonyl]-4-(4-fluorophenyl)piperazine;
1-(4-Fluorophenyl)-4-[[7-(4-fluorophenyl)-4,7-dihydro-5-methylpyrazolo[1,5-a]pyrimidin-6-yl]carbonyl]-piperazine;
N-[4-[6-[[4-(4-Fluorophenyl)-1-piperazinyl]carbonyl]-4,7-dihydro-5-methylpyrazolo[1,5-a]pyrimidin-7-yl]phenyl]acetamide;
1-[[7-[4-(Dimethylamino)phenyl]-4,7-dihydro-5-methylpyrazolo[1,5-a]pyrimidin-6-yl]carbonyl]-4-(4-fluorophenyl)piperazine;
1-[[4,7-Dihydro-7-(4-methoxyphenyl)-5-methylpyrazolo[1,5-a]pyrimidin-6-yl]carbonyl]-4-(4-fluorophenyl)piperazine;
1-[[4,7-Dihydro-5-methyl-7-[4(phenylmethoxy)phenyl]pyrazolo[1,5-a]pyrimidin-6-yl]carbonyl]-4-(4-fluorophenyl)piperazine;
1-[[7-(4-Butoxyphenyl)-4,7-dihydro-5-methylpyrazolo[1,5-a]pyrimidin-6-yl]carbonyl]-4-(4-fluorophenyl)piperazine;

1-[[4,7-Dihydro-5-methyl-7-(2-thienyl)pyrazolo[1,5-a]pyrimidin-6-yl]carbonyl]-4-(4-fluorophenyl)piperazine;

1-[[4,7-Dihydro-5-methyl-7-(3-thienyl)pyrazolo[1,5-a]pyrimidin-6-yl]carbonyl]-4-(4-fluorophenyl)piperazine;

1-[[4,7-Dihydro-5-methyl-7-[4(trifluoromethyl)phenyl]pyrazolo[1,5-a]pyrimidin-6-yl]carbonyl]-4-(4-fluorophenyl)piperazine;

1-[[4,7-Dihydro-5-methyl-7-(4-methylphenyl)pyrazolo[1,5-a]pyrimidin-6-yl]carbonyl]-4-(4-fluorophenyl)piperazine;

1-[[4,7-Dihydro-5-methyl-7-(2-nitrophenyl)pyrazolo[1,5-a]pyrimidin-6-yl]carbonyl]-4-(4-fluorophenyl)piperazine;

1-[[4,7-Dihydro-5-methyl-7-(4-nitrophenyl)pyrazolo[1,5-a]pyrimidin-6-yl]carbonyl]-4-(4-fluorophenyl)piperazine;

1-[[7-(2,6-Difluorophenyl)-4,7-dihydro-5-methylpyrazolo[1,5-a]pyrimidin-6-yl]carbonyl]-4-(4-fluorophenyl)piperazine;

1-[[7-(2,4-Difluorophenyl)-4,7-dihydro-5-methylpyrazolo[1,5-a]pyrimidin-6-yl]carbonyl]-4-(4-fluorophenyl)piperazine;

1-[[7-(2,5-Difluorophenyl)-4,7-dihydro-5-methylpyrazolo[1,5-a]pyrimidin-6-yl]carbonyl]-4-(4-fluorophenyl)piperazine;

1-[[7-(3,5-Difluorophenyl)-4,7-dihydro-5-methylpyrazolo[1,5-a]pyrimidin-6-yl]carbonyl]-4-(4-fluorophenyl)piperazine;

1-[[4,7-Dihydro-5-methyl-7-[2-(phenylmethoxy)phenyl]pyrazolo[1,5-a]pyrimidin-6-yl]carbonyl]-4-(4-fluorophenyl)piperazine;

1-[[7-(3,4-Dimethylphenyl)-4,7-dihydro-5-methyl-pyrazolo[1,5-a]pyrimidin-6-yl]carbonyl]-4-(4-fluorophenyl)piperazine;

1-[[4,7-Dihydro-5-methyl-7-[4-(trifluoromethoxy)phenyl]pyrazolo[1,5-a]pyrimidin-6-yl]carbonyl]-4-(4-fluorophenyl)piperazine;

1-[[4,7-Dihydro-5-methyl-7-[3(trifluoromethoxy)phenyl]pyrazolo[1,5-a]pyrimidin-6-yl]carbonyl]-4-(4-fluorophenyl)piperazine;

1-[[7-(3-Cyanophenyl)-4,7-dihydro-5-methylpyrazolo[1,5-a]pyrimidin-6-yl]carbonyl]-4-(4-fluorophenyl)piperazine;

1-[[4,7-Dihydro-7-(3-methoxyphenyl)-5-methyl-pyrazolo[1,5-a]pyrimidin-6-yl]carbonyl]-4-(4-fluorophenyl)piperazine;

1-[[7-(4-Chlorophenyl)-4,7-dihydro-5-methylpyrazolo[1,5-a]pyrimidin-6-yl]carbonyl]-4-(4-fluorophenyl)piperazine;

1-[[4,7-Dihydro-5-methyl-7-(4-phenoxyphenyl)pyrazolo[1,5-a]pyrimidin-6-yl]carbonyl]-4-(4-fluorophenyl)piperazine;

1-[[4,7-Dihydro-5-methyl-7-(3-nitrophenyl)pyrazolo[1,5-a]pyrimidin-6-yl]carbonyl]-4-(4-fluorophenyl)piperazine;

1-[[4,7-Dihydro-5-methyl-7-(5-methyl-2-furanyl)pyrazolo[1,5-a]pyrimidin-6-yl]carbonyl]-4-(4-fluorophenyl)piperazine;

1-[[4,7-Dihydro-7-(1H-imidazol-2-yl)-5-methylpyrazolo[1,5-a]pyrimidin-6-yl]carbonyl]-4-(4-fluorophenyl)piperazine;

1-[[4,7-Dihydro-5-methyl-7-(1H-pyrrol-2-yl)pyrazolo[1,5-a]pyrimidin-6-yl]carbonyl]-4-(4-fluorophenyl)piperazine;

1-[[4,7-Dihydro-5-methyl-7-(2-pyridinyl)pyrazolo[1,5-a]pyrimidin-6-yl]carbonyl]-4-(4-fluorophenyl)piperazine;

1-[[7-(3-Chloro-4-methoxy-phenyl)-4,7-dihydro-5-methylpyrazolo[1,5-a]pyrimidin-6-yl]carbonyl]-4-(4-fluorophenyl)piperazine;

1-[[4,7-Dihydro-7-(4-methoxy-1,3-benzodioxol-6-yl)-5-methylpyrazolo[1,5-a]pyrimidin-6-yl]carbonyl]-4-(4-fluorophenyl)piperazine;

1-[[4,7-Dihydro-7-[5-(hydroxymethyl)-2-furanyl]-5-methylpyrazolo[1,5-a]pyrimidin-6-yl]carbonyl]-4-(4-fluorophenyl)piperazine;

1-[[4,7-Dihydro-7-(1H-indol-3-yl)-5-methylpyrazolo[1,5-a]pyrimidin-6-yl]carbonyl]-4-(4-fluorophenyl)piperazine;

1-[[4,7-Dihydro-5-methyl-7-(3-pyridinyl)pyrazolo[1,5-a]pyrimidin-6-yl]carbonyl]-4-(4-fluorophenyl)piperazine;

1-[[4,7-Dihydro-5-methyl-7-(3-quinolinyl)pyrazolo[1,5-a]pyrimidin-6-yl]carbonyl]-4-(4-fluorophenyl)piperazine;

1-[[4,7-Dihydro-5-methyl-7-(4-quinolinyl)pyrazolo[1,5-a]pyrimidin-6-yl]carbonyl]-4-(4-fluorophenyl)piperazine;

1-[[7-(2,3-Dihydro-1,4-benzodioxin-6-yl)-4,7-dihydro-5-methylpyrazolo[1,5-a]pyrimidin-6-yl]carbonyl]-4-(4-fluorophenyl)piperazine;

1-[[4,7-Dihydro-5-methyl-7-(2,3,5-trichloro-phenyl)pyrazolo[1,5-a]pyrimidin-6-yl]carbonyl]-4-(4-fluorophenyl)piperazine;

1-[[7-(2,5-Dichlorophenyl)-4,7-dihydro-5-methylpyrazolo[1,5-a]pyrimidin-6-yl]carbonyl]-4-(4-fluorophenyl)piperazine;

1-(4-Fluorophenyl)-4-[[7-(3-furanyl)-4,7-dihydro-5-methylpyrazolo[1,5-a]pyrimidin-6-yl]carbonyl]-piperazine;

1-[[7-(2-Benzofuranyl)-4,7-dihydro-5-methylpyrazolo[1,5-a]pyrimidin-6-yl]carbonyl]-4-(4-fluorophenyl)piperazine;

1-[[4,7-Dihydro-5-methyl-7-(3-methylbenzo[b]thiophen-2-yl)pyrazolo[1,5-a]pyrimidin-6-yl]carbonyl]-4-(4-fluorophenyl)piperazine;

1-[[4,7-Dihydro-5-methyl-7-(2-quinolinyl)pyrazolo[1,5-a]pyrimidin-6-yl]carbonyl]-4-(4-fluorophenyl)piperazine;

1-[[4,7-Dihydro-5-methyl-7-(2-thiazolyl)pyrazolo[1,5-a]pyrimidin-6-yl]carbonyl]-4-(4-fluorophenyl)piperazine;

1-(4-Fluorophenyl)-4-[[7-(2-furanyl)-4,7-dihydro-5-methylpyrazolo[1,5-a]pyrimidin-6-yl]carbonyl]-piperazine;

1-[[4,7-Dihydro-7-[3-methoxy-4-(phenylmethoxy)phenyl]-5-methylpyrazolo[1,5-a]pyrimidin-6-yl]carbonyl]-4-(4-fluorophenyl)piperazine;

1-[[4,7-Dihydro-7-[4-methoxy-3-(phenylmethoxy)phenyl]-5-methylpyrazolo[1,5-a]pyrimidin-6-yl]carbonyl]-4-(4-fluorophenyl)piperazine;

1-[[4,7-Dihydro-5-methyl-7-(2-naphthalenyl)pyrazolo[1,5-a]pyrimidin-6-yl]carbonyl]-4-(4-fluorophenyl)piperazine;

1-[[7-[3,4-Bis(phenylmethoxy)phenyl]-4,7-dihydro-5-methylpyrazolo[1,5-a]pyrimidin-6-yl]carbonyl]-4-(4-fluorophenyl)piperazine;

1-[[7-(1,3-Benzodioxol-5-yl)-4,7-dihydro-5-methyl-pyrazolo[1,5-a]pyrimidin-6-yl]carbonyl]-4-(4-fluorophenyl)piperazine;

1-[[7-[3,5-Bis(trifluoromethyl)phenyl]-4,7-dihydro-5-methylpyrazolo[1,5-a]pyrimidin-6-yl]carbonyl]-4-(4-fluorophenyl)piperazine;

1-[[4,7-Dihydro-5-methyl-7-[5-[1-methyl-3-(trifluoromethyl)-1H-pyrazol-5-yl]-2-thienyl]pyrazolo[1,5-a]pyrimidin-6-yl]carbonyl]-4-(4-fluorophenyl)piperazine;

1-[[7-(5-Ethyl-2-furanyl)-4,7-dihydro-5-methylpyrazolo[1,5-a]pyrimidin-6-yl]carbonyl]-4-(4-fluorophenyl)piperazine;

1-[[7-(2,3-Dihydro-5-benzofuranyl)-4,7-dihydro-5-methylpyrazolo[1,5-a]pyrimidin-6-yl]carbonyl]-4-(4-fluorophenyl)piperazine;

1-[[7-(3-Bromophenyl)-4,7-dihydro-5-methylpyrazolo[1,5-a]pyrimidin-6-yl]carbonyl]-4-(4-fluorophenyl)piperazine;

1-[[4,7-Dihydro-5-methyl-7-[4-(1-pyrrolidinyl)-phenyl]pyrazolo[1,5-a]pyrimidin-6-yl]carbonyl]-4-(4-fluorophenyl)piperazine;

1-[[4,7-Dihydro-5-methyl-7-[4-(1-pyrrolidinyl)-phenyl]pyrazolo[1,5-a]pyrimidin-6-yl]carbonyl]-4-(4-fluorophenyl)piperazine;

1-[[4,7-Dihydro-5-methyl-7-(5-methyl-2-thienyl)pyrazolo[1,5-a]pyrimidin-6-yl]carbonyl]-4-(4-fluorophenyl)piperazine;

1-[[7-(1,3-Benzodioxol-4-yl)-4,7-dihydro-5-methylpyrazolo[1,5-a]pyrimidin-6-yl]carbonyl]-4-(4-fluorophenyl)piperazine;

1-[[7-(5-Chloro-2-thienyl)-4,7-dihydro-5-methylpyrazolo[1,5-a]pyrimidin-6-yl]carbonyl]-4-(4-fluorophenyl)piperazine;

1-[[7-(3,5-Dimethylphenyl)-4,7-dihydro-5-methyl-pyrazolo[1,5-a]pyrimidin-6-yl]carbonyl]-4-(4-fluorophenyl)piperazine;

1-[[7-(2,3-Dichlorophenyl)-4,7-dihydro-2,5-dimethylpyrazolo[1,5-a]pyrimidin-6-yl]carbonyl]-4-(4-fluorophenyl)piperazine;

1-[[7-(3,4-Dichlorophenyl)-4,7-dihydro-5-methyl-pyrazolo[1,5-a]pyrimidin-6-yl]carbonyl]-4-(4-fluorophenyl)piperazine, enantiomer A;

1-[[7-(3,4-Dichlorophenyl)-4,7-dihydro-5-methyl-pyrazolo[1,5-a]pyrimidin-6-yl]carbonyl]-4-(4-fluorophenyl)piperazine, enantiomer B;

1-[[7-(2,3-Dichlorophenyl)-4,7-dihydro-2,5-dimethylpyrazolo[1,5-a]pyrimidin-6-yl]carbonyl]-4-(4-fluorophenyl)piperazine, enantiomer B;

1-[[7-(2,3-Dichlorophenyl)-4,7-dihydro-2,5-dimethylpyrazolo[1,5-a]pyrimidin-6-yl]carbonyl]-4-(4-fluorophenyl)piperazine, enantiomer A;

8-[[7-(3,4-Dichlorophenyl)-4,7-dihydro-5-methylpyrazolo[1,5-a]pyrimidin-6-yl]carbonyl]-1,4-dioxa-8-azaspiro[4.5]decane;

1-[[7-(3,4-Dichlorophenyl)-4,7-dihydro-5-methyl-pyrazolo[1,5-a]pyrimidin-6-yl]carbonyl]-4(2-methoxyphenyl)piperazine;

1-[[7-(3,4-Dichloro-phenyl)-4,7-dihydro-5-methylpyrazolo[1,5-a]-pyrimidin-6-yl]carbonyl]-4-[3-(trifluoromethyl)phenyl]piperazine;

1-[[7-(3,4-Dichlorophenyl)-4,7-dihydro-5-methylpyrazolo[1,5-a]pyrimidin-6-yl]carbonyl]-4-(4-nitrophenyl)piperazine;

1-(4-Acetylphenyl)-4-[[7-(3,4-dichloro-phenyl)-4,7-dihydro-5-methyl-pyrazolo[1,5-a]pyrimidin-6-yl]carbonyl]piperazine;

1-(2-Chlorophenyl)-4-[[7-(3,4-dichloro-phenyl)-4,7-dihydro-5-methyl-pyrazolo[1,5-a]pyrimidin-6-yl]carbonyl]piperazine;

1-[[7-(3,4-Dichlorophenyl)-4,7-dihydro-5-methylpyrazolo[1,5-a]pyrimidin-6-yl]-carbonyl]-4-(4-methoxyphenyl)piperazine;

1-(3,4-Dichlorophenyl)-4-[[7-(3,4-dichloro-phenyl)-4,7-dihydro-5-methylpyrazolo[1,5-a]pyrimidin-6-yl]-carbonyl]piperazine;

1-(3,5-Dichlorophenyl)-4-[[7-(3,4-dichloro-phenyl)-4,7-dihydro-5-methylpyrazolo[1,5-a]pyrimidin-6-yl]-carbonyl]piperazine;

1-(4-Chlorophenyl)-4-[[7-(3,4-dichlorophenyl)-4,7-dihydro-5-methyl-pyrazolo[1,5-a]pyrimidin-6-yl]carbonyl]piperazine;

1-(3-Chlorophenyl)-4-[[7-(3,4-dichlorophenyl)-4,7-dihydro-5-methyl-pyrazolo[1,5-a]pyrimidin-6-yl]carbonyl]piperazine;

1-[[7-(3,4-Dichlorophenyl)-4,7-dihydro-5-methylpyrazolo[1,5-a]pyrimidin-6-yl]car-bonyl]-4-(3-methoxyphenyl)piperazine;

1-[[7-(3,4-Dichlorophenyl)-4,7-dihydro-5-methylpyrazolo[1,5-a]pyrimidin-6-yl]car-bonyl]-4-(4-methylphenyl)piperazine;

1-[[7-(3,4-Dichlorophenyl)-4,7-dihydro-5-methylpyrazolo[1,5-a]-pyrimidin-6-yl]car-bonyl]-4-[4(trifluoromethyl)phenyl]piperazine;

1-[[7-(3,4-Dichlorophenyl)-4,7-dihydro-5-methylpyrazolo[1,5-a]pyrimidin-6-yl]car-bonyl]-4-(2-fluorophenyl)piperazine;

1-[[7-(3,4-Dichlorophenyl)-4,7-dihydro-5-methylpyrazolo[1,5-a]pyrimidin-6-yl]car-bonyl]-4-(3,4-dimethylphenyl)piperazine;

1-[[7-(3,4-Dichlorophenyl)-4,7-dihydro-5-methylpyrazolo[1,5-a]-pyrimidin-6-yl]car-bonyl]-4(3,4-dimethylphenyl)piperazine;

4-[[7-(3,4-Dichlorophenyl)-4,7-dihydro-5-methyl-pyrazolo[1,5-a]pyrimidin-6-yl]carbonyl]-1-piperazinecarboxylic acid phenylmethyl ester;

1-(1,3-Benzodioxol-5-ylmethyl)-4-[[7-(3,4-dichlorophenyl)-4,7-dihydro-5-methylpyrazolo[1,5-a]pyrimidin-6-yl]carbonyl]piperazine;

4-[[7-(3,4-Dichlorophenyl)-4,7-dihydro-5-methylpyrazolo[1,5-a]pyrimidin-6-yl]carbonyl]-1-piperazinecarboxylic acid ethyl ester;

1-[[7-(3,4-Dichlorophenyl)-4,7-dihydro-5-methylpyrazolo[1,5-a]pyrimidin-6-yl]carbonyl]-4-(2-pyridinyl)piperazine;

(2S)-1-[[7-(3,4-Dichlorophenyl)-4,7-dihydro-5-methylpyrazolo[1,5-a]pyrimidin-6-yl]carbonyl]-2-(methoxymethyl)pyrrolidine;

1-[Bis(4-fluorophenyl)-methyl]-4-[[7-(3,4-dichlorophenyl)-4,7-dihydro-5-methyl-pyrazolo[1,5-a]pyrimidin-6-yl]carbonyl]piperazine;

1-[[7-(3,4-Dichlorophenyl)-4,7-dihydro-5-methylpyrazolo[1,5-a]pyrimidin-6-yl]car-bonyl]-4-(2-furanylcarbonyl)piperazine;

1-Cyclohexyl-4-[[7-(3,4-dichlorophenyl)-4,7-dihydro-5-methylpyrazolo[1,5-a]pyrimidin-6-yl]carbonyl]piperazine;

1-[[7-(3,4-Dichlorophenyl)-4,7-dihydro-5-methylpyrazolo[1,5-a]pyrimidin-6-yl]carbonyl]-4-(2-methoxyethyl)piperazine;

1-[[7-(3,4-Dichlorophenyl)-4,7-dihydro-5-methylpyrazolo[1,5-a]pyrimidin-6-yl]carbonyl]-4(9H-fluoren-9-yl)piperazine;

(2R)-1-[[7-(3,4-Dichlorophenyl)-4,7-dihydro-5-methyl-pyrazolo[1,5-a]pyrimidin-6-yl]carbonyl]-2-(methoxymethyl)pyrrolidine;

1-[[7-(3,4-Dichlorophenyl)-4,7-dihydro-5-methylpyrazolo[1,5-a]pyrimidin-6-yl]car-bonyl]-4-(2,3-dimethylphenyl)piperazine;

1-[[7-(3,4-Dichlorophenyl)-4,7-dihydro-5-methylpyrazolo[1,5-a]pyrimidin-6-yl]carbonyl]-1,2,3,4-tetrahydroquinoline;

1-[[7-(3,4-Dichlorophenyl)-4,7-dihydro-5-methylpyrazolo[1,5-a]-pyrimidin-6-yl]carbonyl]-decahydroquinoline;

2-[[7-(3,4-Dichlorophenyl)-4,7-dihydro-5-methylpyrazolo[1,5-a]pyrimidin-6-yl]carbonyl]-1,2,3,4-tetrahydroisoquinoline;

2-[[7-(3,4-Dichlorophenyl)-4,7-dihydro-5-methylpyrazolo[1,5-a]pyrimidin-6-yl]carbonyl]-2,3,4,9-tetrahydro-1H-pyrido[3,4-b]indole;

(2S)-1-[[7-(3,4-Dichlorophenyl)-4,7-dihydro-5-methylpyrazolo[1,5-a]pyrimidin-6-yl]carbonyl]-2-[(phenylamino)methyl]pyrrolidine;

3-[[7-(3,4-Dichlorophenyl)-4,7-dihydro-5-methyl-pyrazolo[1,5-a]pyrimidin-6-yl]carbonyl]thiazole;

1-[[7-(3,4-Dichlorophenyl)-4,7-dihydro-5-methylpyrazolo[1,5-a]pyrimidin-6-yl]carbonyl]-3,4-dihydro-1H-indole;

1-[[7-(3,4-Dichlorophenyl)-4,7-dihydro-5-methylpyrazolo[1,5-a]pyrimidin-6-yl]carbonyl]azetidine;

1-[[7-(3,4-Dichlorophenyl)-4,7-dihydro-5-methylpyrazolo[1,5-a]pyrimidin-6-yl]carbonyl]hexahydro-1H-azepine;

1-[[7-(3,4-Dichlorophenyl)-4,7-dihydro-5-methylpyrazolo[1,5-a]pyrimidin-6-yl]carbonyl]octahydroazocine;

1-[[7-(3,4-Dichlorophenyl)-4,7-dihydro-5-methylpyrazolo[1,5-a]pyrimidin-6-yl]carbonyl]-1,2,3,6-tetrahydropyridine;

1-[[7-(3,4-Dichlorophenyl)-4,7-dihydro-5-methylpyrazolo[1,5-a]pyrimidin-6-yl]carbonyl]-2-methylpyrrolidine;

1-[[7-(3,4-Dichlorophenyl)-4,7-dihydro-5-methylpyrazolo[1,5-a]pyrimidin-6-yl]carbonyl]-2-methylaziridine;

(2S)-1-[[7-(3,4-Dichlorophenyl)-4,7-dihydro-5-methylpyrazolo[1,5-a]pyrimidin-6-yl]carbonyl]-2-[[(2,6-dimethylphenyl)amino]methyl]pyrrolidine;

6-[[7-(3,4-Dichlorophenyl)-4,7-dihydro-5-methylpyrazolo[1,5-a]pyrimidin-6-yl]carbonyl]-1,3,3-trimethyl-6-azabicyclo[3.2.1]octane;

1-[[7-(3,4-Dichlorophenyl)-4,7-dihydro-5-methylpyrazolo[1,5-a]pyrimidin-6-yl]carbonyl]aziridine;

1-[[7-(3,4-Dichlorophenyl)-4,7-dihydro-5-methylpyrazolo[1,5-a]pyrimidin-6-yl]carbonyl]octahydro-1H-azonine;

(2R-trans)-1-[[7-(3,4-Dichlorophenyl)-4,7-dihydro-5-methyl-pyrazolo[1,5-a]pyrimidin-6-yl]carbonyl]-2,5-bis(methoxymethyl)-pyrrolidine;

(2S-trans)-1-[[7-(3,4-Dichlorophenyl)-4,7-dihydro-5-methylpyrazolo[1,5-a]pyrimidin-6-yl]carbonyl]-2,5-bis-(methoxymethyl)pyrrolidine;

1-[[7-(3,4-Dichlorophenyl)-4,7-dihydro-5-methylpyrazolo[1,5-a]pyrimidin-6-yl]carbonyl]-L-prolinamide;

1-[[7-(3,4-Dichlorophenyl)-4,7-dihydro-5-methylpyrazolo[1,5-a]pyrimidin-6-yl]carbonyl]-D-prolinamide;

1-[[7-(3,4-Dichlorophenyl)-4,7-dihydro-5-methylpyrazolo[1,5-a]pyrimidin-6-yl]carbonyl]-2,3-dihydro-2-methyl-1H-indole;

1-[[7-(3,4-Dichlorophenyl)-4,7-dihydro-5-methylpyrazolo[1,5-a]pyrimidin-6-yl]carbonyl]-2,3-dihydro-5-nitro-1H-indole;

1-[[7-(3,4-Dichlorophenyl)-4,7-dihydro-5-methylpyrazolo[1,5-a]pyrimidin-6-yl]carbonyl]-2,3-dihydro-6-nitro-1H-indole;

4-[[7-(3,4-Dichlorophenyl)-4,7-dihydro-5-methyl-pyrazolo[1,5-a]pyrimidin-6-yl]carbonyl]-thiomorpholine;

1-[[7-(3,4-Dichlorophenyl)-4,7-dihydro-5-methylpyrazolo[1,5-a]pyrimidin-6-yl]carbonyl]-L-proline methyl ester;

(2S)-1-[[7-(3,4-Dichlorophenyl)-4,7-dihydro-5-methylpyrazolo[1,5-a]pyrimidin-6-yl]carbonyl]-2(methoxymethyl)pyrrolidine, enantiomer A;

(2S)-1-[[7-(3,4-Dichlorophenyl)-4,7-dihydro-5-methylpyrazolo[1,5-a]pyrimidin-6-yl]carbonyl]-2(methoxymethyl)pyrrolidine, enantiomer B;

1-[[7-(3,4-Dichlorophenyl)-4,7-dihydro-5-methylpyrazolo[1,5-a]pyrimidin-6-yl]carbonyl]-L-proline 1,1-dimethylethyl ester;

1-[[7-(3,4-Dichlorophenyl)-4,7-dihydro-5-methylpyrazolo[1,5-a]pyrimidin-6-yl]carbonyl]-N-(2-naphthalenyl)-L-prolinamide;

1-[[7-(3,4-Dichlorophenyl)-4,7-dihydro-5-methylpyrazolo[1,5-a]pyrimidin-6-yl]carbonyl]-1,2,3,4-tetrahydro-2-methylquinoline;

1-[[7-(3,4-Dichlorophenyl)-4,7-dihydro-5-methylpyrazolo[1,5-a]pyrimidin-6-yl]carbonyl]-6-fluoro-1,2,3,4-tetrahydro-2-methylquinoline;

1-[[7-(3,4-Dichlorophenyl)-4,7-dihydro-5-methylpyrazolo[1,5-a]pyrimidin-6-yl]carbonyl]-L-proline phenylmethyl ester;

1-[[7-(3,4-Dichlorophenyl)-4,7-dihydro-5-methylpyrazolo[1,5-a]pyrimidin-6-yl]carbonyl]-D-proline phenylmethyl ester;

1-[[7-(3,4-Dichlorophenyl)-4,7-dihydro-5-methyl-pyrazolo[1,5-a]pyrimidin-6-yl]carbonyl]-4-hydroxy-L-proline phenylmethyl ester;

1-[[7-(3,4-Dichlorophenyl)-4,7-dihydro-5-methylpyrazolo[1,5-a]pyrimidin-6-yl]carbonyl]-4-(4-fluorophenyl)-2-methylpiperazine;

4-[[3-Chloro-7-(3,4-dichlorophenyl)-4,7-dihydro-5-methyl-pyrazolo[1,5-a]pyrimidin-6-yl]carbonyl]-thiomorpholine;

1-[[3-Chloro-7-(3,4-dichlorophenyl)-4,7-dihydro-5-methyl-pyrazolo[1,5-a]pyrimidin-6-yl]carbonyl]-2,3-dihydro-1H-indole;

1-[[3-Chloro-7-(3,4-dichlorophenyl)-4,7-dihydro-5-methyl-pyrazolo[1,5-a]pyrimidin-6-yl]carbonyl]hexahydro-1H-azepine;

1-[[3-Chloro-7-(3,4-dichlorophenyl)-4,7-dihydro-5-methyl-pyrazolo[1,5-a]pyrimidin-6-yl]carbonyl]-octahydroazocine;

1-[[3-Chloro-7-(3,4-dichlorophenyl)-4,7-dihydro-5-methylpyrazolo[1,5-a]pyrimidin-6-yl]carbonyl]-1,2,3,6-tetrahydropyridine;

[(3R)-1-[[7-(3,4-Dichlorophenyl)-4,7-dihydro-5-methylpyrazolo[1,5-a]pyrimidin-6-yl]carbonyl]-3-pyrrolidinyl]carbamic acid 1,1-dimethylethyl ester;

[(3S)-1-[[7-(3,4-Dichlorophenyl)-4,7-dihydro-5-methylpyrazolo[1,5-a]pyrimidin-6-yl]carbonyl]-3-pyrrolidinyl]carbamic acid 1,1-dimethylethyl ester;

(3R)-1-[[7-(3,4-Dichlorophenyl)-4,7-dihydro-5-methylpyrazolo[1,5-a]pyrimidin-6-yl]carbonyl]-3(dimethylamino)pyrrolidine;

N-[1-[[7-(3,4-Dichlorophenyl)-4,7-dihydro-5-methylpyrazolo[1,5-a]pyrimidin-6-yl]carbonyl]-3-pyrrolidinyl]acetamide;

N-[1-[[7-(3,4-Dichlorophenyl)-4,7-dihydro-5-methylpyrazolo[1,5-a]pyrimidin-6-yl]carbonyl]-3-pyrrolidinyl]-N-methylacetamide;

(2S)-1-[[3-Chloro-7-(3,4-dichlorophenyl)-4,7-dihydro-5-methyl-pyrazolo[1,5-a]pyrimidin-6-yl]carbonyl]-2-(methoxymethyl)pyrrolidine;

1-[[3-Chloro-7-(3,4-dichlorophenyl)-4,7-dihydro-5-methyl-pyrazolo[1,5-a]pyrimidin-6-yl]carbonyl]-decahydroquinoline;

2-[[3-Chloro-7-(3,4-dichlorophenyl)-4,7-dihydro-5-methyl-pyrazolo[1,5-a]pyrimidin-6-yl]carbonyl]-1,2,3,4-tetrahydroisoquinoline;

4-[[3-Chloro-7-(3-chlorophenyl)-4,7-dihydro-5-methyl-pyrazolo[1,5-a]pyrimidin-6-yl]carbonyl]-thiomorpholine;

1-[[7-(3,4-Dichlorophenyl)-4,7-dihydro-5-methyl-pyrazolo[1,5-a]pyrimidin-6-yl]carbonyl]-azacyclotridecane;

(2S)-1-[[7-(3,4-Dichlorophenyl)-4,7-dihydro-5-methyl-2-(trifluoromethyl)pyrazolo-[1,5-a]pyrimidin-6-yl]carbonyl]-2-(methoxymethyl)pyrrolidine;

1-[[3-Chloro-7-(3-chlorophenyl)-4,7-dihydro-5-methyl-pyrazolo[1,5-a]pyrimidin-6-yl]carbonyl]hexahydro-1H-azepine;

1-[[3-Chloro-7-(3-chlorophenyl)-4,7-dihydro-5-methyl-pyrazolo[1,5-a]pyrimidin-6-yl]carbonyl]-octahydroazocine;

1-[[3-Chloro-7-(3-chlorophenyl)-4,7-dihydro-5-methylpyrazolo[1,5-a]pyrimidin-6-yl]carbonyl]-1,2,3,6-tetrahydropyridine;

(2S)-1-[[3-Chloro-7-(3-chlorophenyl)-4,7-dihydro-5-methylpyrazolo[1,5-a]pyrimidin-6-yl]carbonyl]-2(methoxymethyl)pyrrolidine;

1-[[3-Chloro-7-(3-chlorophenyl)-4,7-dihydro-5-methylpyrazolo[1,5-a]pyrimidin-6-yl]carbonyl]-decahydroquinoline;

2-[[3-Chloro-7-(3-chlorophenyl)-4,7-dihydro-5-methylpyrazolo[1,5-a]pyrimidin-6-yl]carbonyl]-1,2,3,4-tetrahydroisoquinoline;

1-[[3-Chloro-7-(2,3-dichlorophenyl)-4,7-dihydro-5-methylpyrazolo[1,5-a]pyrimidin-6-yl]carbonyl]hexahydro-1H-azepine;

1-[[3-Chloro-7-(2,3-dichlorophenyl)-4,7-dihydro-5-methylpyrazolo[1,5-a]pyrimidin-6-yl]carbonyl]-1,2,3,6-tetrahydropyridine;

(2S)-1-[[3-Chloro-7-(2,3-dichlorophenyl)-4,7-dihydro-5-methylpyrazolo[1,5-a]pyrimi-din-6-yl]carbonyl]-2 (methoxymethyl)pyrrolidine;

1-[[7-(3,4-Dichlorophenyl)-4,7-dihydro-5-methyl-2-(trifluoromethyl)pyrazolo[1,5-a]pyrimidin-6-yl]carbonyl]-2,3-dihydro-1H-indole;

1-[[7-(3,4-Dichlorophenyl)-4,7-dihydro-5-methyl-2-(trifluoromethyl)pyrazolo[1,5-a]pyrimidin-6-yl]carbonyl]hexahydro-1H-azepine;

2-[[3-Chloro-7-(2,3-dichlorophenyl)-4,7-dihydro-5-methylpyrazolo[1,5-a]pyrimidin-6-yl]carbonyl]-1,2,3,4-tetrahydroisoquinoline;

1-[[3-Chloro-7-(2,3-dichlorophenyl)-4,7-dihydro-5-methylpyrazolo[1,5-a]pyrimidin-6-yl]carbonyl]-octahydroazocine;

1-[[7-(3,4-Dichlorophenyl)-4,7-dihydro-5-methylpyrazolo[1,5-a]pyrimidin-6-yl]carbonyl]-1,2,3,4-tetrahydro-6-methylquinoline;

1-[(7-Cyclopropyl-4,7-dihydro-5-methyl-pyrazolo[1,5-a]pyrimidin-6-yl)carbonyl]-4-(4-fluorophenyl)piperazine;

1-[[4,7-Dihydro-5-methyl-7-(1-methylethyl)pyrazolo[1,5-a]pyrimidin-6-yl]carbonyl]-4-(4-fluorophenyl)piperazine;

(2S)-1-[[4,7-Dihydro-5-methyl-7-(1-methylethyl)pyrazolo[1,5-a]pyrimidin-6-yl]carbonyl]-2-(methoxymethyl)pyrrolidine;

1-[[4,7-Dihydro-5-methyl-7-(1-methylethyl)pyrazolo[1,5-a]pyrimidin-6-yl]carbonyl]-2,3-dihydro-1H-indole;

1-[[4,7-Dihydro-5-methyl-7-(1-methylethyl)pyrazolo[1,5-a]pyrimidin-6-yl]carbonyl]-1,2,3,6-tetrahydropyridine;

3-[[7-(3,4-Dichlorophenyl)-4,7-dihydro-5-methylpyrazolo[1,5-a]pyrimidin-6-yl]carbonyl]thiazolidine, enantiomer A;

3-[[7-(3,4-Dichlorophenyl)-4,7-dihydro-5-methylpyrazolo[1,5-a]pyrimidin-6-yl]carbonyl]thiazolidine, enantiomer B;

(2S)-1-[[7-(3,4-Dichlorophenyl)-4,7-dihydro-5-methylpyrazolo[1,5-a]pyrimidin-6-yl]carbonyl]-2(phenoxymethyl)pyrrolidine;

(2R)-1-[[7-(3,4-Dichlorophenyl)-4,7-dihydro-5-methylpyrazolo[1,5-a]pyrimidin-6-yl]carbonyl]-2(phenoxymethyl)pyrrolidine;

(2S)-1-[[7-(3,4-Dichlorophenyl)-4,7-dihydro-5-methylpyrazolo[1,5-a]pyrimidin-6-yl]carbonyl]-2-[(4-fluorophenoxy)methyl]-pyrrolidine;

(2R)-1-[[7-(3,4-Dichlorophenyl)-4,7-dihydro-5-methylpyrazolo[1,5-a]pyrimidin-6-yl]carbonyl]-2-[(4-fluorophenoxy)methyl]pyrrolidine;

(2S)-1-[[7-(3,4-Dichlorophenyl)-4,7-dihydro-5-methylpyrazolo[1,5-a]pyrimidin-6-yl]carbonyl]-2-(hydroxydiphenylmethyl)pyrrolidine;

(2R)-1-[[7-(3,4-Dichlorophenyl)-4,7-dihydro-5-methylpyrazolo[1,5-a]pyrimidin-6-yl]carbonyl]-2-(hydroxydiphenylmethyl)pyrrolidine;

1-[[7-(3,4-Dichlorophenyl)-4,7-dihydro-5-methylpyrazolo[1,5-a]pyrimidin-6-yl]carbonyl]-2-(3-pyridinyl)pyrrolidine;

(2S)-1-[[7-(2,3-Dichlorophenyl)-4,7-dihydro-5-methylpyrazolo[1,5-a]pyrimidin-6-yl]carbonyl]-2-(methoxymethyl)pyrrolidine;

1-[[7-(3,4-Dichlorophenyl)-4,7-dihydro-5-methylpyrazolo[1,5-a]pyrimidin-6-yl]carbonyl]-2-phenylpyrrolidine;

3-[[7-(3,4-Dichlorophenyl)-4,7-dihydro-5-methylpyrazolo[1,5-a]pyrimidin-6-yl]car-bonyl]-2-phenylthiazolidine;

3-[[7-(3,4-Dichlorophenyl)-4,7-dihydro-5-methylpyrazolo[1,5-a]pyrimidin-6-yl]carbonyl]-2-thiazolidinecarboxylic acid methyl ester;

2-(4Chlorophenyl)-3-[[7-(3,4-dichlorophenyl)-4,7-dihydro-5-methylpyrazolo[1,5-a]pyrimidin-6-yl]carbonyl]thiazolidine;

8-[[7-(2,3-Dichlorophenyl)-4,7-dihydro-5-methylpyrazolo[1,5-a]pyrimidin-6-yl]car-bonyl]-1-phenyl-1,3,8-triazaspiro[4,5]decan-4-one;

4-(4-Chlorophenyl)-1-[[7-(3,4-dichlorophenyl)-4,7-dihydro-5-methylpyrazolo[1,5-a]pyrimidin-6-yl]carbonyl]-1,2,3,6-tetrahydropyridine;

1-[[7-(3,4-Dichlorophenyl)-4,7-dihydro-5-methylpyrazolo[1,5-a]pyrimidin-6-yl]car-bonyl]-2-(2-phenylethyl)pyrrolidine;

1-[[7-(3,4-Dichlorophenyl)-4,7-dihydro-5-methylpyrazolo[1,5-a]pyrimidin-6-yl]car-bonyl]-2(4-methoxyphenyl)pyrrolidine;

1-[[7-(3,4-Dichlorophenyl)-4,7-dihydro-5-methylpyrazolo[1,5-a]pyrimidin-6-yl]car-bonyl]-2-(2-methoxyphenyl)pyrrolidine;

(3R)1-[[7-(3,4-Dichlorophenyl)-4,7-dihydro-5-methylpyrazolo[1,5-a]pyrimidin-6-yl]carbonyl]-3-phenoxypyrrolidine;

(2S)-2-[(Cyclohexyloxy)methyl]-1-[[7-(3,4-dichlorophenyl)-4,7-dihydro-5-methyl-pyrazolo[1,5-a]pyrimidin-6-yl]carbonyl]pyrrolidine;

1-[[7-(3,4-Dichlorophenyl)-4,7-dihydro-5-methylpyrazolo[1,5-a]pyrimidin-6-yl]car-bonyl]-2-(phenylmethyl)pyrrolidine;

(2S)-1-[[7-(3,4-Dichlorophenyl)-4,7-dihydro-5-methylpyrazolo[1,5-a]pyrimidin-6-yl]carbonyl]-2-(phenoxymethyl)pyrrolidine, diastereomer A;

(2S)-1-[[7-(3,4-Dichlorophenyl)-4,7-dihydro-5-methylpyrazolo[1,5-a]pyrimidin-6-yl]carbonyl]-2-(phenoxymethyl)pyrrolidine, diastereomer B;

1-[[7-(3,4-Dichlorophenyl)-4,7-dihydro-5-methylpyrazolo[1,5-a]pyrimidin-6-yl]car-bonyl]-2-(3-methoxyphenyl)pyrrolidine;

(2S)-2-(Butoxymethyl)-1-[[7-(3,4-dichlorophenyl)-4,7-dihydro-5-methyl-pyrazolo[1,5-a]pyrimidin-6-yl]carbonyl]pyrrolidine;

1-[[7-(3,4-Dichlorophenyl)-4,7-dihydro-5-methylpyrazolo[1,5-a]pyrimidin-6-yl]carbonyl]-2-(2-thienyl)pyrrolidine;

1-[[7-(3,4-Dichlorophenyl)-4,7-dihydro-5-methylpyrazolo[1,5-a]pyrimidin-6-yl]carbonyl]-2-(4-pyridinyl)pyrrolidine;

(2S)-1-[[7-(3,4-Dichlorophenyl)-4,7-dihydro-5-methylpyrazolo[1,5-a]pyrimidin-6-yl]carbonyl]-2-[(methoxymethoxy)-methyl]pyrrolidine;

(2S)-2-(1H-Benzimidazol-1-ylmethyl)-1-[[7-(3,4-dichlorophenyl)-4,7-dihydro-5-methylpyrazolo[1,5-a]pyrimidin-6-yl]carbonyl]pyrrolidine;

1-[[7-(3,4-Dichlorophenyl)-4,7-dihydro-5-methylpyrazolo[1,5-a]pyrimidin-6-yl]carbonyl]-2-(3-furanyl)pyrrolidine;

1-[[7-(3,4-Dichlorophenyl)-4,7-dihydro-5-methylpyrazolo[1,5-a]pyrimidin-6-yl]carbonyl]-2-(2-pyridinyl)pyrrolidine;

(3S)-1-[[7-(3,4-Dichlorophenyl)-4,7-dihydro-5-methylpyrazolo[1,5-a]pyrimidin-6-yl]carbonyl]-3-phenoxypyrrolidine;

(3S)-1-[[7-(3,4-Dichlorophenyl)-4,7-dihydro-5-methylpyrazolo[1,5-a]pyrimidin-6-yl]carbonyl]-3-phenoxypyrrolidine;

(2S)-1-[[7-(3,4-Dichlorophenyl)-4,7-dihydro-5-methyl-2-(trifluoromethyl)pyrazolo[1,5-a]pyrimidin-6-yl]carbonyl]-2-(methoxymethyl)pyrrolidine, enantiomer A;

(2S)-1-[[7-(3,4-Dichlorophenyl)-4,7-dihydro-5-methyl-2-(trifluoromethyl)pyrazolo[1,5-a]-pyrimidin-6-yl]carbonyl]-2-(methoxymethyl)pyrrolidine, enantiomer B;

1-[[7-(3,4-Dichlorophenyl)-4,7-dihydro-5-methylpyrazolo[1,5-a]pyrimidin-6-yl]carbonyl]-L-proline;

(2S)-1-[[7-(3,4-Dichlorophenyl)-4,7di-hydro-5-methyl-2-(trifluoromethyl)pyrazolo[1,5-a]pyrimidin-6-yl]carbonyl]-2-(1-pyrrolidinylmethyl)-pyrrolidine;

1-[[7-(3,4-Dichlorophenyl)-4,7-dihydro-5-methylpyrazolo[1,5-a]pyrimidin-6-yl]carbonyl]-4-(1-naphthalenylsulfonyl)piperazine;

1-[[7-(3,4-Dichlorophenyl)-4,7-dihydro-5-methylpyrazolo[1,5-a]pyrimidin-6-yl]carbonyl]-4-[(4-ethylphenyl)sulfonyl]-piperazine;

1-[(4-Bromo-5-chloro-2-thienyl)sulfonyl]-4-[[7-(3,4-dichlorophenyl)-4,7-dihydro-5-methylpyrazolo[1,5-a]pyrimi-din-6-yl]carbonyl]-piperazine;

1-[[7-(3,4-Dichlorophenyl)-4,7-dihydro-5-methylpyrazolo[1,5-a]pyrimidin-6-yl]car-bonyl]-4-[[2-(trifluoromethoxy)phenyl]sulfonyl]piperazine;

1-[(5-Chloro-3-methylbenzo[b]thiophen-2-yl)sulfonyl]-4-[[7-(3,4-dichlorophenyl)-4,7-dihydro-5-methylpyrazolo[1,5-a]pyrimidin-6-yl]carbonyl]piperazine;

1-[[7-(3,4-Dichlorophenyl)-4,7-dihydro-5-methylpyrazolo[1,5-a]pyrimidin-6-yl]carbonyl]-4-[(3-methoxyphenyl)carbonyl]piperazine;

1-[[7-(3,4-Dichlorophenyl)-4,7-dihydro-5-methylpyrazolo[1,5-a]pyrimidin-6-yl]car-bonyl]-4-(1-oxo-3-phenyl-2-propenyl)-piperazine;

1-[[7-(3,4-Dichlorophenyl)-4,7-dihydro-5-methylpyrazolo[1,5-a]pyrimidin-6-yl]car-bonyl]-4-(4-pyridinylcarbonyl)piperazine;

1-[[7-(2,3-Dichlorophenyl)-4,7-dihydro-4,5-dimethylpyrazolo[1,5-a]pyrimidin-6-yl]carbonyl]-4-phenylpiperazine;

1-[[7-(3,4-Dichlorophenyl)-4,7-dihydro-4,5-dimethylpyrazolo[1,5-a]pyrimidin-6-yl]carbonyl]-4-(4-fluorophenyl)piperazine;

1-[[7-(2,3-Dichlorophenyl)-4,7-dihydro-4,5-dimethylpyrazolo[1,5-a]pyrimidin-6-yl]carbonyl]-4-(4-fluorophenyl)piperazine;

1-[[7-(2,3-Dichlorophenyl)-4,7-dihydro-4,5-dimethylpyrazolo[1,5-a]pyrimidin-6-yl]carbonyl]-4-(4-fluorophenyl)piperazine, enantiomer B;

1-[[7-(2,3-Dichlorophenyl)-4,7-dihydro-4,5-dimethylpyrazolo[1,5-a]pyrimidin-6-yl]carbonyl]-4-(4-fluorophenyl)piperazine, enantiomer A;

1-[[7-(2,3-Dichlorophenyl)-4,7-dihydro-2,4,5-trimethylpyrazolo[1,5-a]pyrimidin-6-yl]carbonyl]-4-(4-fluorophenyl)piperazine;

1-[[7-(2,3-Dichlorophenyl)-4-[(4-fluorophenyl)methyl]-4,7dihydro-2,5-dimethylpyrazolo[1,5-a]pyrimidin-6-yl]carbonyl-4-(4-fluorophenyl)piperazine;

7-(2,3-Dichlorophenyl)-6-[[4-(4-fluorophenyl)-1-piperazinyl]carbonyl]-2,5-dimethylpyrazolo[1,5-a]pyrimidine-4(7H)-acetic acid ethyl ester;

7-(2,3-Dichlorophenyl)-6-[[4-(4-fluorophenyl)-1-piperazinyl]carbonyl]-N,N,2,5-tetramethylpyrazolo[1,5-a]pyrimidine-4(7H)-acetamide;

1-[[7-(2,3-Dichlorophenyl)-4-[2-(dimethylamino)ethyl]-4,7-dihydro-2,5-dimethylpyrazolo[1,5-a]pyrimidin-6-yl]carbonyl]-4-(4-fluorophenyl)piperazine;

1-[[4-(Cyclopropylmethyl)-7-(2,3-dichlorophenyl)-4,7-dihydro-2,5-dimethylpyrazolo[1,5-a]pyrimidin-6-yl]carbonyl]-4-(4-fluorophenyl)piperazine;

7-(2,3-Dichlorophenyl)-6-[[4-(4-fluorophenyl)-1-piperazinyl]carbonyl]-N,N,2,5-tetramethylpyrazolo[1,5-a]pyrimidine-4(7H)-carboxamide;

1-[[7-(2,3-Dichlorophenyl)-4,7-dihydro-4-methyl-5-(trifluoromethyl)pyrazolo[1,5-a]pyrimidin-6-yl]carbonyl]-4-(4-fluorophenyl)piperazine;

1-[[7-(2,3-Dichlorophenyl)-4,7-dihydro-5-(trifluoromethyl)pyrazolo[1,5-a]pyrimidin-6-yl]carbonyl]-4-(4-fluorophenyl)piperazine;

1-[[7-(2,3-Dichlorophenyl)-4,7-dihydro-2-methyl-5-(trifluoromethyl)pyrazolo[1,5-a]pyrimidin-6-yl]carbonyl]-4-(4-fluorophenyl)piperazine;

1-[[7-(2,3-Dichlorophenyl)-4,7-dihydro-2,4-dimethyl-5-(trifluoromethyl)pyrazolo[1,5-a]pyrimidin-6-yl]carbonyl]-4-(4-fluorophenyl)piperazine;

1-[[7-(2,3-Dichlorophenyl)-4,7-dihydro-2,4-dimethyl-5-(trifluoromethyl)pyrazolo[1,5-a]pyrimidin-6-yl]carbonyl]-4-(4-fluorophenyl)piperazine, enantiomer B;

1-[[7-(2,3-Dichlorophenyl)-4,7-dihydro-2,4-dimethyl-5-(trifluoromethyl)pyrazolo[1,5-a]pyrimidin-6-yl]carbonyl]-4-(4-fluorophenyl)piperazine, enantiomer A;

1-[[7-(3,4-Dichlorophenyl)-4,7-dihydro-5-(trifluoromethyl)pyrazolo[1,5-a]pyrimidin-6-yl]carbonyl]-4-(4-fluorophenyl)piperazine;

1-[[7-(3,4-Dichlorophenyl)-4,7-dihydro-2-methyl-5-(trifluoromethyl)pyrazolo[1,5-a]pyrimidin-6-yl]carbonyl]-4-(4-fluorophenyl)piperazine;

1-[[1-Benzoyl-7-(2,3-dichlorophenyl)-1,2,4,7-tetrahydro-5-methyl-2-oxopyrazolo[1,5-a]pyrimidin-6-yl]carbonyl]-4-phenylpiperazine;

1-[[1-Benzoyl-7-(3,4-dichlorophenyl)-1,2,4,7-tetrahydro-5-methyl-2-oxopyrazolo[1,5-a]pyrimidin-6-yl]carbonyl]-4-phenylpiperizine;

1-[[1-Acetyl-7-(3,4-dichlorophenyl)-1,2,4,7-tetrahydro-5-methyl-2-oxopyrazolo[1,5-a]pyrimidin-6-yl]carbonyl]-4-phenylpiperizine;

1-[[7-(3,4-Dichlorophenyl)-1,2,4,7-tetrahydro-5-methyl-2-oxo-1-(1-oxobutyl)-pyrazolo[1,5-a]pyrimidin-6-yl]carbonyl]-4-phenylpiperazine;

1-[[1-(Cyclopropylcarbonyl)-7-(3,4-dichlorophenyl)-1,2,4,7-tetrahydro-5-methyl-2-oxopyrazolo[1,5-a]pyrimidin-6-yl]carbonyl]-4-phenylpiperizine;

1-[[1-(Cyclopropylcarbonyl)-7-(2,3-dichlorophenyl)-1,2,4,7-tetrahydro-5-methyl-2-oxopyrazolo[1,5-a]pyrimidin-6-yl]carbonyl]-4-(4-fluorophenyl)piperazine;

1-[[7-(2,3-Dichlorophenyl)-1,2,4,7-tetra-hydro-5-methyl-1-(3-methyl-1-oxobutyl)-2-oxopyrazolo[1,5-a]pyrimidin-6-yl]carbonyl-4-(4-fluorophenyl)-piperazine;

1-[[7-(2,3-Dichlorophenyl)-(2,2-dimethyl-1-oxopropyl)-1,2,4,7-tetrahydro-5-methyl-2-oxpyrazolo[1,5-a]pyrimidin-6-yl]carbonyl]-4-phenylpiperizine;

1-[[1-(Cyclopropylcarbonyl)-7-(3,4-dichlorophenyl)-1,2,4,7-tetrahydro-5-methyl-2-oxopyrazolo[1,5-a]pyrimidin-6-yl]carbonyl]-4-(4-fluorophenyl)piperazine;

1-[[1-(Cyclobutylcarbonyl)-7-(3,4-dichlorophenyl)-1,2,4,7-tetrahydro-5-methyl-2-oxopyrazolo[1,5-a]pyrimidin-6-yl]carbonyl]-4-(4-fluorophenyl)piperazine;

1-[[7-(3,4-Dichlorophenyl)-1,2,4,7-tetrahydro-5-methyl-1-(2-methyl-1-oxopropyl)-2-oxopyrazolo[1,5-a]pyrimidin-6-yl]carbonyl]-4-(4-fluorophenyl)piperazine;

1-[[7-(2,3-Dichlorophenyl)-1,2,4,7-tetrahydro-5-methyl-1-[(1-methylethyl)sulfonyl]-2-oxopyrazolo[1,5-a]pyrimidin-6-yl]carbonyl]-4-phenylpiperazine;

1-[[7-(3,4-Dichlorophenyl)-1,2,4,7-tetrahydro-5-methyl-1-[(1-methylethyl)sulfonyl]-2-oxopyrazolo[1,5-a]pyrimidin-6-yl]carbonyl]-4-(4-fluorophenyl)piperazine;

7-(2,3-Dichlorophenyl)-4,7-dihydro-5-methyl-N-(1-methylethyl)-2-oxo-6-[(4-phenyl-1-piperazinyl)carbonyl]pyrazolo[1,5-a]pyrimidine-1(2H)-carboxamide;

7-(2,3-Dichlorophenyl)-4,7-dihydro-N,5-dimethyl-2-oxo-6-[(4-phenyl-1-piperazinyl)-carbonyl]pyrazolo[1,5-a]pyrimidine-1(2H)-carboxamide;

7-(2,3-Dichlorophenyl)-4,7-dihydro-5-methyl-2-oxo-6-[(4-phenyl-1-piperazinyl)carbonyl]pyrazolo[1,5-a]pyrimidine-1(2H)-carboxamide;

7-(3,4-Dichlorophenyl)-6-[[4-(4-fluorophenyl)-1-piperazinyl]carbonyl]-4,7-dihydro-N,N,5-trimethyl-2-oxopyrazolo[1,5-a]pyrimidine-1(2H)-carboxamide;

1-[[1-(3-Butenyl)-7-(3,4-dichlorophenyl)-1,2,4,7-tetrahydro-5-methyl-2-oxopyrazolo[1,5-a]pyrimidin-6-yl]carbonyl]-4-(4-fluorophenyl)piperazine;

1-[[7-(3,4-Dichlorophenyl)-1,2,4,7-tetrahydro-5-methyl-2-oxo-1-(2,2,2-trifluoroethyl)pyrazolo-[1,5-a]pyrimidin-6-yl]carbonyl]-4-(4-fluorophenyl)piperazine;

1-[[7-(3,4-Dichlorophenyl)-1,2,4,7tetrahydro-5-methyl-2-oxo-1,4-bis(2,2,2-trifluoromethyl)pyrazolo[1,5-a]pyrimidin-6-yl]carbonyl]-4-(4-fluorophenyl)piperazine;

7-(3,4-Dichlorophenyl)-6-[[4-(4-fluorophenyl)-1-piperazinyl]carbonyl]-4,7-dihydro-5-methyl-2-oxopyrazolo[1,5-a]pyrimidine-1(2H)-carboxylic acid 1-methylethyl ester;

1-[(4,7-Dihydro-5-methylpyrazolo[1,5-a]pyrimidin-6-yl)carbonyl]-4-phenylpiperazine;

7-(3,4-Dichlorophenyl)-6-[[4-(4-fluorophenyl)-1-piperazinyl]carbonyl]-4,7-dihydro-5-methylpyrazolo[1,5-a]pyrimidine-2-carboxylic acid;

7-(3,4-Dichlorophenyl)-N,N-diethyl-6-[[4-(4-fluorophenyl)-1-piperazinyl]carbonyl]-4,7-dihydro-5-methylpyrazolo[1,5-a]pyrimidine-2-carboxamide;

7-(3,4-Dichlorophenyl)-6-[[4-(4-fluorophenyl)-1-piperazinyl]carbonyl]-4,7-dihydro-N-(4-hydroxyphenyl)-5-methylpyrazolo[1,5-a]pyrimidine-2-carboxamide;

1-[(7-(3,4-Dichloro-phenyl)-4,7dihydro-5-methyl-2-[[(2S)-2-(1-pyrrolidinylmethyl)-1-pyrrolidinyl]carbonyl]-pyrazolo[1,5-a]pyrimidin-6-yl]carbonyl]-4-(4-fluorophenyl)piperazine;

7-(3,4-Dichlorophenyl)-6-[[4-(4-fluorophenyl)-1-piperazinyl]carbonyl]-4,7-dihydro-5-methylpyrazolo[1,5-a]pyrimidine-2-carboxamide;

7-(3,4-Dichlorophenyl)-6-[[4-(4-fluorophenyl)-1-piperazinyl]carbonyl]-4,7-dihydro-5-methyl-N-(phenylmethyl)pyrazolo-[1,5-a]pyrimidine-2-carboxamide;

7-(3,4-Dichlorophenyl)-6-[[4-(4-fluorophenyl)-1-piperazinyl]carbonyl]-4,7-dihydro-5-methyl-N-(2-phenylethyl)-pyrazolo[1,5-a]pyri-midine-2-carboxamide;

1-[[2-Cyano-7-(3,4-dichlorophenyl)-4,7-dihydro-5-methylpyrazolo[1,5-a]pyrimidin-6-yl]carbonyl]-4-(4-fluorophenyl)piperazine;

1-[[3-Bromo-7-(2,3-dichlorophenyl)-4,7-dihydro-5-methylpyrazolo[1,5-a]pyrimidin-6-yl]carbonyl]-4-phenylpiperazine;

1-[[3-Chloro-7-(2,3-dichlorophenyl)-4,7-dihydro-5-methylpyrazolo[1,5-a]pyrimidin-6-yl]carbonyl]-4-phenylpiperazine;

1-[[3-Chloro-7-(2,3-dichlorophenyl)-4,7-dihydro-5-methylpyrazolo[1,5-a]pyrimidin-6-yl]carbonyl]-4-(4-fluorophenyl)piperazine;

1-[[3-Chloro-7-(3,4-dichlorophenyl)-4,7-dihydro-5-methylpyrazolo[1,5-a]pyrimidin-6-yl]carbonyl]-4-(4-fluorophenyl)piperazine;

1-[[3-Chloro-7-(2,3-dichlorophenyl)-4,7-dihydro-5-methylpyrazolo[1,5-a]pyrimidin-6-yl]carbonyl]-4-phenylpiperazine, enantiomer B;

1-[[3-Chloro-7-(2,3-dichlorophenyl)-4,7-dihydro-5-methylpyrazolo[1,5-a]pyrimidin-6-yl]carbonyl]-4-phenylpiperizine, enantiomer A;

1-[[3-Chloro-7-(2,3-dichlorophenyl)-4,7-dihydro-5-methylpyrazolo[1,5-a]pyrimidin-6-yl]carbonyl]-4-(4-fluorophenyl)piperazine, enantiomer A;

1-[[3-Chloro-7-(2,3-dichlorophenyl)-4,7-dihydro-5-methylpyrazolo[1,5-a]pyrimidin-6-yl]carbonyl]-4-(4-fluorophenyl)piperazine, enantiomer B;

1-[[3-Chloro-7-(2,3-dichlorophenyl)-4,7-dihydro-2,5-dimethylpyrazolo[1,5-a]pyrimidin-6-yl]carbonyl]-4-(4-fluorophenyl)piperazine, enantiomer A;

1-[[3-Chloro-7-(2,3-dichlorophenyl)-4,7-dihydro-2,5-dimethylpyrazolo[1,5-a]pyrimidin-6-yl]carbonyl]-4-(4-fluorophenyl)piperazine, enantiomer A;

1-[[3-Chloro-7-(3,4-dichlorophenyl)-4,7-dihydro-2,5-dimethylpyrazolo[1,5-a]pyrimidin-6-yl[carbonyl]-4-(4-fluorophenyl)piperazine, enantiomer A;

1-[[3-Chloro-7-(3,4-dichlorophenyl)-4,7-dihydro-2,5-dimethyl-pyrazolo[1,5-a]pyrimidin-6-yl]carbonyl]-4-(4-fluorophenyl)piperazine, enantiomer B;

1-[[7-(3,4-Dichlorophenyl)-4,7-dihydro-5-(methoxymethyl)pyrazolo[1,5-a]pyrimidin-6-yl]carbonyl]-2-(4-fluorophenyl)pyrrolidine;

1-[[7-(3,4-Dichlorophenyl)-4,7-dihydro-5-(methoxymethyl)pyrazolo[1,5-a]pyrimidin-6-yl]carbonyl]-4-(4-fluorophenyl)piperazine;

(2S)-1-[[7-(3,4-Dichlorophenyl)-4,7-dihydro-5-(methoxymethyl)pyrazolo[1,5-a]pyrimidin-6-yl]carbonyl]-2-(methoxymethyl)pyrrolidine;

1-[[5-Cyclohexyl-7-(3,4-dichlorophenyl)-4,7-dihydropyrazolo[1,5-a]pyrimidin-6-yl]carbonyl-4-(4-fluorophenyl)piperazine;

(2S)-1-[[5-Cyclohexyl-7-(3,4-dichlorophenyl)-4,7-dihydropyrazolo[1,5-a]pyrimidin-6-yl]carbonyl]-2-(methoxymethyl)pyrrolidine;

1-[[7-(3,4-Dichlorophenyl)-4,7-dihydro-5-phenylpyrazolo[1,5-a]pyrimidin-6-yl]carbonyl]-4-(4-fluorophenyl)piperazine;

(2S)-1-[[7-(3,4-Dichlorophenyl)-4,7-dihydro-5-phenylpyrazolo[1,5-a]pyrimidin-6-yl]carbonyl]-2-(methoxymethyl)pyrrolidine;

1-[[7-(3,4-Dichlorophenyl)-4,7-dihydro-5-methylpyrazolo[1,5-a]pyrimidin-6-yl]carbonyl]-2-phenylpyrazolidine;

1-[[7-(3,4-Dichlorophenyl)-4,7-dihydro-5-methyl-2-(trifluoromethyl)pyrazolo[1,5-a]pyrimidin-6-yl]carbonyl]-2-(2-thienyl)pyrrolidine;

1-[[7-(3,4-Dichlorophenyl)-4,7-dihydro-5-methyl-2-(trifluoromethyl)pyrazolo[1,5-a]pyrimidin-6-yl]carbonyl]-2-(4-methoxyphenyl)pyrrolidine;

1-[[7-(3,4-Dichlorophenyl)-4,7-dihydro-5-methyl-2-(trifluoromethyl)pyrazolo[1,5-a]pyrimidin-6-yl]carbonyl]-2-(3-furanyl)pyrrolidine;

1-[[7-(3,4-Dichlorophenyl)-4,7-dihydro-5-methyl-2-(trifluoromethyl)pyrazolo[1,5-a]pyrimidin-6-yl]carbonyl]-2-(2-pyridinyl)pyrrolidine;

1-[[7-(3,4-Dichlorophenyl)-4,7-dihydro-5-methyl-2-(trifluoromethyl)pyrazolo[1,5-a]pyrimidin-6-yl]carbonyl]-2-(4-pyridinyl)pyrrolidine;

1-[[7-(3,4-Dichlorophenyl)-4,7-dihydro-5-methyl-2-(trifluoromethyl)pyrazolo[1,5-a]pyrimidin-6-yl]carbonyl]-2-(phenylmethyl)pyrrolidine;

1-[[7-(3,4-Dichlorophenyl)-4,7-dihydro-5-methyl-2-(trifluoromethyl)pyrazolo[1,5-a]pyrimidin-6-yl]carbonyl]-2(2-methoxyphenyl)pyrrolidine;

1-[[7-(3,4-Dichlorophenyl)-4,7-dihydro-5-methyl-2-(trifluoromethyl)pyrazolo[1,5-a]pyrimidin-6-yl]carbonyl]-2-(2-phenylethyl)pyrrolidine;

3-[[7-(3,4-Dichlorophenyl)-4,7dihydro-5-methyl-2-(trifluoromethyl)pyrazolo[1,5-a]pyrimidin-6-yl]carbonyl]thiazolidine;

1-[[7-(3,4-Dichlorophenyl)-4,7dihydro-5-methyl-2-(trifluoromethyl)pyrazolo[1,5-a]pyrimidin-6-yl]carbonyl]-4-methylpiperazine;

8-[[7-(3,4-Dichlorophenyl)-4,7dihydro-5-methyl-2-(trifluoromethyl)pyrazolo[1,5-a]pyrimidin-6-yl]carbonyl]-1,4-dioxa-8-azaspiro[4.5]decane; and 1-[[7-(3,4-Dichlorophenyl)-4,7-dihydro-5-methylpyrazolo[1,5-a]pyrimidin-6-yl]carbonyl]-2-(3-methyl-1,2,4-oxadiazol-5-yl)pyrrolidine.

10. A pharmaceutical composition comprising a compound as defined in claim 1 in combination with one or more components selected from the group consisting of cyclooxygenase inhibitors, fibrinogen antagonists, diuretics, angiotensin converting enzyme inhibitors, angiotensin II antagonists, thrombolytic agents, calcium channel blocking agents, thromboxane receptor antagonists, prostacyclin mimetics and phosphodiesterase inhibitors.

11. A pharmaceutical composition comprising a therapeutically effective amount of at least one compound of claim 1 and a pharmaceutically acceptable vehicle or carrier thereof.

12. A method of treating atrial arrhythmias comprising administering to a patient in need thereof an effective amount of at least one compound of formula I*

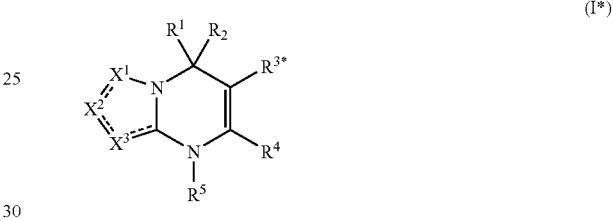

(I*)

enantiomers, diastereomers and pharmaceutically acceptable salts thereof, wherein $X^1$, $X^2$ and $X^3$, together with the atoms to which they are bonded, form a ring selected from:

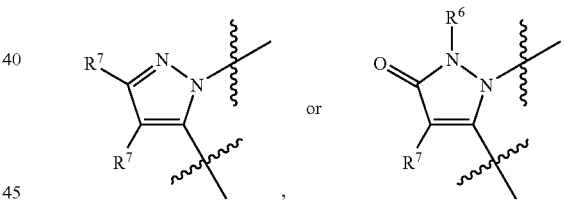

, $R^1$, $R^5$, $R^6$ and $R^7$ are independently selected from groups of the formula $-(CH_2)_n-(Z^1)_m-(CH_2)_p-Z^2$;

$R^2$ is phenyl or substituted phenyl;

$R^4$ is alkyl or substituted alkyl;

$Z^1$ is $-CZ^3Z^4-$, $-O-$, $-NZ^3-$, $-S-$; $-SO-$; $-SO_2-$, $-C(O)-$, $-C(O)Z^3-$, $-C(O)NZ^4$, $-C(S)-$, $-C(=NOZ^3)-$, alkyl, substituted alkyl, alkenyl, substituted alkenyl, alkynyl, substituted alkynyl, carbocyclo, substituted carbocyclo, aryl, substituted aryl, heterocyclo, or substituted heterocyclo;

$Z^2$ is hydrogen, $-OZ^5$, $-OC(O)Z^5$, $-NZ^5-C(O)-Z^6$, $-NZ^5-CO_2-Z^6$, $-NZ^5(C=O)-NZ^6Z^7$, $-NZ^5Z^6$, $-NO_2$, halo, $-CN$, $-C(O)Z^5$, $-CO_2Z^5$, $-C(S)Z^5$, $-(C=NOZ^5)Z^6$, $-C(O)NZ^5Z^6$, $-C(S)NZ^5Z^6$, $-SZ^5$, $-SOZ^5$, $-SO_2Z^5$, $-SO_2NZ^5Z^6$, $-CF_3$, alkyl, substituted alkyl, alkenyl, substituted alkenyl, alkynyl, substituted alkynyl, carbocyclo, substituted carbocyclo, aryl, substituted aryl, heterocyclo, or substituted heterocyclo;

$Z^3$, $Z^4$, $Z^5$, $Z^6$ and $Z^7$ are independently hydrogen, halo, alkyl, substituted alkyl, alkenyl, substituted alkenyl, alkynyl, substituted alkynyl, carbocyclo, substituted carbocyclo, aryl, substituted aryl, heterocyclo, or substituted heterocyclo; or $Z^3$, $Z^4$, $Z^5$, $Z^6$ and $Z^7$ may, in one or more pairs of two, together with the atoms to which they are bonded, form a carbocyclic, substituted carbocyclic, heterocyclic or substituted heterocyclic group;

$R^{3*}$ is —C(O)NZ$^{5*}$Z$^{6*}$;

$Z^{5*}$ and $Z^{6*}$ together with the nitrogen atom to which they are bonded form a heterocyclic group or substituted heterocyclic group, provided that $Z^{5*}$ and $Z^{6*}$ do not together form unsubstituted piperidinyl, substituted piperidinyl, unsubstituted pyrrolidinyl, or unsubstituted morpholinyl;

n and p are independently selected from integers from 0 to 10 wherein, when m is 0, p is also 0;

m is an integer selected from 0 or 1; and q is an integer selected from 1 to 3.

13. A method of claim 12 wherein the atrial arrhythmia is atrial fibrillation.

14. A method of claim 12 wherein the atrial arrhythmia is atrial flutter.

15. A method of treating epilepsy comprising administering to a patient in need thereof an effective amount of at least one compound of the formula I*

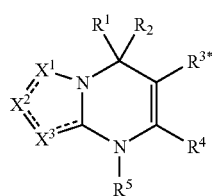

enantiomers, diasteriomers or pharmaceutically acceptable salts thereof, wherein $X^1$, $X^2$ and $X^3$, together with the atoms to which they are bonded, form a ring selected from:

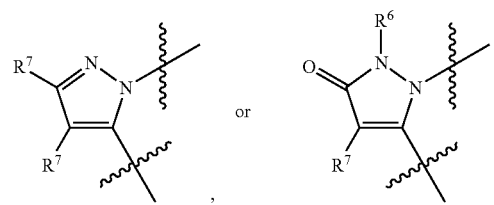

$R^1$, $R^5$, $R^6$ and $R^7$ are independently selected from groups of the formula —(CH$_2$)$_n$-(Z$^1$)$_m$-(CH$_2$)$_p$-Z$^2$;

$R^2$ is phenyl or substituted phenyl;

$R^4$ is alkyl or substituted alkyl;

$Z^1$ is —CZ$^3$Z$^4$-, —O—, —NZ$^3$-, —S—, —SO—, —SO$_2$—, —C(O)—, —C(O)Z$^3$-, —C(O)NZ$^4$, —C(S)—, —C(=NOZ$^3$)-, alkyl, substituted alkyl, alkenyl, substituted alkenyl, alkynyl, substituted alkynyl, carbocyclo, substituted carbocyclo, aryl, substituted aryl, heterocyclo, or substituted heterocyclo;

$Z^2$ is hydrogen, —OZ$^5$, —OC(O)Z$^5$, —NZ$^5$-C(O)-Z$^6$, —NZ$^5$-CO$_2$-Z$^6$, —NZ$^5$(C=O)—NZ$^6$Z$^7$, —NZ$^5$Z$^6$, —NO$_2$, halo, —CN, —C(O)Z$^5$, —CO$_2$Z$^5$, —C(S)Z$^5$, —(C=NOZ$^5$)Z$^6$, —C(O)NZ$^5$Z$^6$, —C(S)NZ$^5$Z$^6$, —SZ$^5$, —SOZ$^5$, —SO$_2$Z$^5$, —SO$_2$NZ$^5$Z$^6$, —CF$_3$, alkyl, substituted alkyl, alkenyl, substituted alkenyl, alkynyl, substituted alkynyl, carbocyclo, substituted carbocyclo, aryl, substituted aryl, heterocyclo, or substituted heterocyclo;

$Z^3$, $Z^4$, $Z^5$, $Z^6$ and $Z^7$ are independently hydrogen, halo, alkyl, substituted alkyl, alkenyl, substituted alkenyl, alkynyl, substituted alkynyl, carbocyclo, substituted carbocyclo, aryl, substituted aryl, heterocyclo, or substituted heterocyclo; or $Z^3$, $Z^4$, $Z^5$, $Z^6$ and $Z^7$ may, in one or more pairs of two, together with the atoms to which they are bonded, form a carbocyclic, substituted carbocyclic, heterocyclic or substituted heterocyclic group;

$R^{3*}$ is —C(O)NZ$^{5*}$Z$^{6*}$;

$Z^{5*}$ and $Z^{6*}$ together with the nitrogen atom to which they are bonded form a heterocyclic group or substituted heterocyclic group, provided that $Z^{5*}$ and $Z^{6*}$ do not together form unsubstituted piperidinyl, substituted piperidinyl, unsubstituted pyrrolidinyl, or unsubstituted morpholinyl;

n and p are independently selected from integers from 0 to 10 wherein, when m is 0, p is also 0;

m is an integer selected from 0 or 1; and q is an integer selected from 1 to 3.

* * * * *